(12) United States Patent
Cisar et al.

(10) Patent No.: US 9,133,148 B2
(45) Date of Patent: Sep. 15, 2015

(54) CARBAMATE COMPOUNDS AND OF MAKING AND USING SAME

(71) Applicants: Abide Therapeutics, Inc., San Diego, CA (US); The Scripps Research Institute, La Jolla, CA (US)

(72) Inventors: Justin S. Cisar, San Diego, CA (US); Cheryl A. Grice, Encinitas, CA (US); Todd K. Jones, Solana Beach, CA (US); Micah J. Niphakis, San Diego, CA (US); Jae Won Chang, San Diego, CA (US); Kenneth M. Lum, San Diego, CA (US); Benjamin F. Cravatt, La Jolla, CA (US)

(73) Assignees: The Scripps Research Institute, La Jolla, CA (US); Abide Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/599,105

(22) Filed: Jan. 16, 2015

(65) Prior Publication Data

US 2015/0148330 A1 May 28, 2015

Related U.S. Application Data

(63) Continuation of application No. 14/369,982, filed as application No. PCT/US2013/020551 on Jan. 7, 2013.

(60) Provisional application No. 61/631,558, filed on Jan. 6, 2012.

(51) Int. Cl.
| | |
|---|---|
| A61K 31/495 | (2006.01) |
| A61K 31/496 | (2006.01) |
| C07D 207/09 | (2006.01) |
| C07D 207/14 | (2006.01) |
| C07D 213/56 | (2006.01) |
| C07D 205/04 | (2006.01) |
| C07D 295/26 | (2006.01) |
| C07D 295/205 | (2006.01) |
| C07D 487/04 | (2006.01) |
| C07D 487/10 | (2006.01) |
| C07D 491/107 | (2006.01) |
| C07D 405/14 | (2006.01) |
| C07D 215/42 | (2006.01) |
| C07D 213/40 | (2006.01) |
| C07C 271/12 | (2006.01) |
| C07D 317/46 | (2006.01) |
| C07D 317/58 | (2006.01) |
| C07D 231/12 | (2006.01) |
| C07D 231/16 | (2006.01) |
| C07D 231/56 | (2006.01) |
| C07D 241/04 | (2006.01) |
| C07D 471/04 | (2006.01) |
| C07D 471/10 | (2006.01) |
| C07D 261/08 | (2006.01) |
| C07D 263/32 | (2006.01) |
| C07D 271/06 | (2006.01) |
| C07D 307/79 | (2006.01) |
| C07D 213/55 | (2006.01) |
| C07D 401/04 | (2006.01) |
| C07D 407/06 | (2006.01) |
| C07D 413/06 | (2006.01) |
| C07C 271/10 | (2006.01) |

(52) U.S. Cl.
CPC ............ *C07D 295/26* (2013.01); *C07C 271/10* (2013.01); *C07C 271/12* (2013.01); *C07D 205/04* (2013.01); *C07D 207/09* (2013.01); *C07D 207/14* (2013.01); *C07D 213/40* (2013.01); *C07D 213/55* (2013.01); *C07D 215/42* (2013.01); *C07D 231/12* (2013.01); *C07D 231/16* (2013.01); *C07D 231/56* (2013.01); *C07D 241/04* (2013.01); *C07D 261/08* (2013.01); *C07D 263/32* (2013.01); *C07D 271/06* (2013.01); *C07D 295/205* (2013.01); *C07D 307/79* (2013.01); *C07D 317/46* (2013.01); *C07D 317/58* (2013.01); *C07D 401/04* (2013.01); *C07D 405/14* (2013.01); *C07D 407/06* (2013.01); *C07D 413/06* (2013.01); *C07D 471/04* (2013.01); *C07D 471/10* (2013.01); *C07D 487/04* (2013.01); *C07D 491/107* (2013.01)

(58) Field of Classification Search
None
See application file for complete search history.

(56) References Cited

U.S. PATENT DOCUMENTS

| 2011/0275650 A1 | 11/2011 | Cravatt et al. |
| 2014/0357693 A1 | 12/2014 | Shaul et al. |
| 2015/0018335 A1 | 1/2015 | Cisar et al. |

FOREIGN PATENT DOCUMENTS

| DE | 1802739 | 6/1969 |
| RU | 2167150 | 5/2001 |

(Continued)

OTHER PUBLICATIONS

Fowler, British Journal of Pharmacology, vol. 166, pp. 1568-1585 (2012).*
Chang et al. Highly Selective Inhibitors of Monoacylglycerol Lipase Bearing a Reactive Group that is Bioisosteric with Endocannabinoid Substrates. Chemistry & Biology 19(5):579-588 (2012).
EP13733636.8 Partial Search Report dated Nov. 25, 2014.

(Continued)

*Primary Examiner* — Emily Bernhardt
(74) *Attorney, Agent, or Firm* — Wilson Sonsini Goodrich & Rosati

(57) ABSTRACT

This disclosure provides piperazine carbamates and compositions which may be modulators of MAGL and/or ABHD6 and their use as medicinal agents, processes for their preparation, and pharmaceutical compositions that include disclosed piperazine carbamates as at least one active agent. The disclosure also provides for method of treating a patient in need thereof, where the patient is suffering from indications such as pain, solid tumor cancer and/or obesity comprising administering a disclosed compound or composition.

29 Claims, No Drawings

(56) References Cited

FOREIGN PATENT DOCUMENTS

| WO | WO89/11794 | 12/1989 |
|---|---|---|
| WO | WO95/17439 | 6/1995 |
| WO | WO01/25188 | 4/2001 |
| WO | WO02/34382 | 5/2002 |
| WO | WO2005/063698 | 7/2005 |
| WO | WO-2005070910 A2 | 8/2005 |
| WO | WO-2005080363 A1 | 9/2005 |
| WO | WO2008/106047 | 9/2008 |
| WO | WO-2009141238 A1 | 11/2009 |
| WO | WO-2010009207 A1 | 1/2010 |
| WO | WO2011/151808 | 12/2011 |
| WO | WO2013/103973 | 7/2013 |

OTHER PUBLICATIONS

Mukhamadieva et al. Search for New Drugs Synthesis and Biological Activity of O-Carbamoylated 1,1,1,3,3,3-Hexafluoroisopropanols as New Specific Inhibitors of Carboxylesterase. Pharmaceutical Chemistry Journal 46(8):461-464 (2012).

PCT/US2013/020551 International Preliminary Report on Patentability dated Jul. 17, 2014.

PCT/US2013/020551 International Search Report dated May 21, 2013.

Science IP Report dated Dec. 11, 2014, provided by CAS Search Service.

South Synthesis and Reactions of Halogenated Thiazole Isocyanates. Journal of Heterocyclic Chemistry 28:1003-1011 (1991).

Studnev et al. Synthesis, Antibacterial and Immunotropic Activity of Poly(fluoroalkyl-N-arylcarbamates. Pharmaceutical Chemistry Journal 36(12):654-657 (2002).

Urry et al. Free-radical chain addition reactions of aldehydes with perfluoro ketones and chloro perfluoro ketones. The Journal of Organic Chemistry 32(2):347-352 (1967).

CR2014-0365 Opposition dated Dec. 5, 2014 (From PCT/US2013/020551).

* cited by examiner

CARBAMATE COMPOUNDS AND OF MAKING AND USING SAME

CROSS REFERENCE TO RELATED APPLICATIONS

This application is a Continuation of application Ser. No. 14/369,982, filed on Jun. 30, 2014, which is a National Phase filing under 35 U.S.C. §371 of PCT International Appl. No. PCT/US2013/020551 and has an international filing date of Jan. 7, 2013, designating the United States of America, which claims priority under 35 U.S.C. §119(a) to U.S. Provisional Application No. 61/631,558, filed Jan. 6, 2012. The entire contents of each of the above-applications are incorporated herein by reference.

BACKGROUND

Monoacylglycerol lipase (MAGL) is a primary enzyme responsible for hydrolyzing endocannabinoids such as 2-AG (2-arachidonoylglycerol), an arachidonate based lipid, in the nervous system. The endocannabinoid system regulates a range of physiological processes, including for example, appetite, pain sensation, inflammation, and memory. Further, disorders such as obesity, chronic pain, anxiety and depression have been linked to regulation of endocannabinoid system signaling activities.

For example, MAGL modulating compounds may be useful in stimulating 2-AG mediated signaling activities, and disorders associated with such signaling activities, including pain, inflammation, metabolic disorders and the like.

However, MAGL modulating compounds to date have typically lacked the selectivity required for general use as in vivo pharmaceutically acceptable agents, particularly, agents that are selective over fatty acid amide hydrolase (FAAH), a primary N-arachidonoyl ethanolamide (AEA) hydrolyzing enzyme. Genetic or pharmacological disruption of FAAH may result in one or more cannabinoid dependent behavioral effects, for example, inflammation, anxiety, depression, or reduction in pain sensation.

Further, it has recently been discovered that MAGL and its free fatty acid products are upregulated in aggressive cancer cells and in primary tumors, where it regulates a fatty acid network that promotes cancer cell migration and tumor growth. Therefore, new, selective inhibitors of MAGL may be useful in the treatment of cancers.

The serine hydrolase α-β-hydrolase domain 6 (ABHD6) is another lipid mediator and also may control accumulation and efficacy of 2-AG at cannabinoid receptors. ABHD6 may be a rate-limiting step of 2-AG signaling and thus is a member of the endocannabinoid signaling system. Therefore, ABHD6 may also be a useful target for cannabinoid dependent disorders, alone or in conjunction with MAGL and/or another serine hydrolase.

SUMMARY

This disclosure provides, for example, compounds and compositions which may be modulators of MAGL and/or ABHD6, and their use as medicinal agents, processes for their preparation, and pharmaceutical compositions that include disclosed compounds as at least one active ingredient. The disclosure also provided for the use of disclosed compounds as medicaments and/or in the manufacture of medicaments for the inhibition of MAGL and/or ABHD6 activity in warm-blooded animals such as humans.

In an embodiment, provided herein are compounds represented by formula I:

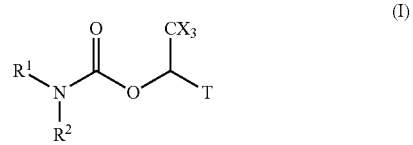

or pharmaceutically acceptable salts, stereoisomers, esters or prodrugs thereof, where $R^1$, $R^2$, T, and X are as defined herein.

The disclosure also provides for methods of treating indications such as pain, solid tumor cancer, or obesity via administration of a disclosed compound. Also provided are pharmaceutical compositions comprising at least one disclosed compound and a pharmaceutically acceptable carrier.

DETAILED DESCRIPTION

This disclosure is directed, at least in part, to MAGL and/or ABHD6 modulators or inhibitors. For example, provided herein are compounds capable of inhibiting MAGL and/or ABHD6.

The features and other details of the disclosure will now be more particularly described. Before further description, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to, allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "aryl" as used herein refers to a mono- or bicyclic carbocyclic ring system with 3-14 carbon atoms having one or two aromatic rings including, but not limited to, phenyl, naphthyl, tetrahydronaphthyl, indanyl, indenyl, and the like.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-7-carbon atoms, referred to herein as $C_{3-7}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-7, 3-6, or 4-6 carbons, referred to herein for example as $C_{3-7}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, oxadiazole, isothiazole, isoxazole, imidazole, indazole, pyrazole, quinoline, triazole, pyridine or pyrimidine etc.

The terms "heterocyclyl" or "heterocyclic group" are art-recognized and refer to saturated or partially unsaturated 4-7 membered ring structures or 8-10 membered bicyclic or spirocyclic ring structures, whose ring structures include one to three heteroatoms, such as nitrogen, oxygen, and sulfur. Where possible, heterocyclyl rings may be linked to the adjacent radical through carbon or nitrogen. A heterocycle may be fused to one or more aryl, or partially unsaturated, or saturated rings. Examples of heterocyclyl groups include, but are not limited to azetidine, benzodioxole, 2,8-diazaspiro[4.5]decan-1-one, 3,4-dihydro-2H-benzo[b][1,4]oxazinedihydrobenzofuran, dihydrofuran, dihydroisobenzofuran, 6,7-dihydro-5H-pyrrolo[3,4-b]pyridine, indoline, morpholine, octahydropyrrolo[1,2-a]pyrazine, 8-oxa-2-azaspiro[4.5]decane, oxetane, 2,3-dihydrobenzofuran, piperazine, piperidine, pyrrolidine, tetrahydrofuran, tetrahydropyran, thiomorpholine, etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. Disclosed compounds may be administered to a mammal, such as a human, but may also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond or arrangement of substituents around a cycloalkyl or heterocyclic ring. The symbol ═════ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds as disclosed herein which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atoms replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino $(C_{2-3})$alkyl.

Similarly, if a compound of this disclosure contains an alcohol functional group, a prodrug can be formed by the replacement of the hydrogen atom of the alcohol group with a group such as $(C_{1-6})$alkylcarbonyloxymethyl, 1-(($C_{1-6}$)alkylcarbonyloxy)ethyl, 1-methyl-1-(($C_{1-6}$)alkylcarbonyloxy)ethyl$(C_{1-6})$alkoxycarbonyloxymethyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O$(C_{1-6})$alkyl)$_2$ or glycosyl (the radical resulting from the removal of a hydroxyl group of the hemiacetal form of a carbohydrate).

I. Carbamate Compounds

In certain embodiments, the present invention provides compounds such as those represented by formula I:

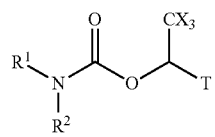
(I)

wherein X is selected independently, for each occurrence, from H, F, Cl or Br; wherein at least three occurrences of X are F;

T is $CX_3$ or

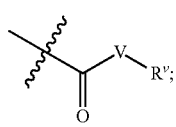

V is O or $NR^a$;

$R^V$ is selected from the group consisting of hydrogen, $C_1$-$C_6$alkyl, $C_2$-$C_6$alkenyl, $C_{3-6}$cycloalkyl, phenyl, heteroaryl, and heterocyclyl, or when $R^a$ and $R^V$ occur together with the nitrogen to which they are attached, form a 4-6 membered heterocyclic ring which may have an additional heteroatom selected from O, S, or N; wherein $C_1$-$C_6$alkyl, $C_2$-$C_6$alkenyl, phenyl, heterocyclic ring and heterocyclyl are optionally substituted by one, two, or three moieties independently selected from the group consisting of halogen, hydroxyl, $C_1$-$C_6$alkyl, cyano, phenyl; and wherein a)

$R^1$ is -$L^1$-$R^6$;

$R^2$ is H or $C_1$-$C_6$alkyl;

$L^1$ is $C_1$-$C_6$alkylene or a bond;

$R^6$ is selected from the group consisting of phenyl, naphthyl, a mono or bicyclic heteroaryl and a mono or bicyclic heterocycle, wherein the heterocycle or heteroaryl has 1, 2 or 3 heteroatoms independently selected from O, S, or N; and $R^6$ is optionally substituted by one, two, three or four moieties independently selected from the group consisting of: halogen, phenyl (optionally substituted by one, two or three moieties independently selected from $R^c$), phenyloxy (optionally substituted by one, two or three moieties independently selected from $R^c$), anilinyl (optionally substituted on a carbon by one, two or three moieties independently selected from $R^c$), hydroxyl, cyano, $C_{1-6}$alkyl (optionally substituted by one, two or three halogens, cyano, or hydroxyl), $C_{1-6}$alkoxy (optionally substituted by one, two or three halogens, cyano, or hydroxyl), $R^aR^bN$—, $R^aR^bN$—SO$_2$—, $R^aR^bN$—C(O)—, $C_{1-6}$alkyl-C(O)NR$^a$—, $R^a$—S(O)$_w$—, $R^a$—S(O)$_w$—NR$^b$— (wherein w is 0, 1 or 2), heteroaryl (optionally substituted by one, two or three moieties independently selected from $R^c$), or heteroaryloxy;

or b)

$R_1$ and $R_2$ taken together with the nitrogen to which they are attached form a moiety selected from:

a 4-7 membered heterocyclic ring A; or a 4-7 membered heterocyclic ring B having an additional nitrogen;

wherein one carbon of ring A has a substituent represented by:

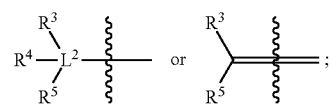

$L^2$ is $C_1$-$C_6$alkylene or $C_1$-$C_6$alkylene-NR$^a$—;

$R^3$ and $R^5$ are each independently selected from phenyl, naphthyl, a mono or bicyclic heteroaryl, and a mono or bicyclic heterocycle, wherein the heterocycle or heteroaryl has 1, 2 or 3 heteroatoms independently selected from O, S, or N; and wherein $R^3$ and $R^5$ may be independently and optionally substituted by one, two, three or four moieties each independently selected from $R^g$;

$R^4$ is selected from the group consisting of H, halogen, hydroxyl, cyano, or $C_1$-$C_5$alkoxy;

A is optionally substituted on another carbon by one, two, three or four substituents each independently selected from $R^d$;

the additional nitrogen of ring B has a substituent represented by:

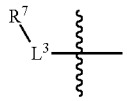

L³ is selected from the group consisting of: a bond, C₁-C₆alkylene, —C(O)—, C₁-C₆alkylene-C(O)—, C(O)—C₁-C₆alkylene-, NRᵃ—C(O)—C₁-C₆alkylene-, C₁-C₆alkylene-O—C(O)—, —S(O)_w—, and C₁-C₆alkylene-S(O)_w—, wherein w is 0, 1, or 2, and wherein C₁-C₆alkylene is optionally substituted by one or two substituents selected from the group consisting of: halogen, hydroxyl, cyano, and an additional R⁷, wherein when L³ is —S(O)_w—, then R⁷ is not H;

R⁷ is selected from the group consisting of: H, phenyl, naphthyl, mono or bicyclic heteroaryl, and mono or bicyclic heterocyclyl, wherein the heteroaryl or the heterocyclyl has 1, 2 or 3 heteroatoms independently selected from O, S, or N; wherein R⁷ is optionally moieties by one, two, three or four moieties each independently selected from Rʰ;

B is optionally substituted on one or more carbons by one, two, three or four moieties each independently selected from Rᵈ;

Rᵃ and Rᵇ may be independently selected, for each occurrence, from the group consisting of hydrogen and C₁₋₃alkyl; wherein C₁₋₃alkyl may optionally be substituted by one or more substituents selected from halogen, cyano, oxo, hydroxyl, heterocycle, and phenyl;

or Rᵃ and Rᵇ, when they occur together with the nitrogen to which they are attached, form a 4-6 membered heterocyclic ring or a 9-10 membered bicyclic heterocycle or spirocyclic ring, which may have an additional heteroatom selected from O, S, or N; wherein the 4-6 membered heterocyclic ring or 9-10 membered bicyclic heterocycle or spirocycle may optionally be substituted by one or more substituents selected from the group consisting of halogen, cyano, oxo, C₁₋₆alkyl, —S(O)_w—C₁₋₆alkyl (where w is 0, 1 or 2), hydroxyl, —NH₂, —NH—C₁₋₆alkyl, —C(O)—C₁₋₆alkyl, and NH—C(O)—C₁₋₆alkyl;

Rᶜ is selected from the group consisting of halogen, cyano, hydroxyl, nitro, C₁₋₆alkyl (optionally substituted by one, two, or three halogens, cyano, or hydroxyl), C₂₋₆alkenyl (optionally substituted by one, two, or three halogens), C₂₋₆alkynyl (optionally substituted by one, two, or three halogens), C₃₋₆cycloalkyl, C₁₋₆alkoxy (optionally substituted by one, two, or three halogens), RᵃRᵇN—, RᵃRᵇN—SO₂—, RᵃRᵇN—C(O)—, Rᵃ—C(O)—NRᵃ—, Rᵃ—C(O)—, Rᵃ—S(O)_w—NRᵇ— (wherein w is 0, 1 or 2), or Rᵃ—S(O)_w— (wherein w is 0, 1 or 2).

Rᵈ is selected from the group consisting of: C₁₋₆alkyl (optionally substituted by one, two or three halogens, or hydroxyl) or RᵃRᵇN—C(O)—;

Rᵍ is selected from the group consisting of: halogen, phenyl, phenyloxy, anilinyl, hydroxyl, cyano, C₁₋₆alkyl (optionally substituted by one, two or three halogens, cyano, or hydroxyl), C₃₋₆cycloalkyl (optionally substituted by one, two or three halogens, cyano, or hydroxyl), C₂₋₆alkenyl (optionally substituted by one, two or three halogens, cyano, or hydroxyl), C₂₋₆alkynyl (optionally substituted by one, two or three halogens, cyano, or hydroxyl) C₁₋₆alkoxy (optionally substituted by one, two or three halogens, cyano, or hydroxyl), Rᵃ—C(O) NRᵃ—, RᵃRᵇN—, RᵃRᵇN—SO₂—, Rᵃ—S(O)_w— (wherein w is 0, 1 or 2), Rᵃ—SO₂—NRᵇ—, RᵃRᵇN—C(O)—, heterocycle (optionally substituted by one, two or three moieties each independently selected from Rᶜ, and connected to R³ or R⁵ through a carbon or heteroatom), or heteroaryl (optionally substituted by one, two or three moieties each independently selected from Rᶜ and connected to R³ or R⁵ through a carbon or heteroatom), or two adjacent Rᵍ groups along with the carbons to which they are attached can be taken together to form a 5- or 6-member heterocyclic or heteroaryl ring optionally substituted with 0, 1 or 2 halogens selected from F or Cl and which may have one or two additional heteroatoms selected from O, S, or N;

Rʰ is selected from the group consisting of: halogen, phenyl (optionally substituted by one, two, or three moieties each independently selected from Rᶜ), phenyloxy (optionally substituted by one, two, or three moieties each independently selected from Rᶜ), hydroxyl, cyano, C₁₋₆alkyl (optionally substituted by one, two or three halogens, cyano, or hydroxyl), C₂₋₆alkenyl (optionally substituted by one, two or three halogens, cyano, or hydroxyl), C₂₋₆alkynyl (optionally substituted by one, two or three halogens, cyano, or hydroxyl), C₁₋₆alkoxy (optionally substituted by one, two or three halogens, cyano, or hydroxyl), RᵃRᵇN—, Rᵃ—C(O) NRᵃ—, RᵃRᵇN—SO₂—, RᵃRᵇN—C(O)—, Rᵃ—S(O)_w— (wherein w is 0, 1 or 2), Rᵃ—SO₂—NRᵇ—, heteroaryl (optionally substituted by one, two or three moieties each independently selected from Rᶜ and connected to R⁷ through a carbon or heteroatom), heterocycle (optionally substituted by one, two or three moieties each independently selected from Rᶜ, and connected to R⁷ through a carbon or heteroatom), or heteroaryloxy (optionally substituted by one, two, or three moieties each independently selected from Rᶜ), or two adjacent Rʰ groups along with the carbons to which they are attached can be taken together to form a 5- or 6-member heterocyclic or heteroaryl ring optionally substituted with 0, 1 or 2 halogens selected from F or Cl and which may have one or two additional heteroatoms selected from O, S, or N;

and pharmaceutically acceptably salts or stereoisomers thereof.

In some embodiments, T is CX₃, and/or Rⱽ is selected from the group consisting of methyl, ethyl, iso-propyl, tert-butyl, benzyl and phenyl. For example, contemplated herein are compounds represented by formula I wherein at least one, two, or three occurrences of X is halogen, e.g., wherein at least two occurrences of X is halogen, or three occurrences of X is halogen, e.g., where X for at least one, two, or three, or at least one occurrence, is fluorine. In some embodiments, for example, formula I may be represented by:

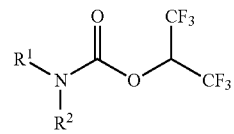

wherein $R^1$ and $R^2$ are provided above; e.g., wherein $R^1$ and $R^2$ taken together with the nitrogen to which they are attached form a 4-7 membered heterocyclic ring, e.g., ring B as described above, having an additional nitrogen that may be substituted as described herein.

In another embodiment, a provided compound is represented by:

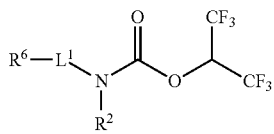

wherein:
$R^2$ is H or $C_1$-$C_3$alkyl;
$L^1$ is —$CH_2$— or —$CH_2$—$CH_2$—; and
$R^6$ is selected from the group consisting of phenyl, naphthyl, indanyl, benzodioxole, benzoxazole, benzoisoxazole, benzimidazole, benzotriazole, oxadiazole, indazole, isooxazole, quinoline, isoquinoline, pyridine, pyrazine, pyrimidine, thienyl, thiazole, benzothiopene, indole, benzothiadiazole, pyrazole, or 3,4-dihydro-2H-benzo[b][1,4]oxazine wherein $R^6$ may be optionally substituted by one, two, three or four moieties each independently selected from the group consisting of halogen, phenyl (optionally substituted by halogen, cyano, methyl or $CF_3$), phenyloxy, hydroxyl, cyano, $C_{1-6}$alkyl (optionally substituted by one, two or three halogens, or hydroxyl), $C_{1-6}$alkoxy (optionally substituted by one, two or three halogens, or hydroxyl), $R^aR^bN$—, $R^aR^bN$—$SO_2$—, $R^a$—$S(O)_w$— (wherein w is 0, 1 or 2), $R^a$—$S(O)_w$—$NR^b$— (wherein w is 0, 1 or 2), $R^aR^bN$—$C(O)$—, $C_{1-6}$alkyl-$C(O)NR^a$—, heteroaryl (optionally substituted by $C_{1-6}$alkyl), or heteroaryloxy.

For example, $R^6$ may be e.g., phenyl, optionally substituted by halogen, cyano, hydroxyl, methoxy, pyridine (optionally substituted by methyl), phenyl, or phenyloxy. $R^6$ for example, may be represented by one of:

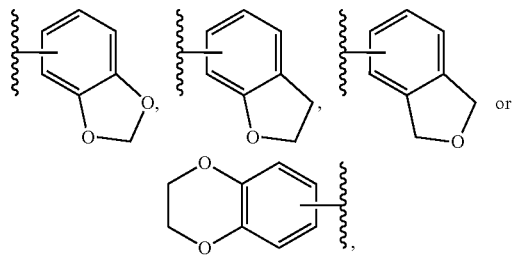

and/or $R^2$ is methyl or ethyl. $L^1$ may be, in certain embodiments, —$CH_2$—.

In some embodiments, $R^6$ is selected from the group consisting of:

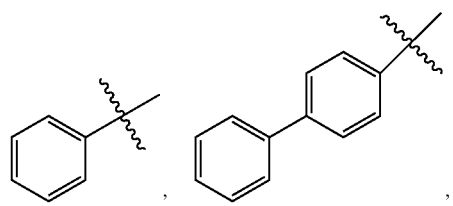

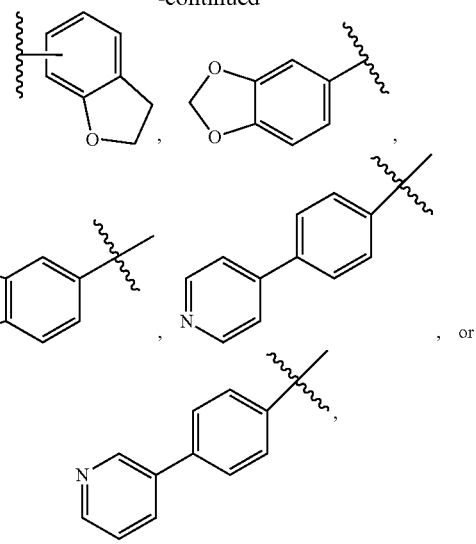

each $R^6$ moiety optionally substituted on a free carbon as described above

In other embodiments, $R^1$ and $R^2$ taken together with the nitrogen to which they are attached form a 4-7 membered heterocyclic ring A wherein one carbon of ring A has a substituent represented by:

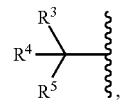

wherein $R^3$, $R^4$, $R^5$ are as described above. For example, contemplated compounds may be represented by:

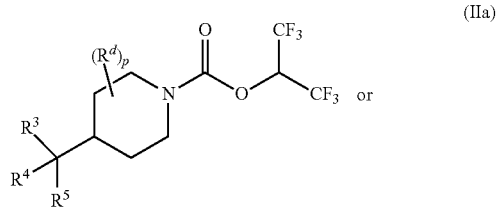

(IIa)

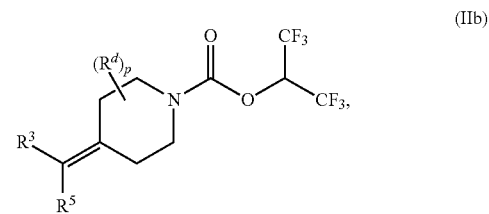

(IIb)

for example, wherein $R^3$ and $R^5$ are described above, or e.g., each independently selected from the group consisting of:

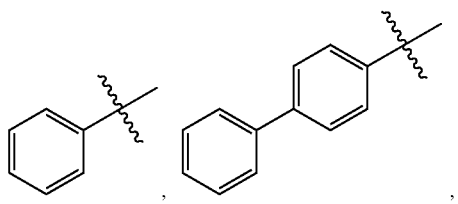

(each moiety optionally substituted on a free carbon as described above); and p is 0, 1, 2, 3 or 4;

$R^d$ is selected from the group consisting of: H, $C_{1-6}$alkyl (optionally substituted by one, two or three halogens, or hydroxyl) or $R^aR^bN$—C(O)—;

In some embodiments, $R^4$ of formula I or IIa may be selected from the group consisting of H, hydroxyl and methoxy. In additional or other embodiments, $R^1$ and $R^2$ taken together with the nitrogen to which they are attached form a 4-7 membered heterocyclic ring B having an additional nitrogen (wherein ring B may be substituted on a carbon and/or nitrogen as described herein)

Also contemplated herein is a compound is represented by:

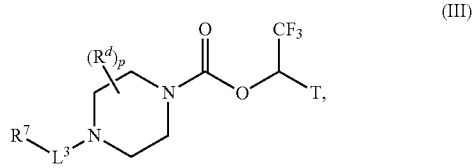

(III)

wherein p is 0, 1, or 2;

T is selected from the group consisting of —C(O)—O-methyl, —C(O)—O-ethyl, —C(O)—O-iso-propyl, —C(O)—O-tert-butyl, —C(O)—O-benzyl and —C(O)—O-phenyl and $CX_3$, wherein X for each occurrence is H or a halogen (e.g., F);

$L^3$ is provided above, e.g., wherein $L^3$ is —CH(phenyl)-, —CH(heteroaryl)-, or —CH(heterocycle)-, or for example, $L^3$ is selected from the group consisting of a bond, $C_1$-$C_3$alkylene (or e.g., $C_1$-$C_2$alkylene or —CH$_2$—), —C(O)—, —CH—C(O)—NH, —S(O)$_w$— (e.g., —S(O)$_2$—), and $C_1$-$C_6$alkylene-S(O)$_w$— e.g., $C_1$-$C_2$alkylene-S(O)$_w$—), wherein w is 0, 1, or 2, and wherein $C_1$-$C_3$alkylene (or e.g., —CH$_2$—), for example is optionally substituted by a substituent selected from the group consisting of: phenyl, biphenyl, phenyloxyphenyl (each optionally substituted by halogen, $C_{1-6}$alkyl (optionally substituted by one, two or three halogens, or hydroxyl), mono or bicyclic heteroaryl having 1, 2 or 3 heteroatoms independently selected from O, S, or N); $R^d$ is provided above, and $R^7$ is selected from the group consisting of phenyl, biphenyl, phenyloxyphenyl, mono or bicyclic heteroaryl or mono or bicyclic heterocyclic ring, wherein the heteroaryl or the heterocyclic ring has 1, 2 or 3 heteroatoms independently selected from O, S, or N; wherein $R^7$ is optionally substituted by one, two, three or four substituents selected from the group consisting of halogen, cyano, phenyl (optionally substituted by one, two, or three substituents selected from the group consisting of: halogen, methyl, ethyl, propyl, t-butyl, cyano or $CF_3$), phenyloxy, hydroxyl, cyano, $C_{1-6}$alkyl (optionally substituted by one, two or three halogens, or hydroxyl), $C_{1-6}$alkoxy (optionally substituted by one, two or three halogens), $R^aR^bN$—, $R^aR^bN$—$SO_2$—, $R^a$—S(O)$_w$—NR$^b$— (wherein w is 0, 1 or 2), $R^aR^bN$—C(O)—, $C_{1-6}$alkyl-C(O)NR$^a$—, heteroaryl (optionally substituted by one or two substituents each selected from $C_{1-6}$alkyl or halogen), or heteroaryloxy (optionally substituted by one or two substituents each selected from $C_{1-6}$alkyl or halogen), and pharmaceutically acceptable salts and stereoisomers thereof.

In certain embodiments, $L^3$ may be —CH—$R^{10}$, (of e.g., formula I or III) wherein $R^{10}$ selected from the group consisting of phenyl, naphthyl, indanyl, benzodioxole, benzoxazole, benzoisoxazole, benzimidazole, benzotriazole, oxadiazole, indazole, isooxazole, quinoline, isoquinoline, pyridine, pyrazine, pyrimidine, thienyl, thiazole, benzothiopene, indole, benzothiadiazole, pyrazole, or 3,4-dihydro-2H-benzo[b][1,4]oxazine, wherein $R^{10}$ may be optionally substituted by one, two or three moieties each independently selected from the group consisting of halogen, phenyl (optionally substituted by halogen, cyano, methyl, methoxy, or $CF_3$), phenyloxy (optionally substituted by halogen, cyano, methyl or $CF_3$), hydroxyl, cyano, $C_{1-6}$alkyl (optionally substituted by one, two or three halogens, or hydroxyl), $C_{1-6}$alkoxy (optionally substituted by one, two or three halogens, cyano or hydroxyl), $R^aR^bN$—, $R^aR^bN$—$SO_2$—, $R^a$—S(O)$_w$—NR$^b$— (wherein w is 0, 1 or 2), $R^aR^bN$—C(O)—, $C_{1-6}$alkyl-C(O)NR$^a$—, heteroaryl (optionally substituted by $C_{1-6}$alkyl), or heteroaryloxy. In other embodiments, $L^3$ is selected from the group consisting of a bond, —CH$_2$—, —S(O)$_2$—, or —C(O)—.

For example, in certain embodiments, $R^7$ and/or $R^{10}$ of formula I or III can be selected from the group consisting of

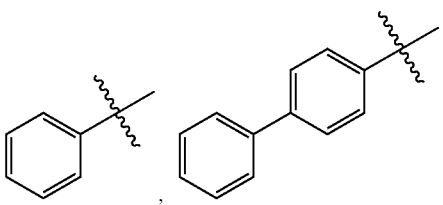

-continued

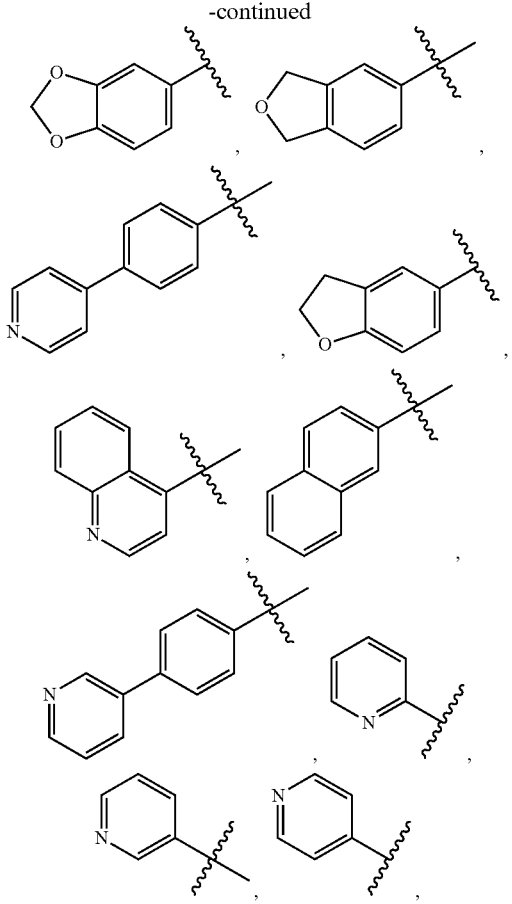

wherein each moiety above can be optionally substituted on a free carbon by one, two, three or four substituents independently selected from $R^b$, described above.

In other embodiments, $R^7$ and/or $R^{10}$ of formula I or III (or $R^3$ and/or $R^5$ of formula II) can be selected from the group consisting of:

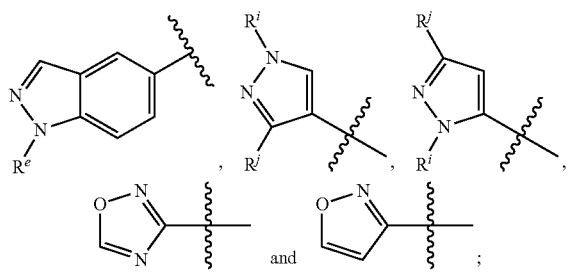

where $R^e$ is selected from the group consisting of H, phenyl (optionally substituted by one, two or three substituents each independently selected from halogen, $C_{1-6}$alkyl (optionally substituted by one, two or three halogens), and $C_{1-6}$alkoxy (optionally substituted by one, two or three halogens)), and $C_{1-6}$alkyl (optionally substituted by one, two or three halogens);

$R^i$ and $R^j$ may be independently selected from the group consisting of: H, CH$_3$, $C_{2-6}$alkyl (optionally substituted by one, two or three moieties independently selected from $R^c$)), phenyl (optionally substituted by one, two or three moieties independently selected from $R^c$), and $C_{3-6}$cycloalkyl (optionally substituted by one, two or three moieties independently selected from $R^c$), where $R^c$ is described above. It is understood that each moiety above can also be optionally substituted on a free carbon, if present, by one, two, three or four substituents independently selected from $R^h$, described above.

In certain embodiments, $R^7$ may be selected from the group consisting of phenyl, naphthyl, indanyl, indazole, isooxazole, quinoline, isoquinoline, pyridine, pyrazine, pyrimidine, thienyl, thiazole, benzothiopene, indole, benzothiadiazole, pyrazole, or 3,4-dihydro-2H-benzo[b][1,4]oxazine, and $R^7$ may be optionally substituted by one, two, three or four substituents selected from the group consisting of halogen, phenyl (optionally substituted by one, two, or three substituents selected from the group consisting of: halogen, methyl, ethyl, propyl, t-butyl, cyano or CF$_3$), phenyloxy, hydroxyl, cyano, $C_{1-6}$alkyl (optionally substituted by one, two or three halogens, or hydroxyl), $C_{1-6}$alkoxy, $R^aR^bN$—, $R^aR^bN$—SO$_2$—, $R^a$—S(O)$_w$—NR$^b$— (wherein w is 0, 1 or 2), $R^aR^bN$—C(O)—, $C_{1-6}$alkyl-C(O)NR$^a$—, heterocycle (optionally substituted by $C_{1-6}$alkyl), heteroaryl (optionally substituted by $C_{1-6}$alkyl), or heteroaryloxy.

Also contemplated herein is a compound represented by:

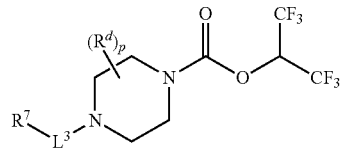

wherein:

p is 0, 1, 2, 3 or 4;

$R^d$ is independently selected for each occurrence from the group consisting of: H, $C_{1-6}$alkyl (optionally substituted by one, two or three halogens) and $R^aR^bN$—C(O)—;

$L^3$ is selected from the group consisting of: a bond, $C_1$-$C_6$alkylene, —C(O)—, $C_1$-$C_6$alkylene-C(O)—, $C_1$-$C_6$alkylene-O—C(O)—, NR$^a$—C(O)—$C_1$-$C_6$alkylene-, —S(O)$_w$—, and $C_1$-$C_6$alkylene-S(O)$_w$—, wherein w is 0, 1, or 2, and wherein $C_1$-$C_6$alkylene is optionally substituted by one or two substituents selected from the group consisting of: halogen, hydroxyl, cyano, and an additional $R^7$;

$R^7$ is selected from the group consisting of: H, phenyl, naphthyl, mono or bicyclic heteroaryl, or mono or bicyclic heterocycle, wherein the heteroaryl or heterocycle has 1, 2 or 3 heteroatoms independently selected from O, S, or N; wherein $R^7$ is optionally substituted by one, two, three or four moieties independently selected from the group consisting of halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by one, two or three halogens, cyano, or hydroxyl), $C_{2-6}$alkenyl (optionally substituted by one, two or three halogens, cyano, or hydroxyl), $C_{1-6}$alkoxy (optionally substituted by one, two or three halogens, cyano, or hydroxyl), $R^aR^bN$—, $R^a$—C(O)NR$^a$—, $R^aR^bN$—SO$_2$—, $R^aR^bN$—C(O)—, $R^a$—S(O)$_w$— (wherein w is 0, 1 or 2), $R^a$—S(O)$_w$—NR$^b$— (wherein w is 0, 1 or 2), heteroaryl (optionally substituted by one, two or three moieties each independently selected from $R^c$) or heteroaryloxy (optionally substituted by one, two, or three moieties each independently selected from $R^c$);

$R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl;

or $R^a$ and $R^b$, when they occur together with the nitrogen to which they are attached, form a 4-6 membered heterocyclic ring or a 9-10 membered bicyclic heterocycle or spirocyclic ring, which may have an additional heteroatom selected from O, S, or N; wherein the 4-6 membered heterocyclic ring or 9-10 membered bicyclic heterocycle or spirocycle may optionally be substituted by one or more substituents selected from the group consisting of halogen, cyano, oxo, $C_{1-6}$alkyl, —S(O)$_w$—$C_{1-6}$alkyl (where w is 0, 1 or 2), hydroxyl, —NH$_2$, and NH—C(O)—$C_{1-6}$alkyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), $R^aR^bN$—, $R^aR^bN$—SO$_2$—, $R^aR^bN$—C(O)—, $R^a$—C(O)—, $R^a$—C(O)—NR$^a$—; $R^a$—S(O)$_w$—NR$^b$— (wherein w is 0, 1 or 2), or $R^a$—S(O)$_w$— (wherein w is 0, 1 or 2).

In an embodiment, a compound provided herein may be represented by:

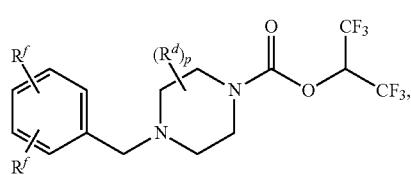
(IV)

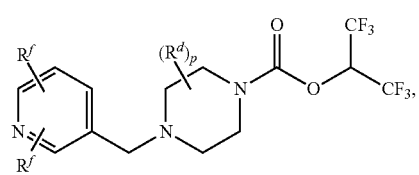
(V)

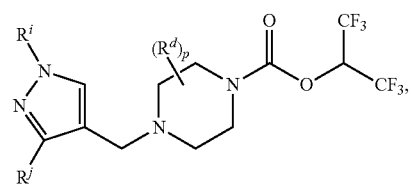
(VI)

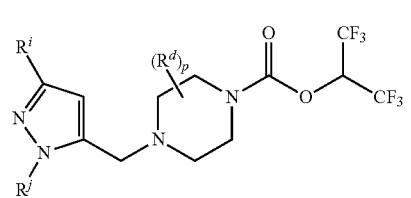
(VII)

wherein p is 0, 1, 2, 3 or 4;

$R^d$ is independently selected for each occurrence from the group consisting of: H, $C_{1-6}$alkyl (optionally substituted by one, two or three halogens) and $R^aR^bN$—C(O)— wherein $R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl; or $R^a$ and $R^b$ together with the nitrogen to which they are attached, form a 4-6 membered heterocyclic ring or a 9-10 membered bicyclic heterocyclic ring or spirocycle, which may have an additional heteroatom selected from O, S, or N; wherein the 4-6 membered heterocyclic ring or 9-10 membered bicyclic heterocyclic ring or spirocycle may optionally be substituted by one or more substituents selected from the group consisting of halogen, cyano, oxo, $C_{1-6}$alkyl, hydroxyl, —NH$_2$, —S(O)$_w$—$C_{1-6}$alkyl (wherein w is 0, 1 or 2), $C_{1-6}$alkyl-C(O)—, and NH—C(O)—$C_{1-6}$alkyl;

$R^f$ is independently selected for each occurrence from H, $R^aR^bN$—, $R^aR^bN$—C(O)—, phenyoxy, phenyl (optionally substituted by one, two or three halogens or methyl); pyridinyl (optionally substituted by one, two or three halogens or methyl) halogen, $C_{1-6}$alkyl (optionally substituted by one, two or three halogens) and $C_{1-6}$alkoxy (optionally substituted by one, two or three halogens) wherein $R^a$ and $R^b$ may be independently selected, for each occurrence, from the group consisting of hydrogen and $C_{1-3}$alkyl; wherein $C_{1-3}$alkyl may optionally be substituted by one or more substituents selected from halogen, cyano, oxo, hydroxyl, heterocycle, and phenyl; or $R^a$ and $R^b$ together with the nitrogen to which they are attached, form a 4-6 membered heterocyclic ring or a 9-10 membered bicyclic heterocyclic ring or spirocycle, which may have an additional heteroatom selected from O, S, or N; wherein the 4-6 membered heterocyclic ring or 9-10 membered bicyclic heterocyclic ring or spirocycle may optionally be substituted by one or more substituents selected from the group consisting of halogen, cyano, oxo, $C_{1-6}$alkyl, hydroxyl, —NH$_2$, —S(O)$_w$—$C_{1-6}$alkyl (wherein w is 0, 1 or 2), $C_{1-6}$alkyl-C(O)—, and NH—C(O)—$C_{1-6}$alkyl;

$R^i$ and $R^j$ may be independently selected from the group consisting of: H, $C_{1-6}$alkyl (optionally substituted by one, two or three moieties independently selected from $R^c$), phenyl (optionally substituted by one, two or three moieties independently selected from $R^c$), and $C_{3-6}$cycloalkyl (optionally substituted by one, two or three moieties independently selected from $R^c$), where $R^c$ is described above. It is understood that each moiety above can also be optionally substituted on a free carbon, if present, by one, two, three or four substituents independently selected from $R^h$, described above and pharmaceutically acceptable salts and stereoisomers thereof. For example, one $R_f$ may be a heterocyclic ring selected from piperidinyl, pyrrolidinyl, morpholinyl, and pyrazole in e.g., compound IV.

In another embodiment, a contemplated compound may be represented by:

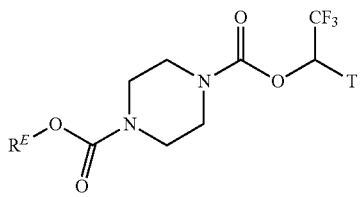

wherein
T is CX$_3$ or

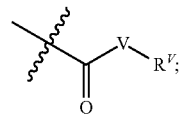

X is independently for each occurrence halogen or H;

V is O or $NR^a$;

$R^V$ is selected from the group consisting of hydrogen, $C_1$-$C_6$alkyl, $C_2$-$C_6$alkenyl, phenyl, and heterocyclyl; wherein $C_1$-$C_6$alkyl, $C_2$-$C_6$alkenyl, phenyl, and heterocyclyl are optionally substituted by one, two, or three moieties independently selected from the group consisting of halogen, hydroxyl, cyano, phenyl and heterocyclyl;

$R^E$ is selected from the group consisting of H, $C_1$-$C_6$alkyl, heterocyclyl or phenyl; wherein $R^E$ is optionally substituted by one, two, or three moieties independently selected from the group consisting of halogen, nitro, $C_1$-$C_6$alkyl, phenyl and heterocyclyl; and stereoisomers or pharmaceutically acceptable salts thereof.

Contemplated herein is a compound represented by:

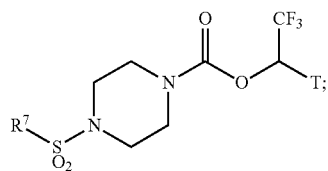

wherein

T is $CX_3$ or

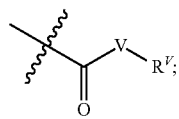

X is independently for each occurrence halogen or H;

V is O or $NR^a$;

$R^V$ is selected from the group consisting of hydrogen, $C_1$-$C_6$alkyl, $C_2$-$C_6$alkenyl, phenyl, and heterocyclyl; wherein $C_1$-$C_6$alkyl, $C_2$-$C_6$alkenyl, phenyl, and heterocyclyl are optionally substituted by one, two, or three moieties independently selected from the group consisting of halogen, hydroxyl, cyano, phenyl and heterocyclyl;

$R^7$ is selected from the group consisting of: H, phenyl, naphthyl, a mono or bicyclic heteroaryl having 1, 2 or 3 heteroatoms independently selected from O, S, or N, or a mono or bicyclic heterocycle having 1, 2 or 3 heteroatoms independently selected from O, S, or N; wherein $R^7$ is optionally substituted by one, two or three moieties independently selected from the group consisting of halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by one, two or three halogens, cyano, or hydroxyl), $C_{2-6}$alkenyl (optionally substituted by one, two or three halogens, cyano, or hydroxyl), $C_{1-6}$alkoxy (optionally substituted by one, two or three halogens, cyano, or hydroxyl), $R^aR^bN-$, $R^a-C(O)NR^a-$, $R^aR^bN-SO_2-$, $R^aR^bN-C(O)-$, $R^a-S(O)_w-$ (wherein w is 0, 1 or 2), $R^a-S(O)_w-NR^b-$ (wherein w is 0, 1 or 2), heteroaryl (optionally substituted by one, two or three moieties each independently selected from $R^c$) or heteroaryloxy (optionally substituted by one, two, or three moieties each independently selected from $R^c$);

$R^a$ and $R^b$ may be independently selected, for each occurrence, from the group consisting of hydrogen and $C_{1-3}$alkyl;

wherein $C_{1-3}$alkyl may optionally be substituted by one or more substituents selected from fluorine, cyano, oxo and hydroxyl;

or $R^a$ and $R^b$, when they occur together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), $R^aR^bN-$, $R^aR^bN-SO_2-$, $R^aR^bN-C(O)-$, $R^a-S(O)_w-NR^b-$ (wherein w is 0, 1 or 2), or $R^a-S(O)_w-$ (wherein w is 0, 1 or 2); and pharmaceutically acceptable salts and stereoisomers thereof.

Procedures for making compounds described herein are provided below with exemplary reference to Schemes 1-15. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art [for example, see Greene, Wuts, Protective Groups in Organic Synthesis, 2nd Ed. (1999)]. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

A general synthetic strategy used to prepare the carbamate compounds of Formula I is depicted in Scheme 1. The activated hexafluoroisopropyl chloroformate, C can be prepared by reacting hexafluoroisopropanol B with triphosgene A in the presence of a base such as diisopropylethyl amine or 2,6-lutidine with catalytic dimethyl aminopyridine in a solvent such as methylene chloride or acetonitrile. The desired $-NR^1R^2$ group (where $R^1$ and $R^2$ are described above) of the carbamate can be installed by reacting the activated chloroformate with the appropriate amine D. The specific $R^1$ and $R^2$ groups are selected based on the desired groups in the final carbamate product E.

SCHEME 1

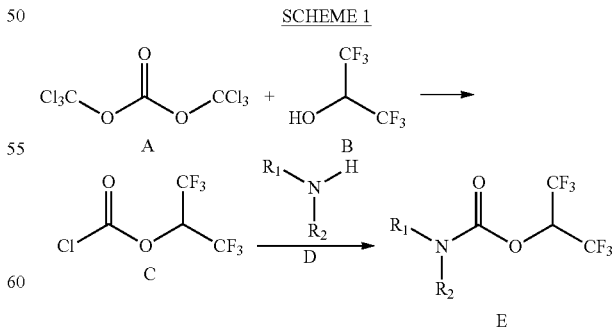

Scheme 2 provides an exemplary synthetic procedure for making the amine starting material utilized in Scheme 1. The desired amine substituent C is derived from the Boc-protected variant F. Removal of the Boc-group is achieved by reaction of the Boc-protected amine with N-methylmorpholine and iodotrimethylsilane or alternatively, by treatment with a 4N solution of HCl in dioxane in a solvent such as CH₂Cl₂ at temperatures ranging from 0 to 25° C. or by treatment with trifluoroacetic acid in a solvent such as CH₂Cl₂.

SCHEME 2

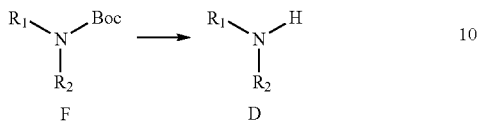

Scheme 3 provides a detailed exemplary synthetic procedure for making carbamate derivatives having a piperidine group of the general structure K. Arylbromide G can be obtained from commercial sources and converted to aryllithium using tert-butyllithium at reduced temperatures. Reacting the aryllithium with ester H provides alcohol I. The alcohol I can be converted to intermediate J according to the representative protocol described in Scheme 2. $R^g$ is described above. Compounds of the general structure K can be prepared according to the representative protocol described above for Scheme 1. Similar chemistry can be executed using heteroarylbromides.

SCHEME 3

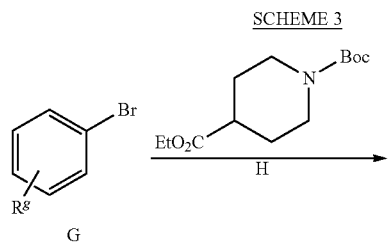

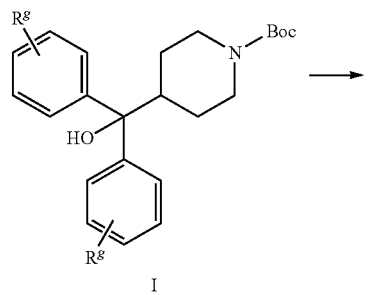

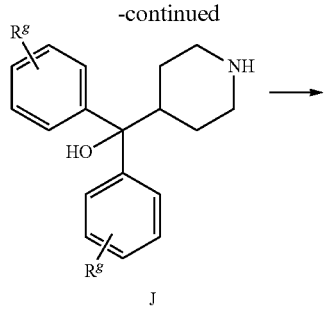

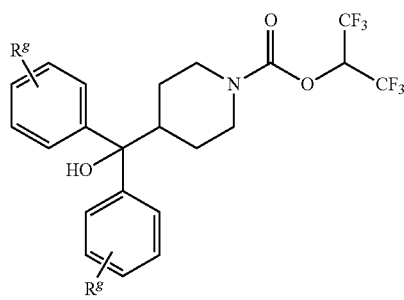

Scheme 4 provides a detailed exemplary synthetic procedure for making carbamates of the general structure M, O, and Q. $R^g$ is described above. Intermediate I can be converted to the methyl ether by treatment with NaH or similar base and methyl iodide in a solvent such as THF to produce intermediate L. Intermediate L may be converted to product M according to the representative protocols described in Schemes 1 and 2 above. Alternatively, intermediate I can be converted to N by treatment with Et₃SiH followed by trifluoroactetic acid. Intermediate N may converted to product O according to the representative protocols described in Scheme 1 above. Additionally, intermediate I can be converted P using trifluoroacetic acid in a solvent such as CH₂Cl₂. Conversion of P to the desired products Q can be achieved according to the representative protocols described in Scheme 1. Similar chemistry can be executed using heteroarylbromides.

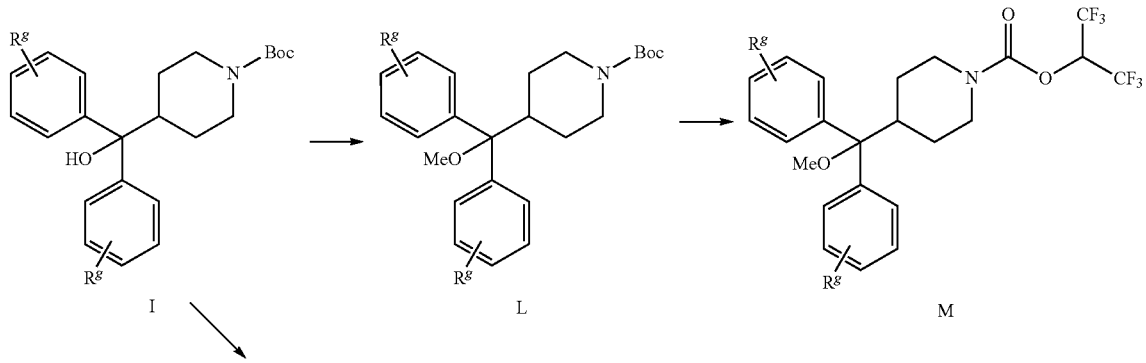

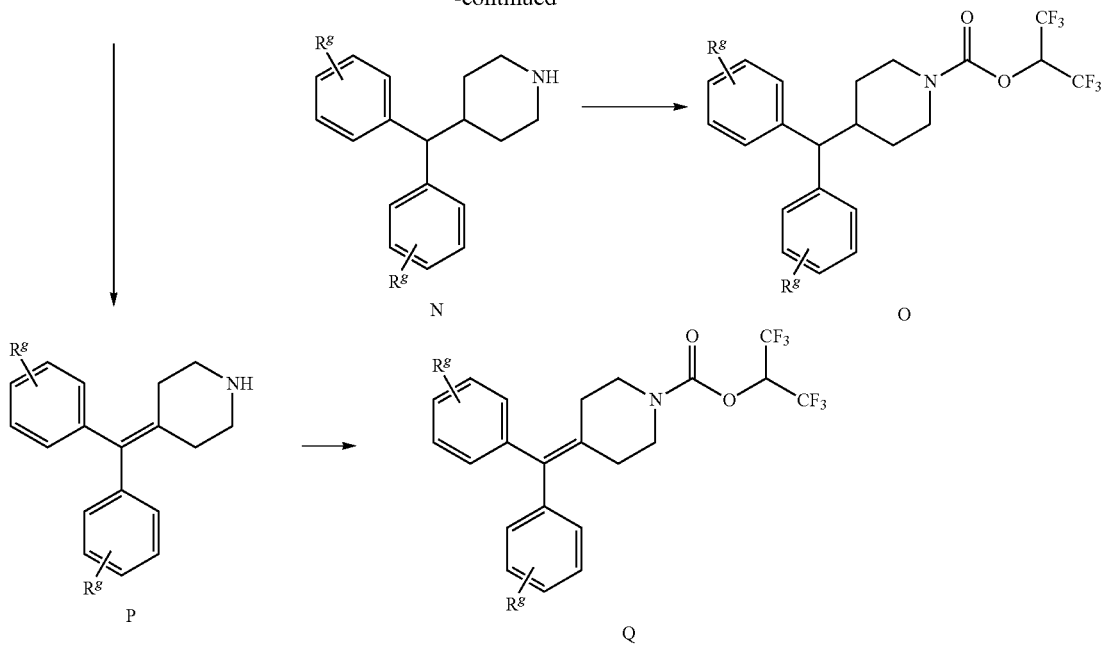

Scheme 5 provides a detailed exemplary synthetic procedure for making carbamate derivatives having a piperazine group of the general structure W. $R^g$ is described above. Arylbromide G can be obtained from commercial sources and converted to aryllithium using either tert-butyllithium or n-butyllithium at reduced temperatures or the Grignard reagent using standard conditions to those skilled in the art or purchased from commercial sources. Reacting the aryllithium or the Grignard reagent with ethyl formate or an appropriate aldehyde R provides alcohol S, which can be symmetrical (utilizing ethyl formate, where $R^g$ are equivalent) or unsymmetrical (utilizing aldehyde R, where $R^g$ are not equivalent). Alcohol S made according to the procedures above or purchased commercially can be converted to the chloro variant T using thionyl chloride, at which point the desired piperazine is installed by treating T with a Boc-protected piperazine in a solvent, such as acetonitrile, with or without and added base, such as potassium carbonate, to give the diarylmethylpiperazine product U. Alternatively, alcohol S can be obtained from a commercially available ketone after reduction with $NaBH_4$ or similar reagent in solvents such as MeOH or $CH_2Cl_2$. The protected diarylmethylpiperazine U was converted to the intermediate V followed by formation of the desired carbamate product W according to the representative protocols described above in Schemes 1 and 2. Similar chemistry can be executed using heteroarylbromides.

SCHEME 5

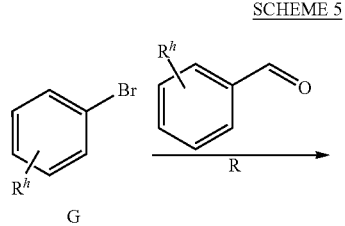

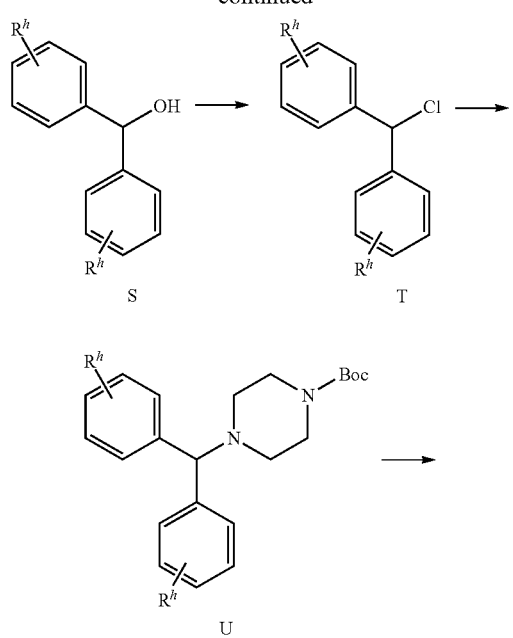

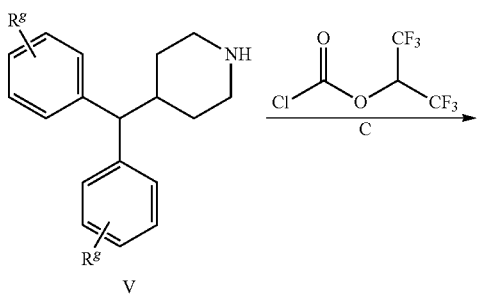

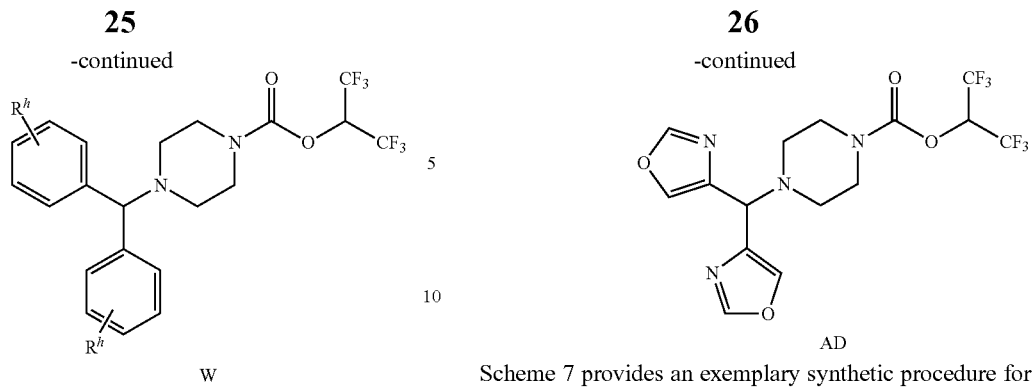

Additionally compounds of the general structure I can be obtained from metalation of commercially available aromatic heterocycles, X, such as oxazole using an alkyllithium such as n-butyllithium as shown in Scheme 6. Allowing the aryllithium to react with an appropriate aldehyde Y provides alcohol Z. Alcohol Z can be converted to the chloro variant, AA using mesyl chloride, at which point the desired piperazine is installed by treating AA with a Boc-protected piperazine to give the diarylmethylpiperazine product AB. The protected diheteroarylmethylpiperazine AB was converted to the desired carbamate product AD according to the representative protocols described above for Scheme 1 and Scheme 2.

Scheme 7 provides an exemplary synthetic procedure for making piperazine carbamate derivatives having sulfonamide groups. Boc-protected piperazine carbamate AE can be prepare utilizing the procedures described above. Removal of the Boc group can be achieved utilizing the representative protocols described in Scheme 2. The desired sulfonyl group can be installed by reacting the free amine with the appropriate arylsulfonyl chloride AF to afford the final product AG. $R^h$ is described above. Similar chemistry can be executed using heteroarylsulfonyl chlorides.

SCHEME 6

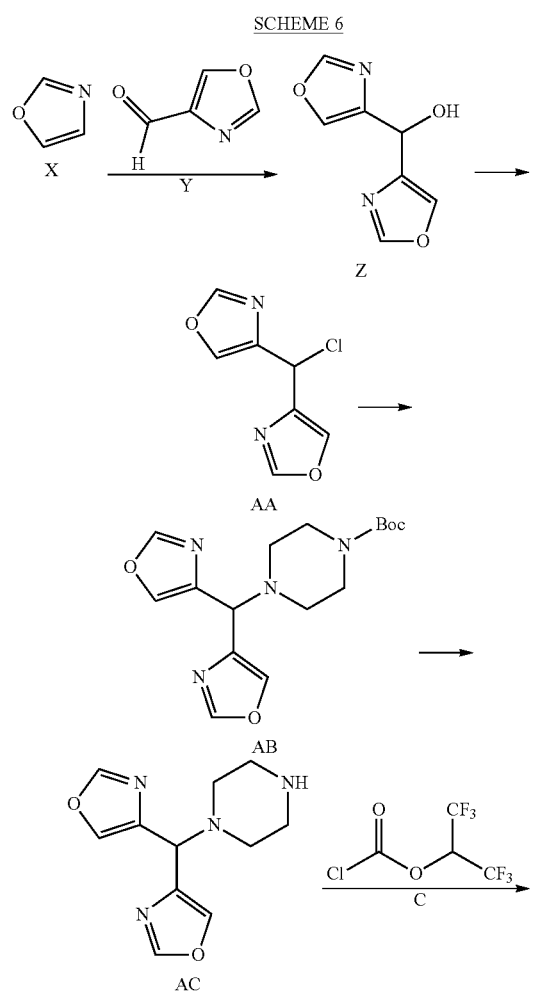

SCHEME 7

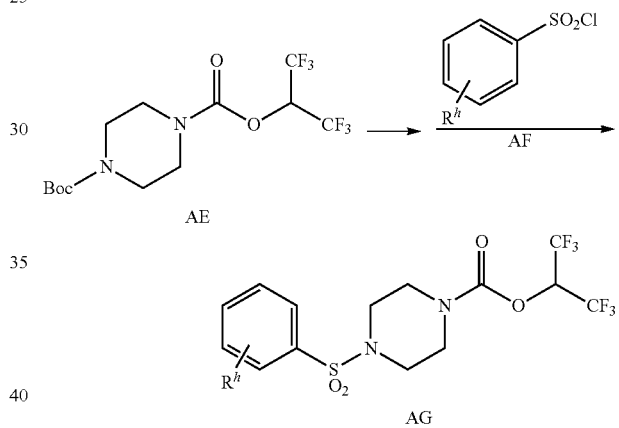

Scheme 8 provides a detailed exemplary synthetic procedure for making carbamate derivatives having a piperazine or substituted piperazine group as the amine substituent. Aldehyde AH, optionally substituted with 1-3 $R^h$ groups (as described above) commercially available or prepared according to the general methods described in Schemes 9, 10, 11 can be allowed to react with amines using a reducing agent such as NaBH(OAc)$_3$, in dichloromethane, dichloroethane, N,N-dimethylformamide or the like in the presence or absence of molecular sieves to yield intermediates AI. Removal of the Boc-protecting group can be achieved as described in Scheme 2 to furnish AJ. Conversion to the desired carbamate product AK can be achieved according to the representative protocols described above for Scheme 1. Similar chemistry can be executed using heteroaryl aldehydes.

SCHEME 8

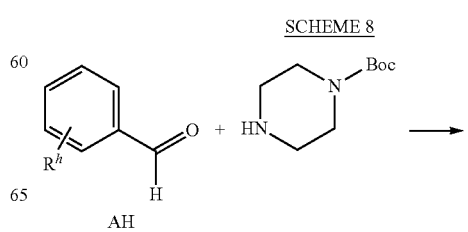

-continued

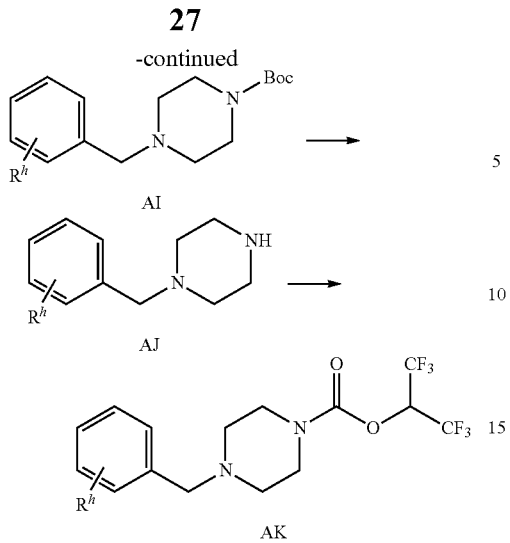

Substituted fluorobenzaldehydes AL may be subjected to nucleophilic aromatic substitution conditions according to the exemplary synthetic procedure described in Scheme 9 using the appropriately substituted fluorobenzaldehyde and the desired amine or phenol in the presence of a base such as potassium carbonate in DMSO or dimethylacetamide at elevated temperature to provide aldehydes AM or AN. $R^h$ is described above and can be independently selected. These aldehydes can be used as variants of aldehydes AH (Scheme 8) for use in preparing substituted piperazine carbamate derivatives AK (Scheme 8).

SCHEME 9

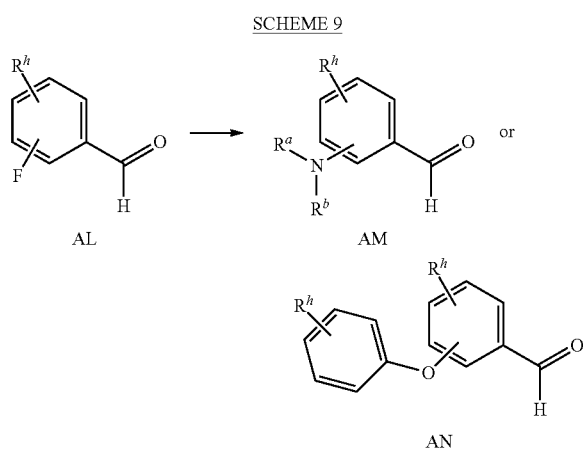

Substituted aldehydes AP may be prepared under palladium cross coupling reactions according to the exemplary synthetic procedure described in Scheme 10 using the appropriately substituted bromobenzaldehyde, AO, and the desired amine in the presence of a Pd catalyst such as $Pd_2(dba)_3$, a ligand such as BINAP, and a base such as sodium t-butoxide, and in a solvent such as toluene at elevated temperature. $R^a$, $R^b$, and $R^h$ are described above. These aldehydes can be used as variants of aldehydes AH (Scheme 8) for use in preparing substituted piperazine carbamate derivatives AK (Scheme 8). Similar chemistry can be executed using heteroaryl aldehydes and heteroaryl boronic acids.

SCHEME 10

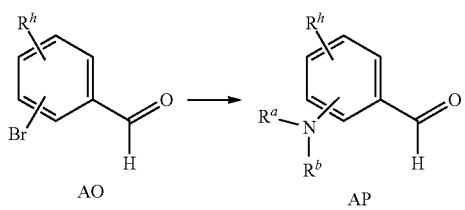

Alternatively, the palladium catalyzed cross coupling can be performed on a substituted aryl bromide after reductive amination with Boc-piperazine as described in exemplary synthetic procedure shown in Scheme 11. $R^a$, $R^b$, $R^c$, and $R^h$ are described above. An appropriately substituted arylbromide carboxaldehyde AQ is allowed to react with Boc-piperazine as described in Scheme 8 to provide AR. Arylbromide AR is treated with the desired amine in the presence of a Pd catalyst such as $Pd_2(dba)_3$, a ligand such as BINAP, and a base such as sodium tert-butoxide, and in a solvent such as toluene at elevated temperature to provide intermediate AS which can then be converted to variants of AK as shown in Scheme 8. Intermediate AR can also be treated with an appropriately substituted arylboronic acid optionally substituted with $R^c$ under palladium cross coupling reactions presence of a Pd catalyst such as $Pd(PPh_3)_4$ or $PdCl_2(dppf).CH_2Cl_2$ in the presence of a base such as potassium carbonate and a solvent such as dioxane or THF/water mixtures at elevated temperatures to generate AT which can then be converted to variants of AK as shown in Scheme 8. Similar chemistry can be executed using heteroaryl aldehydes.

SCHEME 11

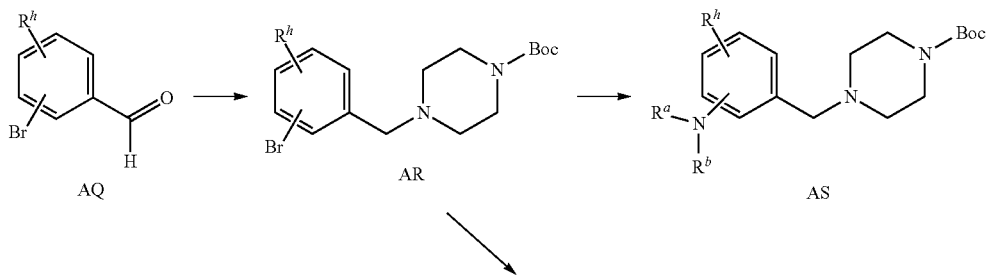

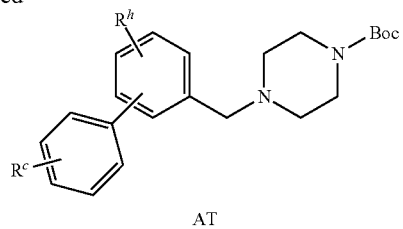

AT

Alternatively, aldehydes of the general structure AU can be allowed to react with amines using a reducing agent such as NaBH(OAc)$_3$, in dichloromethane, dichloroethane, N,N-dimethylformamide or the like in the presence or absence of molecular sieves to yield intermediates AV, as shown in SCHEME 12. $R^a$, $R^b$, and $R^b$ are described above. Intermediates AV may be further reacted with a base such as lithium or sodium hydroxide and in a solvent such as MeOH/water to provide compounds of the general structure AW. Treatment of AW with amines under standard amide coupling conditions using 1-ethyl-3-(3-dimethylaminopropyl)carbodiimide or similar reagent and hydroxybenzotriazole in a solvent such as CH$_2$Cl$_2$ to yield intermediate AX. Conversion to products of Formula I can be achieved according to the protocols described in Scheme 1 and Scheme 2. Similar chemistry can be executed using heteroaryl aldehydes.

SCHEME 12

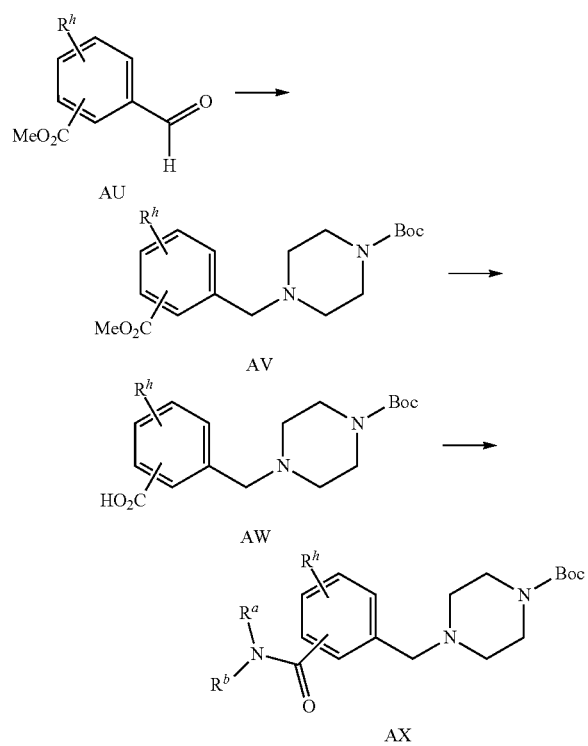

Compounds of the general formula BB can be prepared according to Scheme 13. $R^1$, $R^2$, $R^a$, and $R^b$ are described above. The activated methyl 2-((chlorocarbonyl)oxy)-3,3,3-trifluoropropanoate AY can be prepared by reacting methyl 3,3,3-trifluoro-2-hydroxypropanoate with triphosgene A in the presence of a base such as diisopropylethyl amine or 2,6-lutidine with catalytic dimethyl aminopyridine in a solvent such as methylene chloride or acetonitrile. The desired —NR$^1$R$^2$ group of the carbamate can be installed by reacting the AY with the appropriate amine D. The specific $R^1$ and $R^2$ groups are selected based on the desired groups in the final carbamate product AZ. Further modification of AZ under conditions of hydrolysis using NaOH or similar base in a solvent such as dioxane mixed with water provides BA. Conversion to amide BB can be achieved using conditions similar to those described in Scheme 11 or by treatment with methylamine in THF to provide compounds BB wherein $R^a$ is equal to hydrogen and $R^b$ is equal to Me.

SCHEME 13

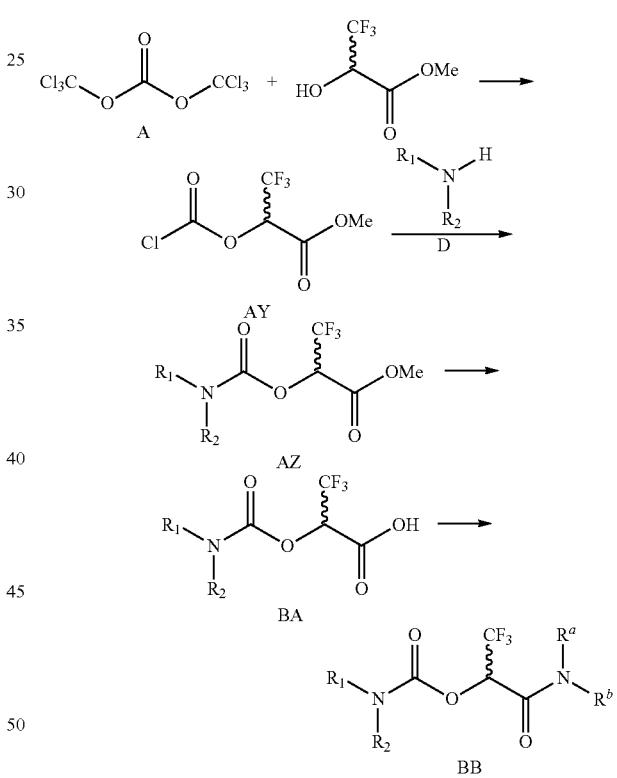

Substituted heteroaryl aldehydes of the general formula BF can be prepared as shown in Scheme 14 and used as shown in Scheme 8 to prepare heteroaryl analogues of AK, for example BG. $R^i$ and $R^j$ may be independently selected, and may be any of e.g., $C_{1-6}$alkyl, aryl, $C_{3-6}$cycloalkyl, etc, or as described above. Commercially available methyl ketones BC can be condensed with commercially available hydrazines or hydrazine salts BD in an alcoholic solvent at room temperature to reflux for hours to overnight to provide hydrazones BE. The hydrazones can then be treated with N-(chloromethylene)-N-methyl-methanaminium chloride in a solvent such as N,N-dimethylformamide and stirred at room temperature to 100° C. overnight. After an aqueous workup, aldehydes BF are generated. These aldehydes can be carried forward to compounds BG as described in Scheme 8.

SCHEME 14

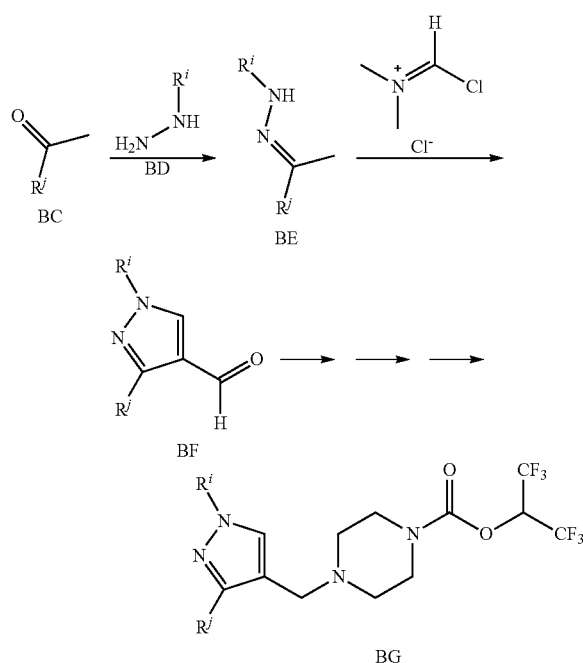

Substituted heteroaryl aldehydes of the general formula BK can be prepared as shown in Scheme 15 and used as shown in Scheme 8 to prepare heteroaryl analogues of AK, for example BL. $R^i$ and $R^j$ may be independently selected, and may be any of e.g., $C_{1-6}$alkyl, aryl, $C_{3-6}$cycloalkyl, etc, or as described above. Commercially available 2,4-dioxo-pentanoic acid esters BH can be condensed with commercially available O-methylhydroxylamine or its salts in an alcoholic solvent at room temperature to reflux for hours to overnight in the presence of molecular sieves to provide oximes BI. The oximes can then be treated with e.g., commercially available hydrazines or hydrazine salts in an alcoholic solvent such as ethanol and stirred at room temperature to reflux overnight to provide esters BJ. The esters can be converted to aldehydes BK through various routes known to those skilled in the art, including direct reduction with di-isobutylaluminum hydride in a solvent such as toluene or dichloromethane at −78° C. to 0° C. followed by aqueous workup, or by reducing to the alcohol with a reducing agent such as lithium borohydride or lithium aluminum hydride in a solvent such as tetrahydrofuran or diethyl ether at −78° C. to room temperature followed by an aqueous workup and oxidizing to the aldehyde with a reagent such as pyridinium chlorochromate or pyridinium dichromate in a solvent such as dichloromethane at 0° C. to reflux Other appropriate oxidants include dimethylsulfoxide with an appropriate activating agent, such as oxalyl chloride at −78° C. to 0° C. in a solvent such as dichloromethane or Dess-Martin periodinane in a solvent such as dichloromethane at room temperature. The resulting aldehydes can be carried forward to compounds BL as described in Scheme 8.

SCHEME 15

Representative contemplated compounds, including salts and/or stereoisomers, are listed in Tables 1, 2, 3, 4 and 5.

TABLE 1

| Compound Number | Structure |
| --- | --- |
| 1a | (structure shown) |

TABLE 1-continued

| Compound Number | Structure |
| --- | --- |
| 1b | 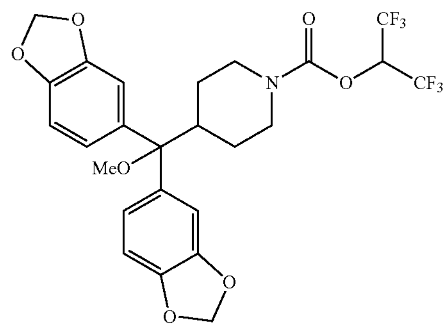 [SMILES: COC(c1ccc2c(c1)OCO2)(c1ccc2c(c1)OCO2)C1CCN(C(=O)OC(C(F)(F)F)C(F)(F)F)CC1] |
| 1c | 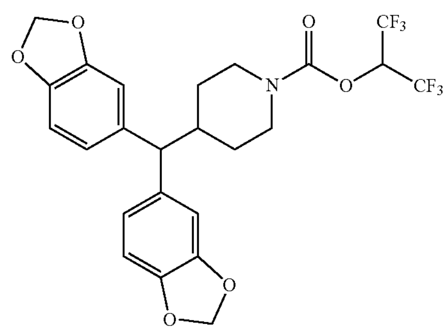 [SMILES: O=C(OC(C(F)(F)F)C(F)(F)F)N1CCC(C(c2ccc3c(c2)OCO3)c2ccc3c(c2)OCO3)CC1] |
| 1d | 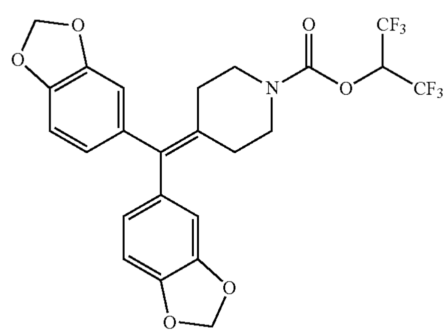 [SMILES: O=C(OC(C(F)(F)F)C(F)(F)F)N1CCC(=C(c2ccc3c(c2)OCO3)c2ccc3c(c2)OCO3)CC1] |
| 1e | 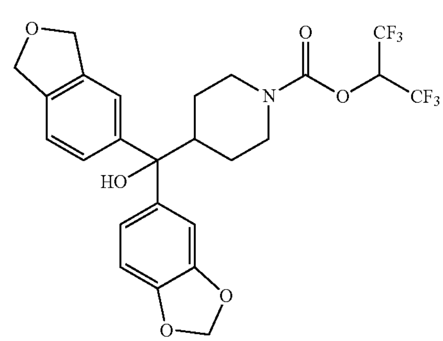 [SMILES: O=C(OC(C(F)(F)F)C(F)(F)F)N1CCC(C(O)(c2ccc3c(c2)COC3)c2ccc3c(c2)OCO3)CC1] |

TABLE 1-continued

| Compound Number | Structure |
| --- | --- |
| 1f | 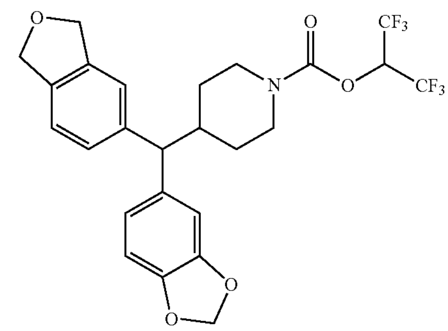 [SMILES: O=C(OC(C(F)(F)F)C(F)(F)F)N1CCC(C(c2ccc3c(c2)COC3)c2ccc3c(c2)OCO3)CC1] |
| 1g | 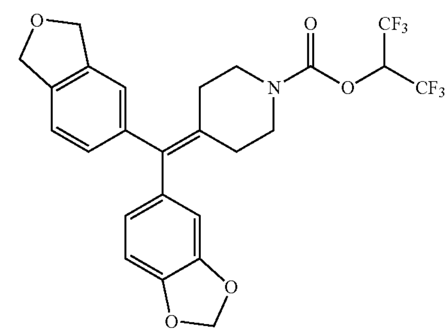 [SMILES: O=C(OC(C(F)(F)F)C(F)(F)F)N1CCC(=C(c2ccc3c(c2)COC3)c2ccc3c(c2)OCO3)CC1] |
| 1h | 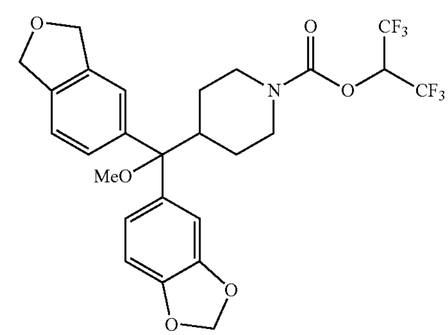 [SMILES: COC(c1ccc2c(c1)COC2)(c1ccc2c(c1)OCO2)C1CCN(C(=O)OC(C(F)(F)F)C(F)(F)F)CC1] |
| 2a | 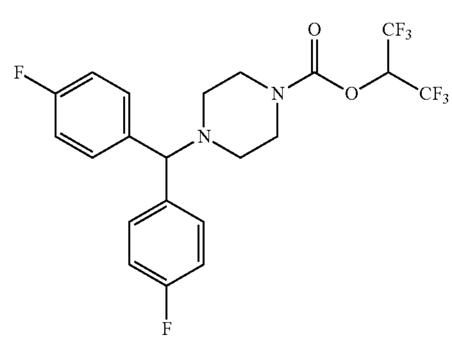 [SMILES: O=C(OC(C(F)(F)F)C(F)(F)F)N1CCN(C(c2ccc(F)cc2)c2ccc(F)cc2)CC1] |

TABLE 1-continued

| Compound Number | Structure |
| --- | --- |
| 2b | 4-Cl-C6H4-CH(4-Cl-C6H4)-N(piperazine)-C(=O)-O-CH(CF3)2 |
| 2c | 4-Br-C6H4-CH(4-Br-C6H4)-N(piperazine)-C(=O)-O-CH(CF3)2 |
| 2d | (benzo[1,3]dioxol-5-yl)2CH-N(piperazine)-C(=O)-O-CH(CF3)2 |
| 2e | (2,3-dihydrobenzofuran-5-yl)2CH-N(piperazine)-C(=O)-O-CH(CF3)2 |

TABLE 1-continued
| Compound Number | Structure |
|---|---|
| 2f | 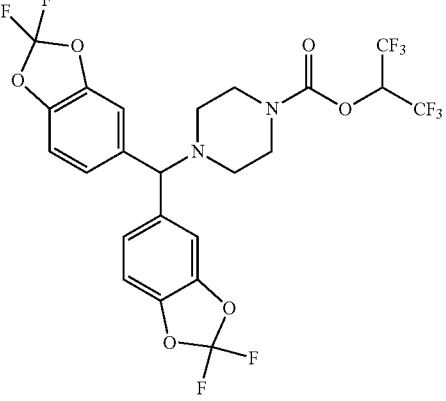 |
| 2g | 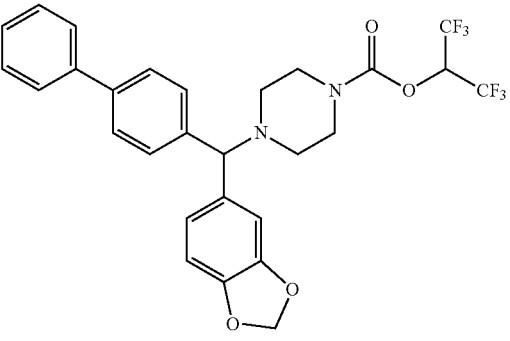 [SMILES: O=C(OC(C(F)(F)F)C(F)(F)F)N1CCN(C(c2ccc(-c3ccccc3)cc2)c2ccc3c(c2)OCO3)CC1] |
| 2h | 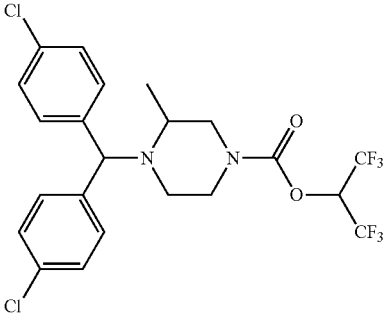 [SMILES: CC1CN(C(=O)OC(C(F)(F)F)C(F)(F)F)CCN1C(c1ccc(Cl)cc1)c1ccc(Cl)cc1] |
| 2i | 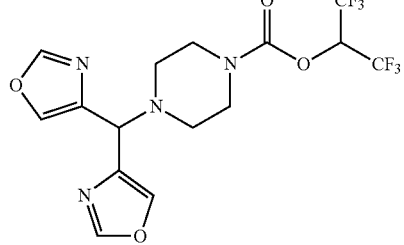 |

TABLE 1-continued
| Compound Number | Structure |
|---|---|
| 2j | 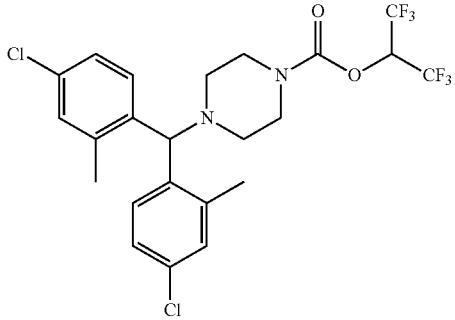 [SMILES: Cc1cc(Cl)ccc1C(c1ccc(Cl)cc1C)N1CCN(C(=O)OC(C(F)(F)F)C(F)(F)F)CC1] |
| 2k | 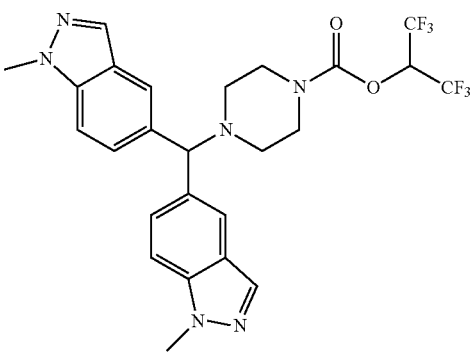 [SMILES: Cn1ncc2cc(C(c3ccc4c(cnn4C)c3)N3CCN(C(=O)OC(C(F)(F)F)C(F)(F)F)CC3)ccc21] |
| 2l | 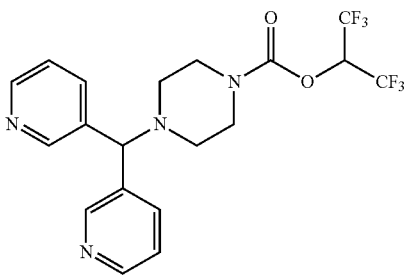 [SMILES: O=C(OC(C(F)(F)F)C(F)(F)F)N1CCN(C(c2cccnc2)c2cccnc2)CC1] |
| 2m | 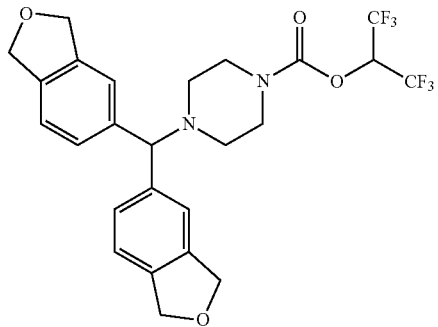 [SMILES: O=C(OC(C(F)(F)F)C(F)(F)F)N1CCN(C(c2ccc3c(c2)COC3)c2ccc3c(c2)COC3)CC1] |
| 3a | 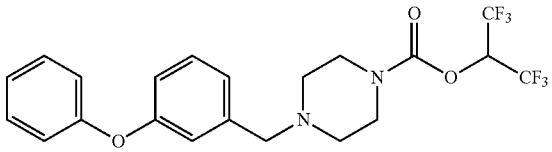 [SMILES: O=C(OC(C(F)(F)F)C(F)(F)F)N1CCN(Cc2cccc(Oc3ccccc3)c2)CC1] |

TABLE 1-continued

| Compound Number | Structure |
|---|---|
| 3b | [biphenyl-CH2-piperazine-C(=O)-O-CH(CF3)2] |
| 3c | [biphenyl-C(=O)-piperazine-C(=O)-O-CH(CF3)2] |
| 3d | [Boc-piperazine-C(=O)-O-CH(CF3)2] |
| 3e | [4-MeO-phenyl-piperazine-C(=O)-O-CH(CF3)2] |
| 3f | [3-(pyridin-4-yl)benzyl-N(Me)-C(=O)-O-CH(CF3)2] |
| 3g | [3-(pyridin-3-yl)benzyl-N(Me)-C(=O)-O-CH(CF3)2] |
| 3h | [2-methylquinolin-4-yl-piperazine-C(=O)-O-CH(CF3)2] |
| 3i | [benzo[d][1,3]dioxol-5-ylmethyl-N(Me)-C(=O)-O-CH(CF3)2] |

TABLE 1-continued

| Compound Number | Structure |
| --- | --- |
| 3j | (structure) |
| 4a | (structure) |
| 4b | (structure) |
| 4c | (structure) |
| 4d | (structure) |
| 4e | (structure) |
| 4f | (structure) |
| 4g | (structure) |

TABLE 1-continued

| Compound Number | Structure |
|---|---|
| 4h | naphthalen-2-yl sulfonyl piperazine carboxylic acid 1,1,1,3,3,3-hexafluoropropan-2-yl ester |
| 4i | 3-(trifluoromethyl)phenylsulfonyl piperazine carboxylic acid 1,1,1,3,3,3-hexafluoropropan-2-yl ester |
| 4j | 2,4,6-trimethylphenylsulfonyl piperazine carboxylic acid 1,1,1,3,3,3-hexafluoropropan-2-yl ester |
| 4k | 2,3,4,6-tetramethylphenylsulfonyl piperazine carboxylic acid 1,1,1,3,3,3-hexafluoropropan-2-yl ester |
| 4l | 3-(trifluoromethoxy)phenylsulfonyl piperazine carboxylic acid 1,1,1,3,3,3-hexafluoropropan-2-yl ester |
| 4m | 3-methoxyphenylsulfonyl piperazine carboxylic acid 1,1,1,3,3,3-hexafluoropropan-2-yl ester |
| 4n | 3-fluorophenylsulfonyl piperazine carboxylic acid 1,1,1,3,3,3-hexafluoropropan-2-yl ester |
| 4o | 3-methylphenylsulfonyl piperazine carboxylic acid 1,1,1,3,3,3-hexafluoropropan-2-yl ester |

TABLE 1-continued
| Compound Number | Structure |
|---|---|
| 4p | 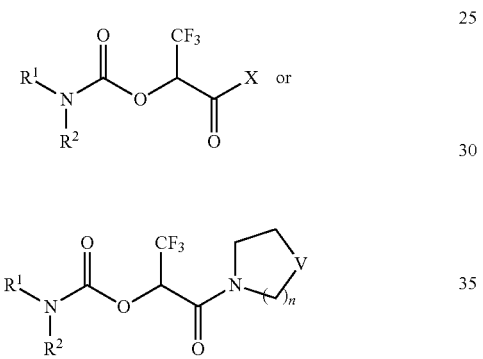 |
| 4q | 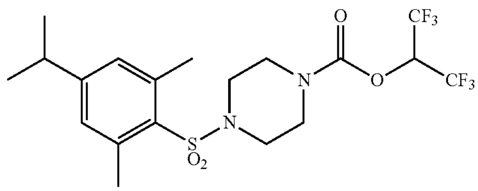 |
In another embodiment, a compound may be represented by:
$X = NR^{N1}R^{N2}$ or $OR$
$R^{N1}$ and $R^{N2}$ = H, methyl, ethyl, isopropyl, tert-butyl, phenyl, or benzyl
$V = CH_2$, $NR^{N1}$ or $O$
n = 1, 2 or 3; wherein $R^1$ and $R^2$ are described above.
TABLE 2
| Compound Number | Structure |
|---|---|
| 5a | 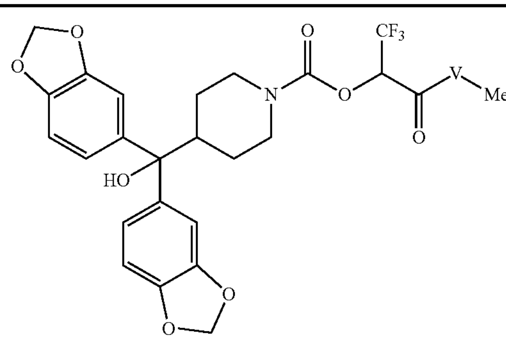 |
$V = NH, N(C_{1-6}alkyl)$ or $O$ TABLE 2-continued
| Compound Number | Structure |
|---|---|
| 5b | 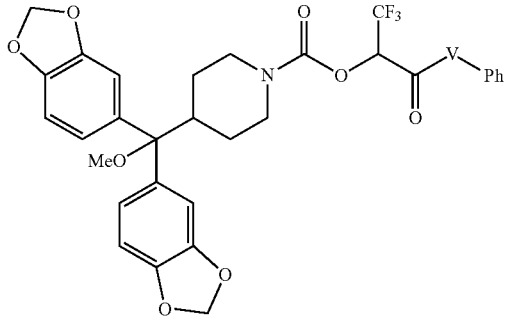  V = NH, N(C$_{1-6}$alkyl) or O |
| 5c | 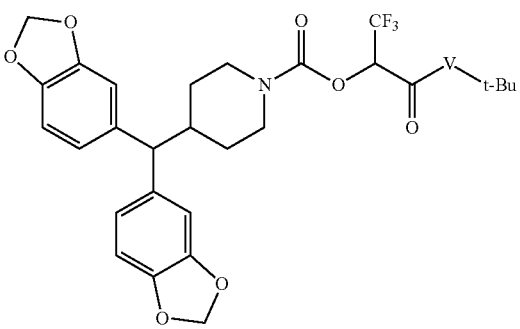  V = NH, N(C$_{1-6}$alkyl) or O |
| 5d | 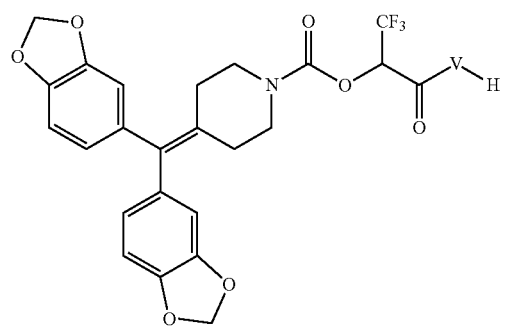  V = NH, N(C$_{1-6}$alkyl) or O |
| 6a | 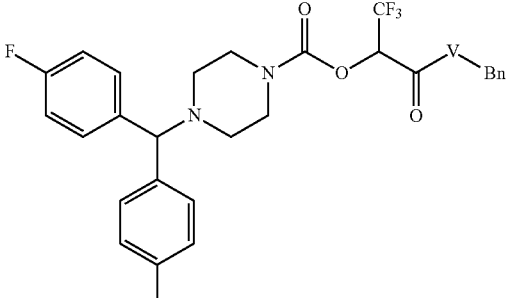  V = NH, N(C$_{1-6}$alkyl) or O |

TABLE 2-continued
| Compound Number | Structure |
|---|---|
| 6b | 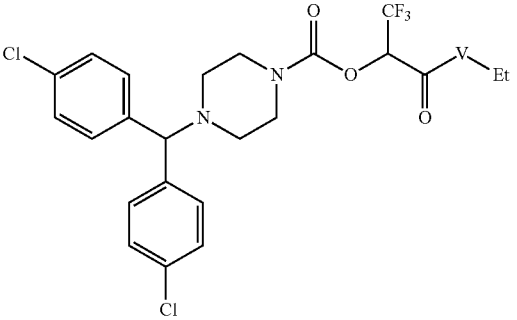<br>V = NH, N(C$_{1-6}$alkyl) or O |
| 6c | 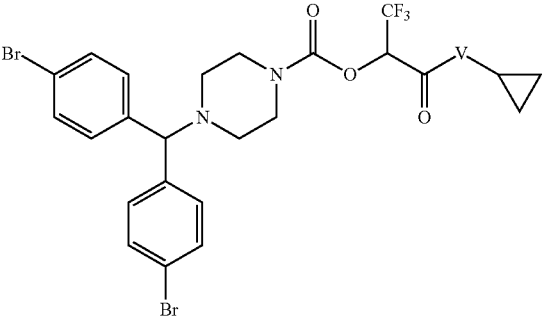<br>V = NH, N(C$_{1-6}$alkyl) or O |
| 6d | 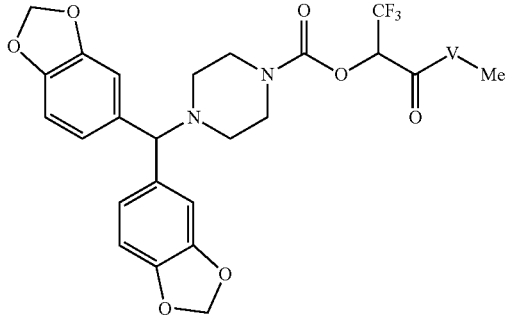<br>V = NH, N(C$_{1-6}$alkyl) or O |
| 6e | 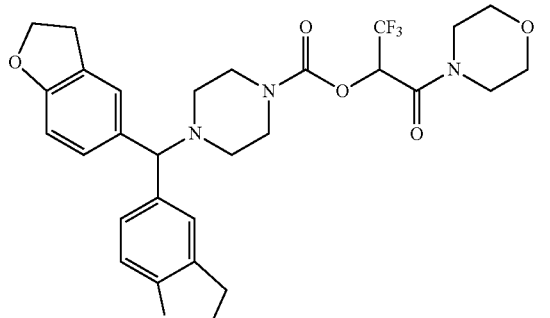 |

TABLE 2-continued

| Compound Number | Structure |
| --- | --- |
| 6f | [Structure with two 2,2-difluoro-1,3-benzodioxole groups connected via CH to piperazine carbamate with CF₃ and V-t-Bu] <br> V = NH, N(C₁₋₆alkyl) or O |
| 6g | [Structure with biphenyl and benzodioxole groups connected via CH to piperazine carbamate with CF₃ and V-H] <br> V = NH, N(C₁₋₆alkyl) or O |
| 6h | [Structure with two 4-chlorophenyl groups connected via CH to piperazine carbamate with CF₃ and OMe] |
| 6i | [Structure with two 4-chlorophenyl groups connected via CH to piperazine carbamate with CF₃ and OH] |

TABLE 2-continued

| Compound Number | Structure |
|---|---|
| 6j | [Structure: bis(4-chlorophenyl)methyl-piperazine-carbamate-CH(CF₃)-C(O)-NHMe] |
| 7a | [Structure: 3-phenoxybenzyl-piperazine-carbamate-CH(CF₃)-C(O)-V-i-Pr]<br>V = NH, N(C₁₋₆alkyl) or O |
| 7b | [Structure: 4-biphenylmethyl-piperazine-carbamate-CH(CF₃)-C(O)-(4-methylpiperazine)] |
| 7c | [Structure: 4-biphenylcarbonyl-piperazine-carbamate-CH(CF₃)-C(O)-V-Ph]<br>V = NH, N(C₁₋₆alkyl) or O |
| 7d | [Structure: Boc-piperazine-carbamate-CH(CF₃)-C(O)-V-Bn]<br>V = NH, N(C₁₋₆alkyl) or O |
| 7e | [Structure: 4-(4-methoxyphenyl)piperazine-carbamate-CH(CF₃)-C(O)-V-Me]<br>V = NH, N(C₁₋₆alkyl) or O |
| 7f | [Structure: 3-(pyridin-4-yl)benzyl-N(Me)-carbamate-CH(CF₃)-C(O)-pyrrolidine] |

TABLE 2-continued

| Compound Number | Structure |
|---|---|
| 7g | 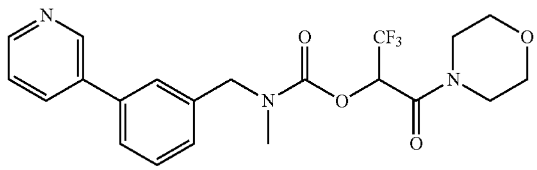 |
| 7h | V = NH, N(C$_{1-6}$alkyl) or O |
| 7i | V = NH, N(C$_{1-6}$alkyl) or O |
| 7j | V = NH, N(C$_{1-6}$alkyl) or O |
| 7k | 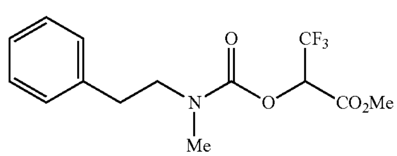 |
| 8a | V = NH, N(C$_{1-6}$alkyl) or O |
| 8b | V = NH, N(C$_{1-6}$alkyl) or O |

TABLE 2-continued
| Compound Number | Structure |
|---|---|
| 8c | 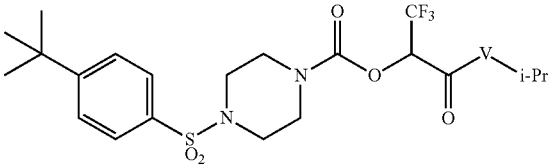<br>V = NH, N(C$_{1-6}$alkyl) or O |
| 8d | 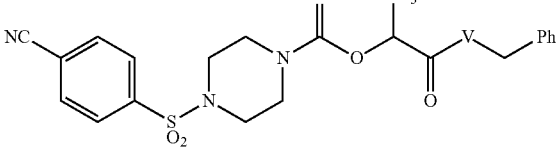<br>V = NH, N(C$_{1-6}$alkyl) or O |
| 8e | 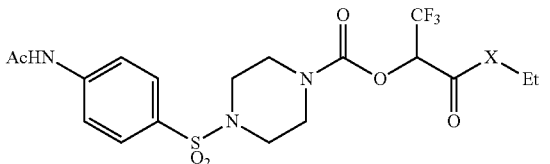<br>V = NH, N(C$_{1-6}$alkyl) or O |
| 8f | 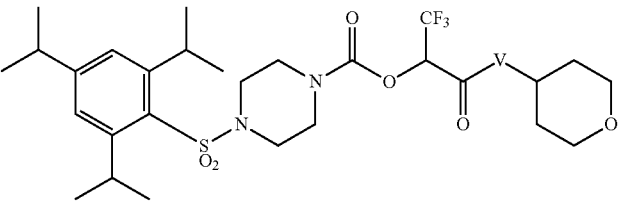<br>V = NH, N(C$_{1-6}$alkyl) or O |
| 8g | 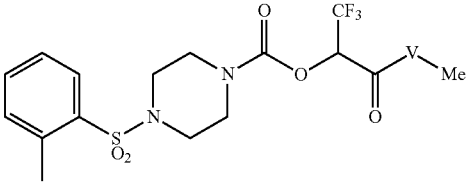<br>V = NH, N(C$_{1-6}$alkyl) or O |
| 8h | 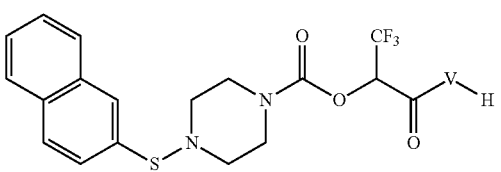<br>V = NH, N(C$_{1-6}$alkyl) or O |

TABLE 2-continued
| Compound Number | Structure |
|---|---|
| 8i | 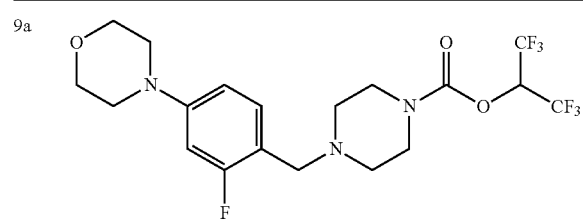 V = NH, N(C$_{1-6}$alkyl) or O |
TABLE 3
| | |
|---|---|
| 9a | 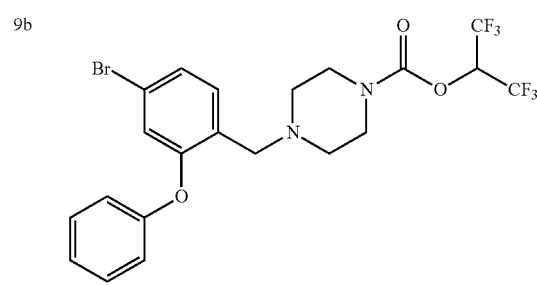 |
| 9b | 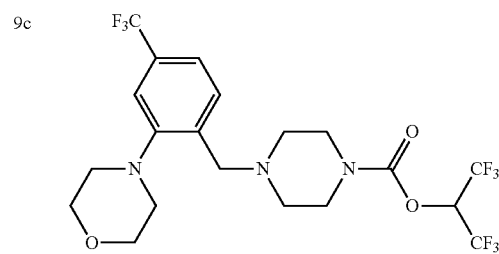 |
| 9c | 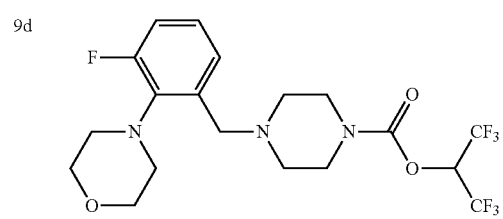 |
| 9d | 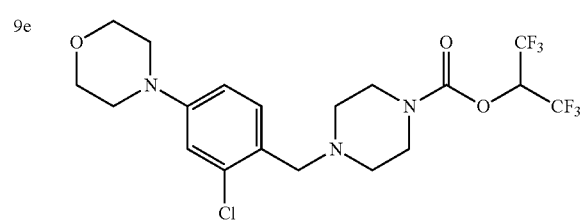 |
| 9e | 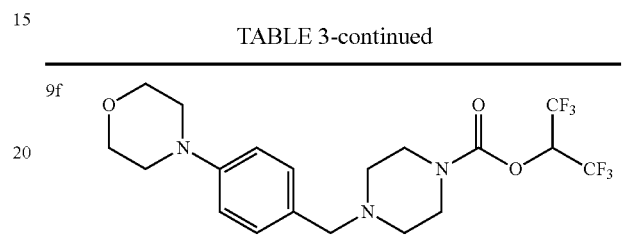 |
TABLE 3-continued
| | |
|---|---|
| 9f | 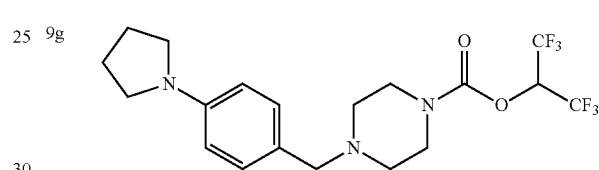 |
| 9g | 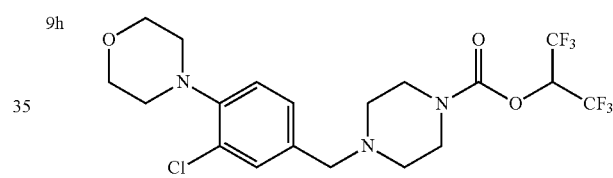 |
| 9h | 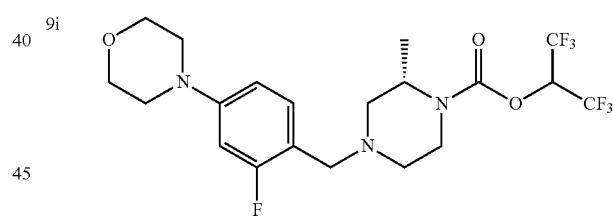 |
| 9i | 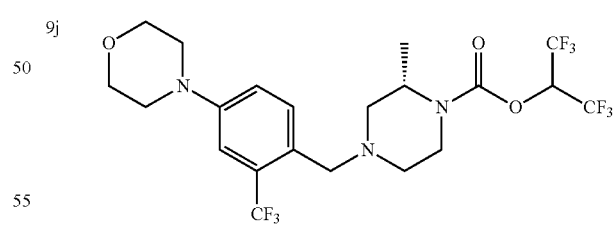 |
| 9j | 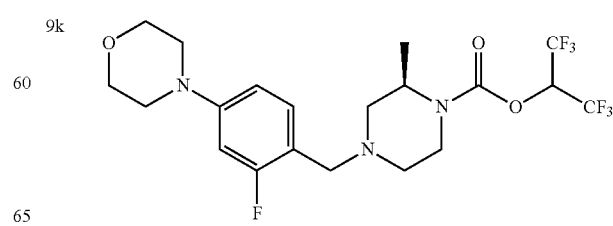 |
| 9k | |

TABLE 3-continued
| | | |
|---|---|---|
| 9l | 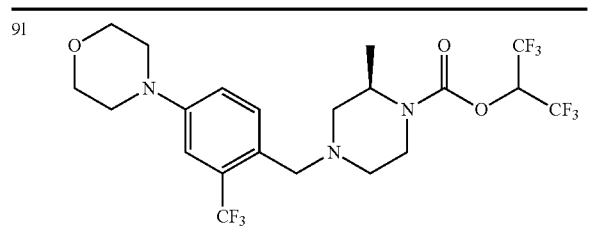 | |
| 9m | | |
| 9n | | |
| 9o | | |
| 9p |  | |
| 9q | | |
| 9r | | |
TABLE 3-continued
| | | |
|---|---|---|
| 9s | 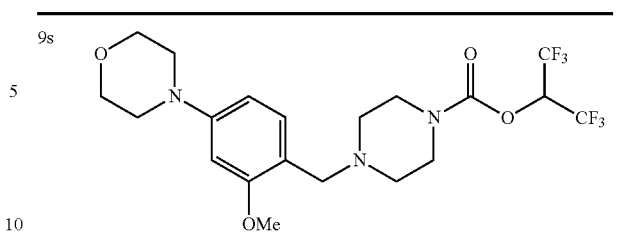 | |
| 9t | | |
| 9u | | |
| 9v | | |
| 9w | | |
| 9x | | |
| 9y | | |

TABLE 3-continued
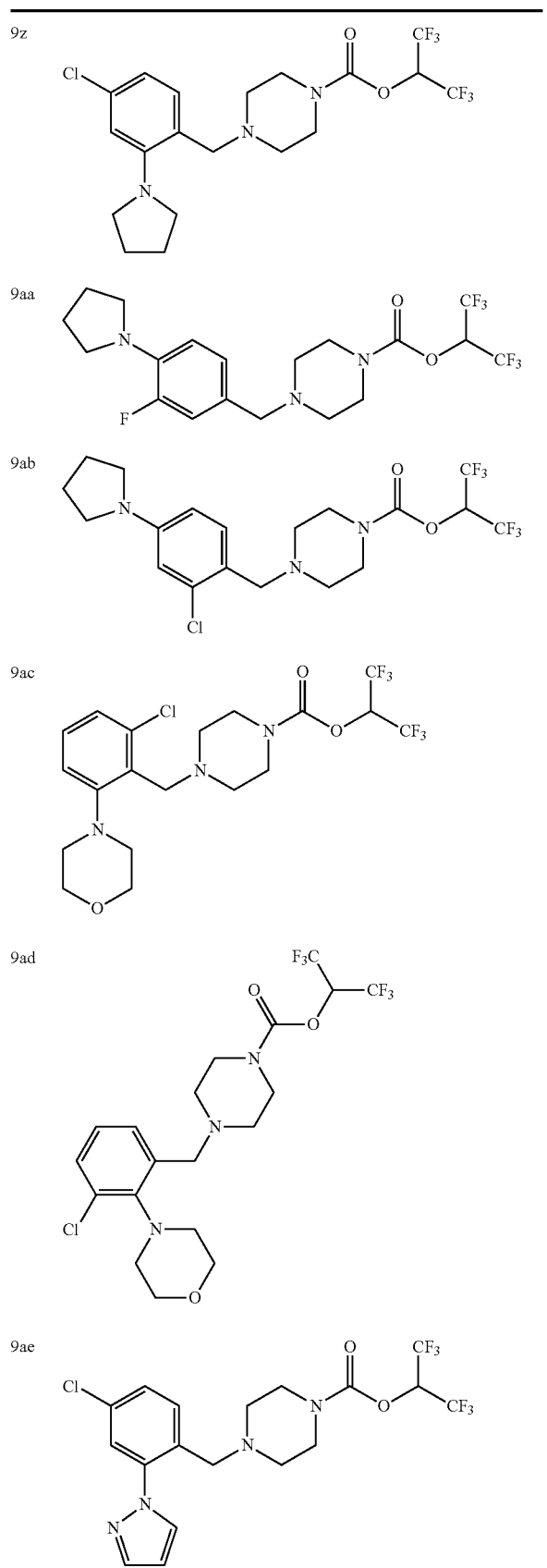
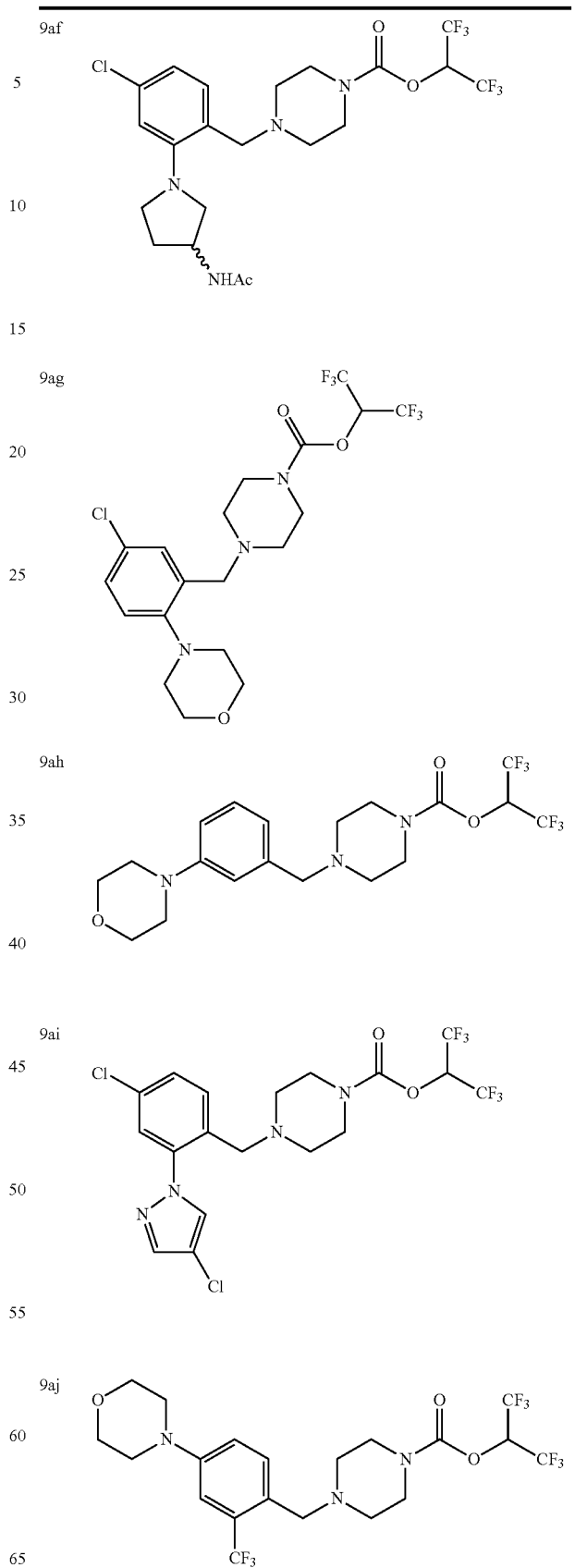

TABLE 3-continued
| | | |
|---|---|---|
| 9ak | 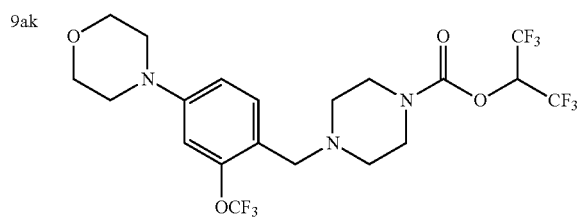 | |
| 9al | 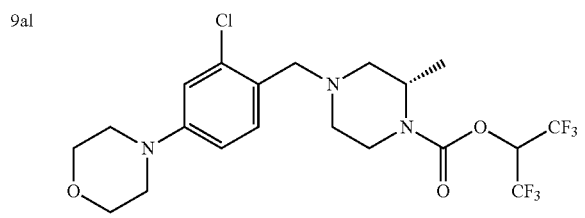 | |
| 9am | 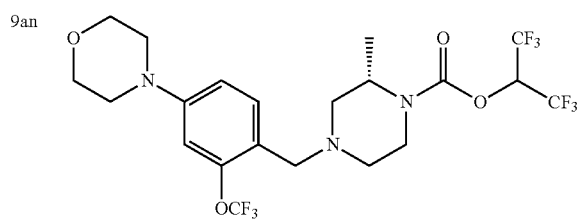 | |
| 9an | | |
| 9ao | 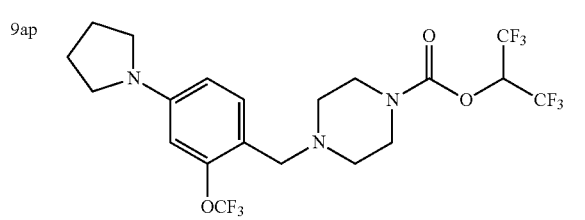 | |
| 9ap | | |
| 9aq | | |
TABLE 3-continued
| | | |
|---|---|---|
| 9ar | 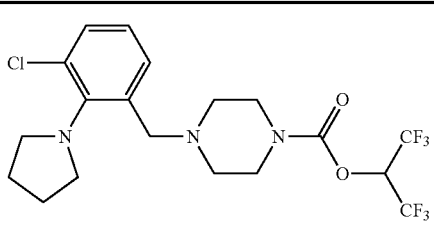 | |
| 9as | 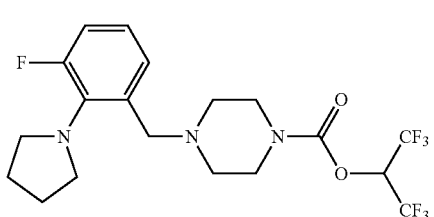 | |
| 9at | | |
| 9au | 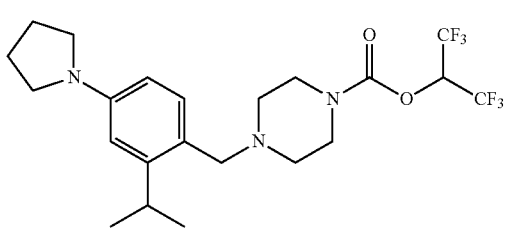 | |
| 9av | | |
| 9aw | 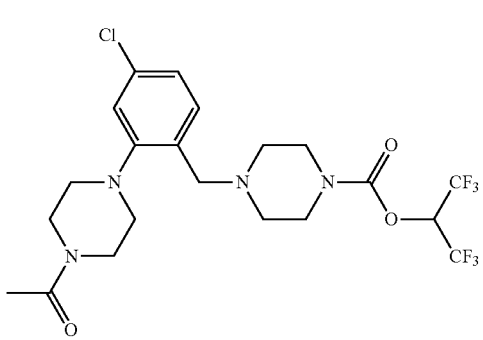 | |

TABLE 3-continued
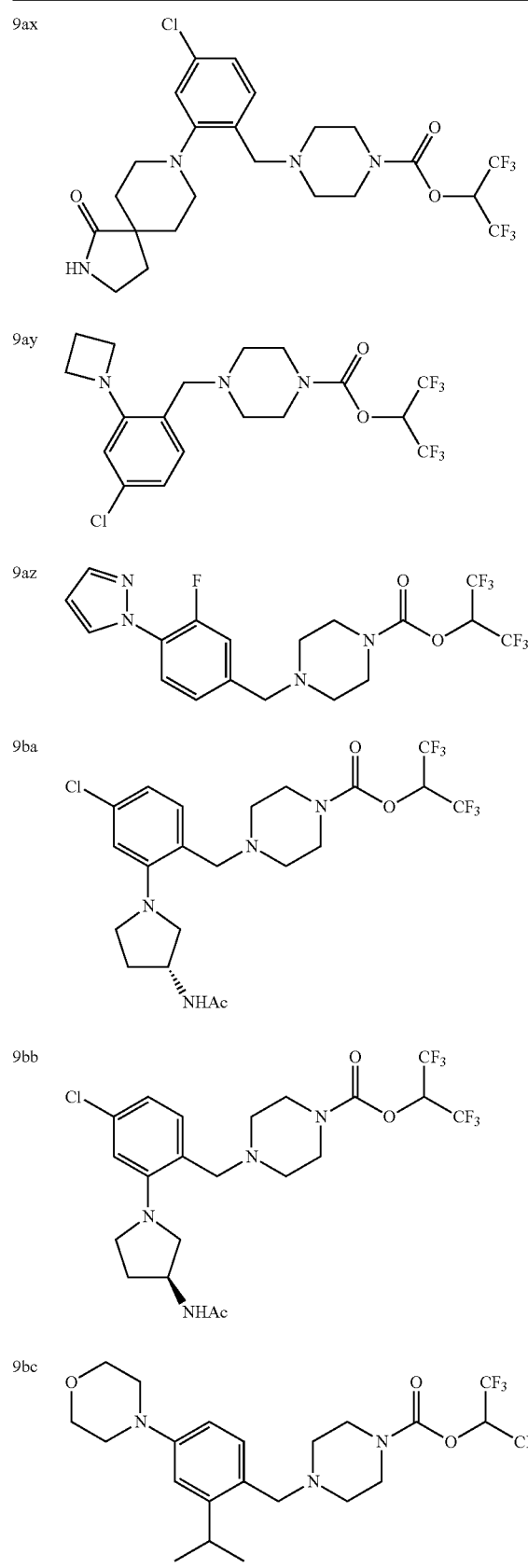
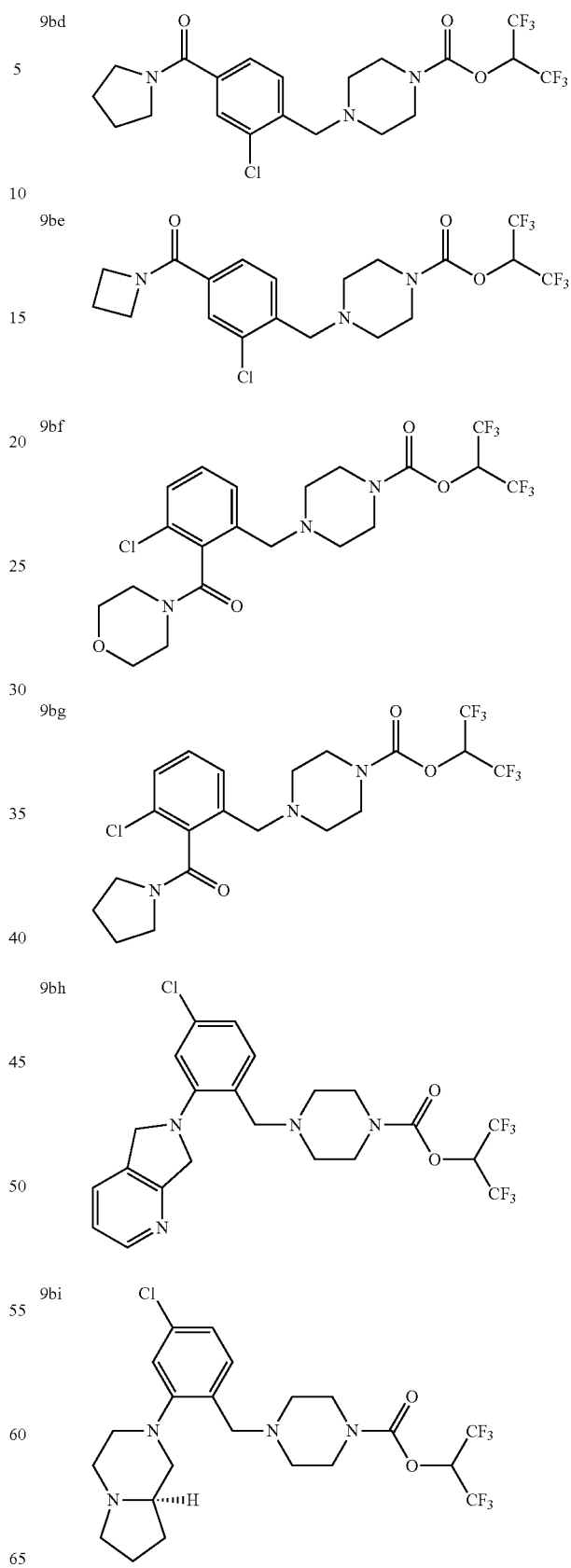

TABLE 3-continued
9bj 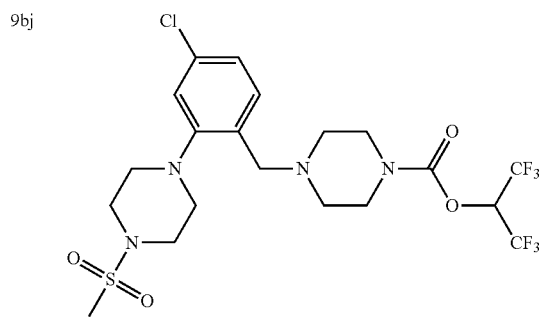
TABLE 4
10a 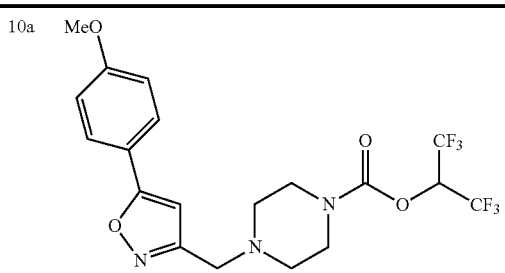
10b 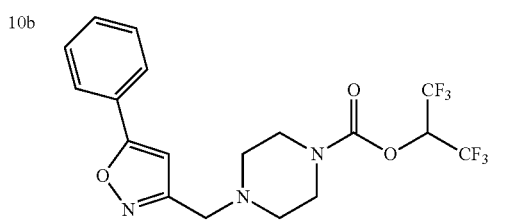
10c 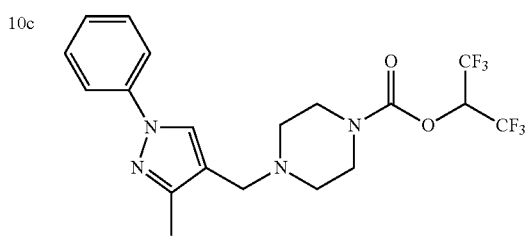
10d 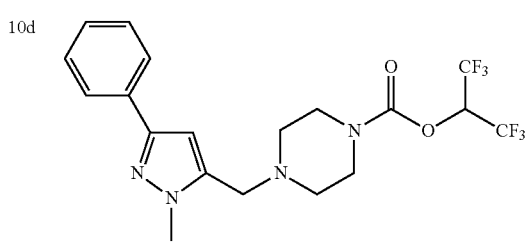
10e 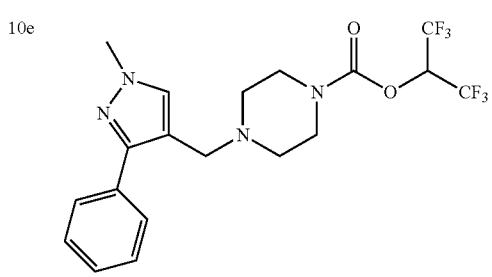
TABLE 4-continued
10f 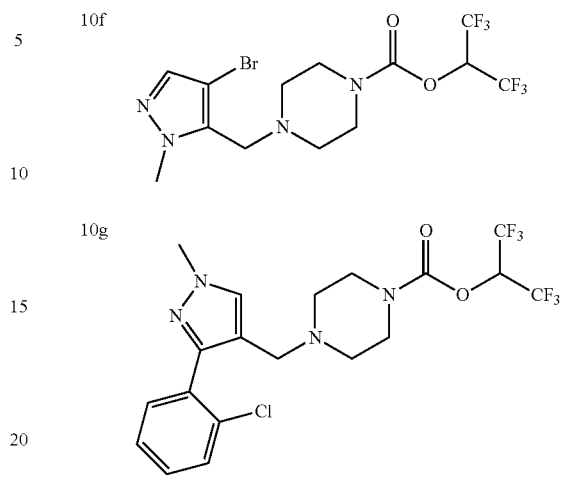
10g 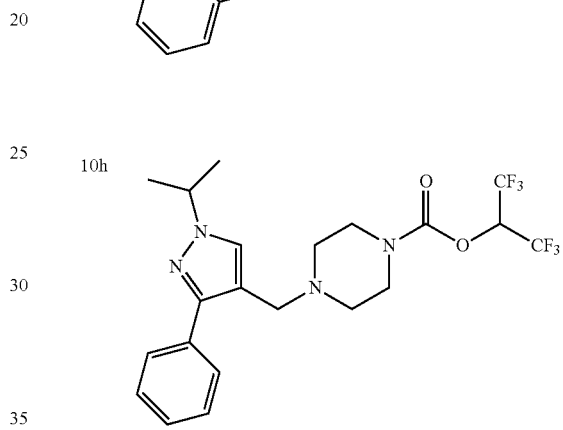
10h 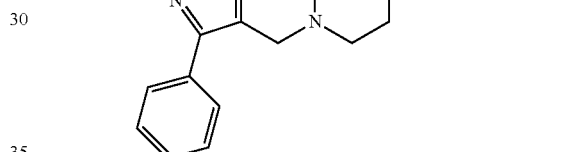
10i 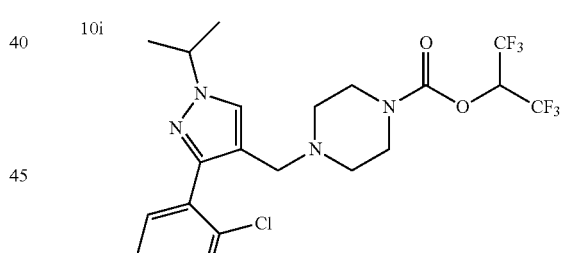
TABLE 5
11a 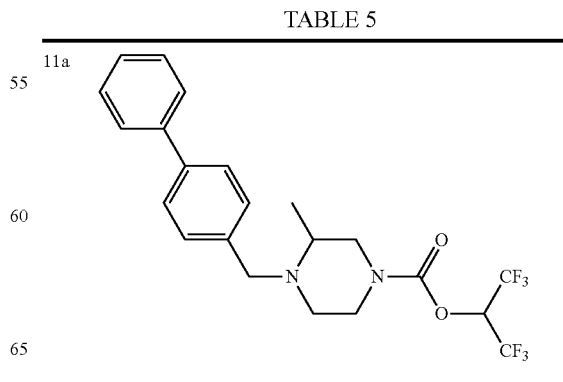

TABLE 5-continued
| | |
|---|---|
| 11b | 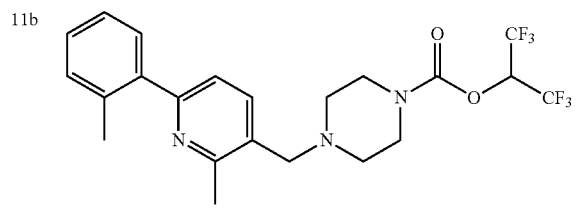 |
| 11c | 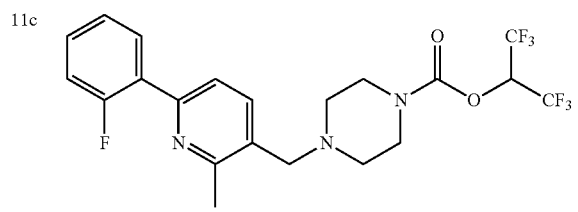 |
| 11d | 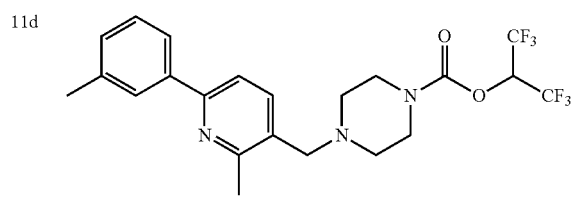 |
| 11e | 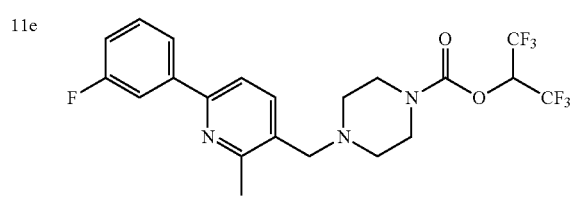 |
| 11f | 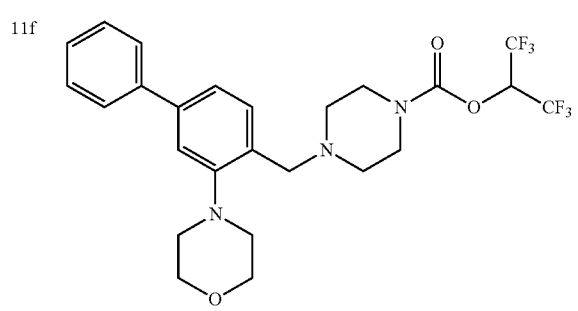 |
| 11g | 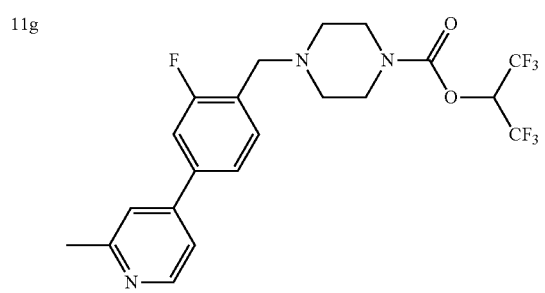 |
| 11h | 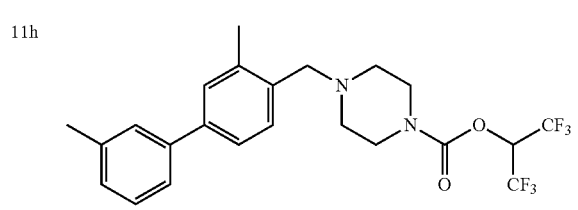 |
| 11i | 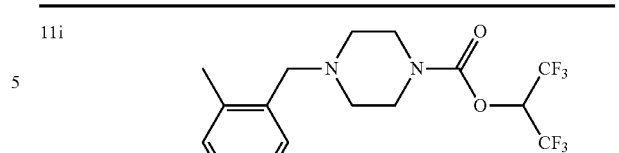 |
| 11j | 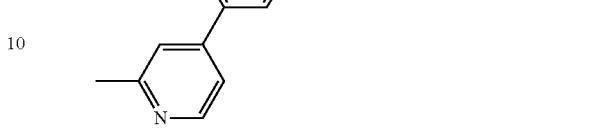 |
| 11k | 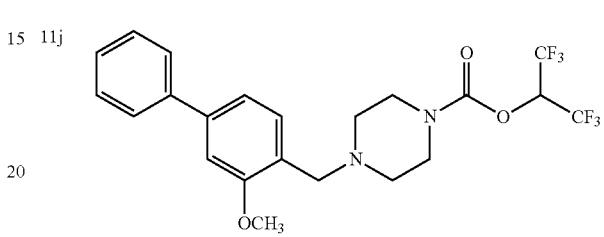 |
| 11l | 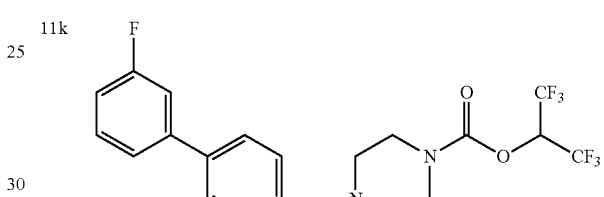 |
| 11m | 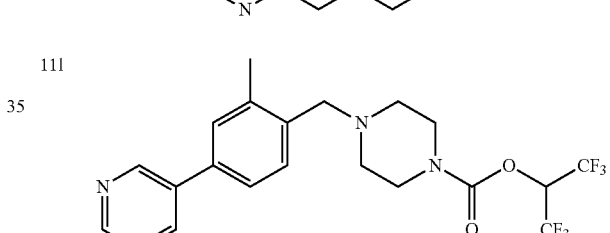 |
| 11n | 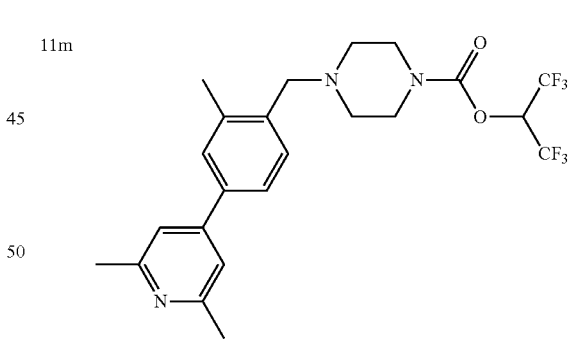 |

TABLE 5-continued
11o 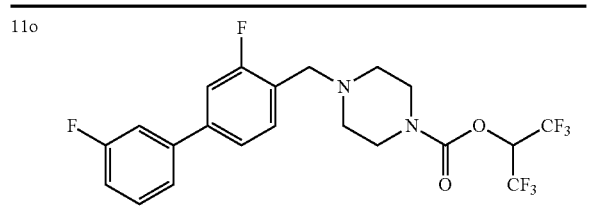
11p 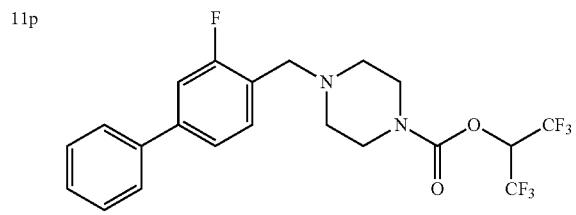
11q 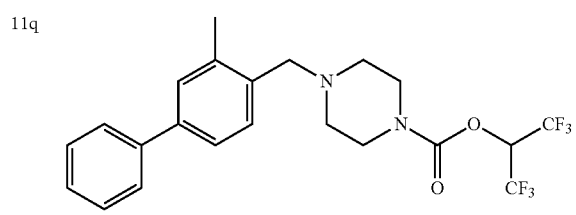
11r 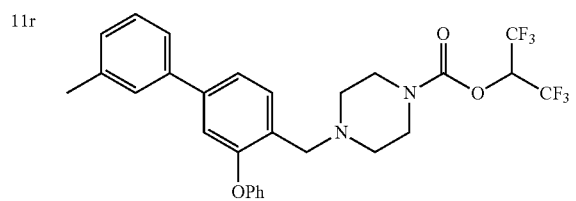
11s 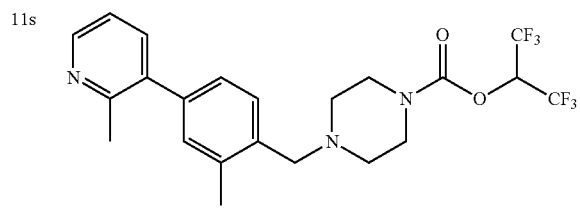
11t 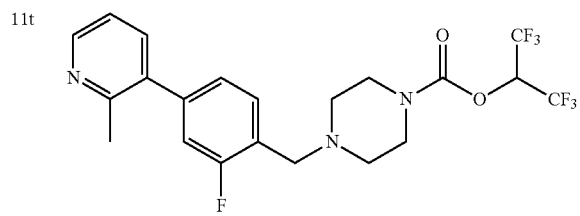
11u 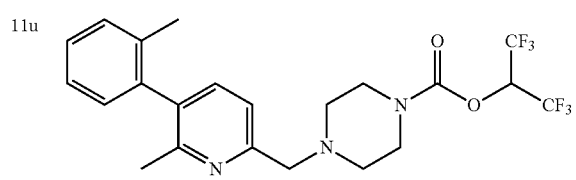
11v 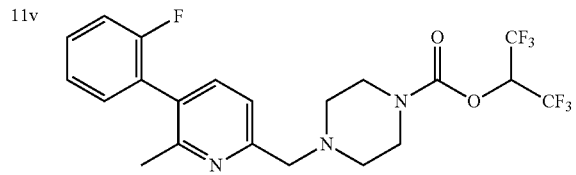
TABLE 5-continued
11w 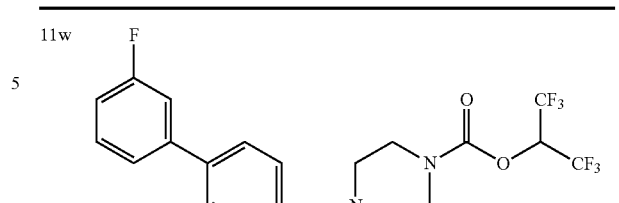
11x 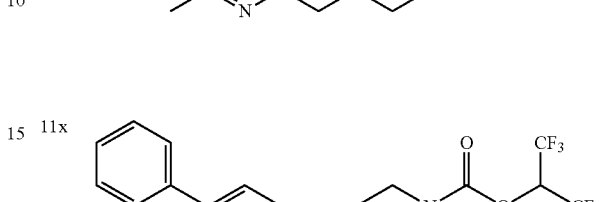
11y 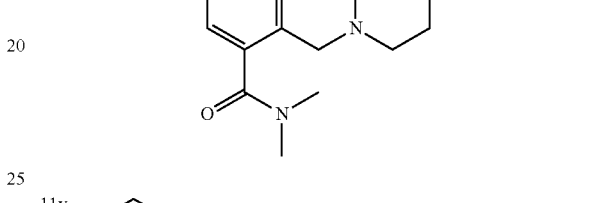
11z 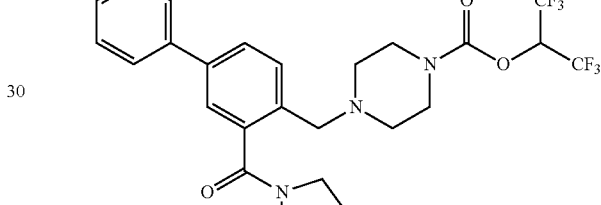
11aa 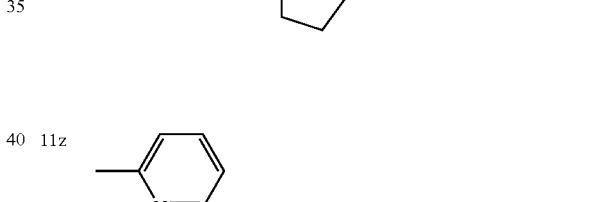

TABLE 5-continued

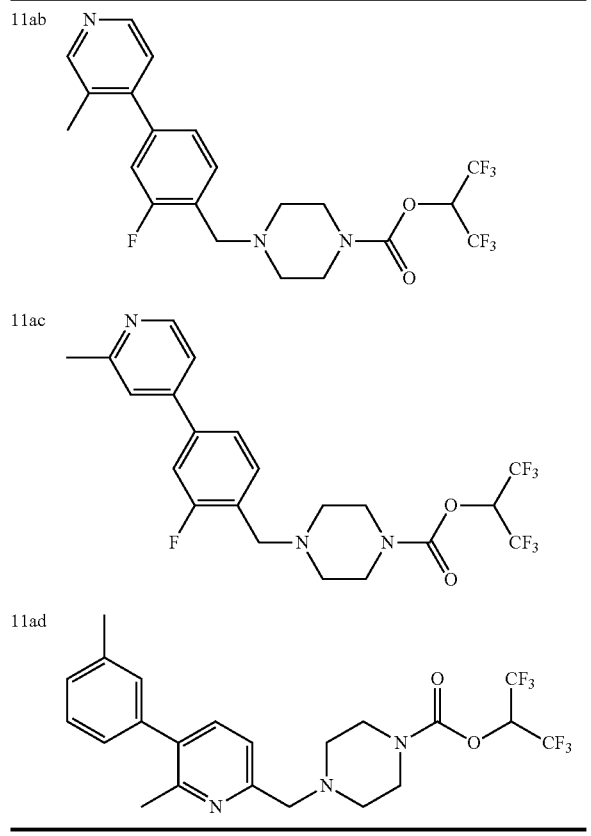

II. Methods

Another aspect of the disclosure provides methods of modulating the activity of MAGL and/or ABHD6. Contemplated methods, for example, comprise exposing said enzyme to a compound described herein. In some embodiments, the compound utilized by one or more of the foregoing methods is one of the generic, subgeneric, or specific compounds described herein, such as a compound of Formula I. The ability of compounds described herein to modulate or inhibit MAGL and/or ABHD6 can be evaluated by procedures known in the art and/or described herein. Another aspect of this disclosure provides methods of treating a disease associated with expression or activity of MAGL and/or ABHD6 in a patient. For example, provided herein are compounds that may be selective in inhibiting MAGL or ABHD6, or both, as compared to inhibition of other serine hydrolases e.g., FAAH, e.g., 10, 100, 1000 or more fold inhibition of MAGL over FAAH. In other embodiments, disclosed compounds may be more selective in inhibition of MAGL as compared to ABHD6.

Also contemplated herein are methods of treating and/or preventing in a patient in need thereof a disorder such as one or more of acute or chronic pain, obesity, metabolic disorders (such as syndrome X), vomiting or nausea, eating disorders such as anorexia and/or bulimia; dislipidaemia, neuropathy such as diabetic neuropathy, pellagric neuropathy, alcoholic neuropathy, Beriberi neuropathy, burning feet syndrome, neurodegenerative disorders such as multiple sclerosis, Parkinson's disease, Huntington's chorea, Alzheimer's disease, amyotrophic lateral sclerosis, epilepsy, sleep disorders, cardiovascular diseases, hypertension, dyslipidemia, atherosclerosis, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, renal ischaemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g., myeloid, lymphoid or monocytic cancers), inflammatory disorders (e.g., bladder inflammation), including inflammatory pain, and/or psychological disorders including anxiety disorders (e.g., panic disorder, acute stress disorder, post-traumatic stress disorder, substance-induced anxiety disorders, obsessive-compulsive disorder, agoraphobia, specific phobia, social phobia. Contemplated methods include administering a pharmaceutically effective amount of a disclosed compound.

In an embodiment, provided herein is a method for treating, ameliorating and/or preventing damage from ischemia, for example, hepatic ischemia or reperfusion in a patient in need thereof, comprising administering a disclosed compound. Methods of treating patients with liver conditions resulting from oxidative stress and/or inflammatory damage are contemplated herein, e.g., contemplated herein are methods of treating liver fibrosis, iron overload, and/or corticosteroid therapy that may result in liver damage, in a patient in need thereof.

For example, provide herein is a method for treating chronic pain such as inflammatory pain, visceral pain, post operative pain, pain related to migraine, osteoarthritis, or rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

For example, contemplated herein are methods for treating neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents) in a patient in need thereof, comprising administering a pharmaceutically effective amount of a disclosed compound.

Also contemplated herein are methods for ameliorating cognitive function in a patient suffering from Down's syndrome or Alzheimer's disease, comprising administering an effective amount of a disclosed compound. Exemplary patients suffering from Down's syndrome may be a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). Such patients may also suffer from further cognitive impairment and/or dementia, and/or seizures which may or may not be due to production of prostaglandins and/or amyloid beta. For example, such patients may also be suffering from, or may have one or more of the following symptoms associated with early-mid or late stage cognitive impairment: loss of language, impairment of social skills, progressive loss of activities of daily living, and may include psychotic behavior. Provided herein, for example, is a method for treating a patient having Down's syndrome or Alzheimer's disease with cognitive impairment, comprising administering an effective amount of a disclosed compound. Such disclosed methods may result in cognitive improvement, for example, measured by IQ or the Arizona Cognitive Test Battery (e.g., measured with a cognitive test battery designed for use in individuals with Down's syndrome). For example, a treated patient using a disclosed method may have at least one of: increased memory, improved memory or improved speech. In some embodiments, such disclosed methods may result in a patient having an increased quality of life as measured by an adaptive behavior scale after said administration.

In other embodiments, a method for at least partially providing a Down's syndrome patient a neuroprotective (such as a disclosed compounds), that may result in delayed onset of neurodegeneration or may substantially prevent neurodegeneration, is provided. Administration to a patient may be initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In certain embodiments, a disclosed compound utilized by one or more of the foregoing methods is one of the generic, subgeneric, or specific compounds described herein, such as a compound of Formula I.

Disclosed compounds may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a contemplated compound disclosed herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

For example, e.g., for contemplated treatment of pain or other contemplated indications (e.g., Alzheimer' or Down's syndrome), a disclosed compound can be co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that may be co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxic.

III. Pharmaceutical Compositions

This disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds disclosed herein may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

All commercially available chemicals were obtained from Aldrich, Acros, Fisher, Fluka, Maybridge or the like and were used without further purification, except where noted. Dry solvents are obtained, for example, by passing these through activated alumina columns. All reactions are typically carried out under an inert nitrogen atmosphere using oven-baked glassware unless otherwise noted. Flash chromatography is performed using 230-400 mesh silica gel 60. NMR spectra were generated on either Varian 400 MHz Bruker 300, Bruker 400, Bruker 500 or Bruker 600 MHz instruments or the like. Chemical shifts are typically recorded in ppm relative to tetramethylsilane (TMS) with multiplicities given as s (singlet), bs (broad singlet), d (doublet), t (triplet), dt (double of triplets), q (quadruplet), qd (quadruplet of doublets), hept (heptuplet), m (multiplet).

Example 1

1,1,1,3,3,3-hexafluoropropan-2-yl 4-(bis(benzo[d][1,3]dioxol-5-yl)(hydroxy)methyl)piperidine-1-carboxylate (1a)

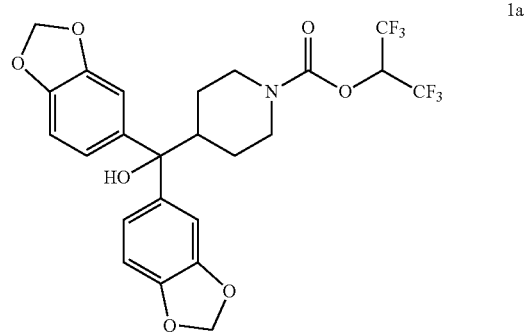

Step 1: Preparation of tert-butyl 4-(dibenzo[d][1,3]dioxol-5-yl(hydroxy)methyl)-piperidine-1-carboxylate

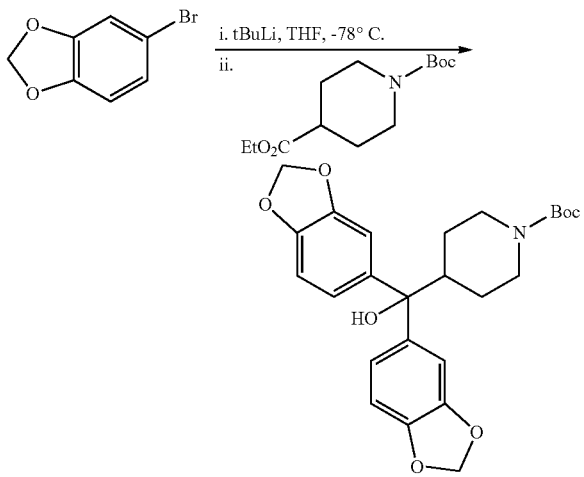

To a stirring solution of 5-bromobenzo-1,3-dioxole (1.77 g, 8.8 mmol) in dry THF (10 mL) at −78° C. under $N_2$ was added tert-butyllithium (10.5 mL, 17.9 mmol, 1.7M in pentane). After 2 h, 1-tert-butyl 4-ethyl piperidine-1,4-dicarboxylate (1.13 g, 4.4 mmol) was added dropwise to the reaction mixture at −78° C. and stirred for 1 h. The reaction mixture was subsequently warmed to room temperature and stirred overnight. The reaction was quenched with saturated aqueous NH₄Cl (30 mL) and the aqueous layer extracted with EtOAc (3×30 mL). The combined organic layers were dried over Na₂SO₄ and concentrated under reduced pressure. The mixture was purified by flash chromatography (10-30% EtOAc/hexanes) to give tert-butyl 4-(bis(benzo[d][1,3]dioxol-5-yl)(hydroxy)methyl)piperidine-1-carboxylate as a white solid (1.3 g, 73%): ¹H NMR 500 MHz (CDCl₃) δ 6.93-6.89 (m, 4H), 6.73 (d, J=8.0 Hz, 2H), 5.91 (s, 4H), 4.14 (bs, 2H), 2.74-2.63 (m, 2H), 2.41-2.34 (m, 1H), 2.04 (s, 1H), 1.55-1.47 (m, 2H), 1.43 (s, 9H), 1.32-1.23 (m, 2H).

Step 2: Preparation of 1,1,1,3,3,3-hexafluoropropan-2-yl 4-(bis(benzo[d][1,3]dioxol-5-yl)(hydroxy)methyl)piperidine-1-carboxylate (1a)

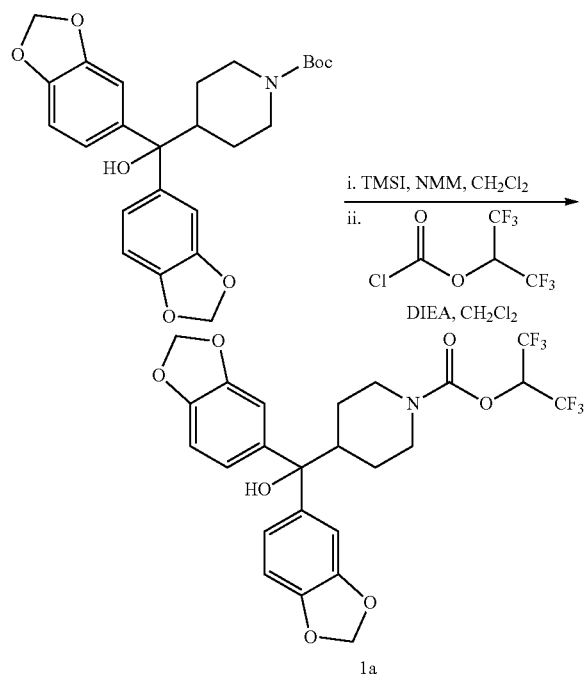

To a solution of tert-butyl 4-(bis(benzo[d][1,3]-dioxol-5-yl)(hydroxy)-methyl)piperidine-1-carboxylate (0.15 mmol) in dry CH₂Cl₂ (8 mL) was added, N-methylmorpholine (82 μL, 0.75 mmol) and iodotrimethylsilane (120 mg, 0.60 mmol). After TLC indicated complete consumption of the starting material, the mixture was poured onto a saturated solution of NaHCO₃ and the product was extracted with CH₂Cl₂ (3×). The combined organic layers were dried over Na₂SO₄ and concentrated under reduced pressure to provide the crude secondary amine, which was used in the next step without further purification.

To a stirring solution of triphosgene (8.2 mg, 0.028 mmol) in CH₂Cl₂ (0.5 mL) was added hexafluoroisopropanol (10 μL, 0.095 mmol) followed by N,N-diisopropylethylamine (30 μL, 0.18 mmol). After 2 h, the secondary amine (0.095 mmol) was added as a solution in CH₂Cl₂ (1 mL) and stirred for another 2 h. The mixture was concentrated under reduced pressure and purified directly by SiO₂ flash chromatography (EtOAc/hexanes) to provide the titled compound: ¹H NMR 400 MHz (CDCl₃) δ 6.91-6.89 (m, 4H), 6.76-6.74 (m, 2H), 5.93 (s, 4H), 5.72 (m, J=6.3, 1H), 4.19 (t, J=15.1, 2H), 2.89 (q, J=14.7, 2H), 2.44 (tt, J=11.8, 3.0, 1H), 1.97 (s, 1H), 1.68-1.58 (m, 2H), 1.41-1.32 (m, 2H); ¹³C NMR 150 MHz (CDCl₃) δ 151.4, 147.97, 147.94, 146.5, 139.62, 139.58, 121.8, 119.9, 118.89, 118.85, 108.08, 108.07, 106.78, 106.73, 101.3, 79.4, 68.4, 68.1, 67.9, 67.7, 45.4, 44.8, 44.3, 26.7, 26.3; HRMS (ESI+) m/z calc'd for [M+Na]⁺ C₂₄H₂₁F₆NO₇: 572.1114. found 572.1111.

Example 2

1,1,1,3,3,3-hexafluoropropan-2-yl 4-(bis(benzo[d][1,3]dioxol-5-yl)(methoxy)methyl)piperidine-1-carboxylate (1b)

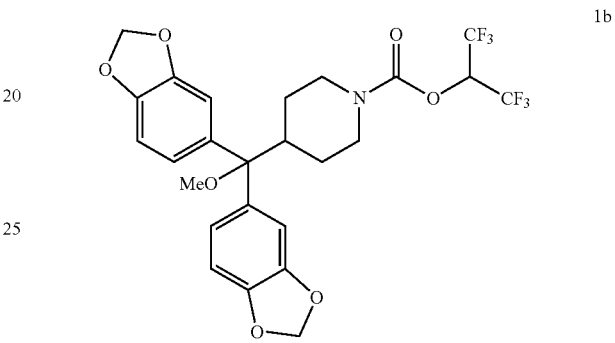

Step 1: Preparation of tert-butyl 4-(dibenzo[d][1,3]dioxol-5-yl(methoxy)methyl)-piperidine-1-carboxylate

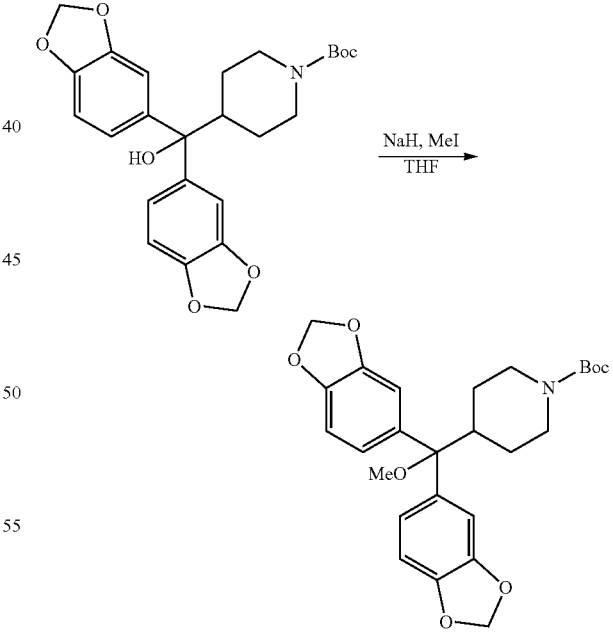

To a slurry of NaH (88 mg, 2.2 mmol, 60% in mineral oil) in dry THF (5.0 mL) was added tert-butyl 4-(bis(benzo[d][1,3]dioxol-5-yl)(hydroxy)methyl)piperidine-1-carboxylate (100 mg, 0.22 mmol). After 30 min, iodomethane (468 mg, 143 mmol) was added and the reaction mixture was stirred for an additional 2 h. The reaction was quenched by the addition of a saturated solution of NH₄Cl (30 mL) and extracted with EtOAc (3×). The combined organic layers were dried over Na₂SO₄ and concentrated under reduced pressure. The crude product was purified by SiO₂ flash chromatography (20% EtOAc/hexanes) to give tert-butyl 4-(bis(benzo[d][1,3]dioxol-5-yl)(methoxy)-methyl)piperidine-1-carboxylate as a clear viscous oil (94 mg, 91%): ¹H NMR 600 MHz (CDCl₃) δ 6.79-6.74 (m, 6H), 5.96-5.95 (m, 4H), 4.08 (bs, 2H), 2.86 (s, 3H), 2.76-2.65 (m, 2H), 2.48-2.43 (m, 1H), 1.76 (d, J=13.2 Hz, 3H), 1.38 (s, 9H), 0.94-0.81 (m, 2H).

Step 2: Preparation of 1,1,1,3,3,3-hexafluoropropan-2-yl 4-(bis(benzo[d][1,3]dioxol-5-yl)(methoxy)methyl)piperidine-1-carboxylate (1b)

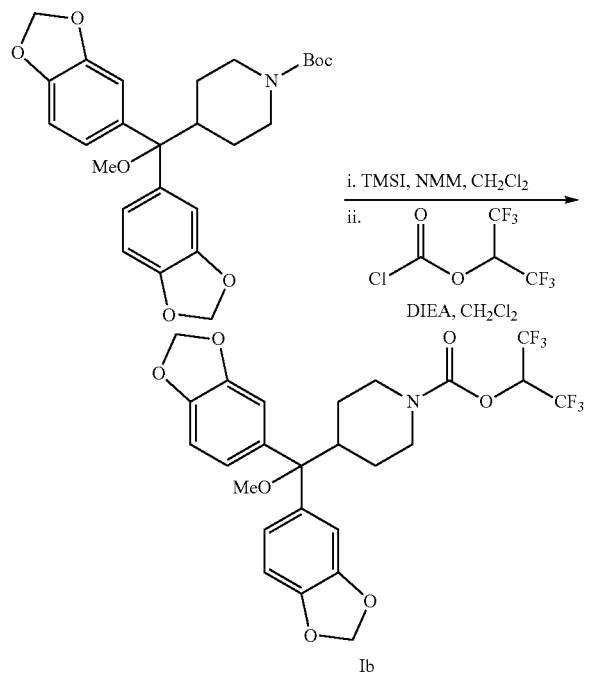

The title compound was prepared from tert-butyl 4-(bis(benzo[d][1,3]-dioxol-5-yl)(methoxy)methyl)piperidine-1-carboxylate according to the representative procedures of Example 1, Step 2: ¹H NMR 500 MHz (CDCl₃) δ 6.88-6.84 (m, 6H), 6.06 (s, 4H), 5.79-5.71 (m, 1H), 4.22 (t, J=15.2 Hz, 2H), 3.06-2.96 (m, 2H), 2.96 (s, 3H), 2.61 (t, J=12.0 Hz, 1H), 1.95 (d, J=13.1 Hz, 2H), 1.10-0.93 (m, 2H); HRMS (ESI+) m/z calc'd for [M+H]⁺ C₂₅H₂₄F₆NO₇: 564.1457. found 564.1460.

Example 3

1,1,1,3,3,3-hexafluoropropan-2-yl 4-(bis(benzo[d][1,3]dioxol-5-yl)methyl)piperidine-1-carboxylate (1c)

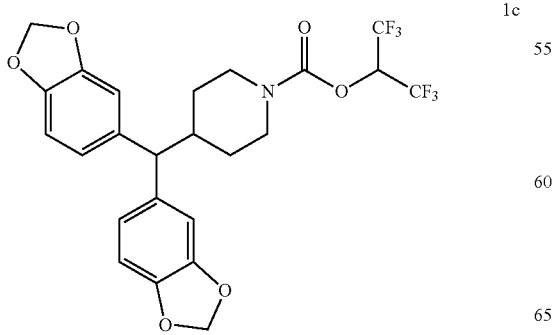

Step 1: Preparation of dibenzo[d][1,3]dioxol-5-yl(piperidin-4-yl)methanol

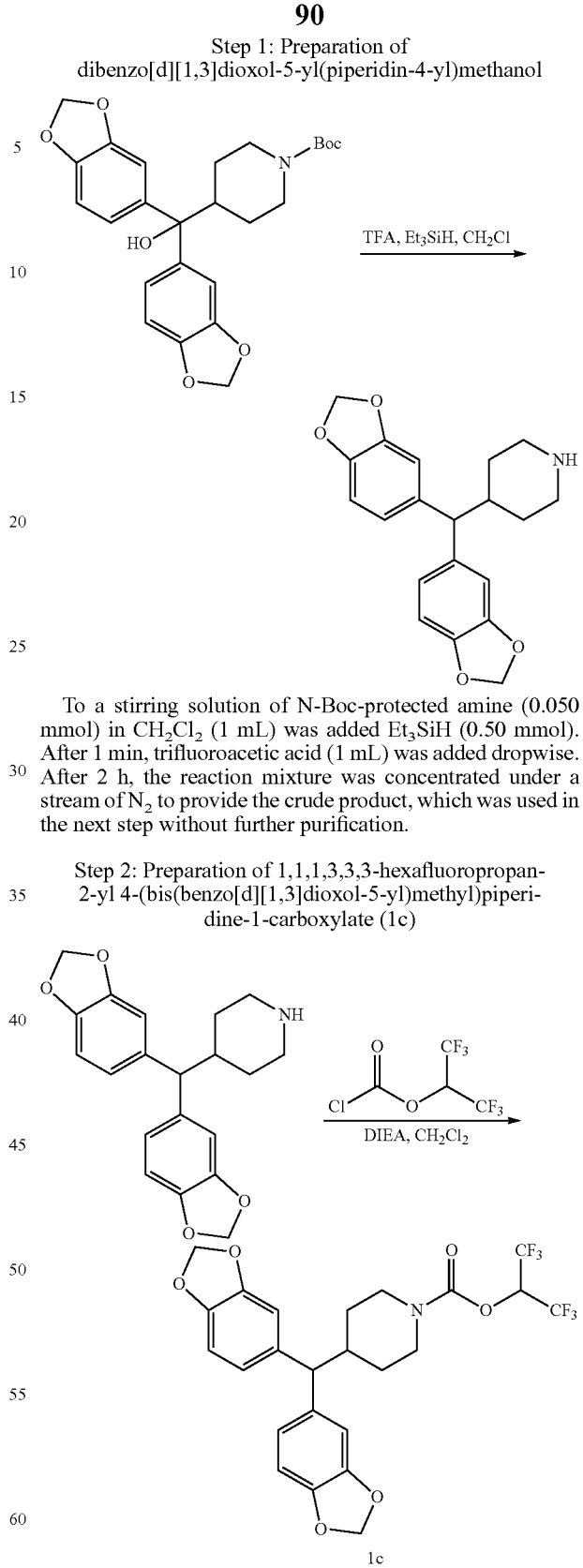

To a stirring solution of N-Boc-protected amine (0.050 mmol) in CH₂Cl₂ (1 mL) was added Et₃SiH (0.50 mmol). After 1 min, trifluoroacetic acid (1 mL) was added dropwise. After 2 h, the reaction mixture was concentrated under a stream of N₂ to provide the crude product, which was used in the next step without further purification.

Step 2: Preparation of 1,1,1,3,3,3-hexafluoropropan-2-yl 4-(bis(benzo[d][1,3]dioxol-5-yl)methyl)piperidine-1-carboxylate (1c)

The title compound was prepared from the crude amine according to the representative procedure of Example 1, Step 2: ¹H NMR 400 MHz (CDCl₃) δ 6.72 (m, 6H), 5.91 (s, 4H), 5.75 (m, 1H), 4.12 (m, 2H), 3.35 (d, J=3.2 Hz, 1H), 2.88 (m, 2H), 2.14 (m, 1H), 1.64 (m, 2H), 1.13 (m, 2H); HRMS m/z calc'd for [M+H]⁺ C₂₄H₂₁F₆NO₆: 534.1346. found 534.1341.

Example 4

1,1,1,3,3,3-hexafluoropropan-2-yl 4-(bis(benzo[d][1,3]dioxol-5-yl)methylene)piperidine-1-carboxylate (1d)

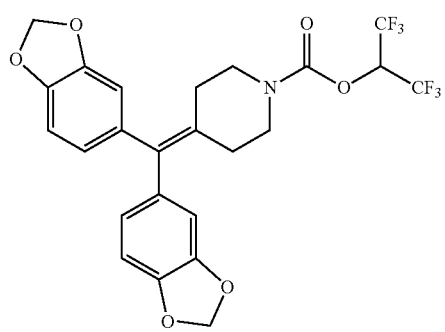

Step 1: Preparation of dibenzo[d][1,3]dioxol-5-yl(piperidin-4-yl)methanol

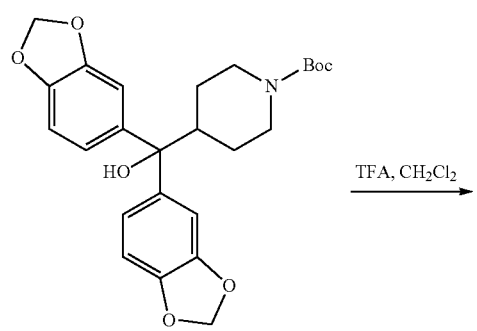

To a stirring solution of N-Boc-protected amine (50 mg, 0.11 mmol) in CH₂Cl₂ (3 mL) was added trifluoroacetic acid (1 mL). After 2 h, the reaction mixture was concentrated under a stream of N₂ to provide the crude product, which was used in the next step without further purification.

Step 2: Preparation of 1,1,1,3,3,3-hexafluoropropan-2-yl 4-(bis(benzo[d][1,3]dioxol-5-yl)methylene)piperidine-1-carboxylate (1d)

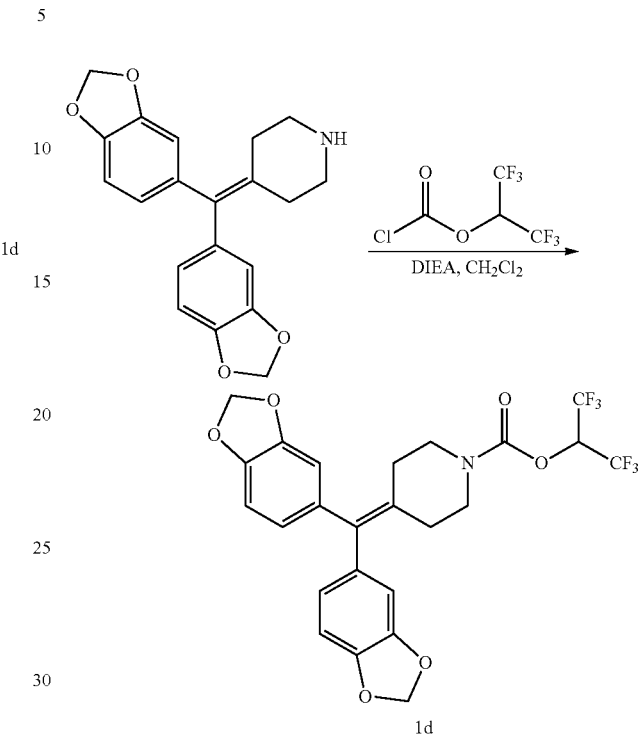

The title compound was prepared from the crude amine according to the representative procedures of Example 1, Step 2: ¹H NMR 600 MHz (CDCl₃) δ 6.74 (dd, J=7.9, 5.4 Hz, 2H), 6.58-6.53 (m, 4H), 5.93 (d, J=2.1 Hz, 4H), 5.76 (dt, J=12.3, 6.1 Hz, 1H), 3.57-3.53 (m, 4H), 2.40 (dt, J=18.1, 5.8 Hz, 4H); HRMS m/z calc'd for [M+H]⁺ C₂₄H₂₀F₆NO₆: 532.1195. found 532.1192.

Example 5

1,1,1,3,3,3-hexafluoropropan-2-yl 4-(bis(4-fluorophenyl)methyl)-piperazine-1-carboxylate (2a)

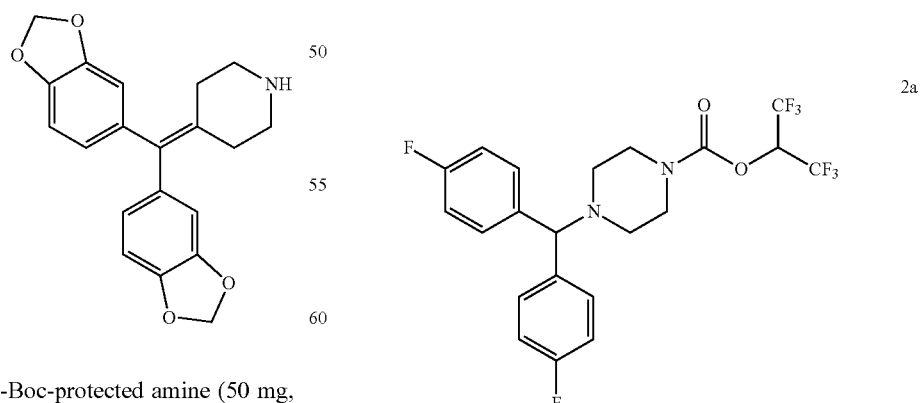

The title compound was synthesized directly from commercially available 1-(bis(4-fluorophenyl)methyl)piperazine according to the representative procedure of Example 1, Step 2: $^1$H NMR 400 MHz (CDCl$_3$) δ 7.33 (m, 4H), 6.98 (m, 4H), 5.72 (m, 1H), 4.25 (s, 1H), 3.55 (m, 4H), 2.38 (m, 4H), HRMS m/z calc'd for [M+H]$^+$ C$_{21}$H$_{18}$F$_8$N$_2$O$_2$: 483.1313. found 483.1315.

Example 6

1,1,1,3,3,3-hexafluoropropan-2-yl 4-(bis(4-chlorophenyl)methyl)-piperazine-1-carboxylate (2b)

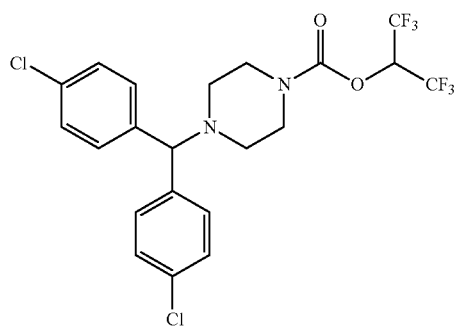

2b

The title compound was synthesized directly from commercially available 1-(bis(4-chlorophenyl)methyl)piperazine according to the representative procedure Example 1, Step 2: $^1$H NMR 400 MHz (CDCl$_3$) δ 7.29 (m, 8H), 5.72 (m, 1H), 4.23 (s, 1H), 3.55 (m, 4H), 2.38 (m, 4H); HRMS m/z calc'd for [M+H]$^+$ C$_{21}$H$_{18}$Cl$_2$F$_6$N$_2$O$_2$: 515.0722. found 515.0725.

Example 7

1,1,1,3,3,3-hexafluoropropan-2-yl 4-(bis(4-bromophenyl)methyl)-piperazine-1-carboxylate (2c)

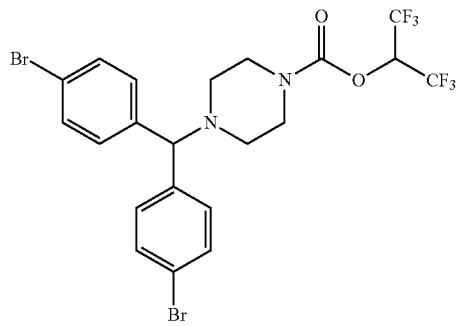

2c

Step 1-2: Preparation of 1-(bis(4-bromophenyl)methyl)piperazine

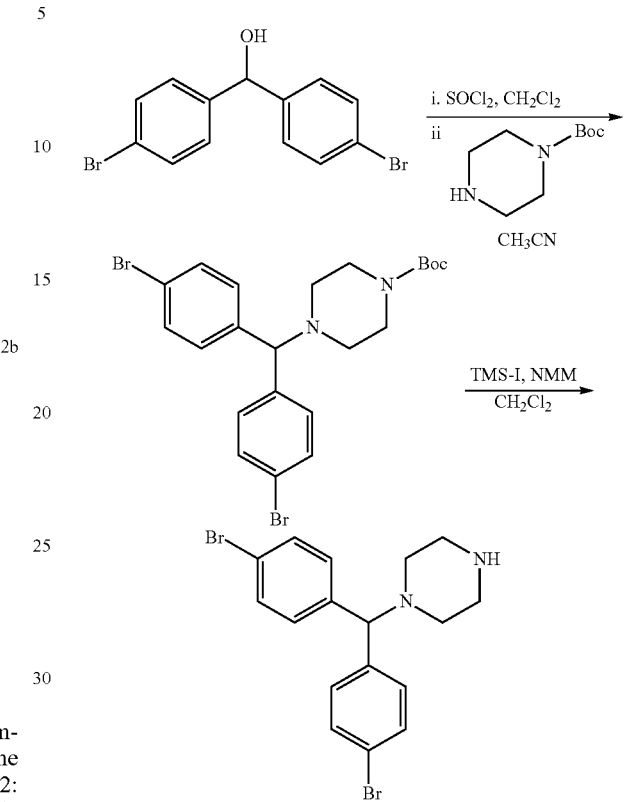

To a stirring solution of bis(4-bromophenyl)methanol (0.060 mmol) in CH$_2$Cl$_2$ (0.3 mL) was added thionyl chloride (40 μL, 0.60 mmol) and the reaction mixture was stirred for 48 h. The reaction was evaporated to dryness under a stream of N$_2$ and the crude product redissolved in acetonitrile (1.0 mL). 1-Boc-piperazine (22.3 mg, 0.12 mmol) was added and the reaction mixture was refluxed for 4 h. The reaction mixture was concentrated under reduced pressure, redissolved in CH$_2$Cl$_2$ and passed through a short pad of SiO$_2$, providing the 1-Boc-4-diphenylmethylpiperazine.

The protected diphenylemethyl-piperazine was treated with TMSI according to the representative protocol for Boc-deprotection as described above in Example 1, Step 2.

Step 3: Preparation of 1,1,1,3,3,3-hexafluoropropan-2-yl 4-(bis(4-bromophenyl))-piperazine-1-carboxylate (2c)

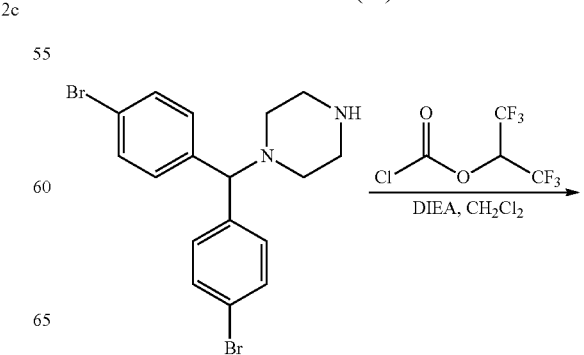

The title compound was synthesized according to the representative procedure of Example 1, Step 2: ¹H NMR 400 MHz (CDCl₃) δ 7.42 (d, J=8.0 Hz, 4H), 7.24 (d, J=8.4 Hz, 4H), 5.72 (m, 1H), 4.21 (s, 1H), 3.55 (m, 4H), 2.38 (m, 4H); HRMS m/z calc'd for [M+H]⁺ C$_{21}$H$_{18}$Br$_2$F$_6$N$_2$O$_2$: 602.9712. found 602.9720.

Example 8

1,1,1,3,3,3-hexafluoropropan-2-yl 4-(bis(benzo[d][1,3]dioxol-5-yl)methyl)piperazine-1-carboxylate (2d)

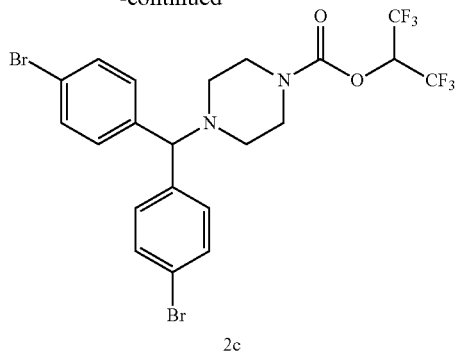

Step 1: Preparation of dibenzo[d][1,3]dioxol-5-ylmethanol

To a stirring solution of tert-butyllithium (1.8 mL, 3.1 mmol, 1.7M in pentane) at −78° C. was added dropwise a solution of 5-bromobenzo-1,3-dioxole (1.5 mmol) in THF (3 mL). After 30 min, benzo-1,3-dioxole-5-carbaldehyde (1.5 mmol) or ethyl formate (0.5 mmol) in THF (1 mL) was added. The mixture was stirred at −78° C. for 1 h and subsequently warmed to room temperature and stirred for an additional 4 h. The reaction was quenched by the addition of a saturated solution of NH₄Cl and extracted with EtOAc (3×). The organic layers were combined, dried over Na₂SO₄ and concentrated under reduced pressure. Purification of the crude oil by flash chromatography (20% EtOAc/hexanes) provided the diphenyl methanol product.

Steps 2-4: Preparation of 1,1,1,3,3,3-hexafluoropropan-2-yl 4-(bis(benzo[d][1,3]-dioxol-5-yl)methyl)piperazine-1-carboxylate (2d)

The title compound was synthesized according to the representative procedures of Example 7: ¹H NMR 400 MHz (CDCl₃) δ 6.90 (m, 2H), 6.80 (d, J=8.0 Hz, 2H), 6.71 (d, J=7.6 Hz, 2H), 5.91 (s, 4H), 5.73 (m, 1H), 4.08 (s, 1H), 3.53 (m, 4H), 2.39 (m, 4H); HRMS m/z calc'd for [M+H]⁺ C$_{23}$H$_{20}$F$_6$N$_2$O$_6$: 535.1298. found 535.1316.

Example 9

1,1,1,3,3,3-hexafluoropropan-2-yl 4-(bis(2,3-dihydrobenzofuran-5-yl)methyl)piperazine-1-carboxylate (2e)

The title compound was synthesized from 5-bromo-2,3-dihydrobenzofuran and ethyl formate according to the representative procedure of Example 8: $^1$H NMR 400 MHz (CDCl$_3$) δ 7.19 (s, 2H), 7.11 (dd, J=8.3, 1.6 Hz, 2H), 6.69 (d, J=8.2 Hz, 2H), 5.72 (7, J=6.2 Hz, 1H), 4.52 (t, J=8.7 Hz, 4H), 4.13-4.09 (m, 1H), 3.52 (d, J=4.2 Hz, 4H), 3.16 (t, J=8.7 Hz, 4H), 2.39 (ddd, J=9.8, 9.8, 5.1 Hz, 4H).

Example 10

1,1,1,3,3,3-hexafluoropropan-2-yl 4-(bis(2,2-difluorobenzo[d][1,3]-dioxol-5-yl)methyl)piperazine-1-carboxylate (2f)

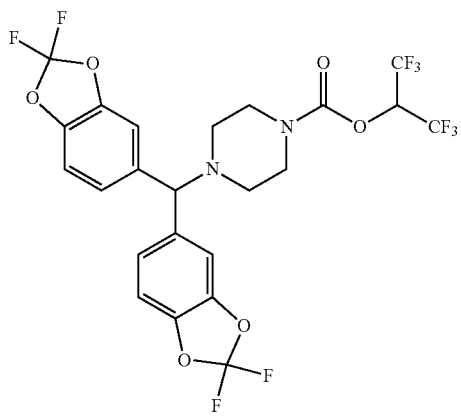

2f

The title compound was synthesized from 5-bromo-2,2-difluorobenzo-[d][1,3]dioxole and ethyl formate according to the representative procedure of Example 8: $^1$H NMR 500 MHz (CDCl$_3$) δ 7.13 (s, 2H), 7.07 (d, J=8.2 Hz, 2H), 6.98 (d, J=8.2 Hz, 2H), 5.72 (7, J=6.2 Hz, 1H), 4.24 (s, 1H), 3.57 (d, J=3.8 Hz, 4H), 2.41 (d, J=17.2 Hz, 4H); HRMS m/z calc'd for [M+H]$^+$ C$_{23}$H$_{16}$F$_{10}$N$_2$O$_6$: 607.0921. found 607.0923.

Example 11

1,1,1,3,3,3-hexafluoropropan-2-yl 4-([1,1'-biphenyl]-4-yl)benzo[d][1,3]-dioxol-5-yl)methyl)piperazine-1-carboxylate (2g)

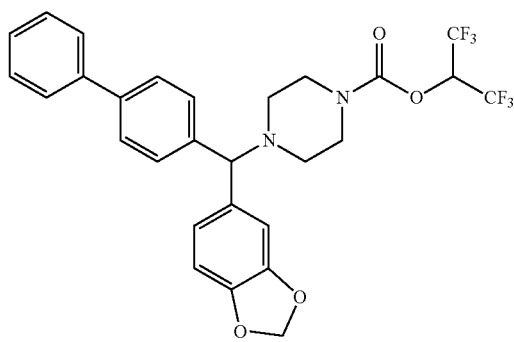

2g

The title compound was synthesized from 5-bromobenzo-1,3-dioxole and 4-phenylbenzaldehyde according to the representative procedure of Example 8: $^1$H-400 MHz (CDCl$_3$) δ 7.55-7.50 (m, 4H), 7.42 (m, 4H), 7.34-7.30 (m, 1H), 6.97 (d, J=1.6 Hz, 1H), 6.87 (dd, J=8.0, 1.6 Hz, 1H), 6.73 (d, J=8.0 Hz, 1H), 5.91 (dd, J=8.8, 1.4 Hz, 2H), 5.73 (7, J=6.2 Hz, 1H), 4.21 (s, 1H), 3.60-3.54 (m, 4H), 2.44 (ddd, J=14.7, 4.8, 4.8 Hz, 4H); HRMS m/z calc'd for [M+H]$^+$ C$_{28}$H$_{24}$F$_6$N$_2$O$_4$: 567.1713. found 567.1712.

Example 12

1,1,1,3,3,3-hexafluoropropan-2-yl 4-(3-phenoxybenzyl)piperazine-1-carboxylate (3a)

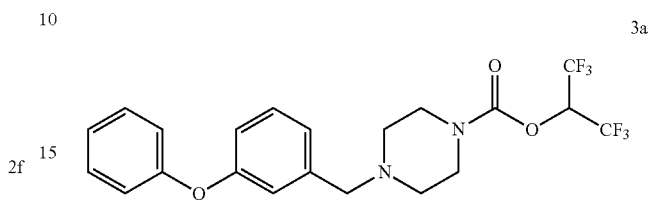

3a

The title compound was synthesized directly from commercially available 1-(3-phenoxybenzyl)piperazine according to the representative procedure of Example 1, Step 2: $^1$H NMR 400 MHz (CDCl$_3$) δ 7.32 (m, 3H), 7.10 (m, 1H), 7.02 (m, 4H), 6.90 (d, J=8.0 Hz, 1H), 5.74 (m, 1H), 3.52 (m, 6H), 2.45 (m, 4H); HRMS m/z calc'd for [M+H]$^+$ C$_{21}$H$_{20}$F$_6$N$_2$O$_3$: 463.1451. found 463.1453.

Example 13

1,1,1,3,3,3-hexafluoropropan-2-yl 4-([1,1'-biphenyl]-4-ylmethyl)-piperazine-1-carboxylate (3b)

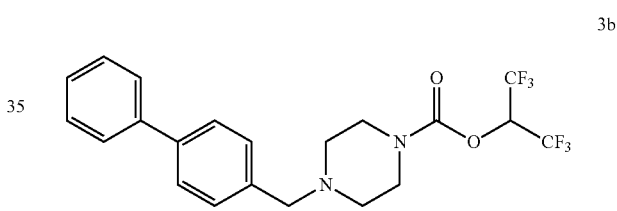

3b

The title compound was synthesized directly from commercially available 1-([1,1'-biphenyl]-4-ylmethyl)piperazine according to the representative procedure of Example 1, Step 2: $^1$H NMR 400 MHz (CDCl$_3$) δ 7.57 (m, 4H), 7.41 (m, 5H), 5.75 (m, 1H), 3.57 (m, 6H), 2.50 (m, 4H); HRMS m/z calc'd for [M+H]$^+$ C$_{21}$H$_{20}$F$_6$N$_2$O$_2$: 447.1502. found 447.1499.

Example 14

1,1,1,3,3,3-hexafluoropropan-2-yl 4-([1,1'-biphenyl]-4-carbonyl)-piperazine-1-carboxylate (3c)

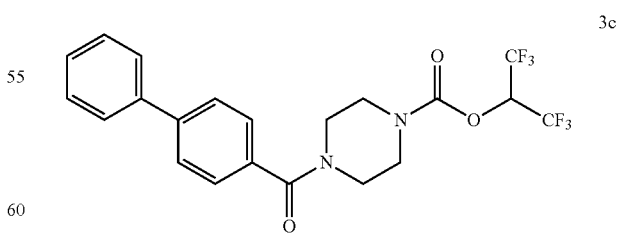

3c

The title compound was synthesized directly from commercially available [1,1'-biphenyl]-4-yl(piperazin-1-yl)methanone according to the representative procedure of Example 1, Step 2: $^1$H NMR 400 MHz (CDCl$_3$) δ 7.65 (d, J=8.0 Hz, 2H), 7.59 (d, J=7.6 Hz, 2H), 7.47 (m, 4H), 7.39 (m, 1H), 5.76 (m, 1H), 3.69 (m, 8H); HRMS m/z calc'd for [M+H]$^+$ C$_{21}$H$_{18}$F$_6$N$_2$O$_3$: 461.1294. found 461.1290.

Example 15

1-tert-butyl 4-(1,1,1,3,3,3-hexafluoropropan-2-yl) piperazine-1,4-dicarboxylate (3d)

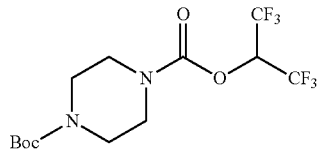 [SMILES: CC(C)(C)OC(=O)N1CCN(C(=O)OC(C(F)(F)F)C(F)(F)F)CC1]

3d

The title compound was synthesized directly from commercially available 1-Boc-piperazine according to the representative procedure of Example 1, Step 2: $^1$H NMR 400 MHz (CDCl$_3$) δ 5.75 (m, 1H), 3.49 (m, 8H), 1.47 (s, 9H); HRMS m/z calc'd for [M+Na]$^+$ C$_{13}$H$_{18}$F$_6$N$_2$O$_4$, 403.1063. found, 403.1066.

Example 16

1,1,1,3,3,3-hexafluoropropan-2-yl 4-(4-methoxyphenyl)piperazine-1-carboxylate (3e)

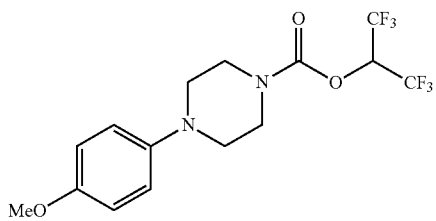 [SMILES: COc1ccc(N2CCN(C(=O)OC(C(F)(F)F)C(F)(F)F)CC2)cc1]

3e

The title compound was synthesized directly from commercially available 1-(4-methoxyphenyl)piperazine according to the representative procedure of Example 1, Step 2: $^1$H NMR 400 MHz (CDCl$_3$) δ 6.89 (m, 4H), 5.77 (s, 1H), 3.77 (s, 3H), 3.70 (m, 4H), 3.06 (m, 4H); HRMS m/z calc'd for [M+H]$^+$ C$_{15}$H$_{16}$F$_6$N$_2$O$_3$: 387.1138. found 387.1143.

Example 17

1,1,1,3,3,3-hexafluoropropan-2-yl methyl(3-(pyridin-4-yl)benzyl)-carbamate (3f)

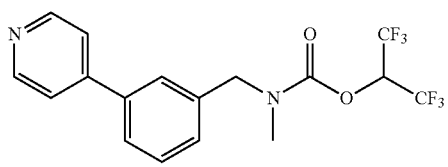 [SMILES: CN(Cc1cccc(-c2ccncc2)c1)C(=O)OC(C(F)(F)F)C(F)(F)F]

3f

The title compound was synthesized directly from commercially available N-methyl-1-(3-(pyridin-4-yl)phenyl) methanamine according to the representative procedure of Example 1, Step 2: $^1$H NMR 400 MHz (CDCl$_3$) δ 7.59 (m, 2H), 7.48 (m, 4H), 7.30 (m, 2H), 5.84 (m, 1H), 4.61 (d, J=4.8 Hz, 2H), 3.00 (s, 3H); HRMS m/z calc'd for [M+H]$^+$ C$_{17}$H$_{14}$F$_6$N$_2$O$_2$: 393.1032. found 393.1034.

Example 18

1,1,1,3,3,3-hexafluoropropan-2-yl methyl(3-(pyridin-3-yl)benzyl)-carbamate (3g)

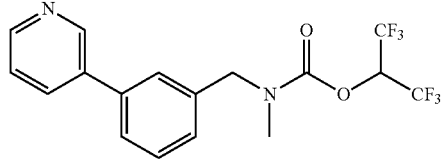 [SMILES: CN(Cc1cccc(-c2cccnc2)c1)C(=O)OC(C(F)(F)F)C(F)(F)F]

3g

The title compound was synthesized directly from commercially available N-methyl-1-(3-(pyridin-3-yl)phenyl) methanamine according to the representative procedure of Example 1, Step 2: $^1$H NMR 400 MHz (CDCl$_3$) δ 7.85 (m, 2H), 7.54 (m, 2H), 7.46 (m, 3H), 7.26 (m, 1H), 5.83 (m, 1H), 4.60 (d, J=5.2 Hz, 2H), 3.00 (s, 3H); HRMS m/z calc'd for [M+H]$^+$ C$_{17}$H$_{14}$F$_6$N$_2$O$_2$: 393.1032. found 393.1026.

Example 19

1,1,1,3,3,3-hexafluoropropan-2-yl 4-(2-methylquinolin-4-yl)piperazine-1-carboxylate (3h)

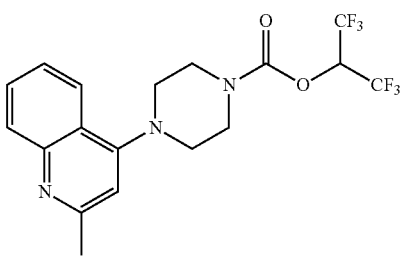 [SMILES: Cc1cc(N2CCN(C(=O)OC(C(F)(F)F)C(F)(F)F)CC2)c2ccccc2n1]

3h

The title compound was synthesized directly from commercially available 2-methyl-4-(piperazin-1-yl)quinoline according to the representative procedure of Example 1, Step 2: $^1$H NMR 400 MHz (CDCl$_3$) δ 8.00 (d, J=8.4 Hz, 1H), 7.94 (d, J=8.4 Hz, 1H), 7.65 (t, J=8.0 Hz, 1H), 7.46 (t, J=8.0 Hz, 1H), 6.76 (s, 1H), 5.80 (m, 1H), 3.86 (m, 6H), 3.23 (m, 2H), 2.69 (s, 3H); HRMS m/z calc'd for [M+H]$^+$ C$_{18}$H$_{17}$F$_6$N$_3$O$_2$: 422.1298. found 422.1292.

Example 20

1,1,1,3,3,3-hexafluoropropan-2-yl(benzo[d][1,3]dioxol-5-ylmethyl)-(methyl)carbamate (3i)

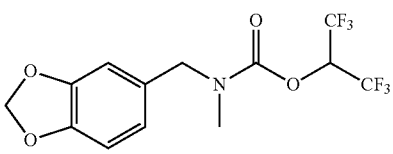 [SMILES: CN(Cc1ccc2c(c1)OCO2)C(=O)OC(C(F)(F)F)C(F)(F)F]

3i

The title compound was synthesized directly from commercially available 1-(benzo[d][1,3]dioxol-5-yl)-N-methylmethanamine according to the representative procedure of Example 1, Step 2: $^1$H NMR 400 MHz (CDCl$_3$) δ 6.77 (m, 1H), 6.70 (m, 2H), 5.96 (s, 2H), 5.80 (m, 1H), 4.41 (d, J=3.6 Hz, 2H), 2.92 (s, 3H); HRMS m/z calc'd for [M+H]⁺ $C_{13}H_{11}F_6NO_4$: 360.0665. found 360.0671.

Example 21

1,1,1,3,3,3-hexafluoropropan-2-yl methyl(3-(5-methyl-1,2,4-oxadiazol-3-yl)benzyl)carbamate (3j)

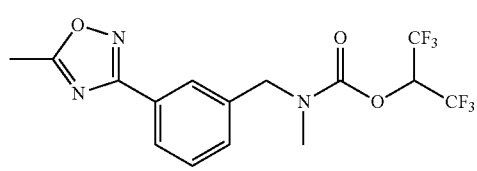 [SMILES: Cc1nc(-c2cccc(CN(C)C(=O)OC(C(F)(F)F)C(F)(F)F)c2)no1]

The title compound was synthesized directly from commercially available N-methyl-1-(3-(5-methyl-1,2,4-oxadiazol-3-yl)phenyl)methanamine according to the representative procedure of Example 1, Step 2: ¹H NMR 400 MHz (CDCl₃) δ 8.02 (m, 1H), 7.93 (m, 1H), 7.49 (m, 1H), 7.36 (m, 1H), 5.83 (m, 1H), 4.59 (d, J=3.2 Hz, 2H), 2.99 (s, 3H), 2.65 (s, 3H); HRMS m/z calc'd for [M+H]⁺ $C_{15}H_{13}F_6N_3O_3$: 398.0926. found 398.0929.

Example 22

1,1,1,3,3,3-hexafluoropropan-2-yl 4-(phenylsulfonyl)piperazine-1-carboxylate (4a)

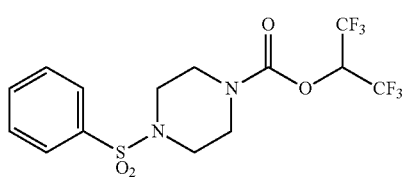 [SMILES: O=C(OC(C(F)(F)F)C(F)(F)F)N1CCN(S(=O)(=O)c2ccccc2)CC1]

Step 1: Preparation of 1,1,1,3,3,3-hexafluoropropan-2-yl piperazine-1-carboxylate

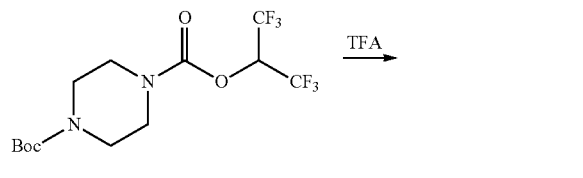

To a solution of 1-tert-butyl 4-(1,1,1,3,3,3-hexafluoropropan-2-yl)piperazine-1,4-dicarboxylate (3d) (42 mg, 0.11 mmol) in CH₂Cl₂ (3.0 mL) was added trifluoroacetic acid (63 mg, 1.54 mmol) at room temperature. After stirring for 12 h, the reaction mixture was treated with a saturated solution of NaHCO₃ and extracted with CH₂Cl₂ (3×). The combined organic layers were washed with brine, dried over MgSO₄, filtered and concentrated to provide the crude deprotected amine, which was used in subsequent reactions without further purification.

Step 2: Preparation of 1,1,1,3,3,3-hexafluoropropan-2-yl 4-(phenylsulfonyl)-piperazine-1-carboxylate (4a)

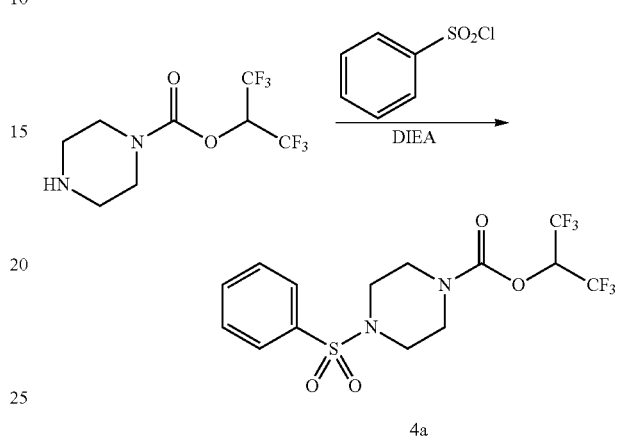

The crude amine was redissolved in CH₂Cl₂ (3.0 mL) and to this solution was added benzenesulfonyl chloride (21 mg, 0.12 mmol) and N,N-diisopropylethylamine (0.058 mL, 0.33 mmol). After stirring for 6 h, the reaction mixture was quenched with a saturated solution of NaHCO₃ and extracted with CH₂Cl₂ (3×). The combined organic layers were washed with brine, dried over MgSO₄, filtered and concentrated under reduced pressure. The crude product was purified by flash column chromatography (10% EtOAc/hexanes) to afford title compound (38 mg, 83% yield) as a white solid: ¹H NMR 400 MHz (CDCl₃) δ 7.76 (d, J=8.4 Hz, 2H), 7.65 (m, 1H), 7.57 (m, 2H), 5.67 (m, 1H), 3.64 (m, 4H), 3.06 (m, 4H); HRMS m/z calc'd for [M+H]⁺ $C_{14}H_{14}F_6N_2O_4S$: 421.065. found 421.0653.

Example 23

1,1,1,3,3,3-hexafluoropropan-2-yl 4-tosylpiperazine-1-carboxylate (4b)

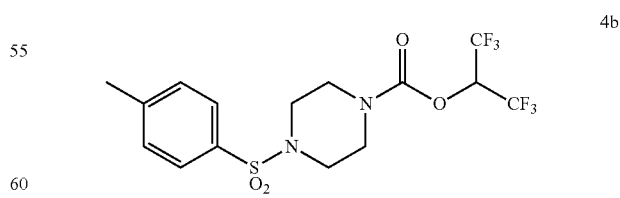

The title compound was synthesized from 1-tert-butyl 4-(1,1,1,3,3,3-hexafluoropropan-2-yl)piperazine-1,4-dicarboxylate (3d) and 4-methylbenzene-1-sulfonyl chloride according to the representative procedure of Example 22: ¹H NMR 400 MHz (CDCl₃) δ 7.64 (d, J=7.2 Hz, 2H), 7.35 (d, J=7.6 Hz, 2H), 5.66 (m, 1H), 3.64 (m, 4H), 3.04 (m, 4H), 2.45 (s, 3H); HRMS m/z calc'd for [M+H]$^+$ C$_{15}$H$_{16}$F$_6$N$_2$O$_4$S: 435.0808. found 435.0815.

Example 24

1,1,1,3,3,3-hexafluoropropan-2-yl 4-((4-(tert-butyl)phenyl)sulfonyl)-piperazine-1-carboxylate (4c)

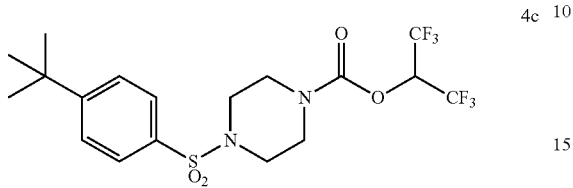

4c

The title compound was synthesized from 1-tert-butyl 4-(1,1,1,3,3,3-hexafluoropropan-2-yl)piperazine-1,4-dicarboxylate (3d) and 4-(tert-butyl)benzene-1-sulfonyl chloride according to the representative procedure of Example 22: $^1$H NMR 400 MHz (CDCl$_3$) δ 7.67 (d, J=7.6 Hz, 2H), 7.55 (d, J=7.6 Hz, 2H), 5.68 (m, 1H), 3.64 (m, 4H), 3.06 (m, 4H), 1.35 (s, 9H); HRMS m/z calc'd for [M+H]$^+$ C$_{18}$H$_{22}$F$_6$N$_2$O$_4$S: 477.1277. found 477.1285.

Example 25

1,1,1,3,3,3-hexafluoropropan-2-yl 4-((4-cyanophenyl)sulfonyl)-piperazine-1-carboxylate (4d)

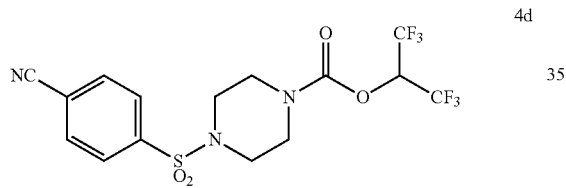

4d

The title compound was synthesized from 1-tert-butyl 4-(1,1,1,3,3,3-hexafluoropropan-2-yl)piperazine-1,4-dicarboxylate (3d) and 4-cyanobenzene-1-sulfonyl chloride according to the representative procedure of Example 22: $^1$H NMR 400 MHz (CDCl$_3$) δ 7.88 (m, 4H), 5.67 (m, 1H), 3.66 (m, 4H), 3.11 (m, 4H); HRMS m/z calc'd for [M+H]$^+$ C$_{15}$H$_{13}$F$_6$N$_3$O$_4$S: 446.0604. found 446.0608.

Example 26

1,1,1,3,3,3-hexafluoropropan-2-yl 4-((4-acetamidophenyl)sulfonyl)-piperazine-1-carboxylate (4e)

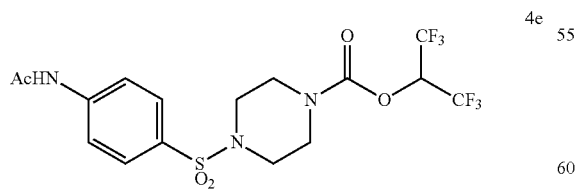

4e

The title compound was synthesized from 1-tert-butyl 4-(1,1,1,3,3,3-hexafluoropropan-2-yl)piperazine-1,4-dicarboxylate (3d) and 4-acetamidobenzene-1-sulfonyl chloride according to the representative procedure of Example 22: $^1$H NMR 400 MHz (CDCl$_3$) δ 7.71 (m, 4H), 7.37 (s, 1H), 5.67 (m, 1H), 3.63 (m, 4H), 3.04 (m, 4H), 2.23 (s, 3H); HRMS m/z calc'd for [M+H]$^+$ C$_{16}$H$_{17}$F$_6$N$_3$O$_5$S: 478.0866. found 478.0868.

Example 27

1,1,1,3,3,3-hexafluoropropan-2-yl 4-((2,4,6-triisopropylphenyl)-sulfonyl)piperazine-1-carboxylate (4f)

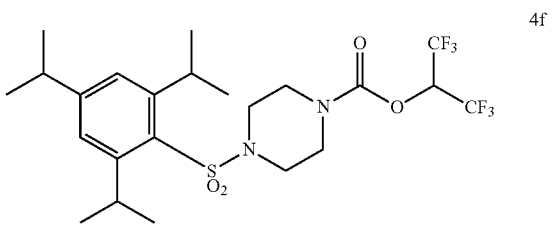 [SMILES: CC(C)c1cc(C(C)C)c(S(=O)(=O)N2CCN(C(=O)OC(C(F)(F)F)C(F)(F)F)CC2)c(C(C)C)c1]

4f

The title compound was synthesized from 1-tert-butyl 4-(1,1,1,3,3,3-hexafluoropropan-2-yl)piperazine-1,4-dicarboxylate (3d) and 4,6-triisopropylbenzene-1-sulfonyl chloride according to the representative procedure of Example 22: $^1$H NMR 400 MHz (CDCl$_3$) δ 7.26 (s, 1H), 7.18 (s, 1H), 5.72 (m, 1H), 4.12 (m, 2H), 3.61 (m, 4H), 3.23 (m, 4H), 2.91 (m, 1H), 1.26 (d, J=6.4 Hz, 18H); HRMS m/z calc'd for [M+H]$^+$ C$_{23}$H$_{32}$F$_6$N$_2$O$_4$S: 547.206. found 547.2064.

Example 28

1,1,1,3,3,3-hexafluoropropan-2-yl 4-(o-tolylsulfonyl)piperazine-1-carboxylate (4g)

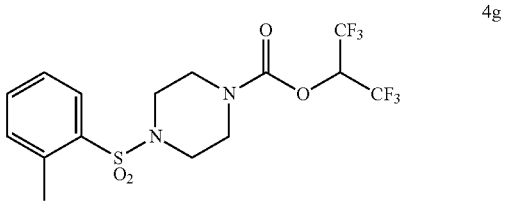 [SMILES: Cc1ccccc1S(=O)(=O)N1CCN(C(=O)OC(C(F)(F)F)C(F)(F)F)CC1]

4g

The title compound was synthesized from 1-tert-butyl 4-(1,1,1,3,3,3-hexafluoropropan-2-yl)piperazine-1,4-dicarboxylate (3d) and 2-methylbenzene-1-sulfonyl chloride according to the representative procedure of Example 22: $^1$H NMR 400 MHz (CDCl$_3$) δ 7.62 (m, 1H), 7.48 (m, 3H), 5.70 (m, 1H), 3.62 (m, 4H), 3.21 (m, 4H), 2.45 (s, 3H); HRMS m/z calc'd for [M+H]$^+$ C$_{15}$H$_{16}$F$_6$N$_2$O$_4$S: 435.0808. found 435.0813.

Example 29

1,1,1,3,3,3-hexafluoropropan-2-yl 4-(naphthalen-2-ylsulfonyl)-piperazine-1-carboxylate (4h)

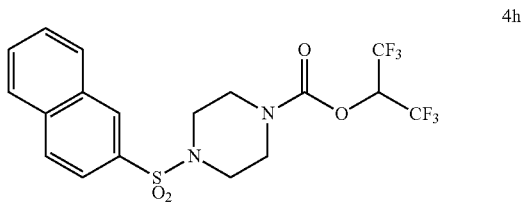 [SMILES: O=C(OC(C(F)(F)F)C(F)(F)F)N1CCN(S(=O)(=O)c2ccc3ccccc3c2)CC1]

4h

The title compound was synthesized from 1-tert-butyl 4-(1,1,1,3,3,3-hexafluoropropan-2-yl)piperazine-1,4-dicarboxylate (3d) and naphthalene-2-sulfonyl chloride according to the representative procedure of Example 22: $^1$H NMR 400 MHz (CDCl$_3$) δ 8.34 (s, 1H), 7.97 (m, 3H), 7.69 (m, 3H), 5.64 (m, 1H), 3.65 (m, 4H), 3.13 (m, 4H); HRMS m/z calc'd for [M+H]$^+$ C$_{18}$H$_{16}$F$_6$N$_2$O$_4$S: 471.0808. found 471.0806.

Example 30

1,1,1,3,3,3-hexafluoropropan-2-yl 4-((3-(trifluoromethyl)phenyl)-sulfonyl)piperazine-1-carboxylate (4i)

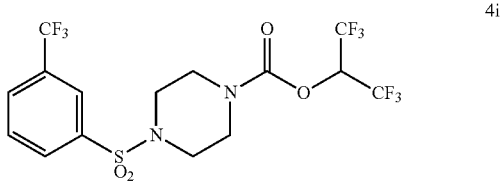 [SMILES: O=C(OC(C(F)(F)F)C(F)(F)F)N1CCN(S(=O)(=O)c2cccc(C(F)(F)F)c2)CC1]

The title compound was synthesized from 1-tert-butyl 4-(1,1,1,3,3,3-hexafluoropropan-2-yl)piperazine-1,4-dicarboxylate (3d) and 3-(trifluoromethyl)-benzene-1-sulfonyl chloride according to the representative procedure of Example 22: $^1$H NMR 400 MHz (CDCl$_3$) δ 8.01 (s, 1H), 7.93 (m, 2H), 7.73 (t, J=8.0 Hz, 1H), 5.66 (m, 1H), 3.67 (m, 4H), 3.10 (m, 4H); HRMS m/z calc'd for [M+H]$^+$ C$_{15}$H$_{13}$F$_9$N$_2$O$_4$S: 489.0525. found 489.0520.

Example 31

1,1,1,3,3,3-hexafluoropropan-2-yl 4-[bis(4-chlorophenyl)methyl]-3-methylpiperazine-1-carboxylate (2h)

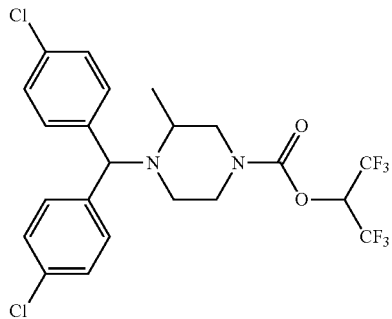 [SMILES: CC1CN(C(=O)OC(C(F)(F)F)C(F)(F)F)CCN1C(c1ccc(Cl)cc1)c1ccc(Cl)cc1]

Step 1: Preparation of 1-chloro-4-[chloro(4-chlorophenyl)methyl]benzene

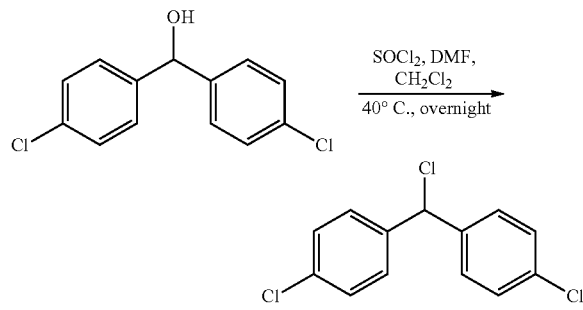

A 1000 mL 3-necked round-bottom flask was charged with bis(4-chlorophenyl)methanol (49.6 g, 196 mmol, 1.00 equiv), N,N-dimethylformamide (5 mL), dichloromethane (100 mL). Liquid thionyl chloride (93.3 g, 790 mmol, 4.00 equiv) was added dropwise. The resulting solution was stirred overnight at 40° C. in an oil bath. The resulting mixture was concentrated under reduced pressure. The residue was chromatographed on a silica gel column with ethyl acetate/petroleum ether (1/5) to provide 47.8 g (88% yield) of 1-chloro-4-[chloro(4-chlorophenyl)methyl]benzene as a gray solid. $^1$HNMR 300 MHz (CDCl$_3$) δ 7.30-7.39 (m, 8H), 6.07 (s, 1H). GCMS (EI, m/z): 270 [M]$^+$.

Step 2: Preparation of tert-butyl 4-[bis(4-chlorophenyl)methyl]-3-methylpiperazine-1-carboxylate

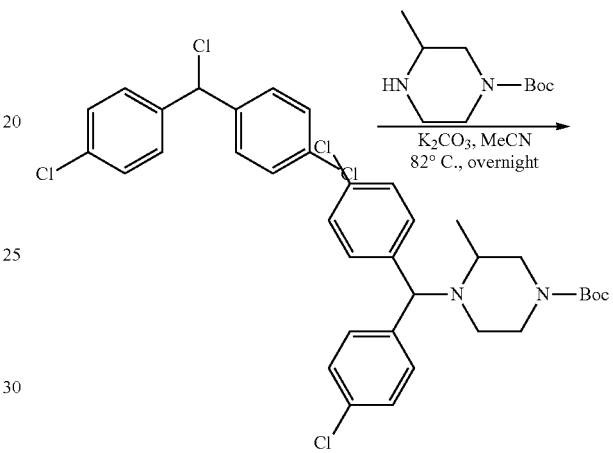

A 100 mL round-bottom flask was charged with tert-butyl 3-methylpiperazine-1-carboxylate (2.00 g, 9.99 mmol, 1.00 equiv), 1-chloro-4-[chloro(4-chlorophenyl)methyl]benzene (5.46 g, 20.1 mmol, 2.01 equiv), potassium carbonate (6.90 g, 49.9 mmol, 5.00 equiv), acetonitrile (30 mL). The resulting solution was stirred overnight at 82° C. in an oil bath. The resulting solution was diluted with H$_2$O (50 mL). The resulting solution was extracted with dichloromethane (3×20 mL) and the organic layers were combined, dried over anhydrous sodium sulfate, filtered and concentrated under reduced pressure. The residue was chromatographed on a silica gel column with ethyl acetate/petroleum ether (1/4) to yield 1.70 g (53% yield) of tert-butyl 4-[bis(4-chlorophenyl)methyl]-3-methylpiperazine-1-carboxylate as a light yellow solid. LCMS: (ESI, m/z): 435 [M+H]$^+$.

Step 3: Preparation of 1-[bis(4-chlorophenyl)methyl]-2-methylpiperazine

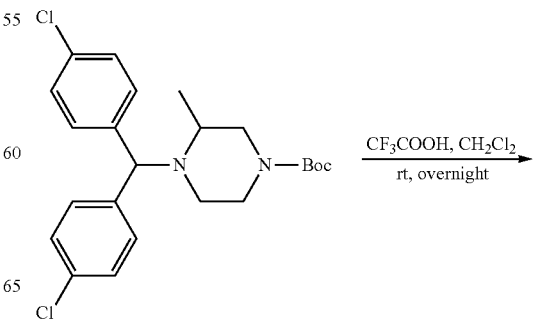

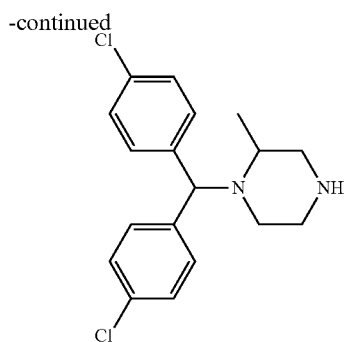

A 50 mL round-bottom flask was charged with tert-butyl 4-[bis(4-chlorophenyl)methyl]-3-methylpiperazine-1-carboxylate (0.800 g, 1.84 mmol, 1.00 equiv), dichloromethane (15 mL). The mixture was cooled to 0° C. and trifluoroacetic acid (2 mL) was added dropwise. The resulting solution was stirred for 3 hours at room temperature and concentrated under reduced pressure to yield 1.60 g (crude) of 1-[bis(4-chlorophenyl)methyl]-2-methylpiperazine as a light yellow semi-solid. LCMS: (ESI, m/z): 335 [M+H]$^+$.

Step 4: Preparation of 1,1,1,3,3,3-hexafluoropropan-2-yl 4-[bis(4-chlorophenyl)methyl]-3-methylpiperazine-1-carboxylate

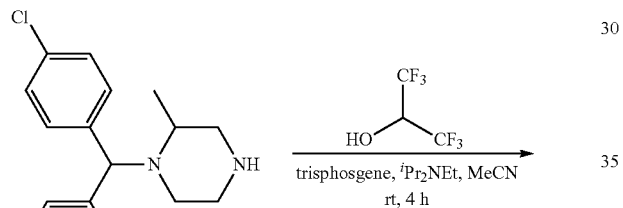

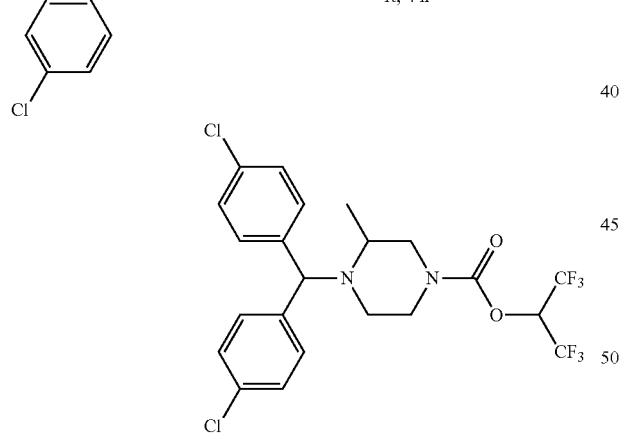

A 50 mL round-bottom flask was charged with 1,1,1,3,3,3-hexafluoropropan-2-ol (336 mg, 2.00 mmol, 1.00 equiv), acetonitrile (20 mL), triphosgene (198 mg, 0.670 mmol, 0.330 equiv). N,N-diisopropylethylamine (942 mg, 7.29 mmol, 3.65 equiv) was added dropwise. The mixture was stirred for 2 hours at room temperature. Then 1-[bis(4-chlorophenyl)methyl]-2-methylpiperazine (670 mg, 2.00 mmol, 1.00 equiv) was added. The resulting solution was stirred for 2 hours at room temperature and diluted with H$_2$O (20 mL). The resulting solution was extracted with dichloromethane (3×20 mL) and the organic layers were combined, washed with water (3×20 mL) and dried over anhydrous sodium sulfate, filtered and concentrated under reduced pressure. The residue was chromatographed on a silica gel column with ethyl acetate/petroleum ether (1/5). The product (218 mg) was purified by preparative HPLC using the following gradient conditions: 20% CH$_3$CN/80% phase A increasing to 80% CH$_3$CN over 10 min, then to 100% CH$_3$CN over 0.1 min, holding at 100% CH$_3$CN for 1.9 min, then reducing to 20% over 0.1 min, and holding at 20% for 1.9 min, on a waters 2767-5 chromatograph. Column: X-bridge Prep C$_{18}$, 19*150 mm Sum; Mobile phase: Phase A: aqueous NH$_4$HCO$_3$ (0.05%); Phase B: CH$_3$CN; Detector, UV220 & 254 nm. Purification resulted in 56.4 mg (5% yield) of 1,1,1,3,3,3-hexafluoropropan-2-yl 4-[bis(4-chlorophenyl)methyl]-3-methylpiperazine-1-carboxylate as a light yellow solid. $^1$H NMR 300 MHz (CDCl$_3$) δ 7.26-7.36 (m, 8H), 5.69-5.77 (m, 1H), 4.56-4.62 (m, 1H), 3.81-3.93 (m, 1H), 3.67-3.75 (m, 1H), 3.34-3.38 (m, 1H), 3.11-3.28 (m, 1H), 2.97 (br, 1H), 2.39-2.58 (m, 2H), 0.95-0.99 (m, 3H). LCMS: (ESI, m/z): 528 [M+H]$^+$.

Example 32

1,1,1,3,3,3-hexafluoropropan-2-yl 4-(bis(oxazol-4-yl)methyl)piperazine-1-carboxylate (2i)

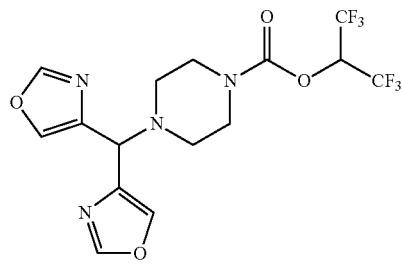 [SMILES: O=C(OC(C(F)(F)F)C(F)(F)F)N1CCN(C(c2cocn2)c2cocn2)CC1]

Step 1: Preparation of bis(oxazol-4-yl)methanol

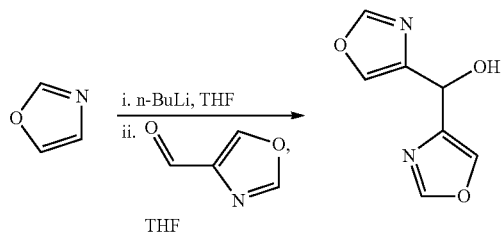 [SMILES: c1cocn1 ; O=Cc1cocn1 ; OC(c1cocn1)c1cocn1 ; "THF"]

A round bottom flask was charged with oxazole (476 μL, 7.2 mmol) and THF (100 mL). The solution was cooled to −78° C. A solution of n-butyllithium (2.3M in hexanes, 3.5 mL, 8.05 mmol) was added dropwise. After stirring at −78° C. for 40 min, a solution of oxazole-4-carbaldehyde (773 mg, 7.96 mmol, in 8 mL THF) was added dropwise. The reaction was allowed to warm to room temperature. After 30 min, the reaction was quenched with sat NH$_4$Cl and extracted with CH$_2$Cl$_2$ (3×). The organics were dried (Na$_2$SO$_4$), filtered, and concentrated under reduced pressure. The residue was chromatographed on a silica gel column (100% CH$_2$Cl$_2$ to 10% MeOH in CH$_2$Cl$_2$) and yielded bis(oxazol-4-yl)methanol (354 mg, 29%) as a light brown solid. $^1$H NMR 400 MHz (CDCl$_3$) δ 7.93 (s, 2H), 7.73 (s, 2H), 5.87 (s, 1H), 3.52 (s, 1H). LCMS (ESI, m/z): 167 [M+H]$^+$.

Step 2: Preparation of tert-butyl 4-(bis(oxazol-4-yl)methyl)piperazine-1-carboxylate

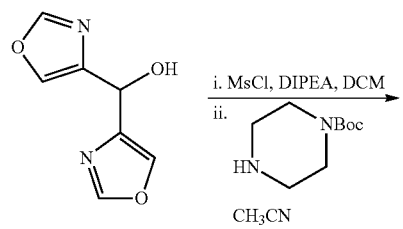

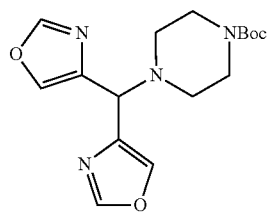

A round bottom flask was charged with bis(oxazol-4-yl)methanol (200 mg, 1.20 mmol), CH$_2$Cl$_2$ (3 mL), and DIPEA (412 μL, 2.41 mmol). The solution was cooled to 0° C. and MsCl (112 μL, 1.45 mmol) was added dropwise. After stirring 0° C. for 30 min, more MsCl (100 μL, 1.29 mmol) was added. After an additional 30 min at 0° C., the reaction was quenched with brine and extracted with CH$_2$Cl$_2$ (3×). The organics were dried (Na$_2$SO$_4$), filtered, and concentrated under reduced pressure yielding the crude alkyl chloride. The crude intermediate was dissolved in CH$_2$Cl$_2$ (3 mL) and treated with tert-butyl piperazine-1-carboxylate (224 mg, 1.20 mmol) and stirred at room temperature. After 48 h at room temperature, the reaction was quenched with brine and extracted with CH$_2$Cl$_2$ (3×). The organics were dried (Na$_2$SO$_4$), filtered, and concentrated under reduced pressure. The residue was chromatographed on a silica gel column (100% CH$_2$Cl$_2$ to 4% MeOH in CH$_2$Cl$_2$) yielding tert-butyl 4-(bis(oxazol-4-yl)methyl)piperazine-1-carboxylate (114 mg, 28%) as a light brown oil. $^1$H NMR 400 MHz (CDC$_3$) δ 7.87 (s, 2H), 7.69 (s, 2H), 4.78 (s, 1H), 3.45-3.37 (m, 4H), 2.53-2.40 (m, 4H), 1.39 (s, 9H). LCMS (ESI, m/z): 335 [M+H]$^+$.

Step 3: Preparation of 1,1,1,3,3,3-hexafluoropropan-2-yl 4-(bis(oxazol-4-yl)methyl)piperazine-1-carboxylate (2i)

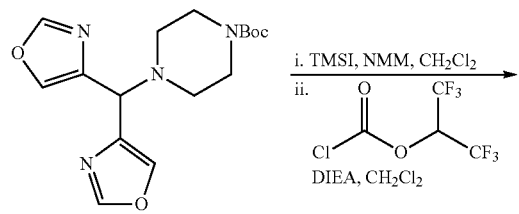

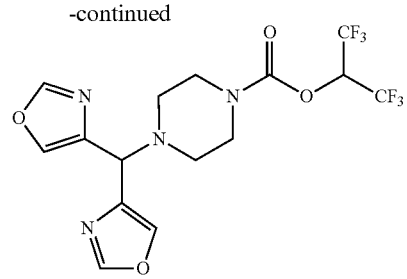

The title compound was prepared from tert-butyl 4-(bis(oxazol-4-yl)methyl)piperazine-1-carboxylate as described in Example 1, step 2 (26 mg, 65%). $^1$H NMR 400 MHz (CDCl$_3$) δ 7.92 (s, 2H), 7.74 (s, 2H), 5.72 (hept, J=6.3 Hz, 1H), 4.86 (s, 1H), 3.65-3.55 (m, 4H), 2.64-2.54 (m, 4H). LCMS (ESI, m/z): 429 [M+H]$^+$.

Example 33

1,1,1,3,3,3-hexafluoropropan-2-yl 4-(bis(4-chloro-2-methylphenyl)methyl)piperazine-1-carboxylate (2j)

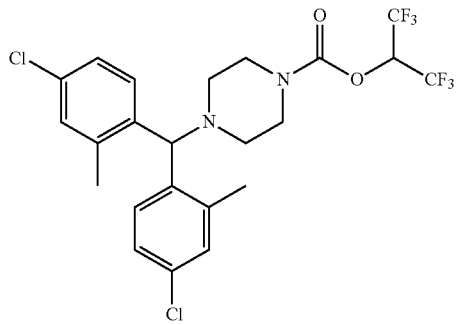 [SMILES: Cc1cc(Cl)ccc1C(c1ccc(Cl)cc1C)N1CCN(C(=O)OC(C(F)(F)F)C(F)(F)F)CC1]

Step 1: Preparation of bis(4-chloro-2-methylphenyl)methanol

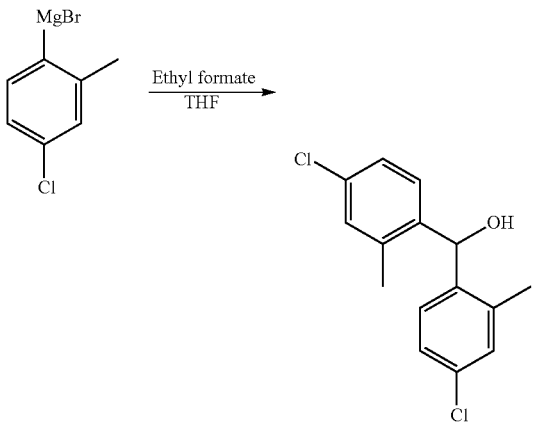

A round bottom flask was charged with a 4-chloro-2-methylphenyl magnesium bromide solution (10 mL of a 0.5M THF solution, 5 mmol) and THF (50 mL). The solution was cooled to −78° C. and an ethyl formate solution (200 μL, 2.50 mmol, in 10 mL THF) was added drop wise. The reaction was allowed to stir at −78° C. for 15 min and allowed to warm to room temperature slowly and stirred for 18 hrs. The reaction was diluted in EtOAc and washed with brine (3×). The organics were dried (Na$_2$SO$_4$), filtered, and concentrated under reduced pressure. The residue was chromatographed on a silica gel column (hexanes to 15% EtOAc in hexanes) and yielded bis(4-chloro-2-methylphenyl)methanol (643 mg, 46%) as a clear cyrstaline solid. $^1$H NMR 400 MHz (CDCl$_3$) δ 7.25-7.14 (m, 6H), 6.07 (s, 1H), 2.26 (s, 6H), 1.57 (s, 2H). LCMS (ESI, m/z): 263 [M+H]$^+$.

Step 2: Preparation of tert-butyl 4-(bis(4-chloro-2-methylphenyl)methyl)piperazine-1-carboxylate

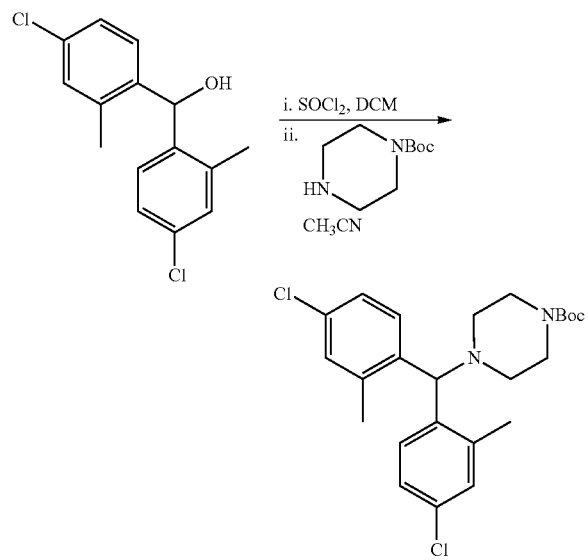

A round bottom flask was charged with bis(4-chloro-2-methylphenyl)methanol (200 mg, 0.711 mmol) and CH$_2$Cl$_2$ (7 mL). Thionyl chloride (100 μL, 1.37 mmol) was added and the reaction was stirred at room temperature for 24 h. The reaction was concentrated. Acetonitrile was added and the reaction was concentrated two times. Acetonitrile (6 mL), tert-butyl piperazine-1-carboxylate (200 mg, 1.07 mmol) and K$_2$CO$_3$ (200 mg, 1.42 mmol) were added and the reaction was heated to 80° C. for 4 h and 120° C. for 18 h. The reaction was poured into brine and extracted with EtOAc (2×). The residue was chromatographed on a silica gel column (100% hexanes to 20% EtOAc) and yielded the title (184 mg, 57%) as a clear oil. $^1$H NMR 400 MHz (CDCl$_3$) δ 7.49 (d, J=8.4 Hz, 2H), 7.16 (d, J=8.4 Hz, 2H), 7.11 (s, 2H), 4.65 (s, 1H), 3.44-3.37 (m, 4H), 2.38 (s, 4H), 2.29 (s, 6H), 1.46 (s, 9H). LCMS (ESI, m/z): 471 [M+H]$^+$.

Step 3: Preparation of 1-(bis(4-chloro-2-methylphenyl)methyl)piperazine

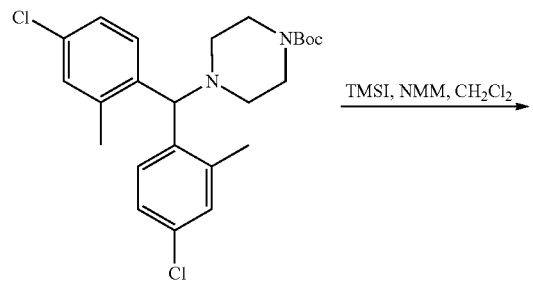

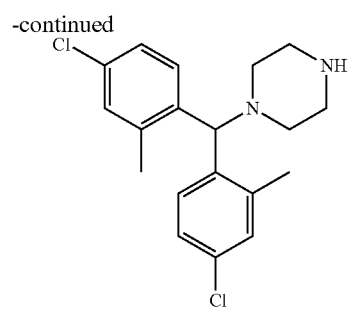

A round bottom flask was charged with tert-butyl 4-(bis(4-chloro-2-methylphenyl)methyl)piperazine-1-carboxylate (184 mg, 409 mmol), CH$_2$Cl$_2$ (5 mL), and NMM (90 μL, 0.819 mmol). Cooled to 0° C. and added TMSI (70 μL, 0.491 mmol) dropwise. After 15 min at 4° C. the reaction was quenched with sat Na$_2$CO$_3$ and extracted with CH$_2$Cl$_2$ (3×). The organics were dried (Na$_2$SO$_4$), filtered, and concentrated. The residue was chromatographed on a silica gel column (100% CH$_2$Cl$_2$ to 6% 2M NH$_3$ in MeOH) and 1-(bis(4-chloro-2-methylphenyl)methyl)piperazine (143 mg, 70%). $^1$H NMR 400 MHz (CDCl$_3$) δ 7.47 (dd, J=8.4, 1.1 Hz, 2H), 7.16-7.11 (m, 1H), 7.11-7.06 (m, 2H), 4.64 (s, 1H), 2.88-2.80 (m, 4H), 2.44-2.33 (m, 5H), 2.28 (s, 7H). LCMS (ESI, m/z): 349 [M+H]$^+$.

Step 4: Preparation of 1,1,1,3,3,3-hexafluoropropan-2-yl 4-(bis(4-chloro-2-methylphenyl)methyl)piperazine-1-carboxylate (2j)

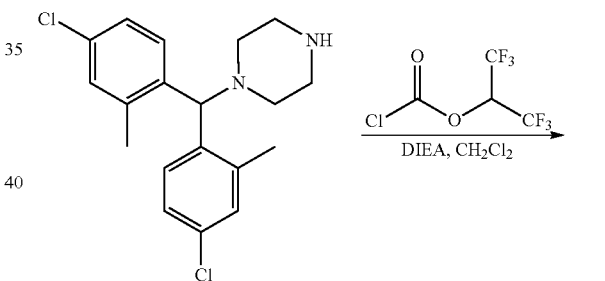

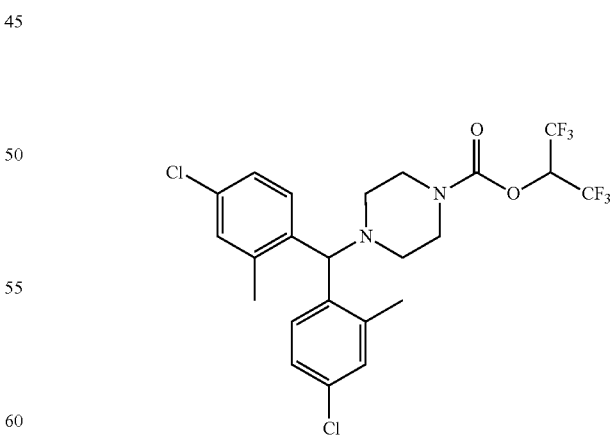

The title compound was prepared from 1-(bis(4-chloro-2-methylphenyl)methyl)piperazine as described in Example 1, step 2 (18 mg, 59%). $^1$H NMR 400 MHz (CDCl$_3$) δ 7.47 (dd, J=8.4, 2.1 Hz, 2H), 7.22-7.16 (m, 2H), 7.16-7.10 (m, 2H), 5.83-5.70 (m, 1H), 4.70 (s, 1H), 3.58-3.50 (m, 4H), 2.51-2.40

(m, 4H), 2.30 (s, 6H). LCMS (ESI, m/z): 263 [bis(4-chloro-2-methylphenyl)methane cation]⁺.

Example 34

1,1,1,3,3,3-hexafluoropropan-2-yl 4-(bis(1-methyl-1H-indazol-5-yl)methyl)piperazine-1-carboxylate (2k)

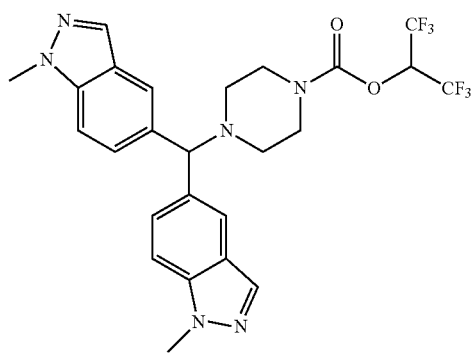 [SMILES: Cn1ncc2cc(C(c3ccc4c(cnn4C)c3)N3CCN(C(=O)OC(C(F)(F)F)C(F)(F)F)CC3)ccc21]

Step 1: Preparation of bis(1-methyl-1H-indazol-5-yl)methanol

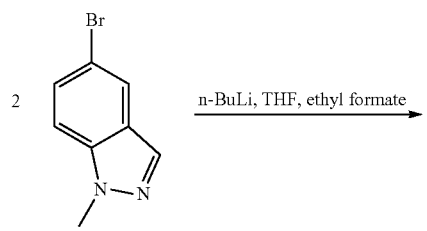

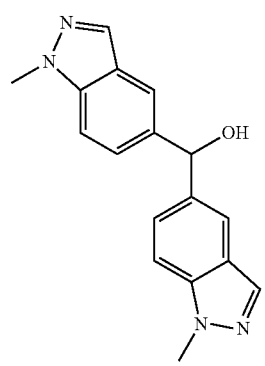

A round bottom flask was charged with 5-bromo-1-methyl-1H-indazole (300 mg, 1.42 mmol) and THF (45 mL). The solution was cooled to −78° C. and a n-butyllithium solution (2.3M in THF, 680 µL, 1.56 mmol) was added dropwise. After 30 min, a solution of ethyl formate (57 µL, 0.697 mmol, in 10 mL THF) was added dropwise, and the reaction was stirred at −78° C. for 10 min and room temperature for 3 h. The reaction was quenched with sat NH₄CL and extracted with EtOAc (3×). The organics were dried (Na₂CO₃), filtered, and concentrated under reduced pressure. The residue was chromatographed on a silica gel column (100% CH₂Cl₂ to 10% MeOH in CH₂Cl₂) and yielded bis(1-methyl-1H-indazol-5-yl)methanol (134 mg, 32%) as a brown oil. ¹H NMR 400 MHz (CDCl₃) δ 7.90 (s, 2H), 7.77 (s, 2H), 7.39 (dd, J=8.7, 1.2 Hz, 2H), 7.31 (d, J=8.7 Hz, 2H), 6.07 (s, 1H), 4.02 (s, 7H). LCMS (ESI, m/z): 293 [M+H]⁺.

Step 2: Preparation of tert-butyl 4-(bis(1-methyl-1H-indazol-5-yl)methyl)piperazine-1-carboxylate

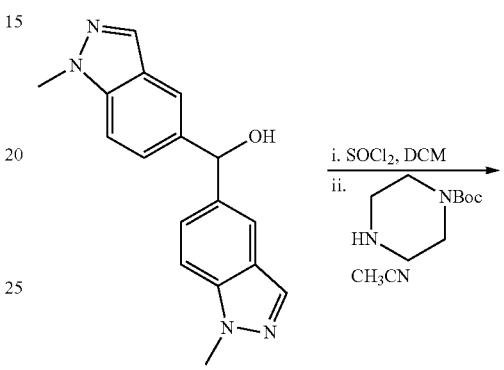

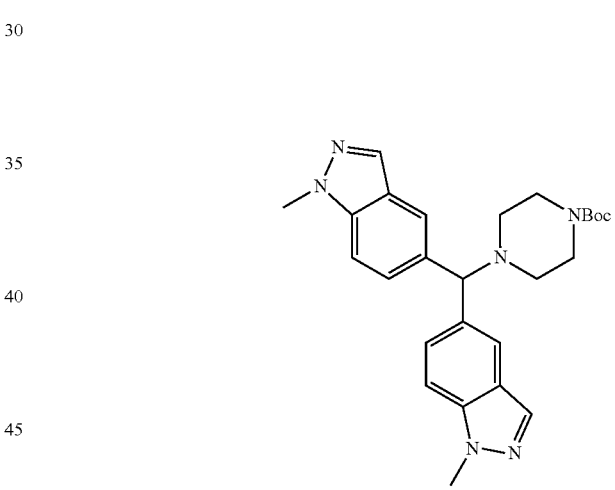

A round bottom flask was charged with bis(1-methyl-1H-indazol-5-yl)methanol (50 mg, 0.17 mmol) and CH₂Cl₂ (5 mL). Thionyl chloride (25 µL, 342 mmol) was added, resulting in a cloudy solution. After 15 min the solution become a clear pink solution and was stirred at room temperature for 48 h. The solution was concentrated under reduced pressure. Acetonitrile was added and the solution was concentrated two times. Acetonitrile (7 mL) and tert-butyl piperazine-1-carboxylate (60 mg, 0.32 mmol) was added and the solution was stirred at room temperature overnight. The reaction was concentrated under reduced pressure and purified by silica chromatography (100% CH₂Cl₂ to 3% MeOH in CH₂Cl₂) yielding tert-butyl 4-(bis(1-methyl-1H-indazol-5-yl)methyl)piperazine-1-carboxylate (53 mg, 56%) as a light brown oil. ¹H NMR 400 MHz (CDCl₃) δ 7.97-7.89 (m, 2H), 7.79 (s, 2H), 7.54 (dd, J=8.8, 1.5 Hz, 2H), 7.32 (d, J=8.7 Hz, 2H), 4.49 (s, 1H), 4.03 (s, 6H), 3.47 (s, 4H), 2.41 (s, 4H), 1.45 (s, 9H). LCMS (ESI, m/z): 483 [M+H]⁺.

Step 3: Preparation of 1,1,1,3,3,3-hexafluoropropan-2-yl 4-(bis(1-methyl-1H-indazol-5-yl)methyl)piperazine-1-carboxylate (2k)

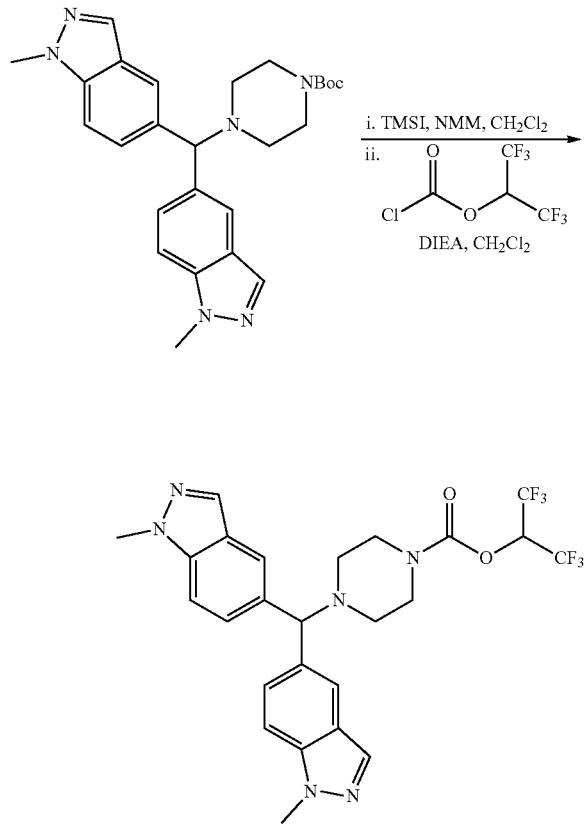 [SMILES: Cn1ncc2cc(C(c3ccc4c(cnn4C)c3)N3CCN(C(=O)OC(C)(C)C)CC3)ccc21 ; O=C(Cl)OC(C(F)(F)F)C(F)(F)F ; Cn1ncc2cc(C(c3ccc4c(cnn4C)c3)N3CCN(C(=O)OC(C(F)(F)F)C(F)(F)F)CC3)ccc21]

The title compound was prepared from tert-butyl 4-(bis(1-methyl-1H-indazol-5-yl)methyl)piperazine-1-carboxylate as described in Example 1, step 2 (12 mg, 35%). $^1$H NMR 400 MHz (CDCl$_3$) δ 7.92 (d, J=7.5 Hz, 2H), 7.77 (d, J=6.7 Hz, 2H), 7.55-7.45 (m, 2H), 7.36-7.28 (m, 2H), 5.80-5.67 (m, 1H), 4.51 (s, 1H), 4.02 (s, 6H), 3.58 (s, 4H), 2.47 (d, J=5.5 Hz, 4H). LCMS (ESI, m/z): 555 [M+H]$^+$.

Example 35

1,1,1,3,3,3-hexafluoropropan-2-yl 4-(di(pyridin-3-yl)methyl)piperazine-1-carboxylate (2l)

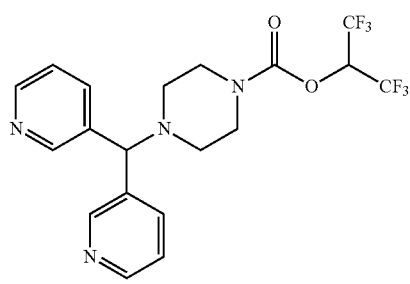 [SMILES: O=C(OC(C(F)(F)F)C(F)(F)F)N1CCN(C(c2cccnc2)c2cccnc2)CC1]

Step 1: Preparation of di(pyridin-3-yl)methanol

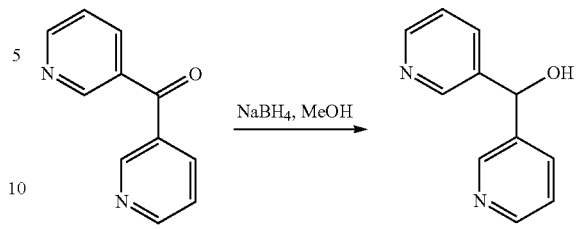

A round bottom flask was charged with di(pyridin-3-yl)methanone (500 mg, 2.72 mmol), MeOH (30 mL), and CH$_2$Cl$_2$ (15 mL) and cooled to 0° C. NaBH$_4$ (51 mg, 1.35 mmol) was added in one portion. The solution was stirred for 1 h at 0° C. and quenched with 1N NaOH and the reaction was extracted with CH$_2$Cl$_2$ (3×). The organic layers were combined, dried over Na$_2$SO$_4$ and concentrated under reduced pressure. Crude di(pyridin-3-yl)methanol (505 mg, 100%) was used in the next step without further purification. $^1$H NMR 400 MHz (CDCl$_3$) δ 8.32 (s, 2H), 8.24 (d, J=4.8 Hz, 2H), 7.47 (d, J=7.9 Hz, 2H), 7.09-7.01 (m, 2H), 5.67 (s, 1H).

Step 2: Preparation of tert-butyl 4-(di(pyridin-3-yl)methyl)piperazine-1-carboxylate

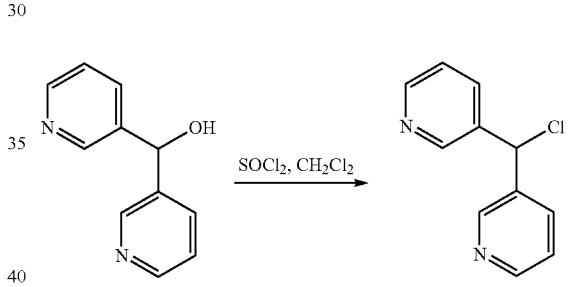

A round bottom flask was charged with di(pyridin-3-yl)methanol (600 mg, 3.22 mmol) and CH$_2$Cl$_2$ (50 mL). Thionyl chloride (353 μl, 4.83 mmol) was added and the reaction was stirred for 18 h at room temperature. The solution was concentrated under reduced pressure. The residue was chromatographed on a silica gel column (100% CH$_2$Cl$_2$ to 5% 2M NH$_3$ in MeOH) and yielded 3,3'-(chloromethylene)dipyridine (415 mg, 64%). $^1$H NMR 400 MHz (CDCl$_3$) δ 8.66 (d, J=2.4 Hz, 2H), 8.59 (dd, J=4.7, 1.6 Hz, 2H), 7.76 (m, 2H), 7.34 (m, 2H), 6.17 (s, 1H).

Step 3: Preparation of tert-butyl 4-(di(pyridin-3-yl)methyl)piperazine-1-carboxylate

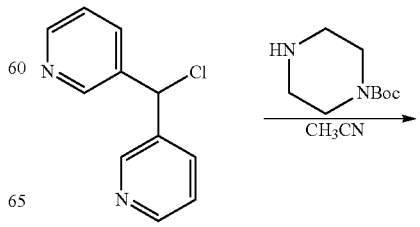

-continued

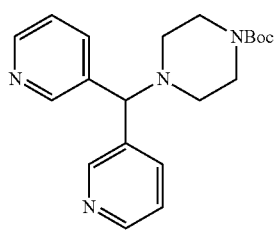

A round bottom flask was charged with 3,3'-(chloromethylene)-dipyridine (415 mg, 2.03 mmol), tert-butyl piperazine-1-carboxylate (1.20 g, 6.45 mmol), and acetonitrile (50 mL). The reaction was heated to 80° C. for 2 hrs, concentrated under reduced pressure, and purified by silica chromatography (100% $CH_2Cl_2$ to 5% 2M $NH_3$ in MeOH) yielding tert-butyl 4-(di(pyridin-3-yl)methyl)piperazine-1-carboxylate (220 mg, 31%). $^1$H NMR 400 MHz ($CDCl_3$) δ 8.64 (d, J=2.0 Hz, 3H), 8.48 (dd, J=4.8, 1.7 Hz, 3H), 7.70 (dt, J=7.9, 1.9 Hz, 3H), 7.24 (ddd, J=7.9, 4.8, 0.7 Hz, 3H), 5.28 (s, 1H), 4.36 (s, 1H), 3.47-3.39 (m, 6H), 2.34 (s, 6H), 1.42 (s, 9H). LCMS (ESI, m/z): 355 [M+H]$^+$.

Step 4: Preparation of 1-(di(pyridin-3-yl)methyl)piperazine

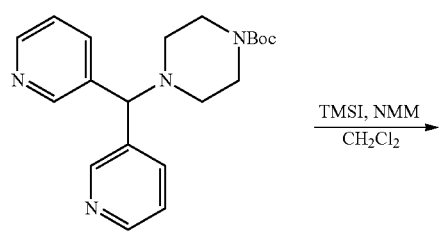

A round bottom flask was charged with tert-butyl 4-(di (pyridin-3-yl)methyl)piperazine-1-carboxylate (220 mg, 0.621 mmol), $CH_2Cl_2$ (20 mL), and NMM (136 µL, 1.23 mmol). The reaction was cooled to 0° C. and TMSI (106 µL, 0.745 mmol) was added dropwise. After 10 min at 0° C., additional TMSI (100 µL, 0.700 mmol) was added. After stirring 10 min at 0° C. the reaction was allowed to warm to room temperature. After 15 min at room temperature the reaction was diluted in $CH_2Cl_2$ and washed (1×) sat $Na_2CO_3$. The organics were dried ($Na_2SO_4$), filtered, and concentrated and yielded 103 mg crude product (0.406 mmol, 65%) as a yellow oil, which was used without further purification in the next step. $^1$H NMR 400 MHz ($CDCl_3$) δ 8.64 (d, J=2.4 Hz, 2H), 8.47 (dd, J=4.8, 1.6 Hz, 2H), 7.70 (dt, J=8.0, 2.0 Hz, 2H), 7.23 (dd, J=7.9, 4.8 Hz, 2H), 4.36 (s, 1H), 2.91 (t, J=4.9 Hz, 4H), 2.38 (t, J=5.0 Hz, 5H). LCMS (ESI, m/z): 255 [M+H]$^+$.

Step 5: Preparation of 1,1,1,3,3,3-hexafluoropropan-2-yl 4-(di(pyridin-3-yl)methyl)piperazine-1-carboxylate (2l)

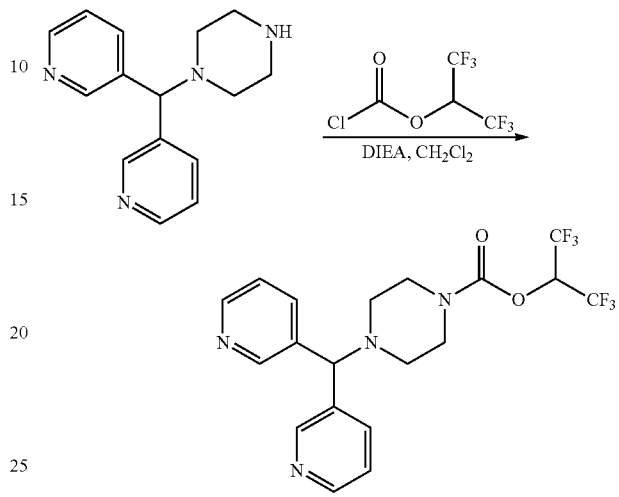

1,1,1,3,3,3-hexafluoropropan-2-yl 4-(di(pyridin-3-yl)methyl)piperazine-1-carboxylate was prepared from 1-(di(pyridin-3-yl)methyl)piperazine as described in Example 1, Step 2 (23 mg, 33%). $^1$H NMR 400 MHz ($CDCl_3$) δ 8.66 (s, 3H), 8.51 (d, J=4.7 Hz, 3H), 7.75-7.67 (m, 3H), 7.27 (t, J=6.3 Hz, 3H), 5.72 (hept, J=6.2 Hz, 1H), 4.41 (s, 1H), 3.58 (d, J=4.4 Hz, 7H), 2.43 (dt, J=10.4, 4.4 Hz, 8H). MS m/z calc'd for [M+H]$^+$ $C_{19}H_{18}F_6N_4O_2$: 449.1. found 449.0.

Example 36

1,1,1-trifluoro-3-methoxy-3-oxopropan-2-yl 4-(bis(4-chlorophenyl)methyl)piperazine-1-carboxylate (6h)

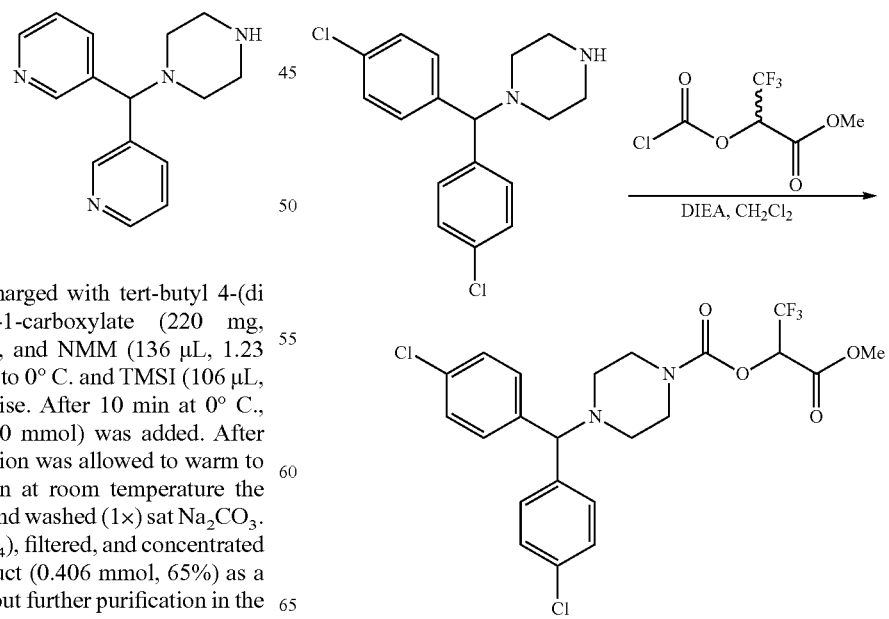

To a stirring solution of triphosgene (65 mg, 0.22 mmol) in CH$_2$Cl$_2$ (5.0 mL) was added methyl-3,3,3-trifluoro-DL-lactate (116 mg, 0.73 mmol) followed by N,N-diisopropylethylamine (0.38 mL, 2.19 mmol). After 2 h, 1-(bis(4-chlorophenyl)methyl)piperazine (160 mg, 0.50 mmol) was added as a solution in CH$_2$Cl$_2$ (2 mL) and stirred for another 2 h. The mixture was concentrated under reduced pressure and purified directly by SiO$_2$ flash chromatography (25% EtOAc/hexanes) to provide the titled compound (156 mg, 62%): $^1$H NMR 500 MHz (CDCl$_3$) δ 7.31 (d, J=8.47 Hz, 4H), 7.26 (d, J=8.41 Hz, 4H), 5.43 (q, J=7.03 Hz, 1H), 4.23 (s, 1H), 3.85 (s, 3H), 3.66-3.46 (m, 4H), 2.44-2.32 (m, 4H); HRMS m/z calc'd for [M+H]$^+$ C$_{22}$H$_{21}$Cl$_2$F$_3$N$_2$O$_4$: 505.0903. found 505.0905.

Example 37

2-((4-(bis(4-chlorophenyl)methyl)piperazine-1-carbonyl)oxy)-3,3,3-trifluoropropanoic acid (6i)

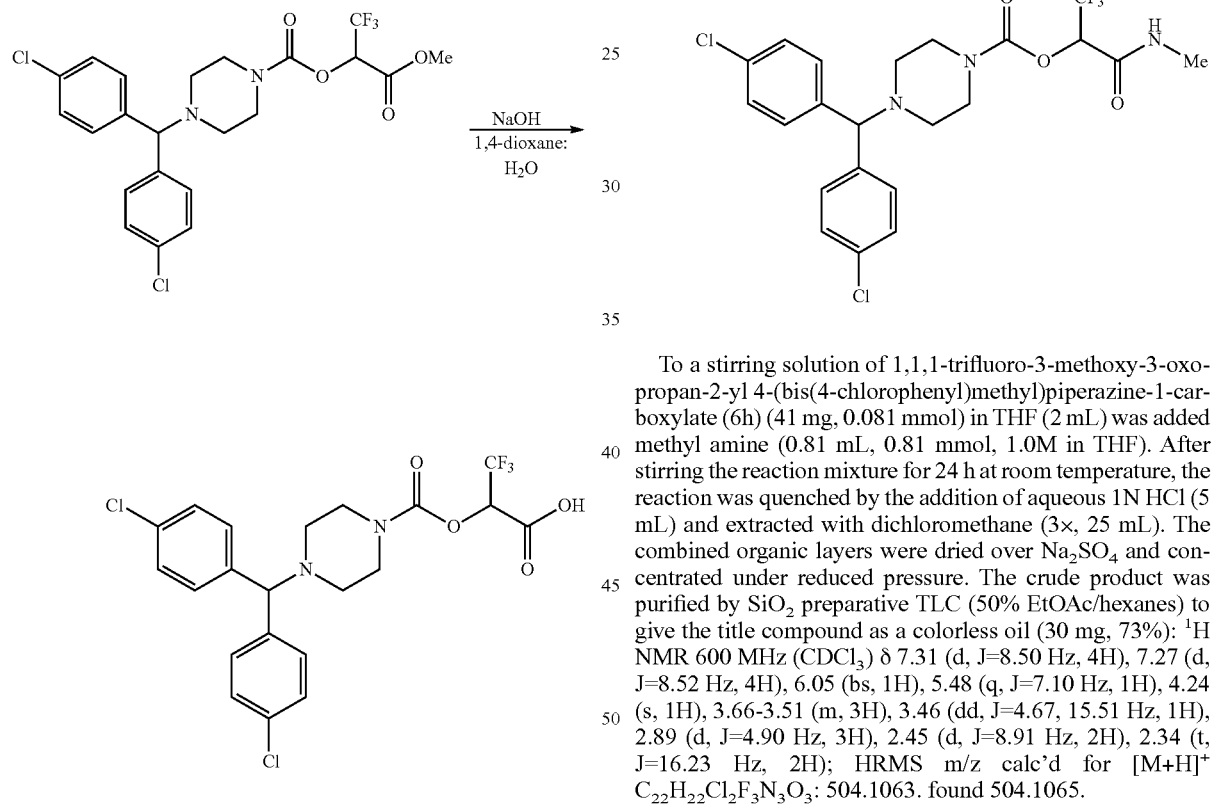

To a stirring solution of 1,1,1-trifluoro-3-methoxy-3-oxopropan-2-yl 4-(bis(4-chlorophenyl)methyl)piperazine-1-carboxylate (6h) (18 mg, 0.036 mmol) in a 1:1 mixture of 1,4-dioxane:water (1 mL) was added NaOH (360 μL, 0.36 mmol, 1.0 N in water). After stirring the reaction mixture overnight at room temperature, the reaction was quenched by the addition of aqueous 1N HCl (5 mL) and extracted with dichloromethane (3×, 25 mL). The combined organic layers were dried over Na$_2$SO$_4$ and concentrated under reduced pressure. The crude product was purified by SiO$_2$ preparative TLC (50% EtOAc/hexanes, 1% HCO$_2$H) to give the title compound as a colorless oil (9.1 mg, 52%): $^1$H NMR (600 MHz (CDCl$_3$) δ 7.42 (d, J=7.32 Hz, 4H), 7.30 (d, J=8.16 Hz, 4H), 5.35 (s, 1H), 4.53 (bs, 1H), 3.78-3.53 (m, 4H), 2.81-2.54 (m, 4H); HRMS m/z calc'd for [M+H]$^+$ C$_{21}$H$_{19}$Cl$_2$F$_3$N$_2$O$_4$: 491.0747. found 491.0735.

Example 38

1,1,1-trifluoro-3-(methylamino)-3-oxopropan-2-yl 4-(bis(4-chlorophenyl)methyl)piperazine-1-carboxylate (6j)

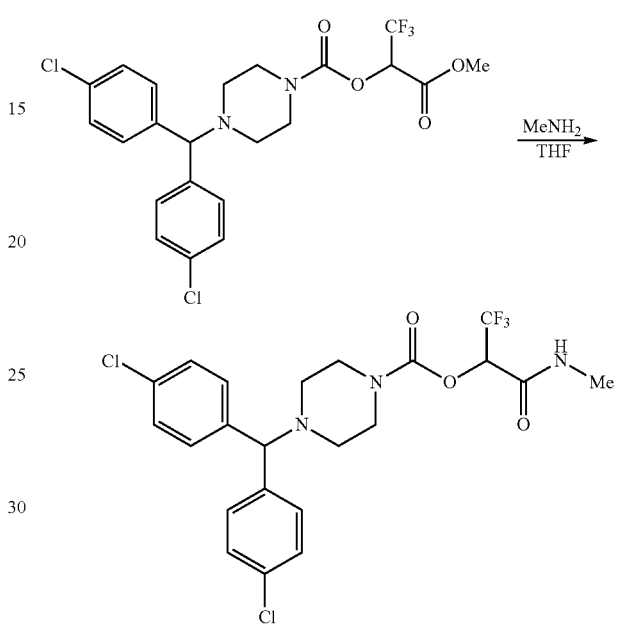

To a stirring solution of 1,1,1-trifluoro-3-methoxy-3-oxopropan-2-yl 4-(bis(4-chlorophenyl)methyl)piperazine-1-carboxylate (6h) (41 mg, 0.081 mmol) in THF (2 mL) was added methyl amine (0.81 mL, 0.81 mmol, 1.0M in THF). After stirring the reaction mixture for 24 h at room temperature, the reaction was quenched by the addition of aqueous 1N HCl (5 mL) and extracted with dichloromethane (3×, 25 mL). The combined organic layers were dried over Na$_2$SO$_4$ and concentrated under reduced pressure. The crude product was purified by SiO$_2$ preparative TLC (50% EtOAc/hexanes) to give the title compound as a colorless oil (30 mg, 73%): $^1$H NMR 600 MHz (CDCl$_3$) δ 7.31 (d, J=8.50 Hz, 4H), 7.27 (d, J=8.52 Hz, 4H), 6.05 (bs, 1H), 5.48 (q, J=7.10 Hz, 1H), 4.24 (s, 1H), 3.66-3.51 (m, 3H), 3.46 (dd, J=4.67, 15.51 Hz, 1H), 2.89 (d, J=4.90 Hz, 3H), 2.45 (d, J=8.91 Hz, 2H), 2.34 (t, J=16.23 Hz, 2H); HRMS m/z calc'd for [M+H]$^+$ C$_{22}$H$_{22}$Cl$_2$F$_3$N$_3$O$_3$: 504.1063. found 504.1065.

Example 39

Methyl 3,3,3-trifluoro-2-((methyl(phenethyl)carbamoyl)oxy)propanoate (7k)

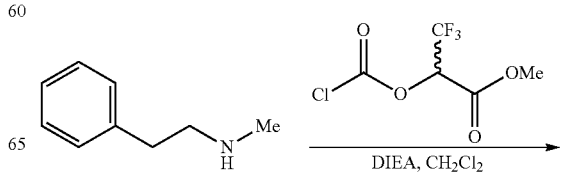

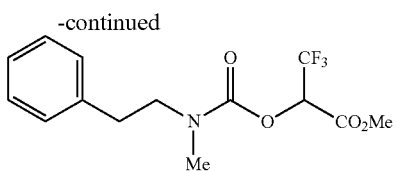

To a stirring solution of triphosgene (20 mg, 0.07 mmol) in CH$_2$Cl$_2$ (5.0 mL) was added methyl-3,3,3-trifluoro-DL-lactate (36 mg, 0.23 mmol) followed by N,N-diisopropylethylamine (120 μL, 0.69 mmol). After 2 h, N-methyl phenethylamine (31 mg, 0.23 mmol) was added as a solution in CH$_2$Cl$_2$ (2 mL) and stirred for another 2 h. The mixture was concentrated under reduced pressure and purified directly by SiO$_2$ flash chromatography (25% EtOAc/hexanes) to provide the titled compound (47 mg, 64%): $^1$H NMR 500 MHz (CDCl$_3$) δ 7.34-7.28 (m, 2H), 7.25-7.18 (m, 3H), 5.51-5.42 (m, 1H), 3.87 (s, 1.8H), 3.86 (s, 1.2H), 3.60-3.46 (m, 2H), 2.96-2.90 (m, 2.5H), 2.90-2.83 (m, 2.5H); HRMS m/z calc'd for [M+H]$^+$ C$_{14}$H$_{16}$F$_3$NO$_4$: 320.1104. found 320.1109.

Example 40

1,1,1,3,3,3-hexafluoropropan-2-yl 4-(2-fluoro-4-morpholinobenzyl)piperazine-1-carboxylate (9a)

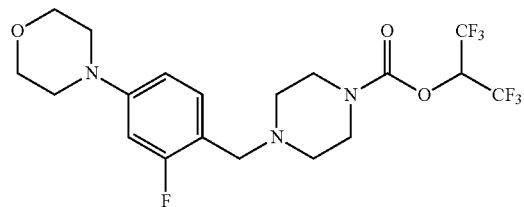

Step 1: Preparation of tert-butyl 4-(2-fluoro-4-morpholinobenzyl)piperazine-1-carboxylate

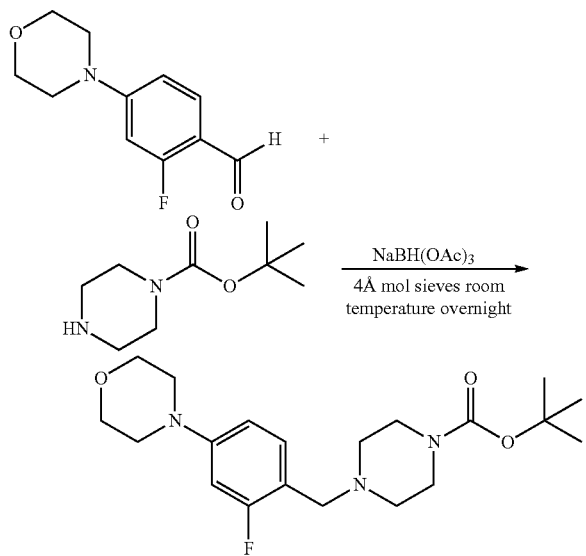

A 50 mL round-bottom flask, equipped with a magnetic stir bar, was charged with tert-butyl-1-piperazine carboxylate (445 mg, 2.39 mmol) under nitrogen. The solid was dissolved in 10 mL dichloromethane (anhydrous) and stirred at room temperature. 2-Fluoro-4-morpholinobenzaldehyde (500 mg, 2.39 mmol) was added followed by molecular sieves (440 mg, 8-12 mesh beads). The reaction was allowed to continue to stir at room temperature for 1 h. At that point, sodium triacetoxyborohydride (557 mg, 2.63 mmol, 1.10 equiv) was added. The reaction was monitored for disappearance of aldehyde by thin layer chromatography. After 15 h, the reaction was quenched with saturated sodium bicarbonate (15 mL). After the addition of dichloromethane (15 mL), the mixture was partitioned into two phases. The aqueous phase was extracted twice with dichloromethane (15 mL). The combined organic layers were dried over anhydrous sodium sulfate, filtered and concentrated. The crude mixture was applied to a chromatography column containing 24 g silica and dichloromethane. A gradient solvent was used from 100% dichloromethane to 10% methanol in dichloromethane to provide 833 mg (92%) of tert-butyl 4-(2-fluoro-4-morpholinobenzyl)piperazine-1-carboxylate as a pale yellow solid. $^1$H NMR 400 MHz (CDCl$_3$) δ 7.22 (t, J=8.4 Hz, 1H), 6.66 (d, J=8.4 Hz, 1H), 6.57 (d, J=13.0 Hz, 1H), 3.90-3.85 (m, 4H), 3.53 (s, 2H), 3.43 (bs, 4H), 3.20-3.15 (m, 4H), 2.41 (bs, 4H), 1.46 (s, 9H).

Step 2: Preparation of 4-(3-fluoro-4-(piperazin-1-ylmethyl)phenyl)morpholine

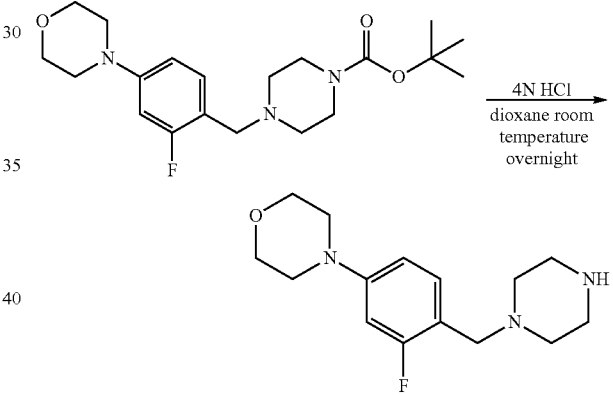

A 100 mL round-bottom flask, equipped with a magnetic stir bar, was charged with tert-butyl 4-(2-fluoro-4-morpholinobenzyl)piperazine-1-carboxylate (819 mg, 2.16 mmol) and dichloromethane (14 mL). The resulting solution was cooled to 0° C. Hydrochloric acid (3.2 mL, 4 N in dioxane) was added via syringe. The ice bath was removed and the resulting cloudy suspension was allowed to stir at room temperature overnight. After 20 h, the white suspension was transferred to a 250 mL Erlenmeyer flask and stirred with saturated aqueous sodium carbonate (30 mL), water (20 mL) and dichloromethane (30 mL) for 30 min. The layers were separated and the aqueous layer was extracted twice with dicholomethane (30 mL). The organic layers were washed with saturated aqueous sodium bicarbonate (30 mL), combined, dried over sodium sulfate and concentrated. The resulting yellow oil was chromatographed on a 24 g silica column with a gradient (100% dichloromethane to 90% dichloromethane/10% methanol containing 2M ammonia) to provide 4-(3-fluoro-4-(piperazin-1-ylmethyl)phenyl)morpholine as a yellow oil (580 mg, 96%). $^1$H NMR 400 MHz (CDCl$_3$) δ 7.22 (t, J=8.5 Hz, 1H), 6.65 (d, J=8.5 Hz, 1H), 6.56 (d, J=13 Hz, 1H)

3.90-3.80 (m, 4H), 3.49 (d, J=14.5 Hz, 2H), 3.20-3.10 (m, 4H), 2.92-2.88 (m, 4H), 2.44 (bs, 4H), 1.64 (s, 1H).

Step 3: Preparation of 1,1,1,3,3,3-hexafluoropropan-2-yl 4-(2-fluoro-4-morpholinobenzyl)piperazine-1-carboxylate (9a)

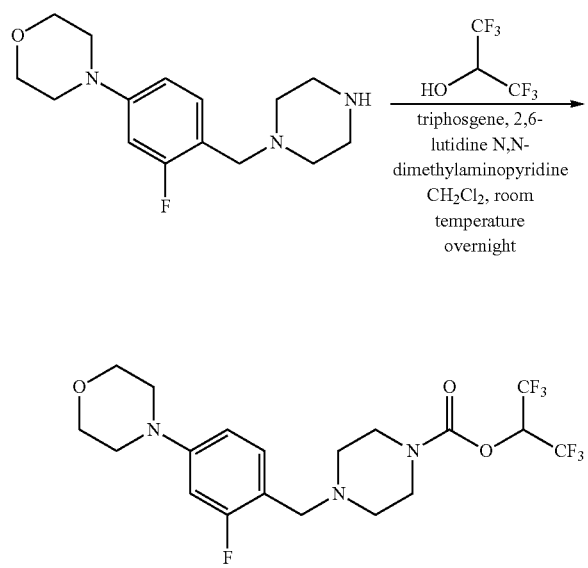

A 10 mL screw cap vial equipped with a magnetic stir bar was charged with triphosgene (22 mg, 0.233 mmol, 0.35 equiv) and dichloromethane (1 mL) under nitrogen and cooled to 0° C. 1,1,1,3,3,3-Hexafluoroisopropanol (29 uL, 0.23 mmol) was added via syringe over 1 min followed by addition of 2,6-lutidine, (52 uL, 0.44 mmol, 2.1 equiv) over 1 min. The latter addition is exothermic and the internal temperature was maintained below 5° C. during the addition. N,N-dimethylaminopyridine (2 mg, 0.1 equiv) was then added to the reaction mixture. The solution remained colorless and the ice bath was removed. The resulting clear solution was allowed to stir at room temperature for 1 h. A separate 10 mL vial, equipped with a magnetic stir bar, was charged with 4-(3-fluoro-4-(piperazin-1-ylmethyl)phenyl) morpholine (59.1 mg, 0.212 mmol) and dichloromethane (1 mL). The chloroformate solution was re-cooled to 0° C. and the amine solution was added to the chloroformate solution over 1 min via syringe. The amine-containing flask was rinsed with dichloromethane (0.25 mL) and the rinsing solution was added to the reaction flask. The ice bath was removed and the clear, colorless reaction was stirred at room temperature overnight. Saturated aqueous sodium bicarbonate (1 mL) was added and the layers were separated. The aqueous layer was washed with dichloromethane (1 mL). The organic layers were combined, concentrated and applied to a 40 g silica gel column to afford 1,1,1,3,3,3-hexafluoropropan-2-yl 4-(2-fluoro-4-morpholinobenzyl)piperazine-1-carboxylate, 54 mg (58%). $^1$H NMR 400 MHz (CDCl$_3$) δ 7.18 (t, J=8.5 Hz, 1H), 6.65 (dd, J=8.5, 2.2 Hz, 1H), 6.56 (dd, J=13.0, 2.2 Hz, 1H), 5.73 (hep, J=6.2 Hz, 1H), 3.88-3.81 (m, 4H), 3.53 (bs, 6H), 3.18-3.07 (m, 4H), 2.52-2.43 (m, 4H). LCMS (ESI, m/z): 194.1 (4-morpholino-2-fluorobenzyl cation).

Example 41

1,1,1,3,3,3-hexafluoropropan-2-yl 4-(4-bromo-2-phenoxybenzyl)piperazine-1-carboxylate (9b)

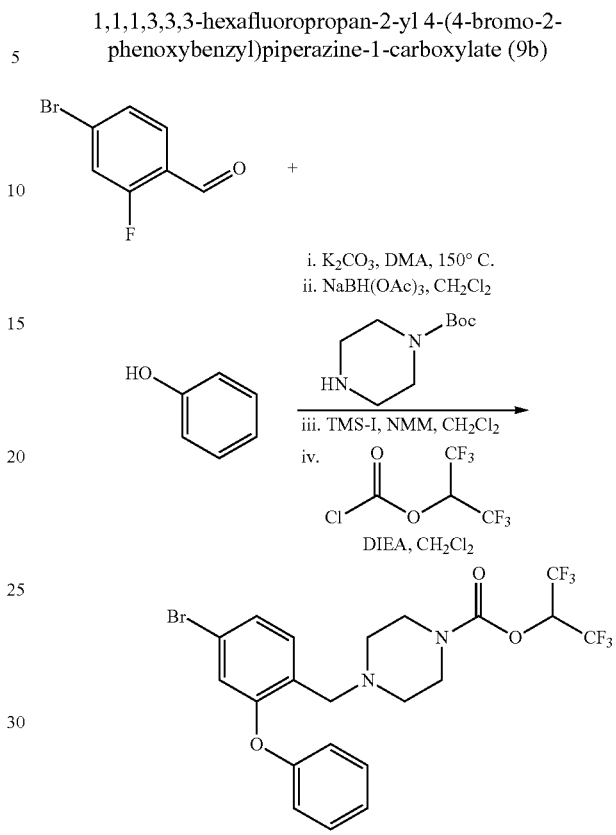

To a sealed tube was added 4-bromo-2-fluorobenzaldehyde (1.0 g, 5.0 mmol, 1.0 equiv), phenol (470 mg, 5.0 mmol, 1.0 equiv), K$_2$CO$_3$ (691 mg, 5.0 mmol, 1.0 equiv) and DMA (10 mL). The reaction was heated to 150° C. and stirred for 4 h. Upon cooling to room temperature, the reaction mixture was poured into a separatory funnel containing brine (250 mL) and the product was extracted with Et$_2$O (250 mL, 3×). The combined organic layers were dried over anhydrous MgSO$_4$ and concentrated under reduced pressure. The remaining residue was used in subsequent steps without further purification. To a stirring solution of the crude aldehyde (610 mg, 2.2 mmol, 1.0 equiv) and N-Boc-piperazine (451 mg, 2.42 mmol, 1.1 equiv) in CH$_2$Cl$_2$ (20 mL) was added NaBH(OAc)$_3$ (699 mg, 3.30 mmol, 1.5 equiv). The reaction was stirred for 2 h at room temperature and subsequently quenched upon addition of aqueous NaOH (20 mL, 1.0 M). The biphasic mixture was vigorously stirred for 30 min and poured into a separatory funnel containing brine (100 mL). The product was extracted with CH$_2$Cl$_2$ (100 mL, 3×) and the combined organic layers were dried over anhydrous MgSO$_4$ and concentrated under reduce pressure to provide a crude colorless oil which was used in subsequent steps without further purification. To a stirring solution of the crude piperazine (290 mg, 0.65 mmol, 1.0 equiv) and NMM (0.42 mL, 3.9 mmol, 6.0 equiv) in CH$_2$Cl$_2$ (10 mL) at 0° C. was added TMS-I (0.28 mL, 1.95 mmol, 3.0 equiv) dropwise. After 1 h, the reaction mixture was quenched with MeOH (1.0 mL) concentrated under a stream of N$_2$. The residue was redissolved in CH$_2$Cl$_2$ (10 mL) and concentrated under reduced pressure providing a crude oil which was used without further purification. The title compound was synthesized according to Example 1, Step 2 from the deprotected amine. Purification of the crude product by flash chromatography (15% EtOAc/hexanes) provided the title compound: ¹H NMR 400 MHz (CDCl₃) δ 7.37-7.34 (m, 3H), 7.24 (s, 1H), 7.14-7.10 (m, 1H), 7.03-7.02 (m, 1H), 6.94-6.91 (m, 2H), 5.73 (septet, J=6.3 Hz, 1H), 3.54 (s, 2H), 3.51-3.48 (m, 4H), 2.50-2.45 (m, 4H), HRMS m/z calc'd for [M+H]⁺ $C_{21}H_{19}BrF_6N_2O_3$: 541.0561. found 541.0558.

Example 42

1,1,1,3,3,3-hexafluoropropan-2-yl 4-[[2-(morpholin-4-yl)-4-(trifluoromethyl)phenyl]methyl]piperazine-1-carboxylate (9c)

Step 1:
2-(morpholin-4-yl)-4-(trifluoromethyl)benzaldehyde

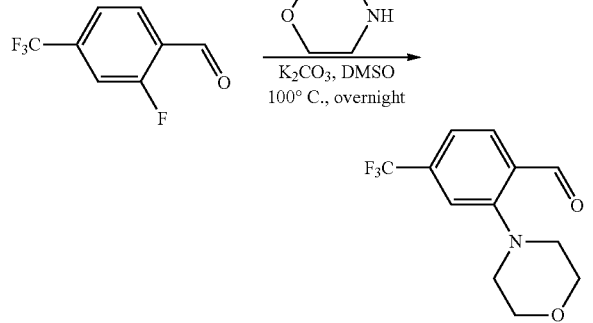

A 100 mL round-bottom flask was charged with 2-fluoro-4-(trifluoromethyl)benzaldehyde (1.90 g, 9.89 mmol, 1.00 equiv), morpholine (1.30 g, 14.9 mmol, 1.51 equiv), potassium carbonate (3.45 g, 25.0 mmol, 2.52 equiv), and dimethyl sulfoxide (20 mL). The resulting solution was stirred overnight at 100° C. in an oil bath and diluted with H₂O (30 mL). The resulting solution was extracted with dichloromethane (2×20 mL) and the organic layers were combined, washed with H₂O (3×20 mL), dried over anhydrous sodium sulfate, filtered and concentrated under reduced pressure. The residue was chromatographed on a silica gel column with ethyl acetate/petroleum ether (1/5) to yield 1.06 g (41% yield) of 2-(morpholin-4-yl)-4-(trifluoromethyl)benzaldehyde as yellow oil. LCMS (ESI, m/z): 260 [M+H]⁺.

Step 2: tert-butyl 4-[[2-(morpholin-4-yl)-4-(trifluoromethyl)phenyl]methyl]piperazine-1-carboxylate

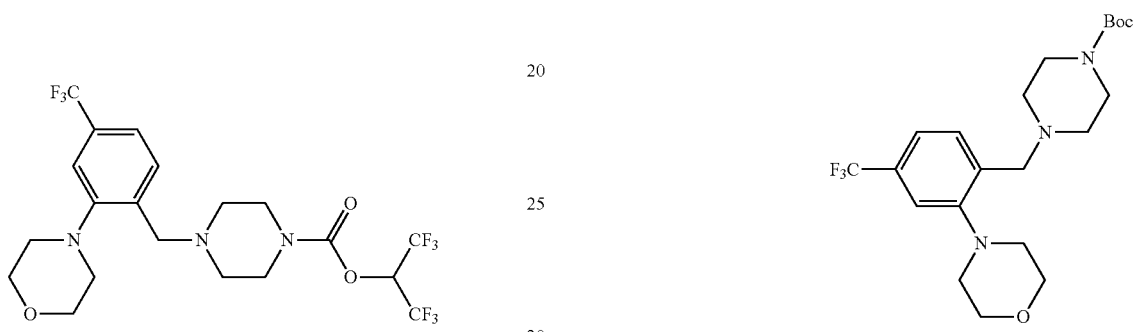

A 100 mL round-bottom flask was charged with 2-(morpholin-4-yl)-4-(trifluoromethyl)benzaldehyde (1.00 g, 3.86 mmol, 1.00 equiv), tert-butyl piperazine-1-carboxylate (0.650 g, 3.51 mmol, 0.91 equiv), dichloromethane (15 mL). The mixture was stirred at room temperature for 0.5 hour. Sodium triacetoxyborohydride (2.23 g, 10.5 mmol, 2.73 equiv) was added. The resulting solution was stirred overnight at room temperature and diluted with dichloromethane (15 mL). The organic layers were washed with H₂O (2×10 mL), dried over anhydrous sodium sulfate, filtered and concentrated under reduced pressure. The residue was chromatographed on a silica gel column with ethyl acetate/petroleum ether (1/4) to yield 1.30 g (78% yield) of tert-butyl 4-[[2-(morpholin-4-yl)-4-(trifluoromethyl)phenyl]methyl]piperazine-1-carboxylate as light yellow oil. LCMS (ESI, m/z): 430 [M+H]⁺

Step 3: 4-[2-(piperazin-1-ylmethyl)-5-(trifluoromethyl)phenyl]morpholine

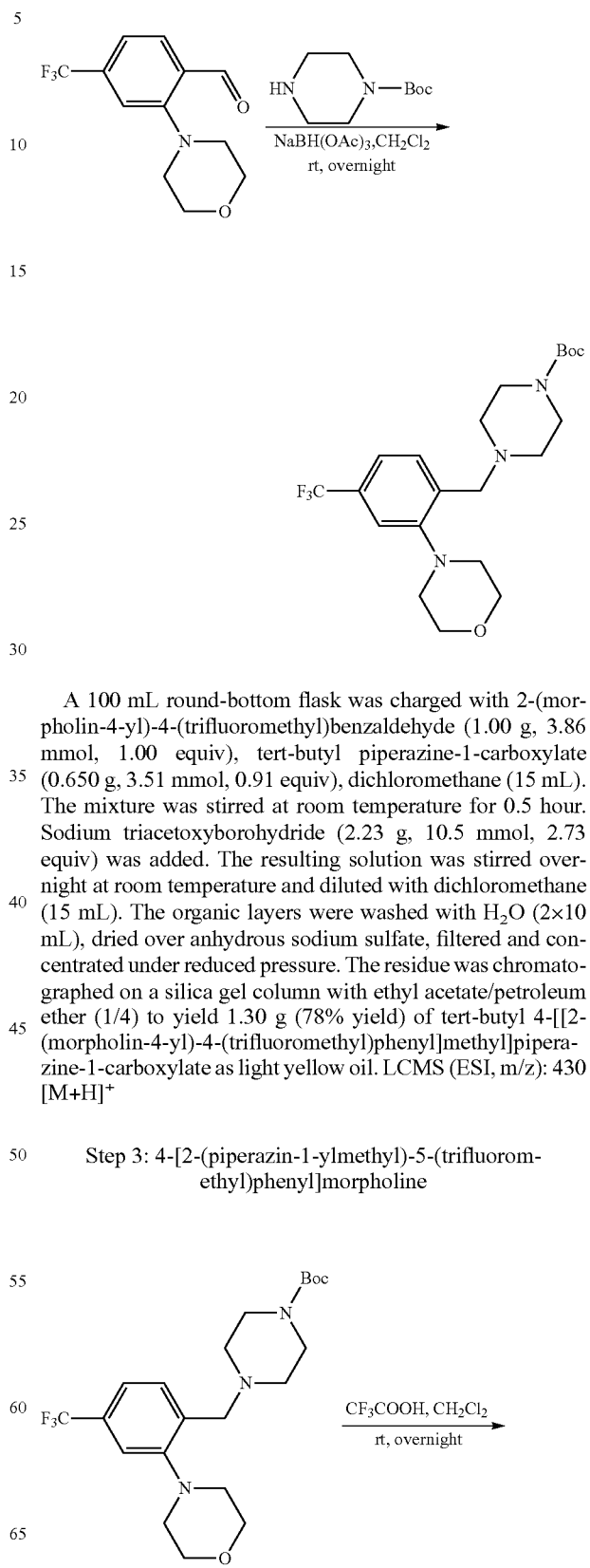

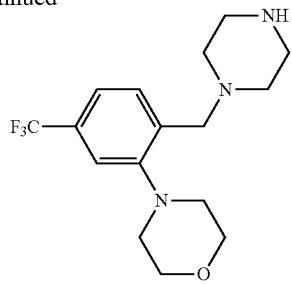

A 100 mL round-bottom flask was charged with tert-butyl 4-[[2-(morpholin-4-yl)-4-(trifluoromethyl)phenyl]methyl]piperazine-1-carboxylate (1.30 g, 3.03 mmol, 1.00 equiv), dichloromethane (20 mL). The mixture was cooled to 0° C. Trifluoroacetic acid (3 mL) was added dropwise. The resulting solution was stirred overnight at room temperature and concentrated under pressure to yield 0.800 g (crude) of 4-[2-(piperazin-1-ylmethyl)-5-(trifluoromethyl)phenyl]morpholine as a light yellow solid. LCMS (ESI, m/z): 330 [M+H]$^+$.

Step 4: 1,1,1,3,3,3-hexafluoropropan-2-yl 4-[[2-(morpholin-4-yl)-4-(trifluoromethyl)phenyl]methyl]piperazine-1-carboxylate

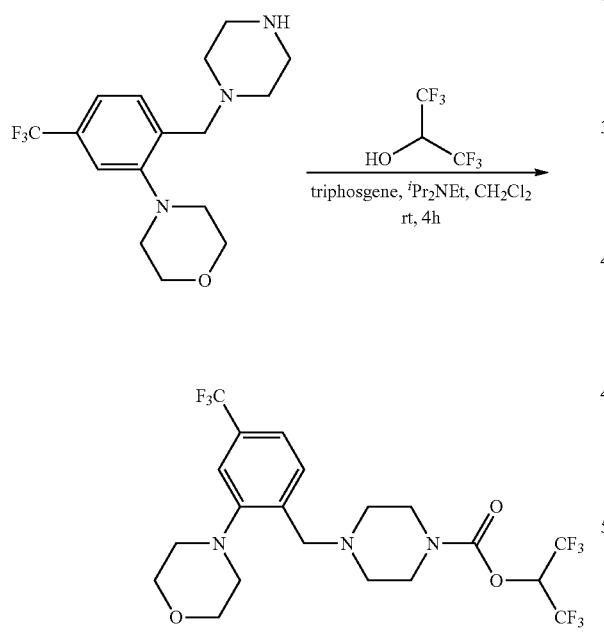

A 50 mL round-bottom flask was charged with 1,1,1,3,3,3-hexafluoropropan-2-ol (168 mg, 1.00 mmol, 1.10 equiv), triphosgene (99.0 mg, 0.330 mmol, 0.33 equiv), dichloromethane (10 mL). N,N-Diisopropylethylamine (381 mg, 2.95 mmol, 3.24 equiv) was added dropwise. The mixture was stirred at room temperature for 2 h. 4-[2-(Piperazin-1-ylmethyl)-5-(trifluoromethyl)phenyl]morpholine (300 mg, 0.910 mmol, 1.00 equiv) was added. The resulting solution was stirred for 2 hours at room temperature and diluted with dichloromethane (20 mL). The resulting mixture was washed with H$_2$O (2×10 mL), dried over anhydrous sodium sulfate, filtered and concentrated under reduced pressure. The residue was chromatographed on a silica gel column with ethyl acetate/petroleum ether (1/3). The crude product (337 mg) was purified by preparative HPLC using the following gradient conditions: 20% CH$_3$CN/80% phase A increasing to 80% CH$_3$CN over 10 min, then to 100% CH$_3$CN over 0.1 min, holding at 100% CH$_3$CN for 1.9 min, then reducing to 20% over 0.1 min, and holding at 20% for 1.9 min, on a waters 2767-5 chromatograph. Column: X-bridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 171.9 mg (35% yield) of 1,1,1,3,3,3-hexafluoropropan-2-yl 4-[[2-(morpholin-4-yl)-4-(trifluoromethyl)phenyl]methyl]piperazine-1-carboxylate as light yellow oil. $^1$H NMR 300 MHz (CDCl$_3$) δ 7.54-7.623 (m, 1H), 7.33-7.42 (m, 2H), 5.72-5.85 (m, 1H), 3.84-3.87 (m, 4H), 3.64 (s, 2H), 3.56-3.57 (m, 4H), 2.96-3.00 (m, 4H), 2.51-2.52 (m, 4H). LCMS (ESI, m/z): 524 [M+H]$^+$.

Example 43

1,1,1,3,3,3-hexafluoropropan-2-yl 4-[[3-fluoro-2-(morpholin-4-yl)phenyl]methyl]piperazine-1-carboxylate (9d)

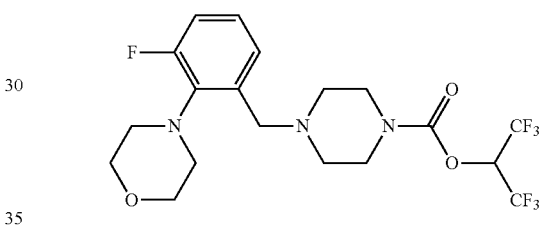

Step 1: Preparation of 3-fluoro-2-(morpholin-4-yl)benzaldehyde

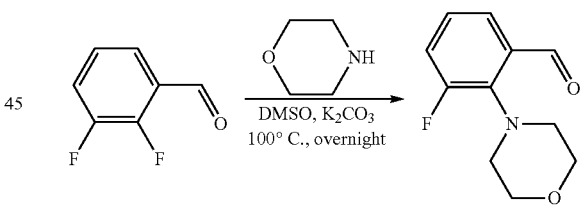

A 100 mL round-bottom flask was charged with 2,3-difluorobenzaldehyde (2.00 g, 14.1 mmol, 1.00 equiv), morpholine (1.84 g, 21.1 mmol, 1.50 equiv), potassium carbonate (4.90 g, 35.4 mmol, 2.52 equiv), and dimethyl sulfoxide (20 mL). The resulting solution was stirred overnight at 100° C. in an oil bath and diluted with H$_2$O (50 mL). The resulting solution was extracted with dichloromethane (3×20 mL) and the organic layers were combined, washed with H$_2$O (3×50 mL), dried over anhydrous sodium sulfate, filtered and concentrated under reduced pressure. The residue was chromatographed on a silica gel column with ethyl acetate/petroleum ether (1/20) to yield 0.840 g (28% yield) of 3-fluoro-2-(morpholin-4-yl)benzaldehyde as a yellow solid. $^1$H NMR 300 MHz, (CDCl$_3$) δ 10.54 (s, 1H), 7.63 (d, J=7.5 Hz, 1H), 7.18-7.34 (m, 2H), 3.85 (br, 4H), 3.23 (br, 4H). LCMS (ESI, m/z): 210 [M+H].

Step 2: Preparation of tert-butyl 4-[[3-fluoro-2-(morpholin-4-yl)phenyl]methyl]piperazine-1-carboxylate

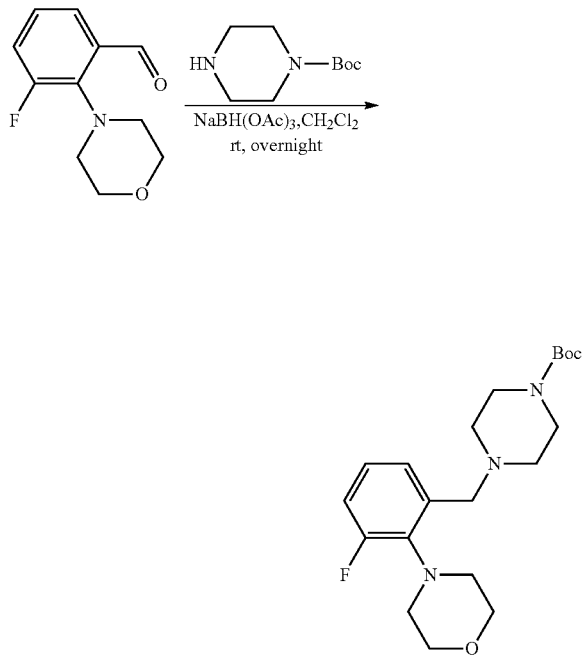

A 50 mL round-bottom flask was charged with 3-fluoro-2-(morpholin-4-yl)benzaldehyde (0.500 g, 2.39 mmol, 1.00 equiv), tert-butyl piperazine-1-carboxylate (404 mg, 2.17 mmol, 0.91 equiv), dichloromethane (10 mL). The mixture was stirred at room temperature for 0.5 hour. Sodium triacetoxyborohydride (1.38 g, 6.51 mmol, 2.72 equiv) was added. The resulting solution was stirred overnight at room temperature and diluted with dichloromethane. The resulting mixture was washed with H$_2$O (3×10 mL), dried over anhydrous sodium sulfate, filtered and concentrated under reduced pressure. The residue was chromatographed on a silica gel column with ethyl acetate/petroleum ether (1/3) to yield 1.00 g (crude) of tert-butyl 4-[[3-fluoro-2-(morpholin-4-yl)phenyl]methyl]piperazine-1-carboxylate as colorless oil. LCMS (ESI, m/z): 380 [M+H]$^+$.

Step 3: Preparation of 4-[2-fluoro-6-(piperazin-1-ylmethyl)phenyl]morpholine

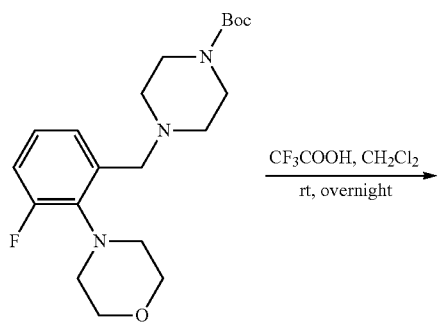

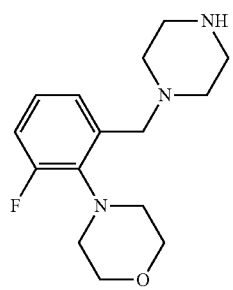

A 100 mL round-bottom flask was charged with tert-butyl 4-[[3-fluoro-2-(morpholin-4-yl)phenyl]methyl]piperazine-1-carboxylate (1.00 g, 2.64 mmol, 1.00 equiv), dichloromethane (20 mL). The mixture was cooled to 0° C. Trifluoroacetic acid (2 mL) was added dropwise at 0° C. The resulting solution was stirred overnight at room temperature and concentrated under reduced pressure to yield 0.600 g (crude) of 4-[2-fluoro-6-(piperazin-1-ylmethyl)phenyl]morpholine as light yellow oil. LCMS (ESI, m/z): 280 [M+H]$^+$.

Step 4: Preparation of 1,1,1,3,3,3-hexafluoropropan-2-yl 4-[[3-fluoro-2-(morpholin-4-yl)phenyl]methyl]piperazine-1-carboxylate (9d)

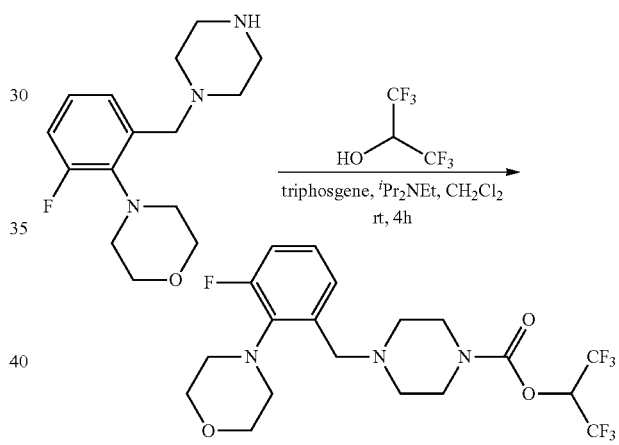

A 50 mL round-bottom flask was charged with 1,1,1,3,3,3-hexafluoropropan-2-ol (120 mg, 0.710 mmol, 1.00 equiv), triphosgene (70.0 mg, 0.240 mmol, 0.33 equiv), dichloromethane (10 mL). N,N-Diisopropylethylamine (338 mg, 2.62 mmol, 3.65 equiv) was added dropwise. The mixture was stirred at room temperature for 2 hours. 4-[2-Fluoro-6-(piperazin-1-ylmethyl)phenyl]morpholine (200 mg, 0.720 mmol, 1.00 equiv) was added. The resulting solution was stirred for 2 hours at room temperature and diluted with H$_2$O (10 mL). The resulting solution was extracted with dichloromethane (3×20 mL) and the organic layers were combined, washed with H$_2$O (3×10 mL), dried over anhydrous sodium sulfate, filtered and concentrated under reduced pressure. The residue was chromatographed on a silica gel column with ethyl acetate/petroleum ether (1/4). The crude product (217 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 125.4 mg (36% yield) of 1,1,1,3,3,3-hexafluoropropan-2-yl 4-[[3-fluoro-2-(morpholin-4-yl)phenyl]methyl]piperazine-1-carboxylate as light yellow oil. $^1$H NMR-300 MHz (CDCl$_3$) δ 7.07-7.18 (m, 2H), 6.94-7.01 (m, 1H), 5.71-5.83 (m, 1H), 3.88 (br, 4H), 3.80 (br, 2H), 3.52-3.54 (m, 4H), 3.10 (br, 4H), 2.49-2.52 (m, 4H). LCMS (ESI, m/z): 474 [M+H]$^+$.

Example 44

1,1,1,3,3,3-hexafluoropropan-2-yl 4-(2-chloro-4-morpholinobenzyl)piperazine-1-carboxylate (9e)

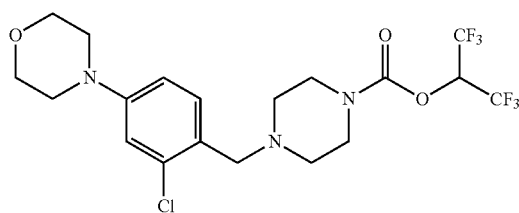 [SMILES: O=C(OC(C(F)(F)F)C(F)(F)F)N1CCN(Cc2ccc(N3CCOCC3)cc2F)CC1]

The title compound was synthesized directly from commercially available 2-chloro-4-morpholinobenzaldehyde and tert-butyl piperazine-1-carboxylate according to the representative procedure of Example 40: $^1$H NMR 400 MHz (CDCl$_3$) δ 7.27 (m, 1H), 6.89 (d, J=2.5 Hz, 1H), 6.79 (dd, J=8.5, 2.5 Hz, 1H), 5.75 (hept, J=6.2 Hz, 1H), 3.92-3.79 (m, 4H), 3.63-3.49 (m, 6H), 3.22-3.09 (m, 4H), 2.53-2.48 (m, 4H). LCMS (ESI, m/z): 210.0 (4-morpholino-2-chlorobenzyl cation).

Example 45

1,1,1,3,3,3-hexafluoropropan-2-yl 4-(4-morpholinobenzyl)piperazine-1-carboxylate (9f)

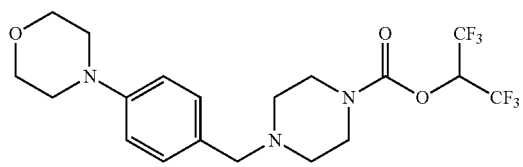 [SMILES: O=C(OC(C(F)(F)F)C(F)(F)F)N1CCN(Cc2ccc(N3CCOCC3)cc2)CC1]

The title compound was synthesized directly from commercially available 4-morpholinobenzaldehyde and tert-butyl piperazine-1-carboxylate according to the representative procedure of Example 40: $^1$H NMR 400 MHz (CDCl$_3$) δ 7.14 (d, J=8.3 Hz, 2H), 6.80 (d, J=8.6 Hz, 2H), 5.79-5.51 (m, 1H), 3.86-3.67 (m, 4H), 3.53-3.43 (m, 4H), 3.39 (s, 2H), 3.15-3.01 (m, 4H), 2.42-2.27 (m, 4H). LCMS (ESI, m/z): 228.5 (4-morpholinobenzyl cation).

Example 46

1,1,1,3,3,3-hexafluoropropan-2-yl 4-(4-(pyrrolidin-1-yl)benzyl)piperazine-1-carboxylate (9g)

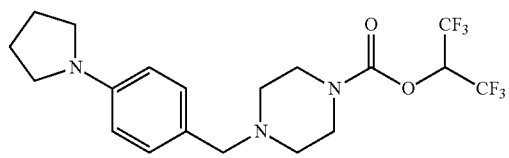 [SMILES: O=C(OC(C(F)(F)F)C(F)(F)F)N1CCN(Cc2ccc(N3CCCC3)cc2)CC1]

The title compound was synthesized directly from commercially available 4-(pyrrolidin-1-yl)benzaldehyde and tert-butyl piperazine-1-carboxylate according to the representative procedure of Example 40: $^1$H NMR 400 MHz (CDCl$_3$) δ 7.07 (d, J=7.9 Hz, 2H), 6.45 (d, J=8.4 Hz, 2H), 5.76-5.56 (m, 1H), 3.47 (s, 4H), 3.37 (s, 2H), 3.26-3.13 (m, 4H), 2.36 (s, 4H), 2.00-1.86 (m, 4H). LCMS (ESI, m/z): 220.6 (4-pyrrolidinobenzyl cation).

Example 47

1,1,1,3,3,3-hexafluoropropan-2-yl 4-(3-chloro-4-morpholinobenzyl)piperazine-1-carboxylate (9h)

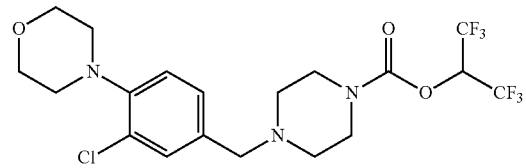 [SMILES: O=C(OC(C(F)(F)F)C(F)(F)F)N1CCN(Cc2ccc(N3CCOCC3)c(Cl)c2)CC1]

The title compound was synthesized directly from commercially available 3-chloro-4-morpholinobenzaldehyde and tert-butyl piperazine-1-carboxylate according to the representative procedure of Example 40. $^1$H NMR 400 MHz (CDCl$_3$) δ 7.35 (s, 1H), 7.17 (d, J=8.2 Hz, 1H), 6.99 (d, J=8.2 Hz, 1H), 5.75 (hept, J=6.2 Hz, 1H), 3.98-3.79 (m, 4H), 3.62-3.54 (m, 4H), 3.45 (s, 2H), 3.14-2.96 (m, 4H), 2.50-2.40 (m, 4H). LCMS (ESI, m/z): 490.1 [M+H]$^+$.

Example 48

1,1,1,3,3,3-hexafluoropropan-2-yl(2S)-4-[[2-fluoro-4-(morpholin-4-yl)phenyl]methyl]-2-methylpiperazine-1-carboxylate (9i)

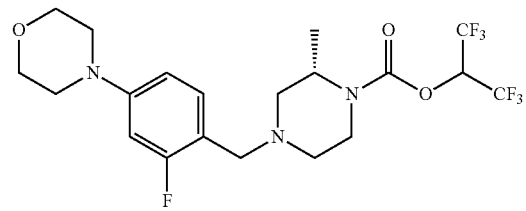 [SMILES: C[C@H]1CN(Cc2ccc(N3CCOCC3)cc2F)CCN1C(=O)OC(C(F)(F)F)C(F)(F)F]

Step 1: Preparation of tert-butyl (2S)-4-[[2-fluoro-4-(morpholin-4-yl)phenyl]methyl]-2-methylpiperazine-1-carboxylate

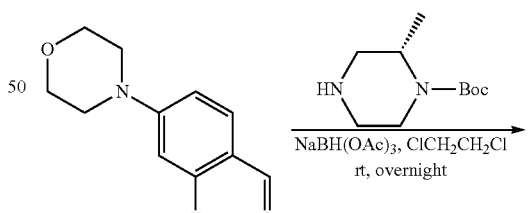

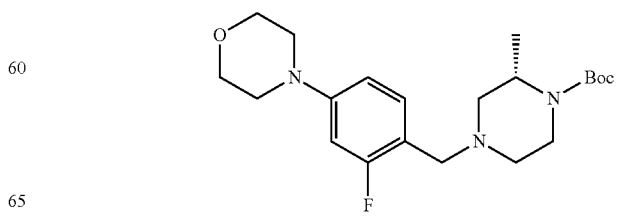

A 100 mL round-bottom flask was charged with 2-fluoro-4-(morpholin-4-yl)benzaldehyde (0.800 g, 3.82 mmol, 1.00 equiv), tert-butyl (2S)-2-methylpiperazine-1-carboxylate (0.840 g, 4.20 mmol, 1.10 equiv), 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The residue was chromatographed on a silica gel column with ethyl acetate/petroleum ether (25/75) to provide 1.40 g (93% yield) of tert-butyl (2S)-4-[[2-fluoro-4-(morpholin-4-yl)phenyl]methyl]-2-methylpiperazine-1-carboxylate as a white solid. LCMS (ESI, m/z): 394 [M+H]$^+$.

Step 2: Preparation of 4-(4-[[(3S)-3-methylpiperazin-1-yl]methyl]-3-(trifluoromethyl)phenyl)morpholine

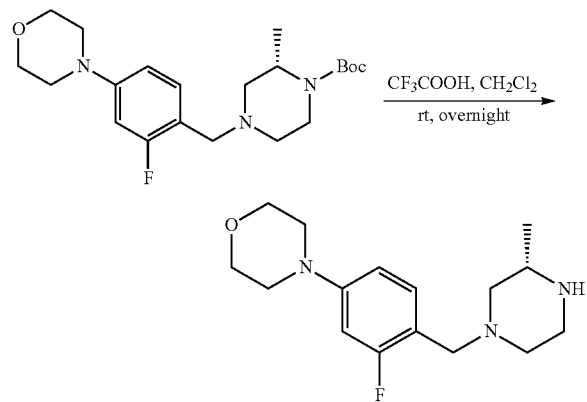

A 100 mL round-bottom flask was charged with tert-butyl (2S)-2-methyl-4-[[4-(morpholin-4-yl)-2-(trifluoromethyl)phenyl]methyl]piperazine-1-carboxylate (1.40 g, 3.16 mmol, 1.00 equiv), dichloromethane (15 mL). Trifluoroacetic acid (3.80 g, 33.3 mmol, 9.40 equiv) was added at 0° C. The resulting solution was stirred overnight at room temperature and concentrated under reduced pressure to yield 0.900 g (83% yield) of 4-(4-[[(3S)-3-methylpiperazin-1-yl]methyl]-3-(trifluoromethyl)phenyl)morpholine as colorless oil. LCMS (ESI, m/z): 294 [M+H]$^+$.

Step 3: Preparation of 1,1,1,3,3,3-hexafluoropropan-2-yl(2S)-4-[[2-fluoro-4-(morpholin-4-yl)phenyl]methyl]-2-methylpiperazine-1-carboxylate (9i)

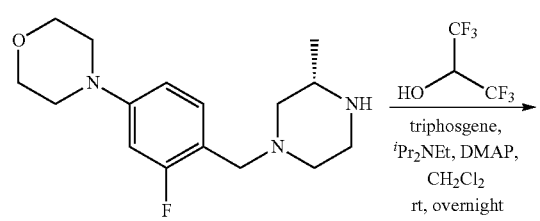

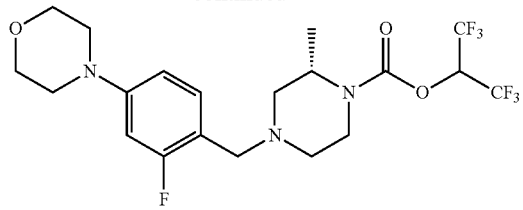

A 100 mL round-bottom flask was charged with triphosgene (142 mg, 0.480 mmol, 0.70 equiv), dichloromethane (15 mL). 1,1,1,3,3,3-hexafluoropropan-2-ol (229 mg, 1.36 mmol, 2.00 equiv) and N-ethyl-N-isopropylpropan-2-amine (352 mg, 2.72 mmol, 4.00 equiv) were added at 0° C. The mixture was stirred for 2 h at room temperature. 4-(3-Fluoro-4-[[(3S)-3-methylpiperazin-1-yl]methyl]phenyl)morpholine (200 mg, 0.68 mmol, 1.00 equiv) and 4-dimethylaminopyridine (83.0 mg, 0.680 mmol, 1.00 equiv) were added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The crude product (500 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 307 mg (92% yield) of 1,1,1,3,3,3-hexafluoropropan-2-yl(2S)-4-[[2-fluoro-4-(morpholin-4-yl)phenyl]methyl]-2-methylpiperazine-1-carboxylate as orange oil. $^1$H NMR 300 MHz (CDCl$_3$) δ 7.19-7.27 (m, 1H), 6.64-6.67 (m, 1H), 6.53-6.58 (m, 1H), 5.72-5.84 (m, 1H), 4.26 (br, 1H), 3.84 (t, J=4.8 Hz, 5H), 3.50 (s, 2H), 3.21-3.29 (m, 1H), 3.15 (t, J=4.8 Hz, 4H), 2.82 (d, J=10.5 Hz, 1H), 2.65 (d, J=11.4 Hz, 1H), 2.22-2.27 (m, 1H), 2.05-2.13 (m, 1H), 1.30 (d, J=6.6 Hz, 3H). LCMS (ESI, m/z): 488 [M+H]$^+$.

Example 49

1,1,1,3,3,3-hexafluoropropan-2-yl(2S)-2-methyl-4-[[4-(morpholin-4-yl)-2-(trifluoromethyl)phenyl]methyl]piperazine-1-carboxylate (9j)

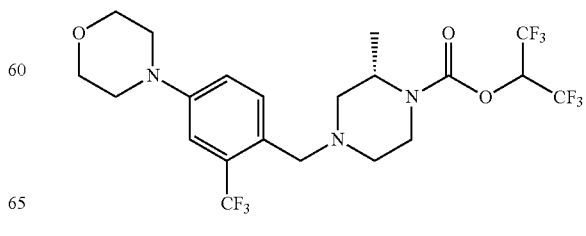

Step 1: Preparation of tert-butyl (2S)-2-methyl-4-[[4-(morpholin-4-yl)-2-(trifluoromethyl)phenyl]methyl]piperazine-1-carboxylate

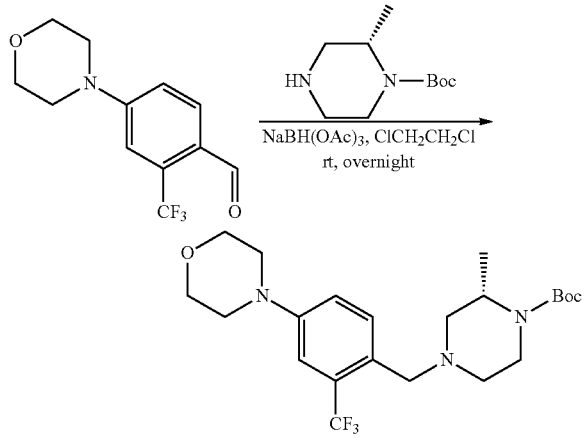

A 100 mL round-bottom flask was charged with 4-(morpholin-4-yl)-2-(trifluoromethyl)benzaldehyde (1.00 g, 3.86 mmol, 1.00 equiv), tert-butyl (2S)-2-methylpiperazine-1-carboxylate (0.850 g, 4.24 mmol, 1.10 equiv), 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (20 mL), extracted with dichloromethane (3×15 mL). The organic layers were combined and washed with brine (50 mL), dried over anhydrous sodium sulfate and concentrated under reduced pressure. The residue was chromatographed on a silica gel column with ethyl acetate/petroleum ether (20/80) to provide 1.70 g (99% yield) of tert-butyl (2S)-2-methyl-4-[[4-(morpholin-4-yl)-2-(trifluoromethyl)phenyl]methyl]piperazine-1-carboxylate as yellow oil. LCMS (ESI, m/z): 444 [M+H]$^+$.

Step 2: Preparation of 4-(4-[[(3S)-3-methylpiperazin-1-yl]methyl]-3-(trifluoromethyl)phenyl)morpholine

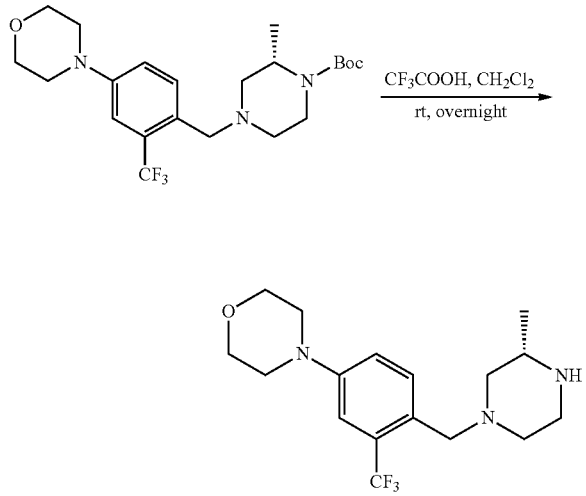

A 100 mL round-bottom flask was charged with tert-butyl (2S)-2-methyl-4-[[4-(morpholin-4-yl)-2-(trifluoromethyl)phenyl]methyl]piperazine-1-carboxylate (1.70 g, 3.83 mmol, 1.00 equiv), dichloromethane (15 mL). Trifluoroacetic acid (3.80 g, 33.3 mmol, 8.70 equiv) was added at 0° C. The resulting solution was stirred overnight at room temperature and concentrated under reduced pressure to yield 1.00 g (crude) of 4-(4-[[(3S)-3-methylpiperazin-1-yl]methyl]-3-(trifluoromethyl)phenyl)morpholine as brown oil. LCMS (ESI, m/z): 344 [M+H]$^+$.

Step 3: Preparation of 1,1,1,3,3,3-hexafluoropropan-2-yl(2S)-2-methyl-4-[[4-(morpholin-4-yl)-2-(trifluoromethyl)phenyl]methyl]piperazine-1-carboxylate (9j)

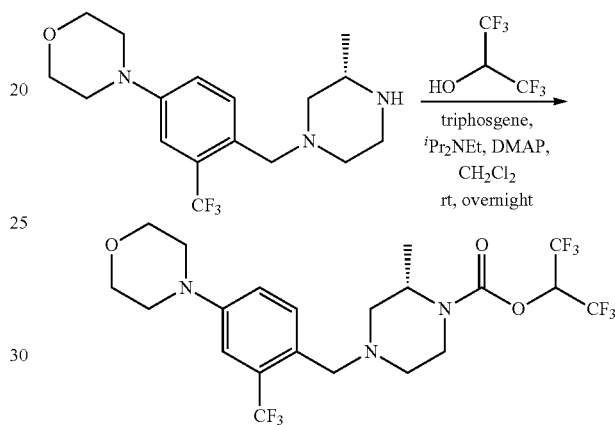

A 100 mL round-bottom flask was charged with triphosgene (121 mg, 0.410 mmol, 0.70 equiv), dichloromethane (20 mL), 1,1,1,3,3,3-hexafluoropropan-2-ol (196 mg, 1.17 mmol, 2.00 equiv) and N-ethyl-N-isopropylpropan-2-amine (602 mg, 4.66 mmol, 8.00 equiv) were added at 0° C. The mixture was stirred for 2 h at room temperature. 4-(4-[[(3S)-3-methylpiperazin-1-yl]methyl]-3-(trifluoromethyl)phenyl)morpholine (200 mg, 0.580 mmol, 1.00 equiv) and 4-dimethylaminopyridine (71.0 mg, 0.580 mmol, 1.00 equiv) were added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The crude product (500 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 228 mg (73% yield) of 1,1,1,3,3,3-hexafluoropropan-2-yl(2S)-2-methyl-4-[[4-(morpholin-4-yl)-2-(trifluoromethyl)phenyl]methyl]piperazine-1-carboxylate as yellow oil. $^1$H NMR 300 MHz (CDCl$_3$) δ 7.58 (d, J=8.7 Hz, 1H), 7.14 (s, 1H), 7.01-7.05 (m, 1H), 5.72-5.84 (m, 1H), 4.27 (br, 1H), 3.87 (t, J=4.8 Hz, 5H), 3.55 (s, 2H), 3.26 (br, 1H), 3.20 (t, J=4.8 Hz, 4H), 2.79 (d, J=10.5 Hz, 1H), 2.63 (d, J=11.4 Hz, 1H), 2.25-2.30 (m, 1H), 2.08-2.16 (m, 1H), 1.31 (d, J=6.6 Hz, 3H). LCMS: (ESI, m/z): 538 [M+H]$^+$.

Example 50

1,1,1,3,3,3-hexafluoropropan-2-yl(2R)-4-[[2-fluoro-4-(morpholin-4-yl)phenyl]methyl]-2-methylpiperazine-1-carboxylate (9k)

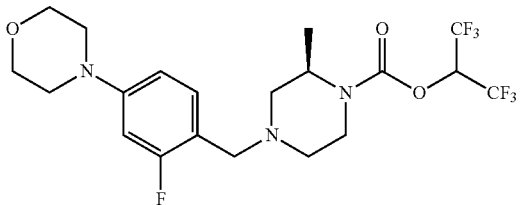 [SMILES: C[C@@H]1CN(Cc2ccc(N3CCOCC3)cc2F)CCN1C(=O)OC(C(F)(F)F)C(F)(F)F]

Step 1: Preparation of tert-butyl (2R)-4-[[2-fluoro-4-(morpholin-4-yl)phenyl]methyl]-2-methylpiperazine-1-carboxylate

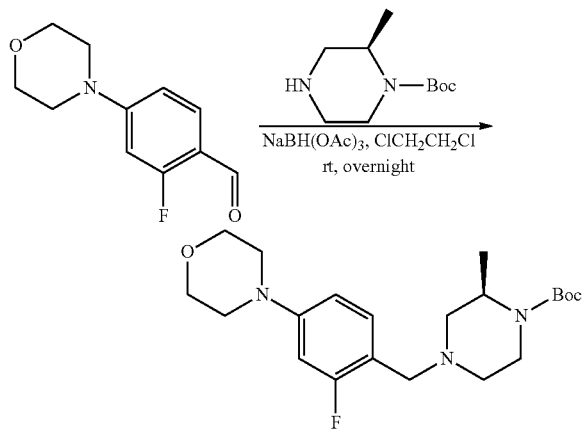

A 100 mL round-bottom flask was charged with 2-fluoro-4-(morpholin-4-yl)benzaldehyde (0.800 g, 3.82 mmol, 1.00 equiv), tert-butyl (2R)-2-methylpiperazine-1-carboxylate (0.840 g, 4.20 mmol, 1.10 equiv), 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The residue was chromatographed on a silica gel column with ethyl acetate/petroleum ether (20/80) to provide 1.40 g (93% yield) of tert-butyl (2R)-4-[[2-fluoro-4-(morpholin-4-yl)phenyl]methyl]-2-methylpiperazine-1-carboxylate as a white solid. LCMS (ESI, m/z): 394 [M+H]$^+$.

Step 2: Preparation of 4-(3-fluoro-4-[[(3R)-3-methylpiperazin-1-yl]methyl]phenyl)morpholine

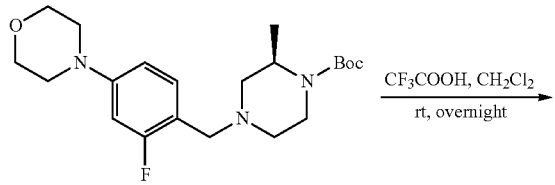

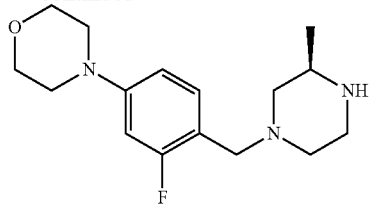

A 100 mL round-bottom flask was charged with tert-butyl (2R)-4-[[2-fluoro-4-(morpholin-4-yl)phenyl]methyl]-2-methylpiperazine-1-carboxylate (1.40 g, 3.56 mmol, 1.00 equiv), dichloromethane (15 mL). Trifluoroacetic acid (3.80 g, 33.3 mmol, 9.40 equiv) was added at 0° C. The resulting solution was stirred overnight at room temperature and concentrated under reduced pressure to yield 0.90 g (86% yield) of 4-(3-fluoro-4-[[(3R)-3-methylpiperazin-1-yl]methyl]phenyl)morpholine as yellow oil. LCMS (ESI, m/z): 294 [M+H]$^+$.

Step 3: Preparation of 1,1,1,3,3,3-hexafluoropropan-2-yl(2R)-4-[[2-fluoro-4-(morpholin-4-yl)phenyl]methyl]-2-methylpiperazine-1-carboxylate (9k)

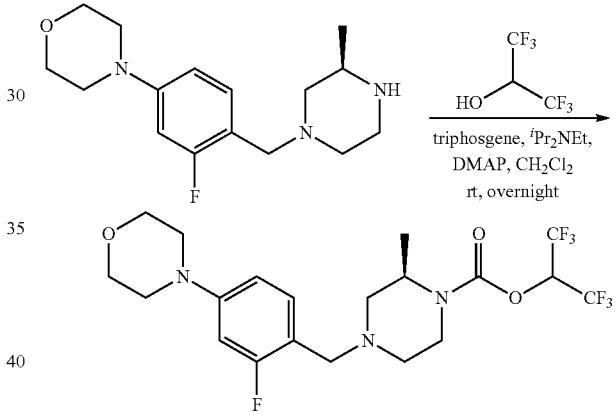

A 100 mL round-bottom flask was charged with triphosgene (142 mg, 0.480 mmol, 0.70 equiv), dichloromethane (15 mL), 1,1,1,3,3,3-hexafluoropropan-2-ol (229 mg, 1.36 mmol, 2.00 equiv) and N-ethyl-N-isopropylpropan-2-amine (352 mg, 2.72 mmol, 4.00 equiv) were added at 0° C. The mixture was stirred for 2 h at room temperature. 4-(3-Fluoro-4-[[(3R)-3-methylpiperazin-1-yl]methyl]phenyl)morpholine (200 mg, 0.68 mmol, 1.00 equiv) and 4-dimethylaminopyridine (83.0 mg, 0.680 mmol, 1.00 equiv) were added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The crude product (500 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 315 mg (95% yield) of 1,1,1,3,3,3-hexafluoropropan-2-yl(2R)-4-[[2-fluoro-4-(morpholin-4-yl)phenyl]methyl]-2-methylpiperazine-1-carboxylate as yellow oil. $^1$H NMR 300 MHz (CDCl$_3$) δ 7.19-7.26 (m, 1H), 6.63-6.67 (m, 1H), 6.53-6.58 (m, 1H), 5.70-5.82 (m, 1H), 4.25 (br, 1H), 3.85 (t, J=4.8 Hz, 5H), 3.49 (s, 2H), 3.20-3.29 (m, 1H), 3.15 (t, J=4.8 Hz, 4H), 2.81 (d, J=10.8 Hz, 1H), 2.65 (d, J=11.4 Hz, 1H), 2.21-2.26 (m, 1H), 2.05-2.13 (m, 1H), 1.30 (d, J=6.6 Hz, 3H). LCMS: (ESI, m/z): 488 [M+H]$^+$.

Example 51

1,1,1,3,3,3-hexafluoropropan-2-yl(2R)-2-methyl-4-[[4-(morpholin-4-yl)-2-(trifluoromethyl)phenyl]methyl]piperazine-1-carboxylate (9l)

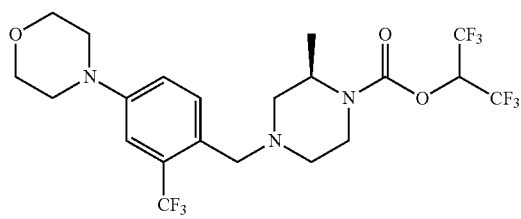 [SMILES: C[C@@H]1CN(Cc2ccc(N3CCOCC3)cc2C(F)(F)F)CCN1C(=O)OC(C(F)(F)F)C(F)(F)F]

Step 1: Preparation of tert-butyl (2R)-2-methyl-4-[[4-(morpholin-4-yl)-2-(trifluoromethyl)phenyl]methyl]piperazine-1-carboxylate

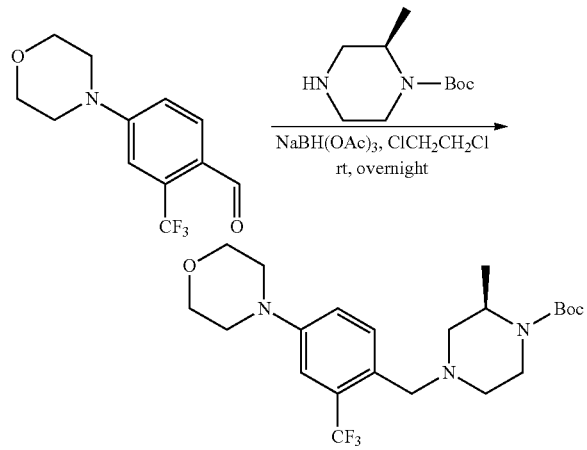

A 100 mL round-bottom flask was charged with 4-(morpholin-4-yl)-2-(trifluoromethyl)benzaldehyde (1.00 g, 3.86 mmol, 1.00 equiv), tert-butyl (2R)-2-methylpiperazine-1-carboxylate (0.850 g, 4.24 mmol, 1.10 equiv), 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The residue was chromatographed on a silica gel column with ethyl acetate/petroleum ether (20/80) to provide 1.70 g (99% yield) of tert-butyl (2R)-2-methyl-4-[[4-(morpholin-4-yl)-2-(trifluoromethyl)phenyl]methyl]piperazine-1-carboxylate as yellow oil. LCMS (ESI, m/z): 444 [M+H]$^+$.

Step 2: Preparation of 4-(4-[[(3R)-3-methylpiperazin-1-yl]methyl]-3-(trifluoromethyl)phenyl)morpholine

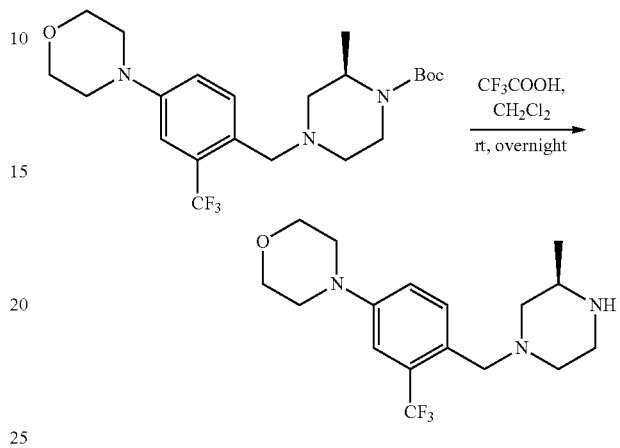

A 100 mL round-bottom flask was charged with tert-butyl (2R)-2-methyl-4-[[4-(morpholin-4-yl)-2-(trifluoromethyl)phenyl]methyl]piperazine-1-carboxylate (1.70 g, 3.83 mmol, 1.00 equiv), dichloromethane (15 mL). Trifluoroacetic acid (3.80 g, 33.3 mmol, 8.70 equiv) was added at 0° C. The resulting solution was stirred overnight at room temperature and concentrated under reduced pressure to yield 1.00 g (crude) of 4-(4-[[(3R)-3-methylpiperazin-1-yl]methyl]-3-(trifluoromethyl)phenyl)morpholine as yellow oil. LCMS (ESI, m/z): 344 [M+H]$^+$.

Step 3: Preparation of 1,1,1,3,3,3-hexafluoropropan-2-yl(2R)-2-methyl-4-[[4-(morpholin-4-yl)-2-(trifluoromethyl)phenyl]methyl]piperazine-1-carboxylate (9l)

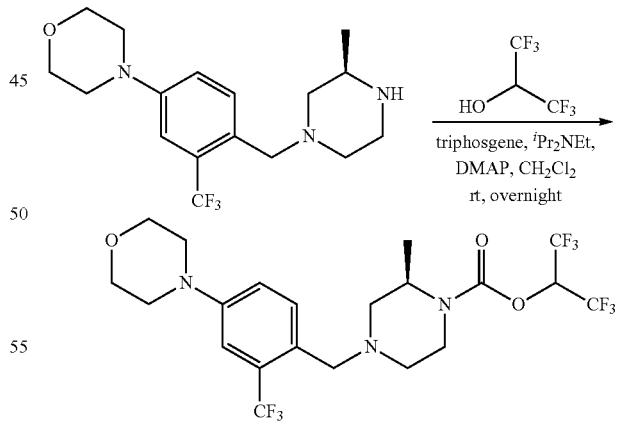

A 100 mL round-bottom flask was charged with triphosgene (121 mg, 0.410 mmol, 0.70 equiv), dichloromethane (15 mL), 1,1,1,3,3,3-hexafluoropropan-2-ol (196 mg, 1.17 mmol, 2.00 equiv) and N-ethyl-N-isopropylpropan-2-amine (301 mg, 2.33 mmol, 4.00 equiv) were added at 0° C. The mixture was stirred for 2 h at room temperature. 4-(4-[[(3R)-3-Methylpiperazin-1-yl]methyl]-3-(trifluoromethyl)phenyl) morpholine (200 mg, 0.580 mmol, 1.00 equiv) and 4-dimethylaminopyridine (71.0 mg, 0.580 mmol, 1.00 equiv) were added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The crude product (500 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 229 mg (73% yield) of 1,1,1,3,3,3-hexafluoropropan-2-yl(2R)-2-methyl-4-[[4-(morpholin-4-yl)-2-(trifluoromethyl)phenyl]methyl]piperazine-1-carboxylate as yellow oil. $^1$H NMR 300 MHz (CDCl$_3$) δ 7.57 (d, J=8.7 Hz, 1H), 7.13 (s, 1H), 7.01-7.05 (m, 1H), 5.71-5.83 (m, 1H), 4.26 (br, 1H), 3.87 (t, J=4.8 Hz, 5H), 3.55 (s, 2H), 3.26-3.30 (m, 1H), 3.20 (t, J=4.8 Hz, 4H), 2.79 (d, J=10.8 Hz, 1H), 2.63 (d, J=11.4 Hz, 1H), 2.25-2.33 (m, 1H), 2.07-2.16 (m, 1H), 1.30 (d, J=6.6 Hz, 3H). LCMS (ESI, m/z): 538 [M+H]$^+$.

Example 52

1,1,1,3,3,3-hexafluoropropan-2-yl 4-[[2-chloro-6-(pyrrolidin-1-yl)phenyl]methyl]piperazine-1-carboxylate (9m)

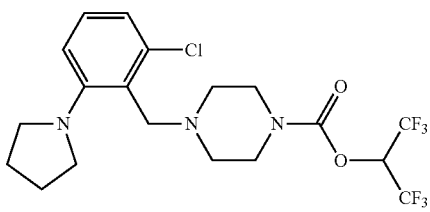 [SMILES: O=C(OC(C(F)(F)F)C(F)(F)F)N1CCN(Cc2c(Cl)cccc2N2CCCC2)CC1]

Step 1: Preparation of 2-chloro-6-(pyrrolidin-1-yl)benzaldehyde

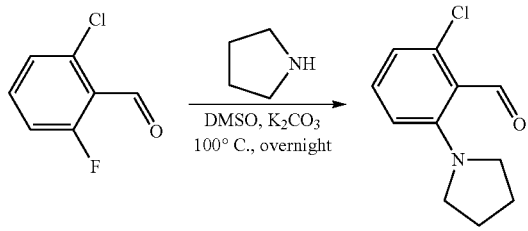 [SMILES: O=Cc1c(F)cccc1Cl ; C1CCNC1 ; O=Cc1c(Cl)cccc1N1CCCC1]

A 100 mL round-bottom flask was charged with 2-chloro-6-fluorobenzaldehyde (2.00 g, 12.6 mmol, 1.00 equiv), pyrrolidine (1.34 g, 18.8 mmol, 1.49 equiv), potassium carbonate (4.34 g, 31.4 mmol, 2.49 equiv), and dimethyl sulfoxide (20 mL). The resulting solution was stirred overnight at 100° C. in an oil bath. Then diluted with H$_2$O (20 mL). The resulting solution was extracted with dichloromethane (3×20 mL) and the organic layers were combined, washed with H$_2$O (3×10 mL), dried over anhydrous sodium sulfate, filtered and concentrated under reduced pressure. The residue was chromatographed on a silica gel column with ethyl acetate/petroleum ether (1/15) to yield 1.40 g (53% yield) of 2-chloro-6-(pyrrolidin-1-yl)benzaldehyde as a yellow solid. $^1$H NMR 300 MHz (CDCl$_3$) δ 10.49 (s, 1H), 7.20-7.25 (m, 1H), 6.73-6.78 (m, 2H), 3.14-3.19 (m, 4H), 1.94-2.02 (m, 4H). LCMS (ESI, m/z): 210 [M+H]$^+$.

Step 2: Preparation of tert-butyl 4-[[2-chloro-6-(pyrrolidin-1-yl)phenyl]methyl]piperazine-1-carboxylate

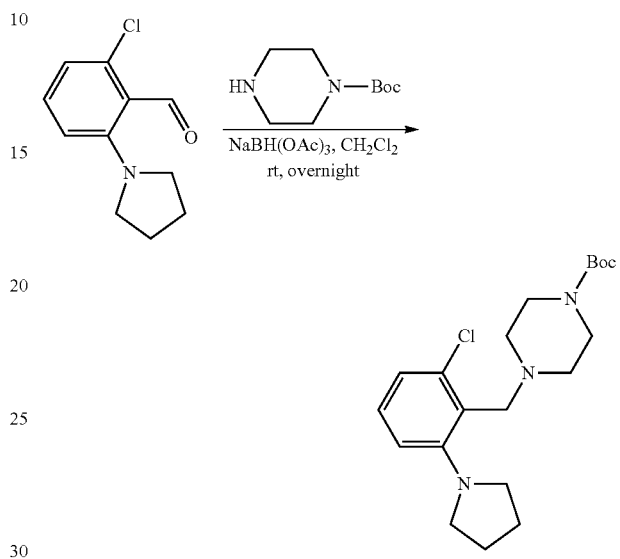

A 100 mL round-bottom flask was charged with 2-chloro-6-(pyrrolidin-1-yl)benzaldehyde (1.40 g, 6.68 mmol, 1.10 equiv), tert-butyl piperazine-1-carboxylate (1.13 g, 6.07 mmol, 1.00 equiv), 1,2-dichloroethane (20 mL). The mixture was stirred 30 min at room temperature. Sodium triacetoxyborohydride (3.85 g, 18.2 mmol, 2.99 equiv) was added. The resulting solution was stirred overnight at room temperature and diluted with 1,2-dichloroethane (20 mL). The resulting solution washed with H$_2$O (2×20 mL), dried over anhydrous sodium sulfate, filtered and concentrated under reduced pressure. The residue was chromatographed on a silica gel column with ethyl acetate/petroleum ether (3/7) to yield 1.95 g (77% yield) of tert-butyl 4-[[2-chloro-6-(pyrrolidin-1-yl)phenyl]methyl]piperazine-1-carboxylate as yellow oil. LCMS (ESI, m/z): 380 [M+H]$^+$.

Step 3: Preparation of 1-[[2-chloro-6-(pyrrolidin-1-yl)phenyl]methyl]piperazine

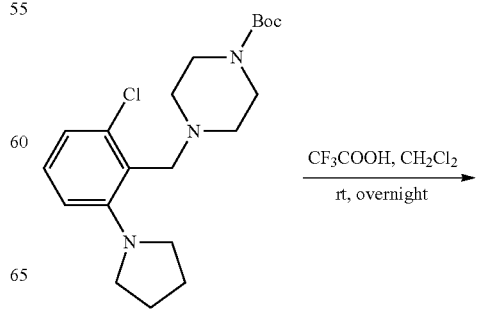

-continued

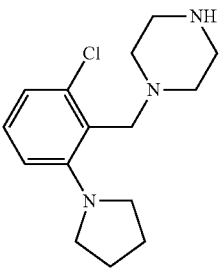

A 100 mL round-bottom flask was charged with tert-butyl 4-[[2-chloro-6-(pyrrolidin-1-yl)phenyl]methyl]piperazine-1-carboxylate (500 mg, 1.32 mmol, 1.00 equiv), dichloromethane (10 mL). The mixture was cooled to 0° C. Trifluoroacetic acid (1 mL) was added dropwise at 0° C. The resulting solution was stirred overnight at room temperature and concentrated under reduced pressure to yield 490 mg (crude) of 1-[[2-chloro-6-(pyrrolidin-1-yl)phenyl]methyl]piperazine as yellow oil. LCMS (ESI, m/z): 280 [M+H]$^+$.

Step 4: Preparation of 1,1,1,3,3,3-hexafluoropropan-2-yl 4-[[2-chloro-6-(pyrrolidin-1-yl)phenyl]methyl]piperazine-1-carboxylate (9m)

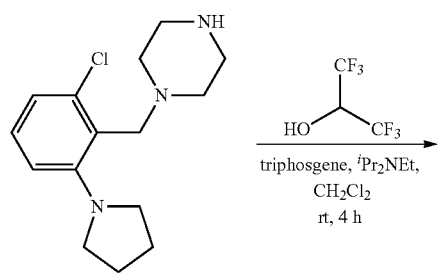

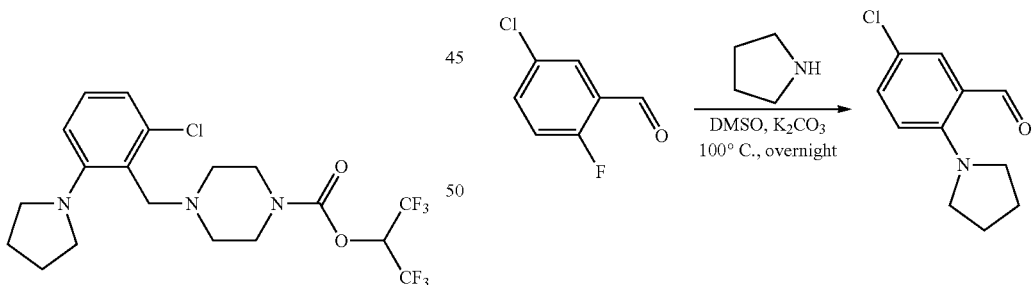

A 50 mL round-bottom flask was charged with 1,1,1,3,3,3-hexafluoropropan-2-ol (126 mg, 0.750 mmol, 1.00 equiv), triphosgene (74.0 mg, 0.250 mmol, 0.33 equiv), dichloromethane (10 mL). N,N-Diisopropylethylamine (290 mg, 2.24 mmol, 2.99 equiv) was added dropwise. The mixture was stirred at room temperature for 2 hours. 1-[[2-Chloro-6-(pyrrolidin-1-yl)phenyl]methyl]piperazine (210 mg, 0.750 mmol, 1.00 equiv) was added. The resulting solution was stirred for 2 hours at room temperature and diluted with H$_2$O (10 mL). The resulting solution was extracted with dichloromethane (3×20 mL) and the organic layers were combined, washed with H$_2$O (3×10 mL), dried over anhydrous sodium sulfate, filtered and concentrated under reduced pressure. The residue was chromatographed on a silica gel column with ethyl acetate/petroleum ether (1/3). The crude product (245 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 119 mg (33% yield) of 1,1,1,3,3,3-hexafluoropropan-2-yl 4-[[2-chloro-6-(pyrrolidin-1-yl)phenyl]methyl]piperazine-1-carboxylate as light yellow oil. $^1$H NMR 300 MHz (CDCl$_3$) δ 7.06-7.14 (m, 1H), 6.94-7.02 (m, 2H), 5.70-5.83 (m, 1H), 3.76 (br, 2H), 3.48 (br, 4H), 3.16-3.20 (m, 4H), 2.50-2.56 (m, 4H), 1.85-1.95 (m, 4H). LCMS (ESI, m/z): 474 [M+H]$^+$.

Example 53

1,1,1,3,3,3-hexafluoropropan-2-yl 4-[[5-chloro-2-(pyrrolidin-1-yl)phenyl]methyl]piperazine-1-carboxylate (9n)

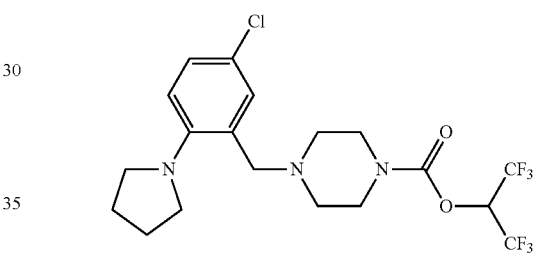

Step 1: Preparation of 5-chloro-2-(pyrrolidin-1-yl)benzaldehyde

A 100 mL round-bottom flask was charged with 5-chloro-2-fluorobenzaldehyde (2.00 g, 12.6 mmol, 1.00 equiv), pyrrolidine (1.34 g, 18.8 mmol, 1.49 equiv), potassium carbonate (4.34 g, 31.4 mmol, 1.92 equiv), and dimethyl sulfoxide (10 mL). The resulting solution was stirred overnight at 100° C. in an oil bath and diluted with H$_2$O (20 mL). The resulting solution was extracted with dichloromethane (3×20 mL) and the organic layers were combined, washed with H$_2$O (3×10 mL), dried over anhydrous sodium sulfate, filtered and concentrated under reduced pressure. The residue was chromatographed on a silica gel column with ethyl acetate/petroleum ether (1/10) to yield 1.80 g (68% yield) of 5-chloro-2-(pyrrolidin-1-yl)benzaldehyde as brown oil. $^1$H NMR 300 MHz (CDCl$_3$) δ 10.05 (s, 1H), 7.66 (d, J=2.4 Hz, 1H), 7.267-7.31

(m, 1H), 6.76 (d, J=9.0 Hz, 1H), 3.29-3.37 (m, 4H), 1.95-2.04 (m, 4H). LCMS (ESI, m/z): 210 [M+H]⁺.

Step 2: Preparation of tert-butyl 4-[[5-chloro-2-(pyrrolidin-1-yl)phenyl]methyl]piperazine-1-carboxylate

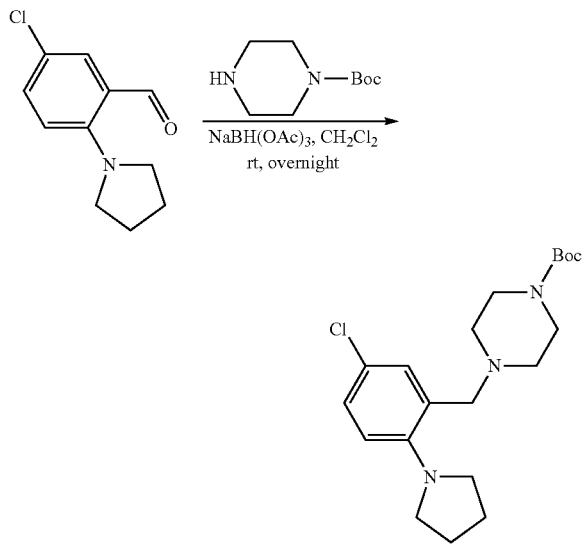

A 100 mL round-bottom flask was charged with 5-chloro-2-(pyrrolidin-1-yl)benzaldehyde (1.80 g, 8.58 mmol, 1.10 equiv), tert-butyl piperazine-1-carboxylate (1.45 g, 7.79 mmol, 1.00 equiv), 1,2-dichloroethane (20 mL). The mixture was stirred 30 min at room temperature. Sodium triacetoxyborohydride (4.96 g, 23.4 mmol, 3.01 equiv) was added. The resulting solution was stirred overnight at room temperature. The resulting mixture was washed with H₂O (2×20 mL), dried over anhydrous sodium sulfate, filtered and concentrated under reduced pressure. The residue was chromatographed on a silica gel column with ethyl acetate/petroleum ether (1/4) to yield 2.50 g (77% yield) of tert-butyl 4-[[5-chloro-2-(pyrrolidin-1-yl)phenyl]methyl]piperazine-1-carboxylate as yellow oil. LCMS (ESI, m/z): 380 [M+H]⁺.

Step 3: Preparation of 1-[[5-chloro-2-(pyrrolidin-1-yl)phenyl]methyl]piperazine

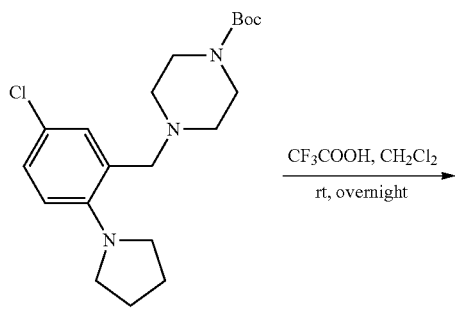

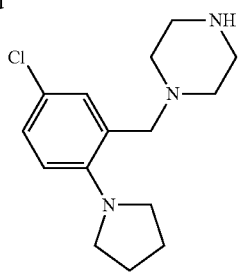

A 100 mL round-bottom flask was charged with tert-butyl 4-[[5-chloro-2-(pyrrolidin-1-yl)phenyl]methyl]piperazine-1-carboxylate (500 mg, 1.32 mmol, 1.00 equiv), dichloromethane (10 mL). The mixture was cooled to 0° C. Trifluoroacetic acid (1 mL) was added dropwise at 0° C. The resulting solution was stirred overnight at room temperature. The resulting mixture was concentrated under reduced pressure to yield 490 mg (crude) of 1-[[5-chloro-2-(pyrrolidin-1-yl)phenyl]methyl]piperazine as a brown solid. LCMS (ESI, m/z): 280 [M+H]⁺.

Step 4: Preparation of 1,1,1,3,3,3-hexafluoropropan-2-yl 4-[[5-chloro-2-(pyrrolidin-1-yl)phenyl]methyl]piperazine-1-carboxylate (9n)

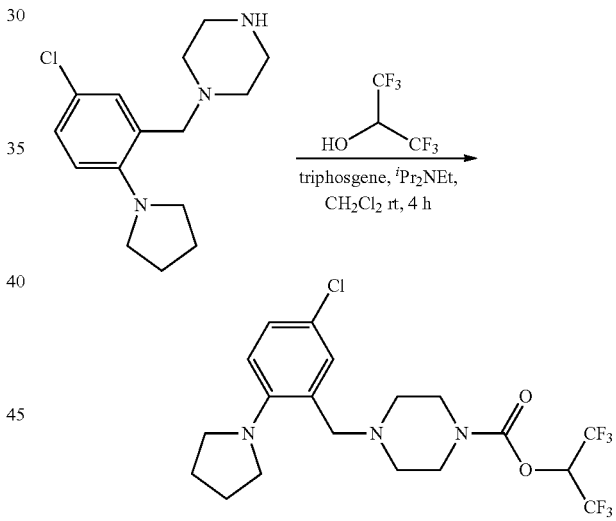

A 50 mL round-bottom flask was charged with 1,1,1,3,3,3-hexafluoropropan-2-ol (126 mg, 0.750 mmol, 1.00 equiv), triphosgene (74.0 mg, 0.250 mmol, 0.33 equiv), dichloromethane (10 mL). N,N-Diisopropylethylamine (290 mg, 2.24 mmol, 2.99 equiv) was added dropwise at room temperature. The mixture was stirred at room temperature for 2 h. 1-[[5-Chloro-2-(pyrrolidin-1-yl)phenyl]methyl]piperazine (210 mg, 0.750 mmol, 1.00 equiv) was added. The resulting solution was stirred for 2 hours at room temperature and diluted with H₂O (10 mL). The resulting solution was extracted with dichloromethane (3×10 mL) and the organic layers were combined, washed with H₂O (3×5 mL), dried over anhydrous sodium sulfate, filtered and concentrated under reduced pressure. The residue was chromatographed on a silica gel column with ethyl acetate/petroleum ether (1/3). The crude product (150 mg) was purified by preparative HPLC using the following gradient conditions: 20% CH₃CN/

80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep $C_{18}$, 19*150 mm 5 um; Mobile phase: Phase A: aqueous NH₄HCO₃ (0.05%); Phase B: CH₃CN; Detector, UV220 & 254 nm. Purification resulted in 51.5 mg (14% yield) of 1,1,1,3,3,3-hexafluoropropan-2-yl 4-[[5-chloro-2-(pyrrolidin-1-yl)phenyl]methyl]piperazine-1-carboxylate as light yellow oil. ¹H NMR 300 MHz (CDCl₃) δ 7.42 (d, J=2.4 Hz, 1H), 7.09-7.13 (m, 1H), 6.85 (d, J=8.9 Hz, 1H), 5.69-5.82 (m, 1H), 3.52-3.58 (m, 6H), 3.10-3.14 (m, 4H), 2.46-2.49 (m, 4H), 1.86-1.96 (m, 4H). LCMS (ESI, m/z): 474 [M+H]⁺.

Example 54

1,1,1,3,3,3-hexafluoropropan-2-yl 4-(4-chlorobenzyl)piperazine-1-carboxylate (9o)

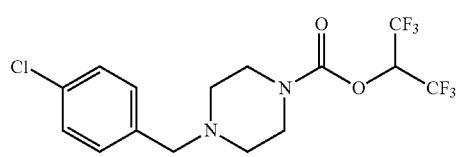

Step 1: Preparation of tert-butyl 4-(4-chlorobenzyl)piperazine-1-carboxylate

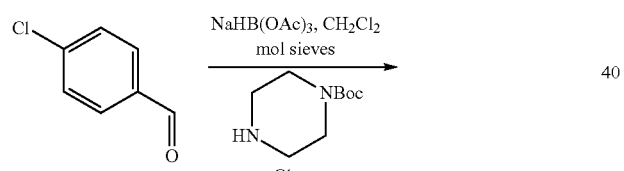

The title compound was prepared from 4-chlorobenzaldehyde as described in Example 40, Step 1 (800 mg, 96%): ¹H NMR 400 MHz (CDCl₃) δ 7.39-7.23 (m, 5H), 3.53-3.41 (m, 6H), 2.44-2.36 (m, 4H), 1.47 (s, 9H). LCMS (ESI, m/z): 311 [M+H]⁺.

Step 2: Preparation of 1,1,1,3,3,3-hexafluoropropan-2-yl 4-(4-chlorobenzyl)piperazine-1-carboxylate (9o)

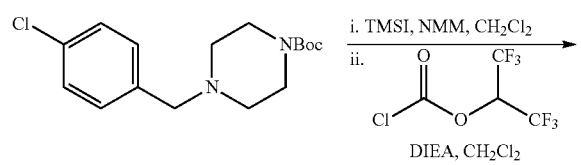

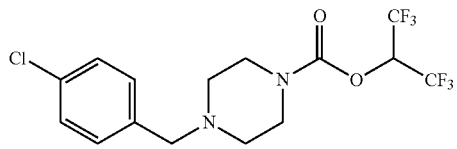 [SMILES: O=C(OC(C(F)(F)F)C(F)(F)F)N1CCN(Cc2ccc(Cl)cc2)CC1]

The title compound was prepared from tert-butyl 4-(4-chlorobenzyl)piperazine-1-carboxylate as described in Example 1, step 2 (24 mg, 24%). ¹H NMR 400 MHz (CDCl₃) δ 7.26-7.11 (m, 5H), 5.68 (hept, J=6.3 Hz, 1H), 3.52-3.38 (m, 6H), 2.36 (m, 4H). LCMS (ESI, m/z): 405 [M+H]⁺.

Example 55

1,1,1,3,3,3-hexafluoropropan-2-yl 4-(2-methyl-4-morpholinobenzyl)piperazine-1-carboxylate (9p)

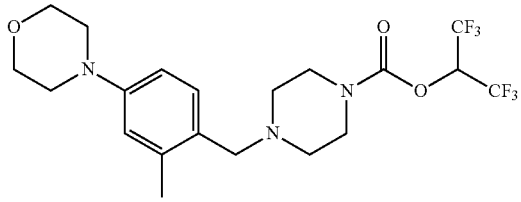 [SMILES: Cc1cc(N2CCOCC2)ccc1CN1CCN(C(=O)OC(C(F)(F)F)C(F)(F)F)CC1]

Step 1: Preparation of tert-butyl 4-(2-methyl-4-morpholinobenzyl)piperazine-1-carboxylate

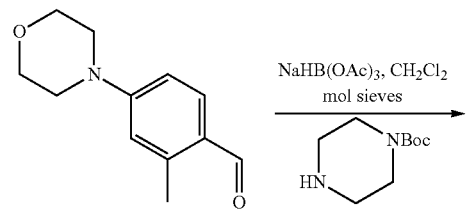

The title compound was prepared from 2-methyl-4-morpholinobenzaldehyde as described in Example 40, Step 1 (130 mg, 16%): ¹H NMR 400 MHz (CDCl₃) δ 7.14 (d, J=8.3 Hz, 1H), 6.78-6.73 (m, 1H), 6.71 (dd, J=8.3, 2.5 Hz, 1H), 3.91-3.84 (m, 4H), 3.41 (s, 6H), 3.20-3.13 (m, 4H), 2.37 (d, J=6.4 Hz, 7H), 1.48 (s, 9H), 1.28 (t, J=7.1 Hz, 1H).

Step 2: Preparation of 1,1,1,3,3,3-hexafluoropropan-2-yl 4-(2-methyl-4-morpholinobenzyl)piperazine-1-carboxylate (9p)

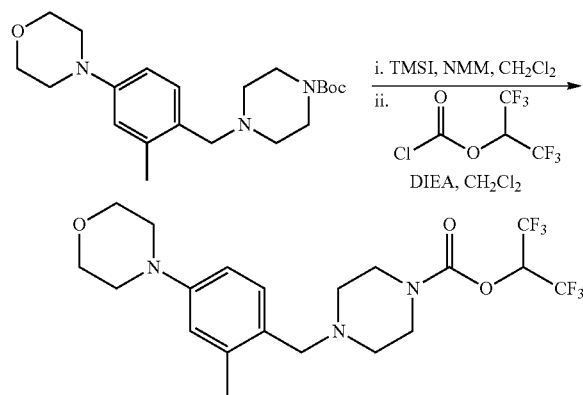

The title compound was prepared from 1 tert-butyl 4-(2-methyl-4-morpholinobenzyl)piperazine-1-carboxylate as described in Example 1, step 2 (25 mg, 20%). $^1$H NMR 400 MHz (CDCl$_3$) δ 7.13 (d, J=8.3 Hz, 1H), 6.80-6.70 (m, 3H), 5.78 (hept, J=6.3 Hz, 1H), 3.92-3.85 (m, 4H), 3.58-3.49 (m, 4H), 3.44 (s, 2H), 3.21-3.14 (m, 4H), 2.45 (dt, J=10.2, 4.9 Hz, 4H), 2.37 (s, 3H). LCMS (ESI, m/z): 470 [M+H]$^+$.

Example 56

1,1,1,3,3,3-hexafluoropropan-2-yl 4-(4-bromo-2-(piperidin-1-yl)benzyl)piperazine-1-carboxylate (9q)

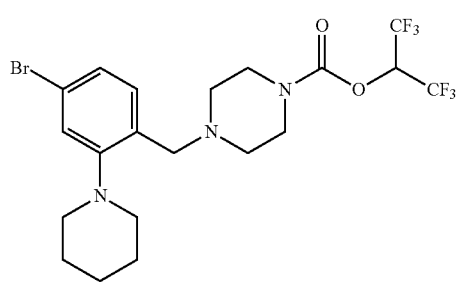 [SMILES: O=C(OC(C(F)(F)F)C(F)(F)F)N1CCN(Cc2ccc(Br)cc2N2CCCCC2)CC1]

Step 1: Preparation of 3-bromo-5-(piperidin-1-yl)benzaldehyde

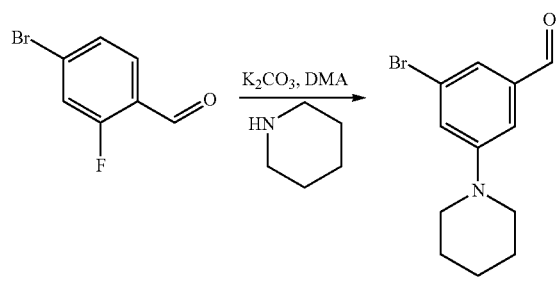 [SMILES: O=Cc1ccc(Br)cc1F ; C1CCNCC1 ; O=Cc1cc(Br)cc(N2CCCCC2)c1]

A 20 mL screwtop vial was charged with 4-bromo-2-fluorobenzaldehyde (200 mg, 0.985 mmol), piperadine (116 µL, 1.19 mmol), and DMA (1 mL). The reaction was heated to 120° C. for 3 h. The reaction was diluted in EtOAc and extracted with brine (3×). The organics were dried (Na$_2$SO$_4$), filtered, and concentrated under reduced pressure. The residue was chromatographed on a silica gel column (0% to 20% EtOAc in hexanes) and yielded 4-bromo-2-(pyrrolidin-1-yl)benzaldehyde (242 g, 92%). $^1$H NMR 400 MHz (CDCl$_3$) δ 10.21 (s, 1H), 7.66 (dd, J=8.3, 2.4 Hz, 1H), 7.31-7.17 (m, 2H), 4 (m, 4H), 1.78 (m, 4H), 1.71-1.60 (m, 2H). LCMS (ESI, m/z): 268 [M+H]$^+$.

Step 2: Preparation of tert-butyl 4-(4-bromo-2-(piperidin-1-yl)benzyl)piperazine-1-carboxylate

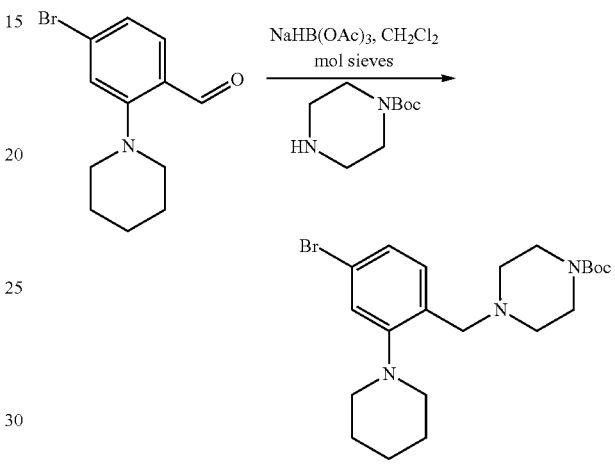

The title compound was prepared from 5-phenylisoxazole-3-carbaldehyde as described in Example 40, Step 1 (302 mg, 92%): $^1$H NMR 400 MHz (CDCl$_3$) δ 7.33 (d, J=8.7 Hz, 1H), 7.20-7.13 (m, 3H), 3.50 (s, 2H), 3.46-3.38 (m, 7H), 2.93-2.81 (m, 7H), 2.46-2.38 (m, 6H), 1.78-1.63 (m, 8H), 1.66-1.52 (m, 5H), 1.48 (s, 12H). LCMS (ESI, m/z): 538 [M+H]$^+$.

Step 3: Preparation of 1,1,1,3,3,3-hexafluoropropan-2-yl 4-(4-bromo-2-(piperidin-1-yl)benzyl)piperazine-1-carboxylate (9q)

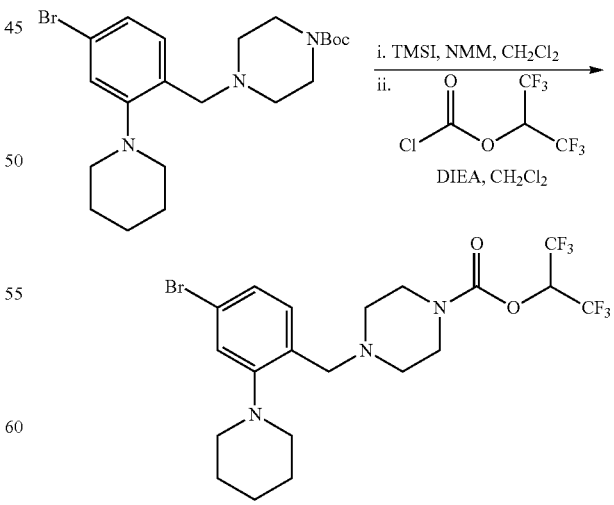

The title compound was prepared from tert-butyl 4-((5-phenylisoxazol-3-yl)methyl)piperazine-1-carboxylate as described in Example 1, step 2 (19 mg, 24%). $^1$H NMR 400

MHz (CDCl₃) δ 7.23 (d, J=8.1 Hz, 1H), 7.12-7.05 (m, 2H), 5.68 (hept, J=6.2 Hz, 1H), 3.51-3.42 (m, 6H), 2.79-2.71 (m, 4H), 2.45-2.35 (m, 4H), 1.67-1.46 (m, 5H). LCMS (ESI, m/z): 532 [M+H]⁺.

Example 57

1,1,1,3,3,3-hexafluoropropan-2-yl 4-(4-bromo-2-morpholinobenzyl)piperazine-1-carboxylate (9r)

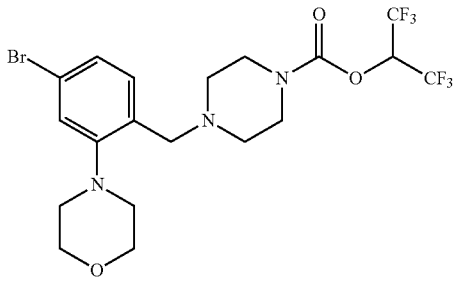 [SMILES: O=C(OC(C(F)(F)F)C(F)(F)F)N1CCN(Cc2ccc(Br)cc2N2CCOCC2)CC1]

Step 1: Preparation of 3-bromo-5-morpholinobenzaldehyde

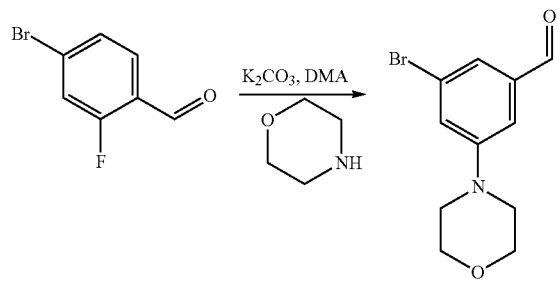 [SMILES: O=Cc1ccc(Br)cc1F ; C1COCCN1 ; O=Cc1cc(Br)cc(N2CCOCC2)c1]

The title compound was prepared from 4-bromo-2-fluorobenzaldehyde (200 mg, 0.985 mmol) as described in Example 56, Step 1 (180 mg, 68%). ¹H NMR 400 MHz (CDCl₃) δ 10.26 (s, 1H), 7.69 (dd, J=8.2, 2.7 Hz, 1H), 7.35-7.23 (m, 2H), 3.96-3.88 (m, 4H), 3.15-3.03 (m, 4H). LCMS (ESI, m/z): 270 [M+H]⁺.

Step 2: Preparation of tert-butyl 4-(4-bromo-2-morpholinobenzyl)piperazine-1-carboxylate

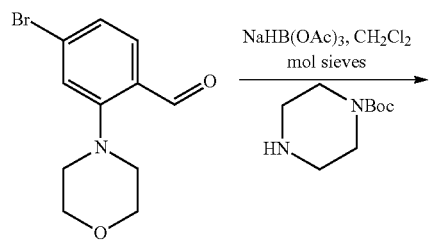

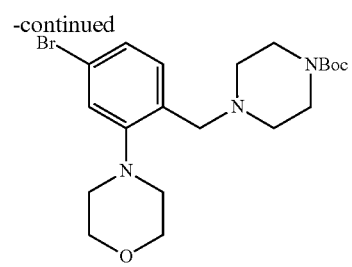

The title compound was prepared from 3-bromo-5-morpholinobenzaldehyde (200 mg, 0.741 mmol) as described in Example 40, Step 1 (230 mg, 71%). ¹H NMR 400 MHz (CDCl₃) δ 7.23 (d, J=8.0 Hz, 1H), 7.16-7.08 (m, 2H), 3.79-3.71 (m, 4H), 3.42 (s, 2H), 3.31 (m, 4H), 2.92-2.85 (m, 4H), 2.33 (m, 4H), 1.38 (s, 9H). LCMS (ESI, m/z): 440 [M+H]⁺.

Step 3: Preparation of 1,1,1,3,3,3-hexafluoropropan-2-yl 4-(4-bromo-2-morpholinobenzyl)piperazine-1-carboxylate (9r)

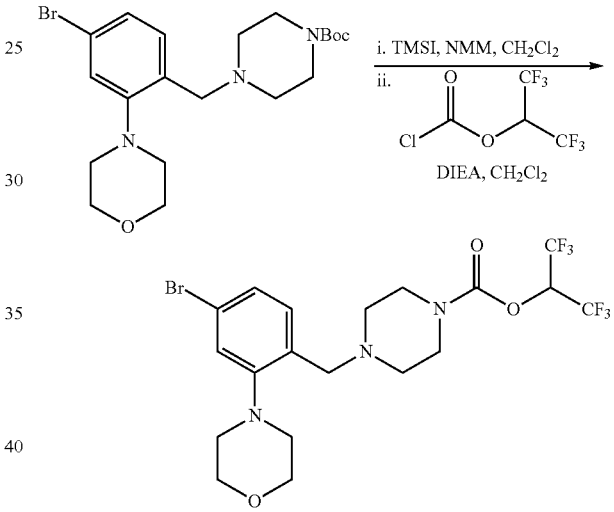

The title compound was prepared from tert-butyl 4-(4-bromo-2-morpholinobenzyl)piperazine-1-carboxylate (50 mg, 0.147 mmol) as described in Example 1, step 2 (22 mg, 28%). ¹H NMR 400 MHz (CDCl₃) δ 7.36-7.18 (m, 3H), 5.82-5.70 (m, 1H), 3.88-3.80 (m, 4H), 3.54 (s, 6H), 2.99-2.91 (m, 4H), 2.49 (s, 4H). LCMS (ESI, m/z): 535 [M+H]⁺.

Example 58

1,1,1,3,3,3-hexafluoropropan-2-yl 4-(2-methoxy-4-morpholinobenzyl)piperazine-1-carboxylate (9s)

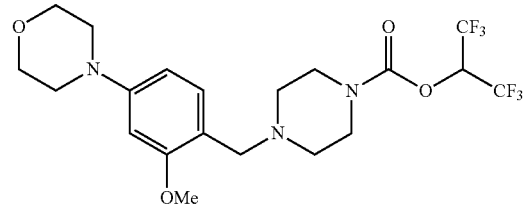 [SMILES: COc1cc(N2CCOCC2)ccc1CN1CCN(C(=O)OC(C(F)(F)F)C(F)(F)F)CC1]

The title compound was synthesized directly from commercially available 2-methoxy-4-morpholinobenzaldehyde and tert-butyl piperazine-1-carboxylate according to the representative procedure of Example 40: $^1$H NMR 400 MHz (CDCl$_3$) δ 7.16 (d, J=8.2 Hz, 1H), 6.55-6.37 (m, 2H), 5.74 (hept, J=6.3 Hz, 1H), 3.89-3.83 (m, 4H), 3.81 (s, 3H), 3.61-3.43 (m, 6H), 3.24-3.09 (m, 4H), 2.51-2.44 (m, 4H). LCMS (ESI, m/z): 206.1 (morpholino-2-methoxybenzyl cation)

Example 59

1,1,1,3,3,3-hexafluoropropan-2-yl 4-(4-chloro-2-morpholinobenzyl)piperazine-1-carboxylate (9t)

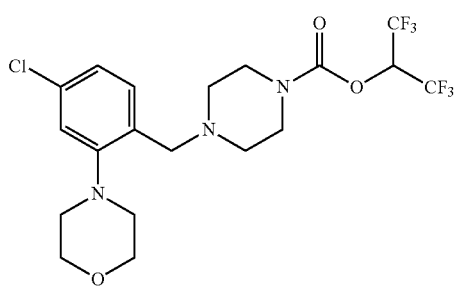 [SMILES: O=C(OC(C(F)(F)F)C(F)(F)F)N1CCN(Cc2ccc(Cl)cc2N2CCOCC2)CC1]

Step 1: Preparation of
3-chloro-5-morpholinobenzaldehyde

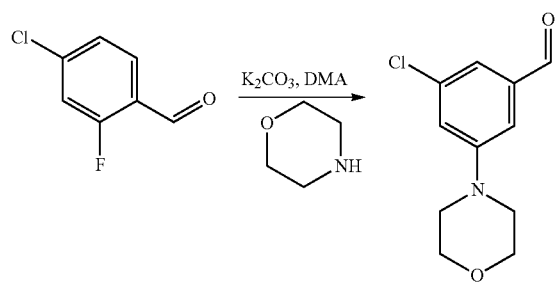 [SMILES: O=Cc1ccc(Cl)cc1F ; C1COCCN1 ; O=Cc1cc(Cl)cc(N2CCOCC2)c1]

The title compound was prepared from 4-chloro-2-fluorobenzaldehyde and morpholine as described in Example 56, Step 1 (2.21 g, 77%). $^1$H NMR 400 MHz (CDCl$_3$) δ 10.21 (s, 1H), 7.73 (d, J=8.3 Hz, 1H), 7.20-6.96 (m, 2H), 4.11-3.77 (m, 4H), 3.17-2.96 (m, 4H). LCMS (ESI, m/z): 226 [M+H]$^+$.

Step 2: Preparation of tert-butyl 4-(4-chloro-2-morpholinobenzyl)piperazine-1-carboxylate

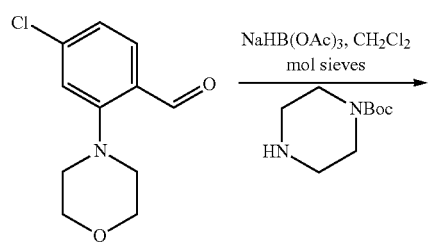

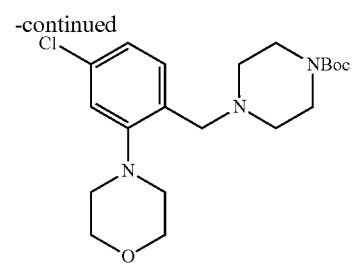

The title compound was prepared from 4-chloro-2-morpholinobenzaldehyde (2.21 g, 9.79 mmol) as described in Example 40, Step 1 (2.73 g, 70%). $^1$H NMR 400 MHz (CDCl$_3$) δ 7.38 (d, J=7.6 Hz, 1H), 7.11-7.04 (m, 3H), 3.88-3.82 (m, 8H), 3.53 (s, 3H), 3.43-3.37 (m, 6H), 3.02-2.95 (m, 8H), 2.42 (s, 4H), 1.48 (s, 9H). LCMS (ESI, m/z): 396 [M+H]$^+$.

Step 3: Preparation of 1,1,1,3,3,3-hexafluoropropan-2-yl 4-(4-chloro-2-morpholinobenzyl)piperazine-1-carboxylate (9t)

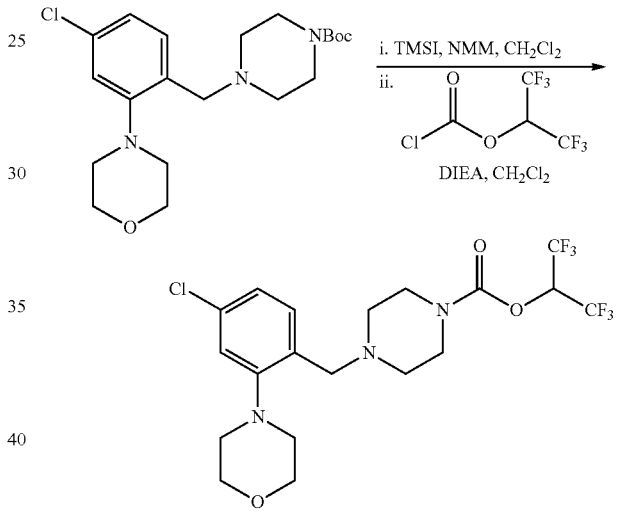

The title compound was prepared from tert-butyl 4-(4-chloro-2-morpholinobenzyl)piperazine-1-carboxylate as described in Example 1, step 2 (116 mg, 86%). $^1$H NMR 400 MHz (CDCl$_3$) δ 7.40-7.33 (m, 1H), 7.10-7.03 (m, 2H), 5.74 (h, J=6.3 Hz, 1H), 3.86-3.79 (m, 4H), 3.53 (d, J=7.0 Hz, 5H), 2.98-2.90 (m, 4H), 2.47 (dt, J=9.8, 5.1 Hz, 4H). LCMS (ESI, m/z): 490 [M+H]$^+$.

Example 60

1,1,1,3,3,3-hexafluoropropan-2-yl 4-(2-methyl-4-(pyrrolidin-1-yl)benzyl)piperazine-1-carboxylate (9u)

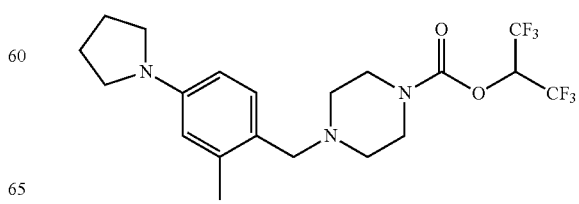

The title compound was synthesized directly from commercially available 2-methyl-4-(pyrrolidin-1-yl)benzaldehyde and tert-butyl piperazine-1-carboxylate according to the representative procedure of Example 40. ¹H NMR 400 MHz (CDCl₃) δ 7.02 (d, J=8.2 Hz, 1H), 6.45-6.29 (m, 2H), 5.75 (hept, J=6.2 Hz, 1H), 3.54-3.48 (m, 4H), 3.40 (s, 2H), 3.30-3.24 (m, 4H), 2.46-2.38 (m, 4H), 2.34 (s, 3H), 2.02-1.94 (m, 4H). LCMS (ESI, m/z): 454.1 [M+H]⁺.

Example 61

1,1,1,3,3,3-hexafluoropropan-2-yl 4-(4-methoxybenzyl)piperazine-1-carboxylate (9v)

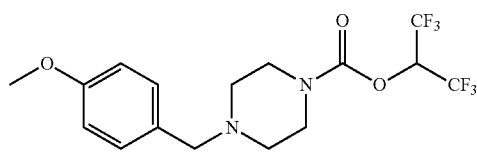 [SMILES: COc1ccc(CN2CCN(C(=O)OC(C(F)(F)F)C(F)(F)F)CC2)cc1]

The title compound was synthesized directly from commercially available 4-methoxybenzaldehyde and tert-butyl piperazine-1-carboxylate according to the representative procedure of Example 40: ¹H NMR 400 MHz (CDCl₃) δ 7.25-7.17 (m, 2H), 6.86 (dd, J=8.7, 2.2 Hz, 2H), 5.81-5.64 (hept, J=6.2 Hz, 1H), 3.80 (s, 3H), 3.59-3.49 (m, 4H), 3.46 (s, 2H), 2.49-2.35 (m, 4H). LCMS (ESI, m/z): 401.1 [M+H]⁺.

Example 62

1,1,1,3,3,3-hexafluoropropan-2-yl 4-(4-methylbenzyl)piperazine-1-carboxylate (9w)

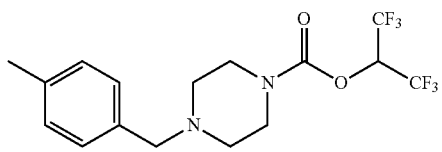 [SMILES: Cc1ccc(CN2CCN(C(=O)OC(C(F)(F)F)C(F)(F)F)CC2)cc1]

The title compound was synthesized directly from commercially available 4-methylbenzaldehyde and tert-butyl piperazine-1-carboxylate according to the representative procedure of Example 40: ¹H NMR 400 MHz (CDCl₃) δ 7.23-7.10 (m, 4H), 5.74 (hept, J=6.24 Hz, 1H) 3.58-3.52 (m, 4H), 3.49 (s, 2H), 2.48-2.41 (m, 4H), 2.34 (s, 3H). LCMS (ESI, m/z): 385.0 [M+H]⁺.

Example 63

1,1,1,3,3,3-hexafluoropropan-2-yl 4-(4-bromo-2-(pyrrolidin-1-yl)benzyl)piperazine-1-carboxylate (9x)

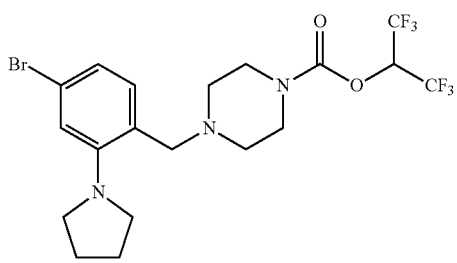

Step 1: Preparation of 4-bromo-2-(pyrrolidin-1-yl)benzaldehyde

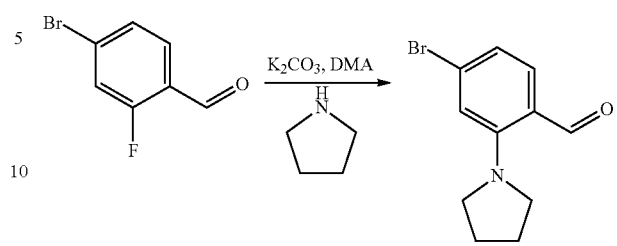

The title compound was prepared from 4-chloro-2-fluorobenzaldehyde and pyrroldine as described in Example 56, Step 1 (1.0 g, 80%). ¹H NMR 400 MHz (CDCl₃) δ 10.04 (d, J=1.2 Hz, 1H), 7.56 (dd, J=8.4, 1.5 Hz, 1H), 7.00 (d, J=1.4 Hz, 1H), 6.93 (dd, J=8.4, 1.5 Hz, 1H), 3.41-3.33 (m, 4H), 2.02 (tt, J=5.1, 2.1 Hz, 4H). LCMS (ESI, m/z): 254 [M+H]⁺.

Step 2: Preparation of tert-butyl 4-(4-bromo-2-(pyrrolidin-1-yl)benzyl)piperazine-1-carboxylate

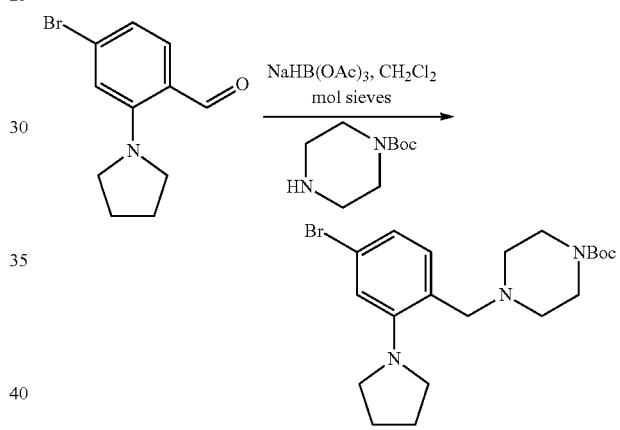

The title compound was prepared from 4-bromo-2-(pyrrolidin-1-yl)benzaldehyde as described in Example 40, Step 1 (1.2 g, 72%). ¹H NMR 400 MHz (CDCl₃) δ 7.31-7.23 (m, 1H), 7.02-6.93 (m, 2H), 3.50-3.37 (m, 6H), 3.23 (t, J=6.5 Hz, 4H), 2.39 (m, 4H), 1.99-1.88 (m, 4H), 1.47 (s, 9H). LCMS (ESI, m/z): 424 [M+H]⁺.

Step 3: Preparation of 1,1,1,3,3,3-hexafluoropropan-2-yl 4-(4-bromo-2-(pyrrolidin-1-yl)benzyl)piperazine-1-carboxylate (9x)

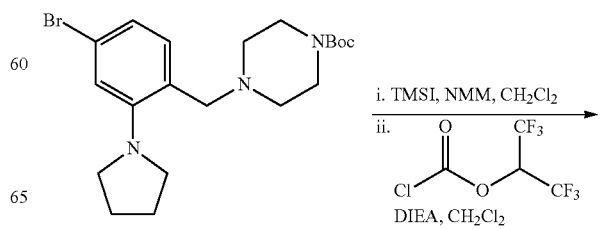

-continued

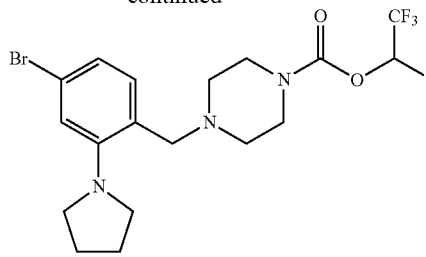

The title compound was prepared from tert-butyl 4-(4-bromo-2-(pyrrolidin-1-yl)benzyl)piperazine-1-carboxylate according to the representative procedures of Example 1, Step 2: $^1$H NMR 400 MHz (CDCl$_3$) δ 7.26 (dd, J=8.1, 3.7 Hz, 1H), 7.05-6.95 (m, 2H), 5.79 (hept, J=6.0 Hz, 1H), 3.62-3.44 (m, 6H), 3.27-3.18 (m, 4H), 2.53-2.41 (m, 4H), 2.01-1.88 (m, 4H). LCMS (ESI, m/z): 518 [M+H]$^+$.

Example 64

1,1,1,3,3,3-hexafluoropropan-2-yl 4-(2-morpholinobenzyl)piperazine-1-carboxylate (9y)

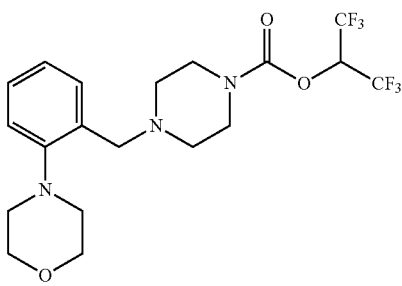 [SMILES: O=C(OC(C(F)(F)F)C(F)(F)F)N1CCN(Cc2ccccc2N2CCOCC2)CC1]

The title compound was synthesized directly from commercially available 2-morpholinobenzaldehyde and tert-butyl piperazine-1-carboxylate according to the representative procedure of Example 40: $^1$H NMR 400 MHz (CDCl$_3$) δ 7.44 (d, J=6.5 Hz, 1H), 7.36-7.26 (m, 4H), 7.13 (dd, J=13.2, 7.3 Hz, 2H), 5.78 (hept, J=6.3 Hz, 1H), 3.92-3.82 (m, 4H), 3.63 (s, 2H), 3.56-3.50 (m, 4H), 3.05-2.94 (m, 4H), 2.54-2.47 (m, 4H). LCMS (ESI, m/z): 456.1 [M+H]$^+$.

Example 65

1,1,1,3,3,3-hexafluoropropan-2-yl 4-(4-chloro-2-(pyrrolidin-1-yl)benzyl)piperazine-1-carboxylate (9z)

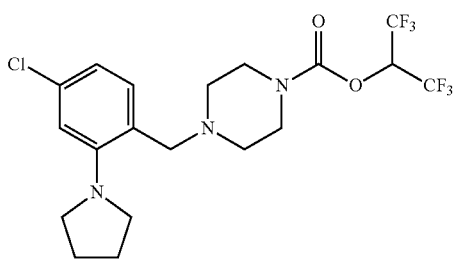 [SMILES: O=C(OC(C(F)(F)F)C(F)(F)F)N1CCN(Cc2ccc(Cl)cc2N2CCCC2)CC1]

Step 1: Preparation of 4-chloro-2-(pyrrolidin-1-yl)benzaldehyde

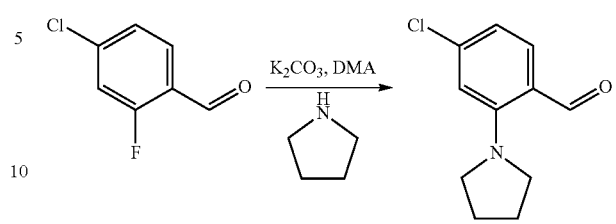

The title compound was prepared from 4-chloro-2-fluorobenzaldehyde and pyrroldine according to the representative procedures of Example 56, Step 1: $^1$H NMR 400 MHz (CDCl$_3$) δ 10.04 (s, 1H), 7.64 (d, J=8.1 Hz, 1H), 6.82 (s, 1H), 6.77 (d, J=8.4 Hz, 1H), 3.41-3.33 (m, 4H), 2.06-1.96 (m, 4H). LCMS (ESI, m/z): 210 [M+H]$^+$.

Step 2: Preparation of tert-butyl 4-(4-chloro-2-(pyrrolidin-1-yl)benzyl)piperazine-1-carboxylate

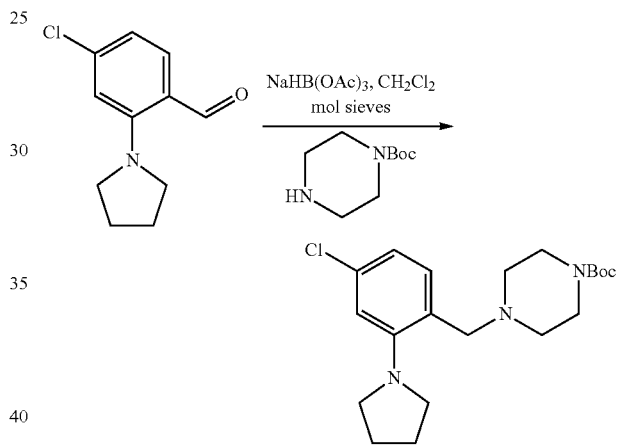

The title compound was prepared from tert-butyl 4-(4-chloro-2-(pyrrolidin-1-yl)benzyl)piperazine-1-carboxylate according to the representative procedures of Example 40, Step 1: $^1$H NMR 400 MHz (CDCl$_3$) δ 7.32 (d, J=8.2 Hz, 1H), 6.88-6.79 (m, 2H), 3.49 (s, 2H), 3.43 (t, J=4.9 Hz, 4H), 3.24 (ddd, J=6.5, 4.2, 2.1 Hz, 4H), 2.39 (d, J=6.0 Hz, 4H), 1.94 (td, J=5.5, 4.8, 2.9 Hz, 4H), 1.47 (d, J=1.4 Hz, 9H). LCMS (ESI, m/z): 380 [M+H]$^+$.

Step 3: Preparation of 1,1,1,3,3,3-hexafluoropropan-2-yl 4-(4-chloro-2-(pyrrolidin-1-yl)benzyl)piperazine-1-carboxylate (9z)

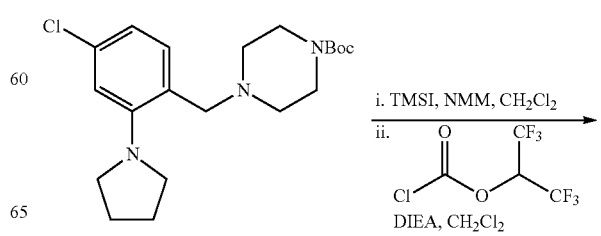

159

-continued

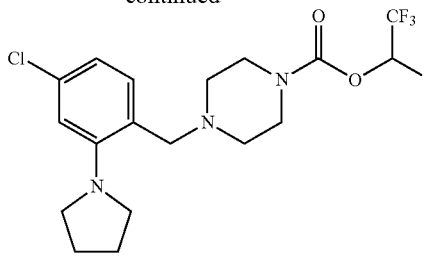

The title compound was prepared from tert-butyl 4-(4-chloro-2-(pyrrolidin-1-yl)benzyl)piperazine-1-carboxylate according to the representative procedures of Example 1, Step 2: $^1$H NMR 400 MHz (CDCl$_3$) δ 7.34-7.26 (m, 1H), 6.90-6.80 (m, 2H), 5.78 (hept, J=6.2 Hz, 1H), 3.61-3.54 (m, 4H), 3.52 (s, 2H), 3.27-3.19 (m, 4H), 2.47 (m, 4H), 2.00-1.87 (m, 4H). LCMS (ESI, an/z): 474 [M+H]$^+$.

Example 66

1,1,1,3,3,3-hexafluoropropan-2-yl 4-(3-fluoro-4-(pyrrolidin-1-yl)benzyl)piperazine-1-carboxylate (9aa)

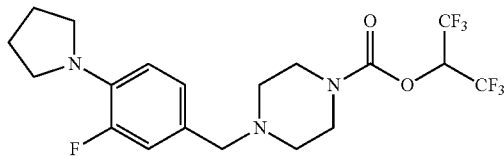 [SMILES: O=C(OC(C(F)(F)F)C(F)(F)F)N1CCN(Cc2ccc(N3CCCC3)c(F)c2)CC1]

The title compound was synthesized directly from commercially available 3-fluoro-4-(pyrrolidin-1-yl)benzaldehyde and tert-butyl piperazine-1-carboxylate according to the representative procedure of Example 40: $^1$H NMR 400 MHz (CDCl$_3$) δ 7.03-6.81 (m, 2H), 6.60 (t, J=8.7 Hz, 1H), 5.74 (hept, J=6.3 Hz, 1H), 3.563-3.53 (m, 4H), 3.46-3.29 (m, 6H), 2.51-2.36 (m, 4H), 2.06-1.83 (m, 4H). LCMS (ESI, m/z): 458.1 [M+H]$^+$.

Example 67

1,1,1,3,3,3-hexafluoropropan-2-yl 4-[[2-chloro-4-(pyrrolidin-1-yl)phenyl]methyl]piperazine-1-carboxylate (9ab)

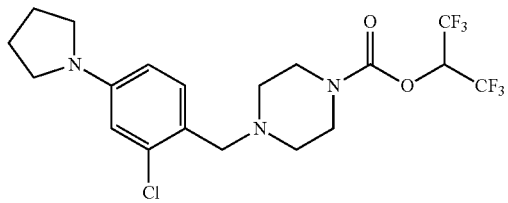 [SMILES: O=C(OC(C(F)(F)F)C(F)(F)F)N1CCN(Cc2ccc(N3CCCC3)cc2Cl)CC1]

160

Step 1: Preparation of 2-chloro-4-(pyrrolidin-1-yl)benzaldehyde

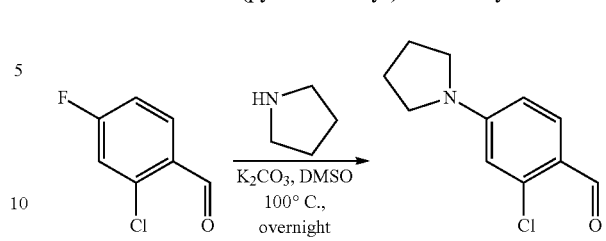

A 100 mL round-bottom flask was charged with 2-chloro-4-fluorobenzaldehyde (2.50 g, 15.8 mmol, 1.00 equiv), pyrrolidine (2.20 g, 30.9 mmol, 2.00 equiv), potassium carbonate (4.40 g, 31.8 mmol, 2.00 equiv), DMSO (50 mL). The resulting solution was stirred overnight at 100° C., diluted with H$_2$O (50 mL), extracted with ethyl acetate (3×30 mL). The organic layers were combined and washed with brine (100 mL), dried over anhydrous sodium sulfate and concentrated under reduced pressure. The residue was chromatographed on a silica gel column with ethyl acetate/petroleum ether (20/80) to provide 2.40 g (73% yield) of 2-chloro-4-(pyrrolidin-1-yl)benzaldehyde as a yellow solid. LCMS: (ESI, m/z): 210 [M+H]$^+$.

Step 2: Preparation of tert-butyl 4-[[2-chloro-4-(pyrrolidin-1-yl)phenyl]methyl]piperazine-1-carboxylate

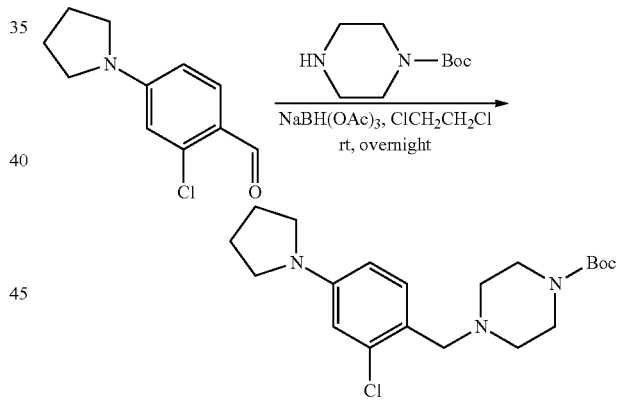

A 100 mL round-bottom flask was charged with 2-chloro-4-(pyrrolidin-1-yl)benzaldehyde (0.600 g, 2.86 mmol, 1.00 equiv), tert-butyl piperazine-1-carboxylate (0.590 g, 3.15 mmol, 1.10 equiv), 1,2-dichloroethane (15 mL). The mixture was stirred for 30 min at room temperature. Sodium triacetoxyborohydride (1.80 g, 8.49 mmol, 3.00 equiv) was added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The residue was chromatographed on a silica gel column with ethyl acetate/petroleum ether (20/80) to provide 0.900 g (83% yield) of tert-butyl 4-[[2-chloro-4-(pyrrolidin-1-yl)phenyl]methyl]piperazine-1-carboxylate as colorless oil. LCMS (ESI, m/z): 380 [M+H]⁺.

Step 3: Preparation of 1-[[2-chloro-4-(pyrrolidin-1-yl)phenyl]methyl]piperazine

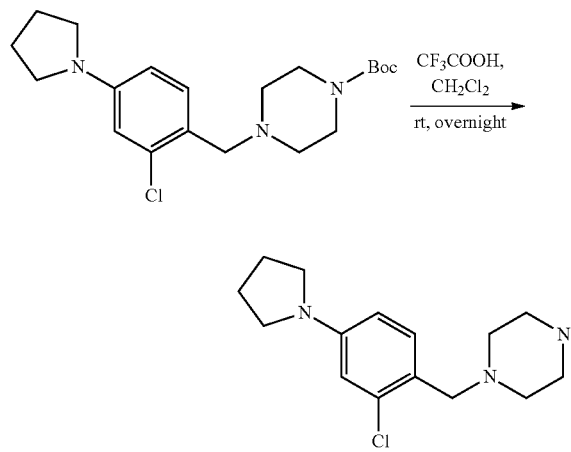

A 50 mL round-bottom flask was charged with tert-butyl 4-[[2-chloro-4-(pyrrolidin-1-yl)phenyl]methyl]piperazine-1-carboxylate (0.270 g, 0.710 mmol, 1.00 equiv), dichloromethane (10 mL). Trifluoroacetic acid (3.00 g, 26.3 mmol, 37.00 equiv) was added at 0° C. The resulting solution was stirred overnight at room temperature and concentrated under reduced pressure to yield 0.160 g (crude) of 1-[[2-chloro-4-(pyrrolidin-1-yl)phenyl]methyl]piperazine as yellow oil. LCMS (ESI, m/z): 280 [M+H]⁺.

Step 4: 1,1,1,3,3,3-hexafluoropropan-2-yl 4-[[2-chloro-4-(pyrrolidin-1-yl)phenyl]methyl]piperazine-1-carboxylate (9ab)

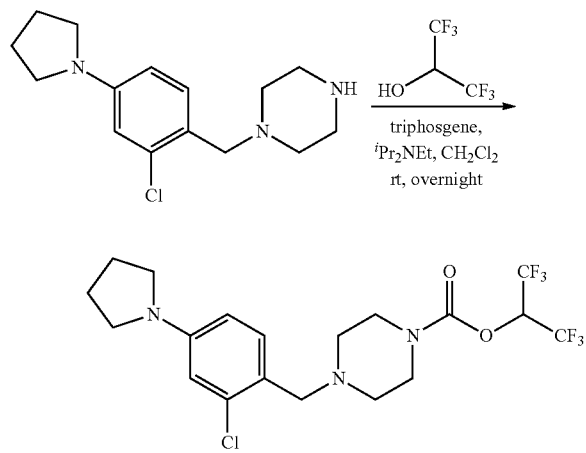

A 100 mL round-bottom flask was charged with triphosgene (119 mg, 0.400 mmol, 0.70 equiv), dichloromethane (15 mL). 1,1,1,3,3,3-Hexafluoropropan-2-ol (193 mg, 1.15 mmol, 2.00 equiv) and N-ethyl-N-isopropylpropan-2-amine (592 mg, 4.58 mmol, 8.00 equiv) were added at 0° C. The mixture was stirred for 2 h at room temperature. 1-[[2-chloro-4-(pyrrolidin-1-yl)phenyl]methyl]piperazine (160 mg, 0.570 mmol, 1.00 equiv) was added. The resulting solution was stirred overnight at room temperature, diluted with H₂O (10 mL), extracted with dichloromethane (3×10 mL). The organic layers were combined and washed with brine (50 mL), dried over anhydrous sodium sulfate and concentrated under reduced pressure. The crude product (300 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm 5 um; Mobile phase: Phase A: aqueous NH₄HCO₃ (0.05%); Phase B: CH₃CN; Detector, UV220 & 254 nm. Purification resulted in 106 mg (39% yield) of 1,1,1,3,3,3-hexafluoropropan-2-yl 4-[[2-chloro-4-(pyrrolidin-1-yl)phenyl]methyl]piperazine-1-carboxylate as yellow oil. ¹H NMR 300 MHz (CDCl₃) δ 7.18 (d, J=8.4 Hz, 1H), 6.54 (s, 1H), 6.40-6.44 (m, 1H), 5.71-5.80 (m, 1H), 3.54-3.56 (m, 6H), 3.23-3.33 (m, 4H), 2.47-2.52 (m, 4H), 1.96-2.04 (m, 4H). LCMS (ESI, m/z): 474 [M+H]⁺.

Example 68

1,1,1,3,3,3-hexafluoropropan-2-yl 4-[[2-chloro-6-(morpholin-4-yl)phenyl]methyl]piperazine-1-carboxylate (9ac)

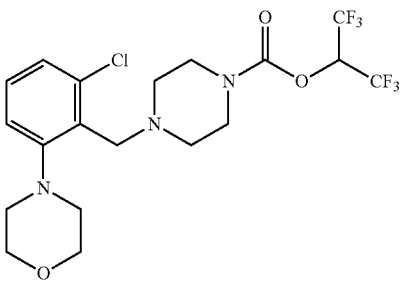 [SMILES: O=C(OC(C(F)(F)F)C(F)(F)F)N1CCN(Cc2c(Cl)cccc2N2CCOCC2)CC1]

Step 1: 2-chloro-6-(morpholin-4-yl)benzaldehyde

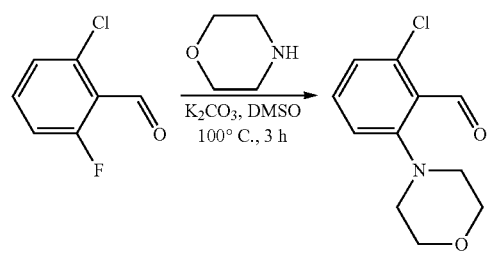 [SMILES: O=Cc1c(F)cccc1Cl ; C1COCCN1 ; O=Cc1c(Cl)cccc1N1CCOCC1]

A 100 mL round-bottom flask was charged with 2-chloro-6-fluorobenzaldehyde (8.00 g, 50.5 mmol, 1.00 equiv), morpholine (6.60 g, 75.8 mmol, 1.50 equiv), potassium carbonate (17.4 g, 126 mmol, 2.50 equiv), and dimethyl sulfoxide (50 mL). The resulting solution was stirred for 3 hour at 100° C. in an oil bath and then diluted with H₂O (50 mL). The resulting mixture was extracted with ethyl acetate (3×100 mL) and the organic layers were combined, washed with H₂O (2×50 mL), dried over anhydrous sodium sulfate, filtered and concentrated under reduced pressure. The residue was chromatographed on a silica gel column with ethyl acetate/petroleum ether (1/9) to yield 5.00 g (44%) of 2-chloro-6-(morpholin-4-yl)benzaldehyde as a yellow solid. LCMS (ESI, m/z): 226 [M+H]+.

Step 2: Preparation of tert-butyl 4-[[2-chloro-6-(morpholin-4-yl)phenyl]methyl]piperazine-1-carboxylate

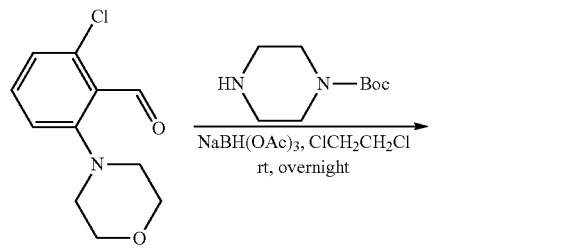

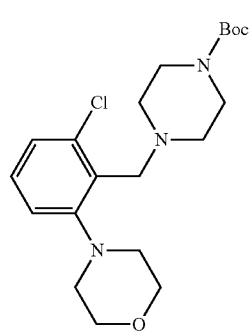

A 100 mL round-bottom flask was charged with 2-chloro-6-(morpholin-4-yl)benzaldehyde (1.34 g, 5.92 mmol, 1.00 equiv), tert-butyl piperazine-1-carboxylate (1.00 g, 5.37 mmol, 0.910 equiv), 1,2-dichloroethane (30 mL). The mixture was stirred at room temperature for 0.5 hour. Sodium triacetoxyborohydride (3.42 g, 16.1 mmol, 2.72 equiv) was added. The resulting solution was stirred overnight at room temperature and diluted with 1,2-dichloroethane (20 mL). The resulting mixture was washed with H$_2$O (2×30 mL), dried over anhydrous sodium sulfate, filtered and concentrated under reduced pressure. The residue was chromatographed on a silica gel column with ethyl acetate/petroleum ether (1/2) to yield 1.80 g (77% yield) of tert-butyl 4-[[2-chloro-6-(morpholin-4-yl)phenyl]methyl]piperazine-1-carboxylate as colorless oil. LCMS (ESI, m/z): 396 [M+H]+.

Step 3: Preparation of 4-[3-chloro-2-(piperazin-1-ylmethyl)phenyl]morpholine

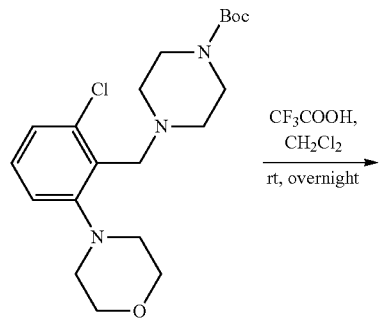

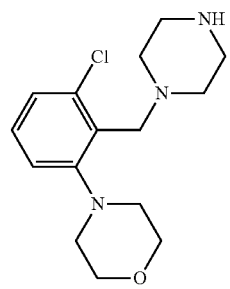

A 50 mL round-bottom flask was charged with tert-butyl 4-[[2-chloro-6-(morpholin-4-yl)phenyl]methyl]piperazine-1-carboxylate (1.80 g, 4.55 mmol, 1.00 equiv), dichloromethane (30 mL). The mixture was cooled to 0° C. and then trifluoroacetic acid (5 mL) was added dropwise at 0° C. The resulting solution was stirred overnight at room temperature and concentrated under reduced pressure to provide 0.990 g (crude) of 4-[3-chloro-2-(piperazin-1-ylmethyl)phenyl]morpholine as light yellow oil. LCMS (ESI, m/z): 296 [M+H]+.

Step 4: Preparation of 1,1,1,3,3,3-hexafluoropropan-2-yl 4-[[2-chloro-6-(morpholin-4-yl)phenyl]methyl]piperazine-1-carboxylate (9ac)

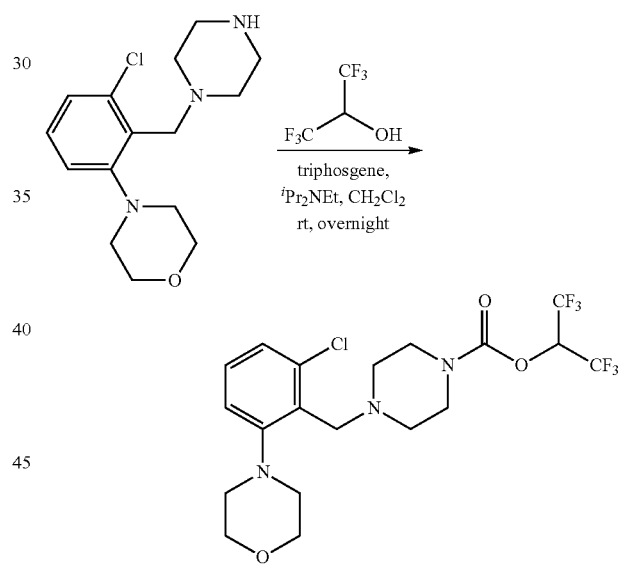

A 50 mL round-bottom flask was charged with 1,1,1,3,3,3-hexafluoropropan-2-ol (168 mg, 1.00 mmol, 0.99 equiv), triphosgene (99.0 mg, 0.330 mmol, 0.330 equiv), dichloromethane (10 mL). N,N-Diisopropylethylamine (471 mg, 3.64 mmol, 3.59 equiv) was added dropwise. The mixture was stirred at room temperature for 2 hours. 4-[3-Chloro-2-(piperazin-1-ylmethyl)phenyl]morpholine (300 mg, 1.01 mmol, 1.00 equiv) was added. The resulting solution was stirred for 2 hours at room temperature and diluted with H$_2$O (30 mL). The resulting solution was extracted with dichloromethane (3×10 mL) and the organic layers were combined, dried over anhydrous sodium sulfate, filtered and concentrated under reduced pressure. The residue was chromatographed on a silica gel column with ethyl acetate/petroleum ether (1/1). The crude product (204 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 273 mg (55% yield) of 1,1,1,3,3,3-hexafluoropropan-2-yl 4-[[2-chloro-6-(morpholin-4-yl)phenyl]methyl]piperazine-1-carboxylate as light yellow oil. $^1$H NMR 300 MHz (CDCl$_3$) δ 7.17-7.25 (m, 1H), 7.09-7.12 (m, 2H), 5.73-5.86 (m, 1H), 3.78-3.84 (m, 6H), 3.47 (d, J=6.0 Hz, 4H), 3.00 (br, 4H), 2.60 (br, 4H). LCMS (ESI, m/z): 490 [M+H]$^+$.

Example 69

1,1,1,3,3,3-hexafluoropropan-2-yl 4-[[3-chloro-2-(morpholin-4-yl)phenyl]methyl]piperazine-1-carboxylate (ad)

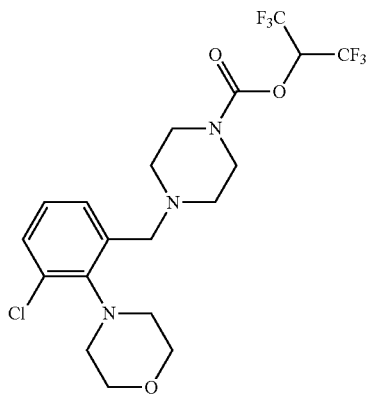 [SMILES: O=C(OC(C(F)(F)F)C(F)(F)F)N1CCN(Cc2cccc(Cl)c2N2CCOCC2)CC1]

Step 1: Preparation of 3-chloro-2-(morpholin-4-yl)benzaldehyde

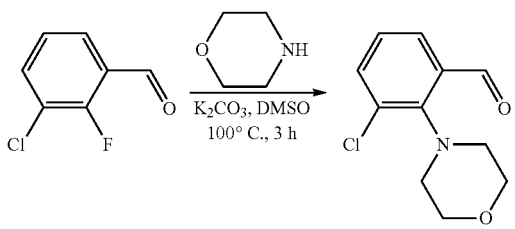

A 100 mL round-bottom flask was charged with 3-chloro-2-fluorobenzaldehyde (3.00 g, 18.9 mmol, 1.00 equiv), morpholine (2.50 g, 28.7 mmol, 1.52 equiv), potassium carbonate (6.50 g, 47.0 mmol, 2.49 equiv), and dimethyl sulfoxide (30 mL). The resulting solution was stirred for 3 hours at 100° C. in an oil bath and diluted with H$_2$O (30 mL). The resulting solution was extracted with dichloromethane (3×20 mL) and the organic layers were combined, washed with H$_2$O (2×50 mL), dried over anhydrous sodium sulfate, filtered and concentrated under reduced pressure. The residue was chromatographed on a silica gel column with ethyl acetate/petroleum ether (1/20) to provide 1.40 g (33% yield) of 3-chloro-2-(morpholin-4-yl)benzaldehyde as a yellow solid. LCMS (ESI, m/z): 226 [M+H]$^+$.

Step 2: Preparation of tert-butyl 4-[[3-methyl-2-(morpholin-4-yl)phenyl]methyl]piperazine-1-carboxylate

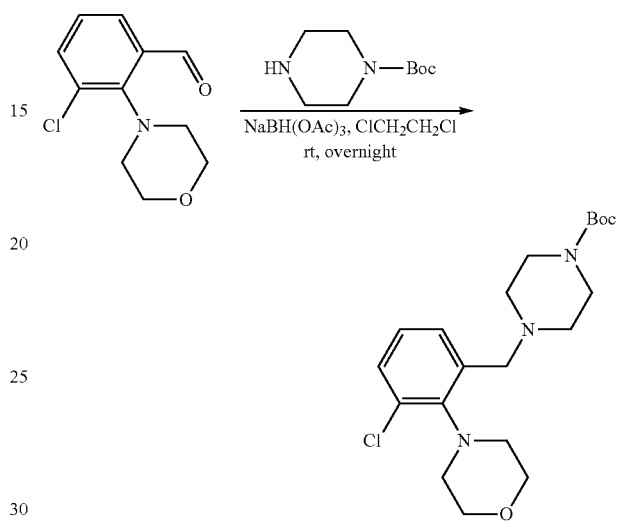

A 100 mL round-bottom flask was charged with 3-methyl-2-(morpholin-4-yl)benzaldehyde (1.34 g, 6.51 mmol, 1.00 equiv), tert-butyl piperazine-1-carboxylate (1.00 g, 5.37 mmol, 0.82 equiv), 1,2-dichloromethane (30 mL). The mixture was stirred at room temperature for 0.5 hour. Sodium triacetoxyborohydride (3.42 g, 16.1 mmol, 2.48 equiv) was added. The resulting solution was stirred for 2 h at room temperature and diluted with 1,2-dichloromethane (30 mL). The resulting solution was washed with H$_2$O (2×30 mL), dried over anhydrous sodium sulfate, filtered and concentrated under reduced pressure. The residue was chromatographed on a silica gel column with ethyl acetate/petroleum ether (1/3) to provide 0.800 g (34% yield) of tert-butyl 4-[[3-methyl-2-(morpholin-4-yl)phenyl]methyl]piperazine-1-carboxylate as light red oil. LCMS (ESI, m/z): 396 [M+H]$^+$.

Step 3: Preparation of 4-[2-chloro-6-(piperazin-1-ylmethyl)phenyl]morpholine

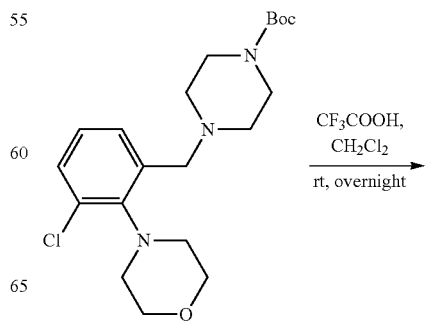

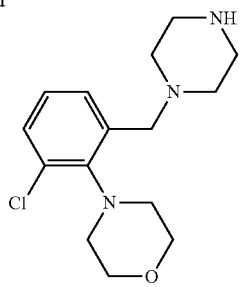

A 50 mL round-bottom flask was charged with tert-butyl 4-[[3-chloro-2-(morpholin-4-yl)phenyl]methyl]piperazine-1-carboxylate (800 mg, 2.02 mmol, 1.00 equiv), dichloromethane (15 mL). The mixture was cooled to 0° C. Trifluoroacetic acid (2.5 mL) was added dropwise at 0° C. The resulting solution was stirred overnight at room temperature and concentrated under reduced pressure to yield 580 mg (crude) of 4-[2-chloro-6-(piperazin-1-ylmethyl)phenyl]morpholine as colorless oil. LCMS (ESI, m/z): 296 [M+H]$^+$.

Step 4: Preparation of 1,1,1,3,3,3-hexafluoropropan-2-yl 4-[[3-chloro-2-(morpholin-4-yl)phenyl]methyl]piperazine-1-carboxylate (9ad)

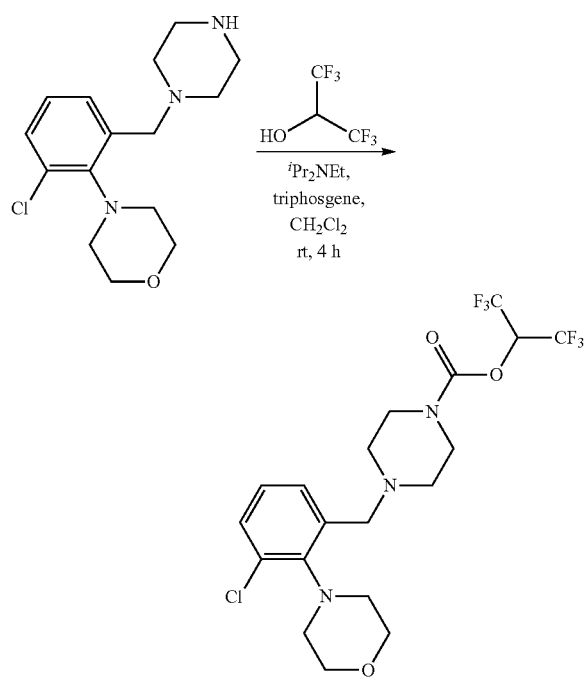

A 50 mL round-bottom flask was charged with 1,1,1,3,3,3-hexafluoropropan-2-ol (168 mg, 1.00 mmol, 1.02 equiv), triphosgene (99.0 mg, 0.330 mmol, 0.33 equiv), dichloromethane (10 mL). N,N-Diisopropylethylamine (471 mg, 3.64 mmol, 3.72 equiv) was added dropwise. The mixture was stirred at room temperature for 2 hours. 4-[2-Chloro-6-(piperazin-1-ylmethyl)phenyl]morpholine (290 mg, 0.980 mmol, 1.00 equiv) was added dropwise. The resulting solution was stirred for 2 hours at room temperature and diluted with water (20 mL). The resulting solution was extracted with dichloromethane (3×10 mL) and the organic layers were combined, dried over anhydrous sodium sulfate, filtered and concentrated under reduced pressure. The residue was chromatographed on a silica gel column with ethyl acetate/petroleum ether (1/1). The crude product (313 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 134 mg (27% yield) of 1,1,1,3,3,3-hexafluoropropan-2-yl 4-[[3-chloro-2-(morpholin-4-yl)phenyl]methyl]piperazine-1-carboxylate as light yellow oil. $^1$H NMR 300 MHz (CDCl$_3$) δ 7.27 (d, J=3.0 Hz, 2H), 7.06-7.11 (m, 1H), 5.71-5.84 (m, 1H), 3.87-3.90 (m, 2H), 3.53-3.78 (m, 10H), 2.78 (d, J=10.8 Hz, 2H), 2.48-2.49 (m, 4H). LCMS (ESI, m/z): 490 [M+H]$^+$.

Example 70

1,1,1,3,3,3-hexafluoropropan-2-yl 4-(4-chloro-2-(1H-pyrazol-1-yl)benzyl)piperazine-1-carboxylate (9ae)

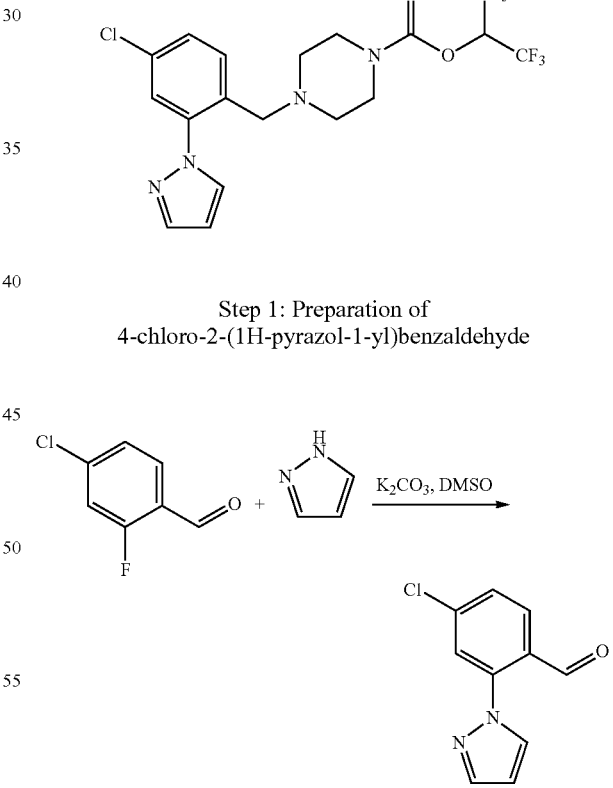

Step 1: Preparation of 4-chloro-2-(1H-pyrazol-1-yl)benzaldehyde

A 20 mL vial with a screw-top was charged with 4-bromo-2-fluorobenzaldehyde (500 mg, 2.70 mmol), pyrazole (258 mg, 3.79 mmol), and DMSO (3 mL). The reaction was heated to 120° C. for 3.5 h. The reaction was diluted in EtOAc and extracted with brine (3×). The organics were dried (Na$_2$SO$_4$), filtered, and concentrated under reduced pressure. The residue was chromatographed on a silica gel column (0 to 10%

EtOAc in hexanes) and yielded 4-chloro-2-(1H-pyrazol-1-yl)benzaldehyde (350 mg, 46%). $^1$H NMR 400 MHz (CDCl$_3$) δ 10.04 (s, 1H), 7.98 (d, J=8.4 Hz, 1H), 7.86 (d, J=2.5 Hz, 1H), 7.82 (d, J=1.8 Hz, 1H), 7.53 (d, J=1.9 Hz, 1H), 7.48 (ddd, J=8.4, 1.9, 0.7 Hz, 1H), 6.58 (t, J=2.2 Hz, 1H). LCMS (ESI, m/z): 207 [M+H]$^+$.

Step 2: Preparation of tert-butyl 4-(4-chloro-2-(1H-pyrazol-1-yl)benzyl)piperazine-1-carboxylate

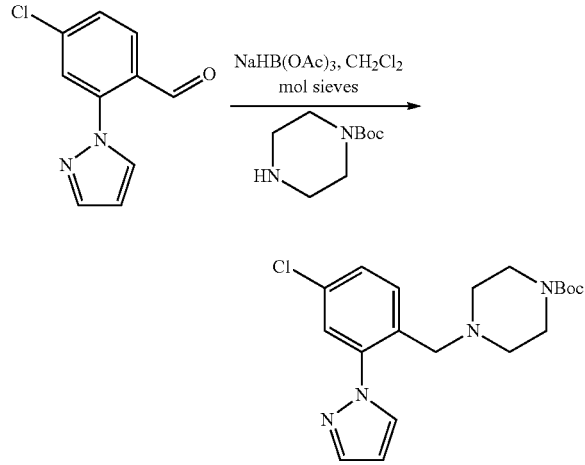

The title compound was prepared from 4-chloro-2-(1H-pyrazol-1-yl)benzaldehyde (180 mg, 0.871 mmol) as described in Example 40, Step 1 (210 mg, 64%). $^1$H NMR 400 MHz (CDCl$_3$) δ 7.93 (d, J=2.4 Hz, 1H), 7.71-7.68 (m, 2H), 7.44 (dd, J=5.2, 3.0 Hz, 3H), 7.32 (dd, J=8.3, 2.1 Hz, 1H), 6.41 (dd, J=2.8, 1.4 Hz, 2H), 3.43-3.29 (m, 9H), 2.34-2.26 (m, 7H), 1.42 (s, 11H). LCMS (ESI, m/z): 377 [M+H]$^+$.

Step 3: Preparation of 1,1,1,3,3,3-hexafluoropropan-2-yl 4-(4-chloro-2-(1H-pyrazol-1-yl)benzyl)piperazine-1-carboxylate (9ae)

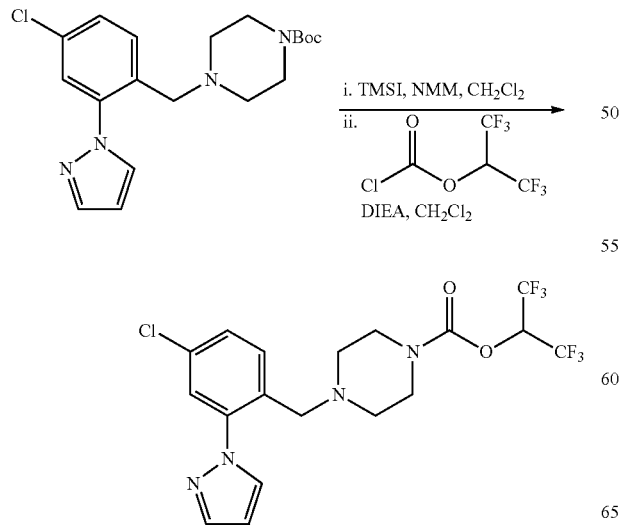

The title compound was prepared from tert-butyl 4-(4-chloro-2-(1H-pyrazol-1-yl)benzyl)piperazine-1-carboxylate (52 mg, 0.158) as described in Example 1, step 2, (38 mg, 53%). $^1$H NMR 400 MHz (CDCl$_3$) δ 7.88 (d, J=2.3 Hz, 1H), 7.73 (d, J=1.7 Hz, 1H), 7.50-7.44 (m, 2H), 7.38 (dd, J=8.2, 2.2 Hz, 1H), 6.49-6.43 (m, 1H), 5.74 (hept, J=6.2 Hz, 1H), 3.54-3.44 (m, 6H), 2.44-2.34 (m, 4H). LCMS (ESI, m/z): 471 [M+H]$^+$.

Example 71

1,1,1,3,3,3-hexafluoropropan-2-yl 4-(2-(3-acetamidopyrrolidin-1-yl)-4-chlorobenzyl)piperazine-1-carboxylate (9af)

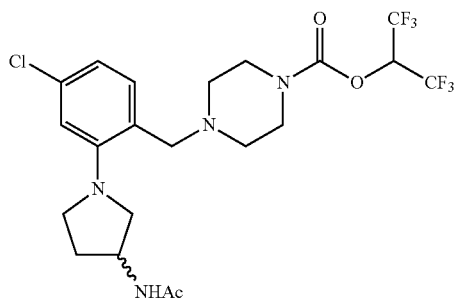 [SMILES: CC(=O)NC1CCN(c2cc(Cl)ccc2CN2CCN(C(=O)OC(C(F)(F)F)C(F)(F)F)CC2)C1]

Step 1: Preparation of N-(1-(5-chloro-2-formylphenyl)pyrrolidin-3-yl)acetamide

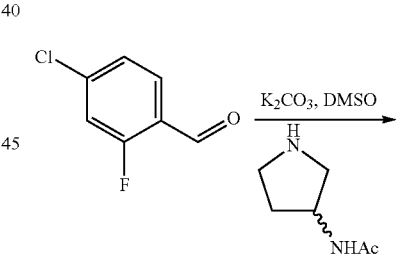

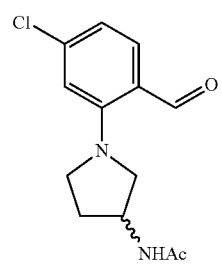

The title compound was prepared from 4-chloro-2-fluorobenzaldehyde (500 mg, 3.15 mmol) as described in Example 70, Step 1 (646 mg, 77%). $^1$H NMR 400 MHz (CDCl$_3$) δ 9.95 (s, 1H), 7.62 (d, J=8.3 Hz, 1H), 6.91-6.75 (m, 2H), 6.66 (s, 1H), 4.62-4.52 (m, 1H), 3.61-3.50 (m, 2H), 3.37-3.22 (m, 2H), 2.35-2.21 (m, 1H), 2.06-2.00 (m, 2H), 1.99 (s, 3H). LCMS (ESI, m/z): 267 [M+H]+.

Step 2: Preparation of tert-butyl 4-(2-(3-acetamidopyrrolidin-1-yl)-4-chlorobenzyl)piperazine-1-carboxylate

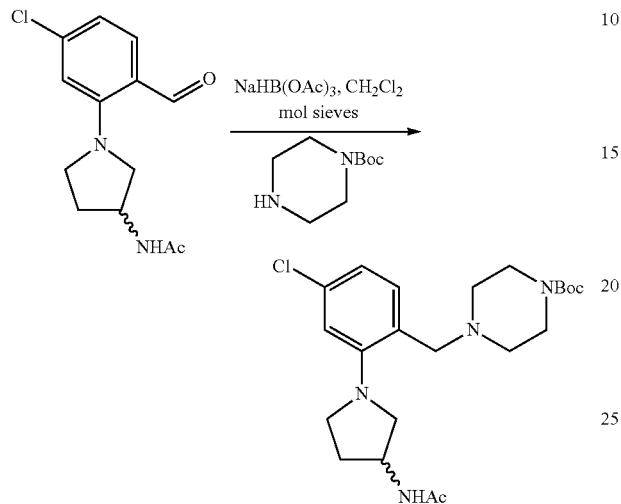

The title compound was prepared from N-(1-(5-chloro-2-formylphenyl)pyrrolidin-3-yl)acetamide as described in Example 40, Step 1 (346 mg, 33%). $^1$H NMR 400 MHz (CDCl$_3$) δ 7.27 (d, J=8.5 Hz, 1H), 6.90-6.80 (m, 3H), 6.14 (d, J=7.3 Hz, 1H), 4.64-4.45 (m, 1H), 3.49-3.34 (m, 8H), 3.20-3.07 (m, 2H), 2.42-2.34 (m, 4H), 2.34-2.23 (m, 1H), 1.98 (s, 3H), 1.90-1.78 (m, 1H), 1.45 (s, 9H). LCMS (ESI, m/z): 437 [M+H]+.

Step 3: Preparation of 1,1,1,3,3,3-hexafluoropropan-2-yl 4-(2-(3-acetamidopyrrolidin-1-yl)-4-chlorobenzyl)piperazine-1-carboxylate (9af)

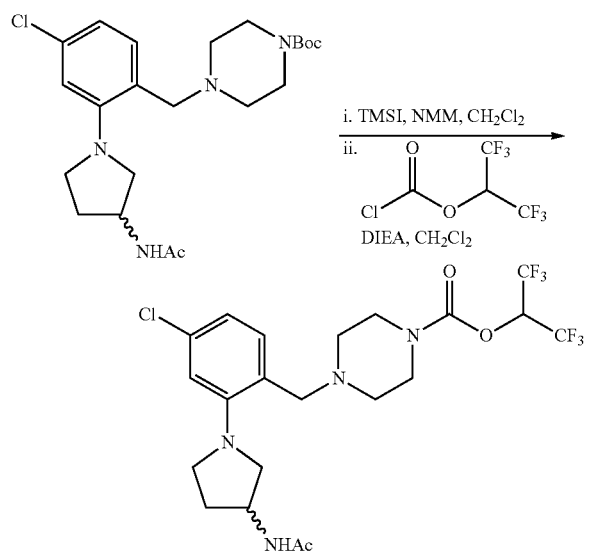

The title compound was prepared from tert-butyl 4-(2-(3-acetamidopyrrolidin-1-yl)-4-chlorobenzyl)piperazine-1-carboxylate as described in Example 1, step 2 (35 mg, 62%). $^1$H NMR 400 MHz (CDCl$_3$) δ 7.32-7.26 (m, 1H), 6.89 (dd, J=8.1, 2.0 Hz, 1H), 6.85 (d, J=2.0 Hz, 1H), 5.89 (d, J=7.0 Hz, 1H), 5.76 (hept, J=6.2 Hz, 1H), 4.61-4.48 (m, 1H), 3.60-3.52 (m, 4H), 3.51-3.43 (m, 3H), 3.38 (m, 1H), 3.15 (td, J=8.6, 5.3 Hz, 2H), 2.50-2.40 (m, 4H), 2.32 (m, 1H), 1.99 (s, 3H), 1.91-1.78 (m, 1H). LCMS (ESI, m/z): 531 [M+H]+.

Example 72

1,1,1,3,3,3-hexafluoropropan-2-yl 4-[[5-chloro-2-(morpholin-4-yl)phenyl]methyl]piperazine-1-carboxylate (ag)

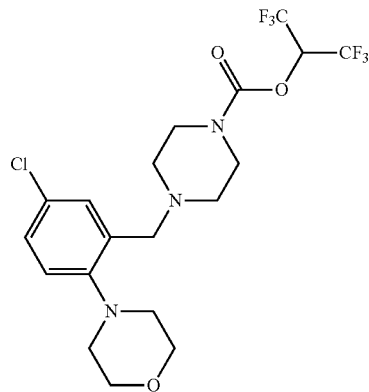 [SMILES: O=C(OC(C(F)(F)F)C(F)(F)F)N1CCN(Cc2cc(Cl)ccc2N2CCOCC2)CC1]

Step 1: Preparation of 5-chloro-2-(morpholin-4-yl)benzaldehyde

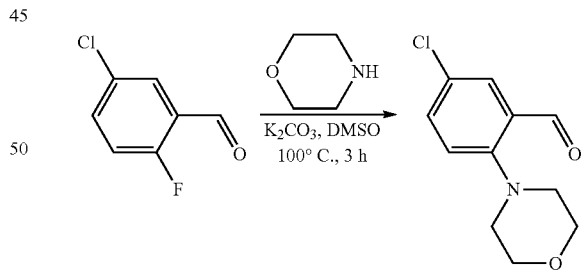

A 50 mL round-bottom flask was charged with 5-chloro-2-fluorobenzaldehyde (3.00 g, 18.9 mmol, 1.00 equiv), morpholine (2.50 g, 28.7 mmol, 1.52 equiv), potassium carbonate (6.50 g, 47.0 mmol, 2.49 equiv), methyl sulfoxide (20 mL). The resulting solution was stirred overnight at 100° C. in an oil bath and diluted with H$_2$O (50 mL). The resulting solution was extracted with dichloromethane (3×20 mL) and the organic layers were combined, washed with H$_2$O (2×50 mL), dried over anhydrous sodium sulfate, filtered and concentrated under reduced pressure. The residue was chromatographed on a silica gel column with ethyl acetate/petroleum ether (1/9) to provide 3.24 g (76% yield) of 5-chloro-2-(morpholin-4-yl)benzaldehyde as brown oil. LCMS (ESI, m/z): 226 [M+H]$^+$.

Step 2: Preparation of tert-butyl 4-[[5-chloro-2-(morpholin-4-yl)phenyl]methyl]piperazine-1-carboxylate

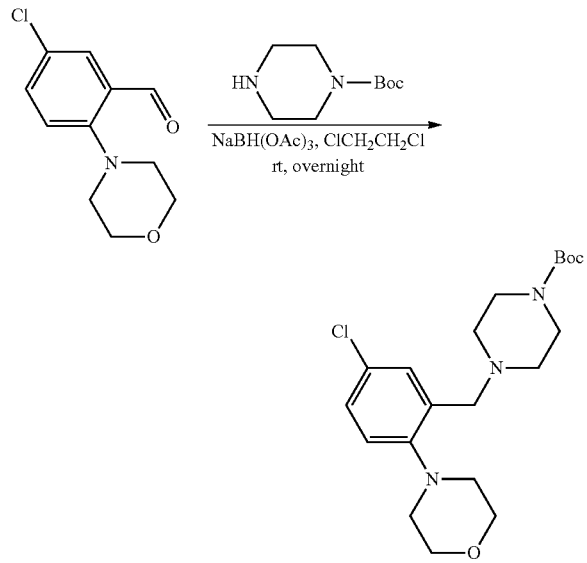

A round-bottom flask was charged with 5-chloro-2-(morpholin-4-yl)benzaldehyde (1.60 g, 7.09 mmol, 1.00 equiv), tert-butyl piperazine-1-carboxylate (1.20 g, 6.43 mmol, 0.910 equiv), 1,2-dichloromethane (20 mL). The mixture was stirred at room temperature for 0.5 hour. Sodium triacetoxyborohydride (4.09 g, 19.3 mmol, 2.72 equiv) was added. The resulting solution was stirred overnight at room temperature and diluted with H$_2$O (50 mL). The resulting solution was extracted with dichloromethane (2×20 mL), the organic layers were combined, dried over anhydrous sodium sulfate, filtered and concentrated under reduced pressure. The residue was chromatographed on a silica gel column with ethyl acetate/petroleum ether (1/4) to yield 2.90 g (crude) of tert-butyl 4-[[5-chloro-2-(morpholin-4-yl)phenyl]methyl]piperazine-1-carboxylate as yellow oil. LCMS (ESI, m/z): 396 [M+H]$^+$.

Step 3: 4-[4-chloro-2-(piperazin-1-ylmethyl)phenyl]morpholine

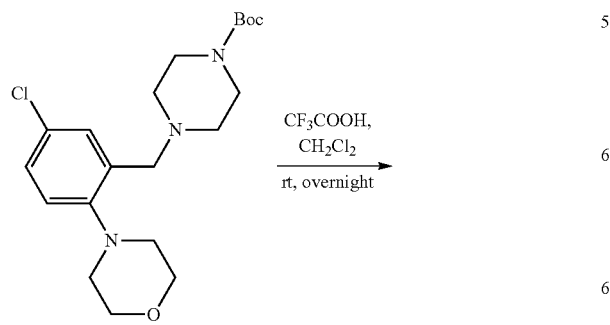

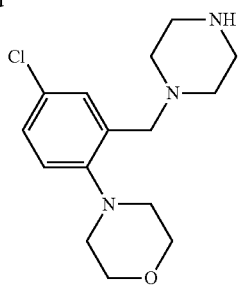

A 100 mL round-bottom flask was charged with tert-butyl 4-[[5-chloro-2-(morpholin-4-yl)phenyl]methyl]piperazine-1-carboxylate (2.90 g, 7.32 mmol, 1.00 equiv), dichloromethane (35 mL). The mixture was cooled to 0° C. and trifluoroacetic acid (7 mL) was added dropwise. The resulting solution was stirred overnight at room temperature. The resulting solution was concentrated under reduced pressure to yield 2.60 g (crude) of 4-[4-chloro-2-(piperazin-1-ylmethyl)phenyl]morpholine as light yellow oil. LCMS (ESI, m/z): 296 [M+H]$^+$.

Step 4: 1,1,1,3,3,3-hexafluoropropan-2-yl 4-[[5-chloro-2-(morpholin-4-yl)phenyl]methyl]piperazine-1-carboxylate (ag)

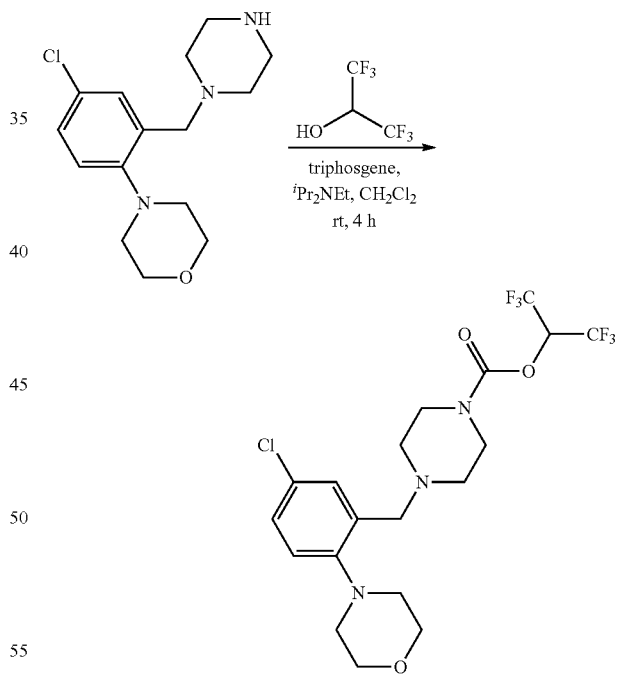

A 50 mL round-bottom flask was charged with 1,1,1,3,3,3-hexafluoropropan-2-ol (168 mg, 1.00 mmol, 1.00 equiv), triphosgene (99.0 mg, 0.330 mmol, 0.33 equiv), dichloromethane (10 mL). N,N-Diisopropylethylamine (417 mg, 3.23 mmol, 3.18 equiv) was added dropwise. The mixture was stirred for 2 hours at room temperature. 4-[4-Chloro-2-(piperazin-1-ylmethyl)phenyl]morpholine (300 mg, 1.01 mmol, 1.00 equiv) was added dropwise. The resulting solution was stirred for 2 hours at room temperature and diluted with water (20 mL). The resulting solution was extracted with dichloromethane (2×10 mL) and the organic layers were combined, dried over anhydrous sodium sulfate, filtered and concentrated under reduced pressure. The residue was chromatographed on a silica gel column with ethyl acetate/petroleum ether (1/3). The crude product (206 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 aqueous NH$_4$HCO$_3$ (0.05%); Phase B: CH$_3$CN; Detector, UV220 & 254 nm. Purification resulted in 91.9 mg (18% yield) of 1,1,1,3,3,3-hexafluoropropan-2-yl 4-[[5-chloro-2-(morpholin-4-yl)phenyl]methyl]piperazine-1-carboxylate as a white solid. $^1$HNMR 300 MHz (CDCl$_3$) δ 7.45 (s, 1H), 7.23 (d, J=9.0 Hz, 1H), 7.04 (d, J=9.0 Hz, 1H), 5.69-5.81 (m, 1H), 3.81-3.84 (m, 4H), 3.56 (br, 6H), 2.88-2.91 (m, 4H), 2.50 (br, 4H). LCMS (ESI, m/z): 490 [M+H]$^+$.

Example 73

1,1,1,3,3,3-hexafluoropropan-2-yl 4-(3-morpholinobenzyl)piperazine-1-carboxylate (9ah)

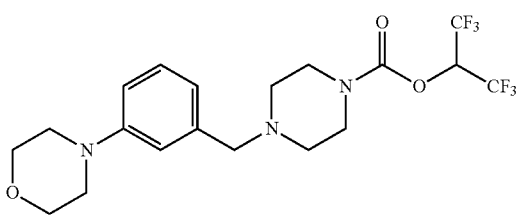 [SMILES: O=C(OC(C(F)(F)F)C(F)(F)F)N1CCN(Cc2cccc(N3CCOCC3)c2)CC1]

The title compound was synthesized directly from commercially available 3-morpholinobenzaldehyde and tert-butyl piperazine-1-carboxylate according to the representative procedure of Example 40: $^1$H NMR 400 MHz (CDCl$_3$) δ 7.16 (t, J=7.7 Hz, 1H), 6.84-6.73 (m, 3H), 5.68 (h, J=6.2 Hz, 1H), 3.83-3.77 (m, 4H), 3.52-3.44 (m, 4H), 3.42 (s, 2H), 3.13-3.08 (m, 4H), 2.43-2.35 (m, 4H). LCMS (ESI, m/z): 456.1 [M+H]$^+$.

Example 74

1,1,1,3,3,3-hexafluoropropan-2-yl 4-(4-chloro-2-(4-chloro-1H-pyrazol-1-yl)benzyl)piperazine-1-carboxylate (9ai)

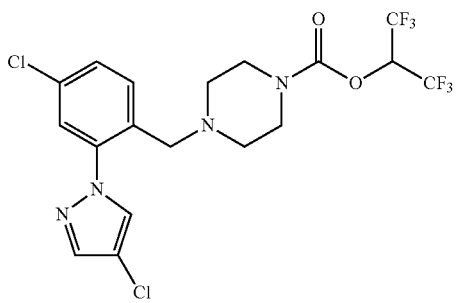 [SMILES: O=C(OC(C(F)(F)F)C(F)(F)F)N1CCN(Cc2ccc(Cl)cc2-n2cc(Cl)cn2)CC1]

Step 1: Preparation of 4-chloro-2-(4-chloro-1H-pyrazol-1-yl)benzaldehyde

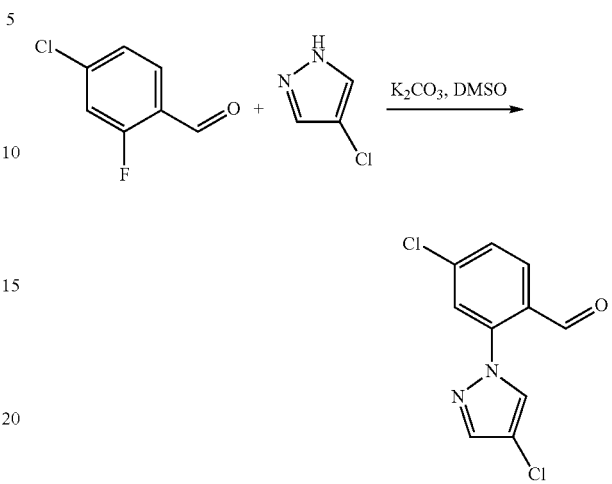

The title compound was prepared from 4-bromo-2-fluorobenzaldehyde and 4-chloropyrazole as described in Example 70, Step 1 (478 mg, 63%). $^1$H NMR 400 MHz (CDCl$_3$) δ 10.08-10.01 (m, 1H), 8.00 (d, J=8.3 Hz, 1H), 7.91-7.86 (m, 1H), 7.76 (s, 1H), 7.53 (m, 2H). LCMS (ESI, m/z): 250 [M+H]$^+$.

Step 2: Preparation of tert-butyl 4-(4-chloro-2-(4-chloro-1H-pyrazol-1-yl)benzyl)piperazine-1-carboxylate

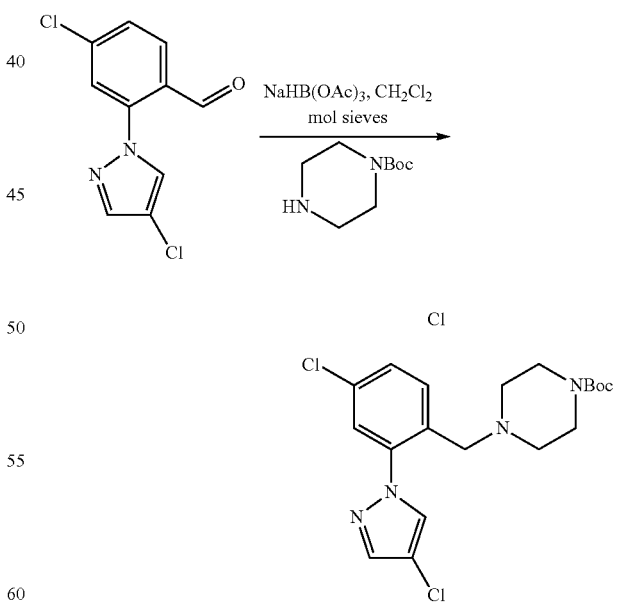

The title compound was prepared from tert-butyl 4-(4-chloro-2-(4-chloro-1H-pyrazol-1-yl)benzyl)piperazine-1-carboxylate according to the representative procedures of Example 40, Step 1. $^1$H NMR 400 MHz (CDCl$_3$) δ 8.13 (s, 1H), 7.64 (s, 1H), 7.48 (d, J=2.1 Hz, 1H), 7.42 (d, J=8.3 Hz, 1H), 7.35 (dd, J=8.3, 2.1 Hz, 1H), 3.43-3.35 (m, 6H), 2.38-2.31 (m, 4H), 1.45 (s, 10H). LCMS (ESI, an/z): 411 [M+H]⁺.

Step 3: Preparation of 1-(4-chloro-2-(4-chloro-1H-pyrazol-1-yl)benzyl)piperazine

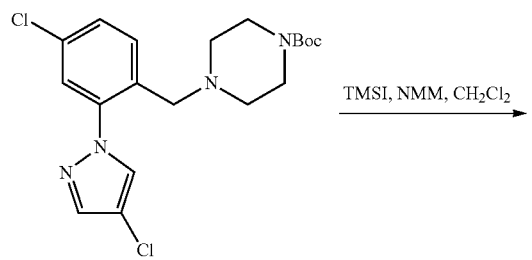

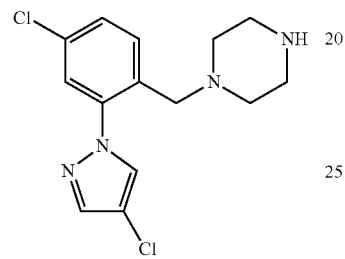

The title compound was prepared from tert-butyl 4-(4-chloro-2-(4-chloro-1H-pyrazol-1-yl)benzyl)piperazine-1-carboxylate as described in Example 33, step 3 (227 mg, 88%) as a white solid. ¹H NMR 400 MHz (CDCl₃) δ 8.24 (s, 1H), 7.63 (s, 1H), 7.50-7.46 (m, 1H), 7.38 (d, J=8.3 Hz, 1H), 7.36-7.30 (m, 1H), 3.32 (s, 2H), 2.84 (t, J=4.7 Hz, 4H), 2.37 (s, 4H). LCMS (ESI, m/z): 311 [M+H]⁺.

Step 4: Preparation of 1,1,1,3,3,3-hexafluoropropan-2-yl 4-(4-chloro-2-(4-chloro-1H-pyrazol-1-yl)benzyl)piperazine-1-carboxylate (9ai)

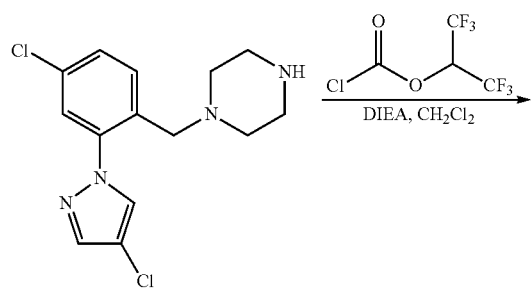

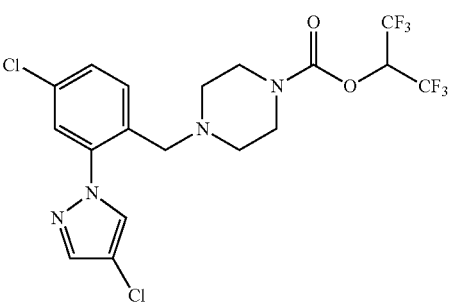

The title compound was prepared from 1-(4-chloro-2-(4-chloro-1H-pyrazol-1-yl)benzyl)piperazine according to the representative procedures of Example 1, Step 2. ¹H NMR 400 MHz (CDCl₃) δ 8.00 (s, 1H), 7.67 (s, 1H), 7.50-7.42 (m, 3H), 7.40 (d, J=8.3 Hz, 1H), 5.75 (hept, J=6.4 Hz, 1H), 3.53 (d, J=4.4 Hz, 7H), 3.45 (s, 3H), 2.44 (d, J=8.5 Hz, 6H). LCMS (ESI, m/z): 505 [M+H]⁺.

Example 75

1,1,1,3,3,3-hexafluoropropan-2-yl 4-[[4-(morpholin-4-yl)-2-(trifluoromethyl)phenyl]methyl]piperazine-1-carboxylate (aj)

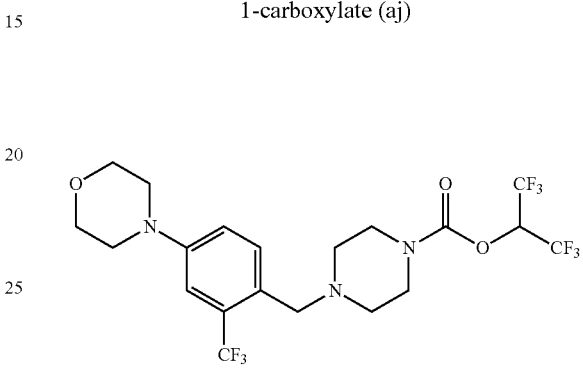

Step 1: Preparation of 4-(morpholin-4-yl)-2-(trifluoromethyl)benzaldehyde

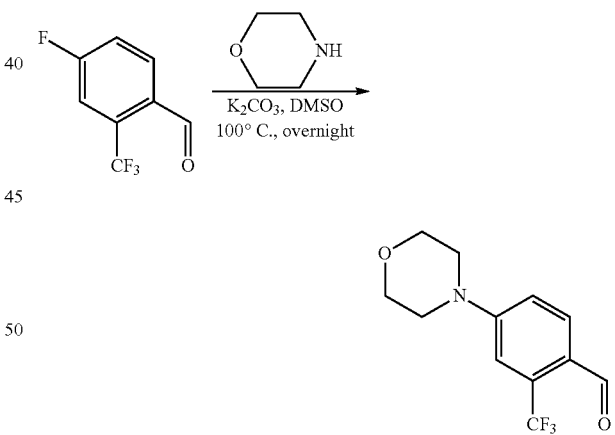

A 100 mL round-bottom flask was charged with 4-fluoro-2-(trifluoromethyl)benzaldehyde (1.00 g, 5.21 mmol, 1.00 equiv), morpholine (0.500 g, 5.74 mmol, 1.10 equiv), potassium carbonate (1.40 g, 10.1 mmol, 2.00 equiv), DMSO (15 mL). The resulting solution was stirred overnight at 100° C., diluted with H₂O (10 mL), extracted with ethyl acetate (3×10 mL). The organic layers were combined and washed with brine (1×50 mL), dried over anhydrous sodium sulfate and concentrated under reduced pressure. The residue was chromatographed on a silica gel column with ethyl acetate/petroleum ether (25/75) to provide 1.00 g (74% yield) of 4-(morpholin-4-yl)-2-(trifluoromethyl)benzaldehyde as a yellow solid. LCMS (ESI, m/z): 260 [M+H]$^+$.

Step 2: Preparation of tert-butyl 4-[[4-(morpholin-4-yl)-2-(trifluoromethyl)phenyl]methyl]piperazine-1-carboxylate

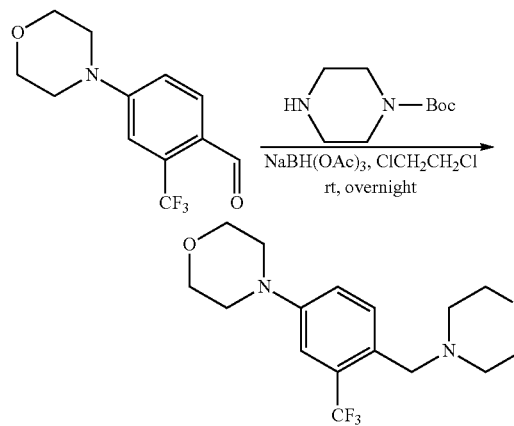

A 100 mL round-bottom flask was charged with 4-(morpholin-4-yl)-2(trifluoromethyl)benzaldehyde (1.00 g, 3.86 mmol, 1.00 equiv), tert-butyl piperazine-1-carboxylate (0.720 g, 3.86 mmol, 1.00 equiv), 1,2-dichloroethane (15 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The residue was chromatographed on a silica gel column with ethyl acetate/petroleum ether (25/75) to provide 1.60 g (97% yield) of tert-butyl 4-[[4-(morpholin-4-yl)-2-(trifluoromethyl)phenyl]methyl]piperazine-1-carboxylate as yellow oil. LCMS (ESI, m/z): 430 [M+H]$^+$.

Step 3: Preparation of 4-[4-(piperazin-1-ylmethyl)-3-(trifluoromethyl)phenyl]morpholine

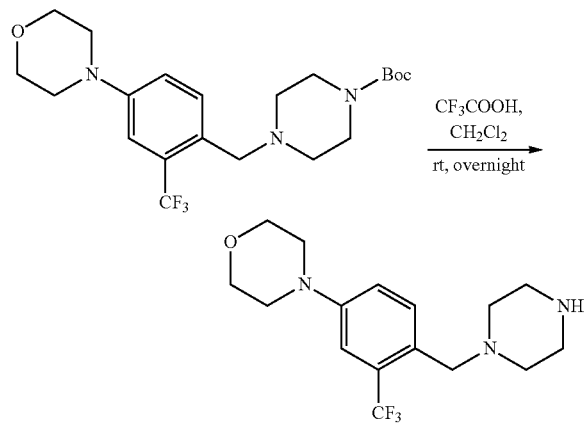

A 100 mL round-bottom flask was charged with tert-butyl 4-[[4-(morpholin-4-yl)-2-(trifluoromethyl)phenyl]methyl]piperazine-1-carboxylate (1.60 g, 3.73 mmol, 1.00 equiv), dichloromethane (10 mL). Trifluoroacetic acid (3.10 g, 27.2 mmol, 7.30 equiv) was added at 0° C. The resulting solution was stirred overnight at room temperature and concentrated under reduced pressure to yield 1.00 g (81% yield) of 4-[4-(piperazin-1-ylmethyl)-3-(trifluoromethyl)phenyl]morpholine as yellow oil. LCMS (ESI, m/z): 330 [M+H]$^+$.

Step 4: Preparation of 1,1,1,3,3,3-hexafluoropropan-2-yl 4-[[4-(morpholin-4-yl)-2-(trifluoromethyl)phenyl]methyl]piperazine-1-carboxylate (aj)

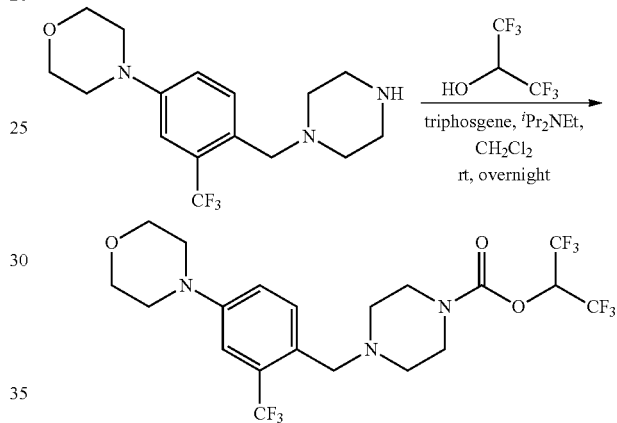

A 100 mL round-bottom flask was charged with triphosgene (126 mg, 0.420 mmol, 0.70 equiv), dichloromethane (20 mL), 1,1,1,3,3,3-hexafluoropropan-2-ol (204 mg, 1.21 mmol, 2.00 equiv) and N-ethyl-N-isopropylpropan-2-amine (627 mg, 4.86 mmol, 8.00 equiv) were added at 0° C. The mixture was stirred for 2 h at room temperature. 4-[4-(piperazin-1-ylmethyl)-3-(trifluoromethyl)phenyl]morpholine (200 mg, 0.610 mmol, 1.00 equiv) was added. The resulting solution was stirred overnight at room temperature, diluted with H$_2$O (10 mL), extracted with dichloromethane (3×10 mL). The organic layers were combined and washed with brine (50 mL), dried over anhydrous sodium sulfate and concentrated under reduced pressure. The crude product (300 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 57.4 mg (18% yield) of 1,1,1,3,3,3-hexafluoropropan-2-yl 4-[[4-(morpholin-4-yl)-2-(trifluoromethyl)phenyl]methyl]piperazine-1-carboxylate as yellow oil. $^1$H NMR 300 MHz (CDCl$_3$) δ 7.57 (d, J=8.7 Hz, 1H), 7.14 (s, 1H), 7.01-7.04 (m, 1H), 5.70-5.82 (m, 1H), 3.87 (t, J=4.8 Hz, 4H), 3.55-3.60 (m, 6H), 3.19 (t, J=4.8 Hz, 4H), 2.45-2.47 (m, 4H). LCMS (ESI, m/z): 524 [M+H]$^+$.

Example 76

1,1,1,3,3,3-hexafluoropropan-2-yl 4-[[4-(morpholin-4-yl)-2-(trifluoromethoxy)phenyl]methyl]piperazine-1-carboxylate (9ak)

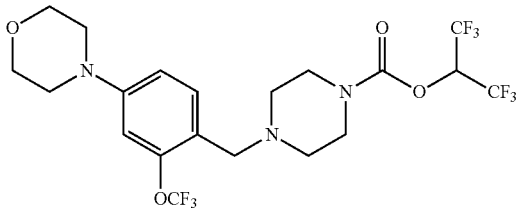

Step 1: Preparation of 4-(morpholin-4-yl)-2-(trifluoromethoxy)benzaldehyde

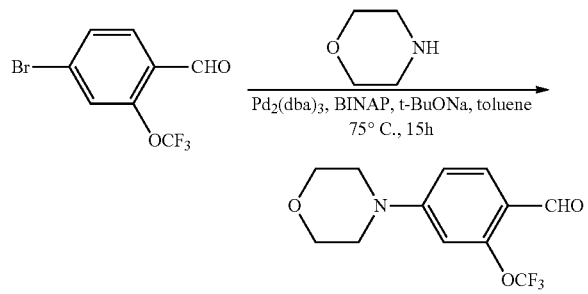

A 500 mL round-bottom flask was purged with and maintained under an inert atmosphere of nitrogen then charged with 4-bromo-2-(trifluoromethoxy)benzaldehyde (8.00 g, 29.7 mmol, 1.00 equiv), morpholine (2.59 g, 29.7 mmol, 1.00 equiv), t-BuONa (4.28 g, 44.5 mmol, 1.50 equiv), Pd$_2$(dba)$_3$ (1.36 g, 1.49 mmol, 0.05 equiv), BINAP (1.85 g, 2.97 mmol, 0.10 equiv), toluene (150 mL). The resulting solution was stirred for 15 h at 75° C. in an oil bath. The reaction progress was monitored by LCMS. The resulting solution was diluted with 50 mL of water and extracted with ethyl acetate (3×30 mL). The organic layers were combined, dried over anhydrous sodium sulfate, filtered and concentrated under reduced pressure. The residue was chromatographed on a silica gel column with ethyl acetate/petroleum ether (1/4) to provide 0.800 g (10% yield) of 4-(morpholin-4-yl)-2-(trifluoromethoxy)benzaldehyde as a yellow solid. LCMS (ESI, m/z): 276 [M+H]$^+$.

Step 2: Preparation of tert-butyl 4-[[4-(morpholin-4-yl)-2-(trifluoromethoxy)phenyl]methyl]piperazine-1-carboxylate

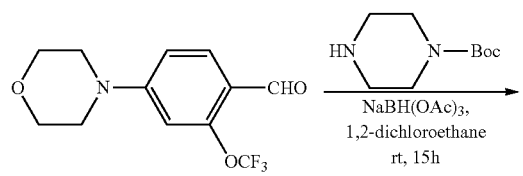

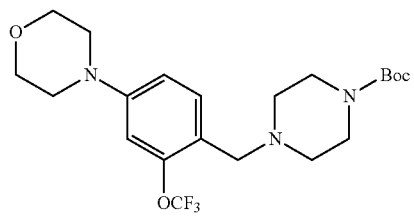

A 40 mL vial was charged with 4-(morpholin-4-yl)-2-(trifluoromethoxy)benzaldehyde (400 mg, 1.45 mmol, 1.00 equiv), tert-butyl piperazine-1-carboxylate (270 mg, 1.45 mmol, 1.00 equiv), 1,2-dichloroethane (15 mL). The resulting solution was stirred for 1 h at room temperature. Sodium triacetoxyhydroborate (925 mg, 4.36 mmol, 3.00 equiv) was added. The resulting solution was stirred for 15 hours at room temperature. The reaction progress was monitored by LCMS. The resulting solution was diluted with 15 mL of water. The resulting solution was extracted with dichloromethane (3×15 mL) and the organic layers combined, dried over anhydrous sodium sulfate, filtered and concentrated under reduced pressure. The residue was chromatographed on a silica gel column with ethyl acetate/petroleum ether (1/3) to provide 590 mg (91% yield) of tert-butyl 4-[[4-(morpholin-4-yl)-2-(trifluoromethoxy)phenyl]methyl]piperazine-1-carboxylate as yellow oil. LCMS (ESI, m/z): 446 [M+H]$^+$.

Step 3: Preparation of 4-[4-(piperazin-1-ylmethyl)-3-(trifluoromethoxy)phenyl]morpholine

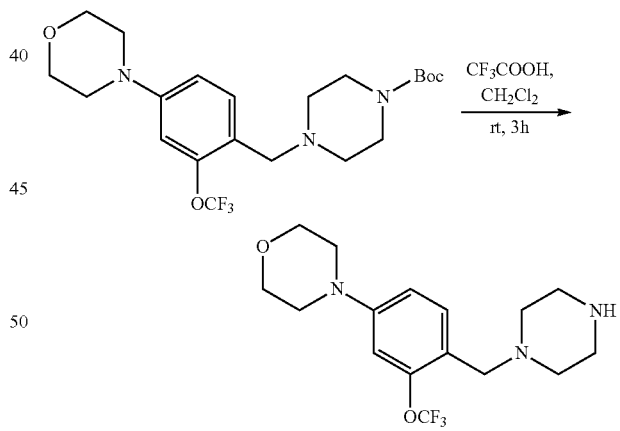

A 50 mL round-bottom flask was charged with a solution of tert-butyl 4-[[4-(morpholin-4-yl)-2-(trifluoromethoxy)phenyl]methyl]piperazine-1-carboxylate (590 mg, 1.32 mmol, 1.00 equiv) in dichloromethane (15 mL). Trifluoroacetic acid (262 mg, 2.30 mmol, 1.74 equiv) was added dropwise at 0° C. The resulting solution was stirred for 3 h at room temperature. The reaction progress was monitored by LCMS. The resulting mixture was concentrated under reduced pressure to provide 445 mg (crude) of 4-[4-(piperazin-1-ylmethyl)-3-(trifluoromethoxy)phenyl]morpholine as light yellow oil. LCMS (ESI, m/z): 346 [M+H]$^+$.

183

Step 4: Preparation of 1,1,1,3,3,3-hexafluoropropan-2-yl 4-[[4-(morpholin-4-yl)-2-(trifluoromethoxy)phenyl]methyl]piperazine-1-carboxylate (9ak)

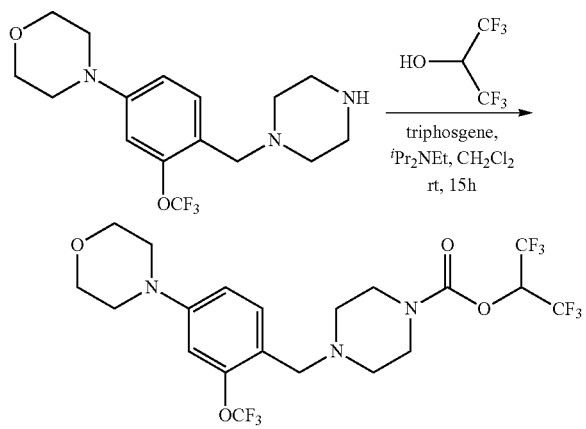

A 50 mL round-bottom flask was charged with a solution of triphosgene (122 mg, 0.410 mmol, 0.71 equiv) in dichloromethane (20 mL). 1,1,1,3,3,3-Hexafluoropropan-2-ol (195 mg, 1.16 mmol, 2.00 equiv) and N,N-di-isopropylethylamine (598 mg, 4.63 mmol, 7.99 equiv) were added sequentially dropwise at 0° C. The resulting solution was stirred for 2 h at room temperature. 4-[4-(piperazin-1-ylmethyl)-3-(trifluoromethoxy)phenyl]morpholine (200 mg, 0.580 mmol, 1.00 equiv) was added. The resulting solution was stirred at room temperature. The reaction progress was monitored by LCMS. The resulting solution was diluted with $H_2O$ (15 mL). The resulting solution was extracted with dichloromethane (3×15 mL) and the organic layers were combined, dried over anhydrous sodium sulfate, filtered and concentrated under reduced pressure. The crude product (381 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep $C_{18}$, 19*150 mm 5 um; Mobile phase: Phase A: aqueous $NH_4HCO_3$ (0.05%); Phase B: $CH_3CN$; Detector, UV220 & 254 nm. Purification resulted in 185 mg (59% yield) of 1,1,1,3,3,3-hexafluoropropan-2-yl 4-[[4-(morpholin-4-yl)-2-(trifluoromethoxy)phenyl]methyl]piperazine-1-carboxylate as light yellow oil. $^1$H NMR 300 MHz (CDCl$_3$) δ 7.34 (d, J=8.4 Hz, 1H), 6.74-6.83 (m, 2H), 5.72-5.80 (m, 1H), 3.86 (t, J=4.6 Hz, 4H), 3.52 (s, 6H), 3.16 (t, J=4.8 Hz, 4H), 2.46 (d, J=4.2 Hz, 4H). LCMS (ESI, m/z): 260 [M–$C_8H_9F_6N_2O_2$]$^+$.

Example 77

1,1,1,3,3,3-hexafluoropropan-2-yl(2S)-4-[[2-chloro-4-(morpholin-4-yl)phenyl]methyl]-2-methylpiperazine-1-carboxylate (9al)

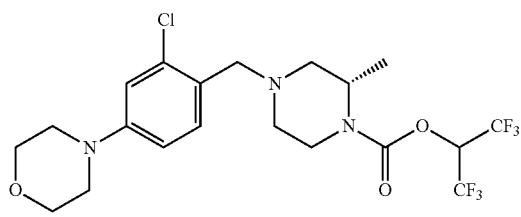 [SMILES: C[C@H]1CN(Cc2ccc(N3CCOCC3)cc2Cl)CCN1C(=O)OC(C(F)(F)F)C(F)(F)F]

184

Step 1: tert-butyl (2S)-4-[[2-chloro-4-(morpholin-4-yl)phenyl]methyl]-2-methylpiperazine-1-carboxylate

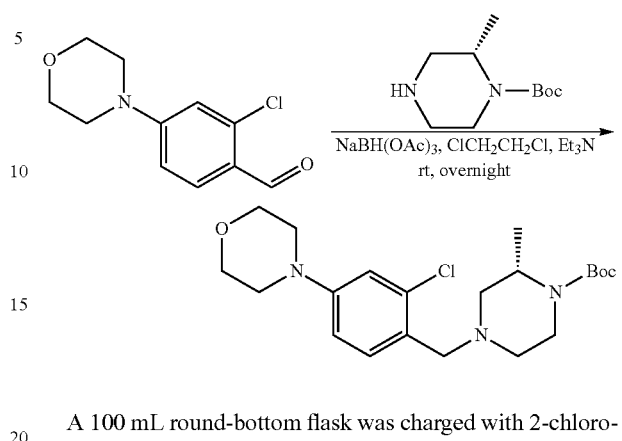

A 100 mL round-bottom flask was charged with 2-chloro-4-(morpholin-4-yl)benzaldehyde (0.800 g, 3.54 mmol, 1.00 equiv), tert-butyl (2S)-2-methylpiperazine-1-carboxylate (0.783 g, 3.91 mmol, 1.10 equiv), 1,2-dichloroethane (20 mL). The mixture was stirred for 30 min at room temperature. Sodium triacetoxyborohydride (2.26 g, 10.7 mmol, 3.00 equiv) was added. The resulting solution was stirred overnight at room temperature, diluted with $H_2O$ (30 mL), extracted with dichloromethane (3×30 mL) and the organic layers were combined, dried over $Na_2SO_4$, filtered and concentrated under reduced pressure. The residue was chromatographed on a silica gel column with ethyl acetate/petroleum ether (25/75) to provide 1.20 g (74% yield) of tert-butyl (2S)-4-[[2-chloro-4-(morpholin-4-yl)phenyl]methyl]-2-methylpiperazine-1-carboxylate as a white solid. LCMS (ESI, m/z): 410 [M+H]$^+$.

Step 2: Preparation of 4-(3-chloro-4-[[(3S)-3-methylpiperazin-1-yl]methyl]phenyl)morpholine

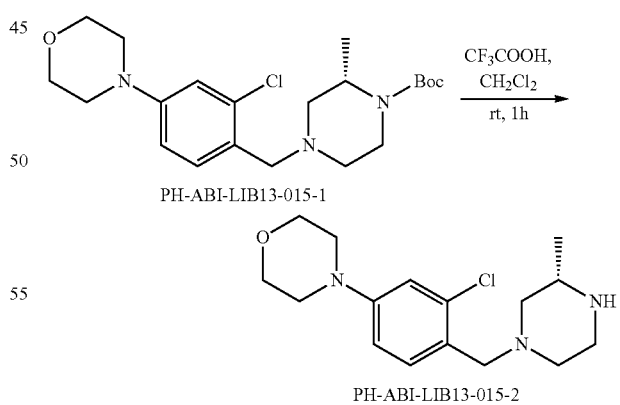

A 100 mL round-bottom flask was charged with tert-butyl (2S)-4-[[2-chloro-4-(morpholin-4-yl)phenyl]methyl]-2-methylpiperazine-1-carboxylate (1.20 g, 2.93 mmol, 1.00 equiv), trifluoroacetic acid (4 mL), dichloromethane (20 mL). The resulting solution was stirred for 1 h at room temperature and concentrated under reduced pressure to yield 0.910 g (crude) of 4-(3-chloro-4-[[(3S)-3-methylpiperazin-1-yl]methyl]phenyl)morpholine as light yellow oil. LCMS (ESI, m/z): 310 [M+H]+.

Step 3: Preparation of 1,1,1,3,3,3-hexafluoropropan-2-yl(2S)-4-[[2-chloro-4-(morpholin-4-yl)phenyl]methyl]-2-methylpiperazine-1-carboxylate (9al)

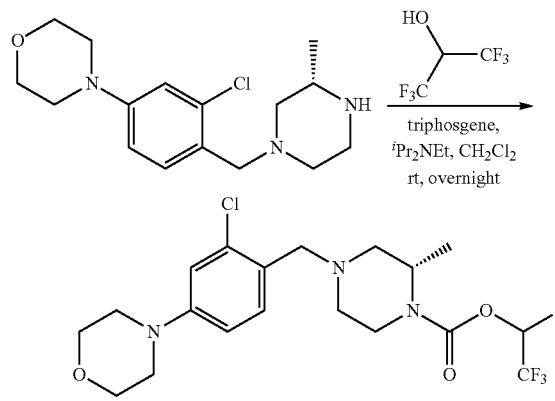

A 100 mL round-bottom flask was charged with dichloromethane (20 mL), triphosgene (86.0 mg, 0.290 mmol, 0.300 equiv). 1,1,1,3,3,3-Hexafluoropropan-2-ol (163 mg, 0.970 mmol, 1.00 equiv) and N,N-diisopropylethylamine (238 mg, 1.84 mmol, 1.90 equiv) were added. The mixture was stirred for 2 h at room temperature. 4-(3-Chloro-4-[[(3S)-3-methylpiperazin-1-yl]methyl]phenyl)morpholine (300 mg, 0.970 mmol, 1.00 equiv) was added. The resulting solution was stirred overnight at room temperature, diluted with H2O (20 mL), extracted with dichloromethane (3×15 mL) and the organic layers were combined, dried over Na2SO4, filtered and concentrated under reduced pressure. The crude product (180 mg) was purified by preparative HPLC using the following gradient conditions: 20% CH3CN/80% Phase A increasing to 80% CH3CN over 10 min, then to 100% CH3CN over 0.1 min, holding at 100% CH3CN for 1.9 min, then reducing to 20% CH3CN over 0.1 min, and holding at 20% for 1.9 min, on a Waters 2767-5 Chromatograph. Column: Xbridge Prep C18, 19*150 mm 5 um; Mobile phase: Phase A: aqueous NH4HCO3 (0.05%); Phase B: CH3CN; Detector, UV220 & 254 nm. Purification resulted in 77.5 mg (15% yield) of 1,1,1,3,3,3-hexafluoropropan-2-yl(2S)-4-[[2-chloro-4-(morpholin-4-yl)phenyl]methyl]-2-methylpiperazine-1-carboxylate as light yellow oil. 1H NMR 400 MHz (CDCl3) δ 7.28-7.30 (m, 1H), 6.88 (d, J=2.4 Hz, 1H), 6.77-6.80 (m, 1H), 5.73-5.79 (m, 1H), 4.26 (br, 1H), 3.84 (t, J=4.8 Hz, 5H), 3.48-3.56 (m, 2H), 3.25 (br, 1H), 3.15 (t, J=5.2 Hz, 4H), 2.80-2.82 (m, 1H), 2.66 (d, J=10.8 Hz, 1H), 2.28-2.31 (m, 1H), 2.10-2.16 (m, 1H), 1.30 (d, J=6.8 Hz, 3H). LCMS (ESI, m/z): 504 [M+H]+.

Example 78

1,1,1,3,3,3-hexafluoropropan-2-yl(2R)-4-[[2-chloro-4-(morpholin-4-yl)phenyl]methyl]-2-methylpiperazine-1-carboxylate (9am)

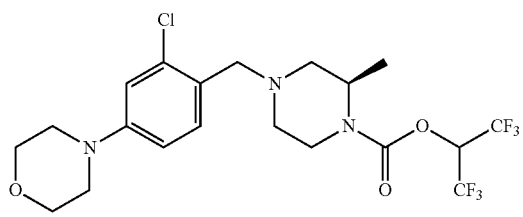 [SMILES: C[C@@H]1CN(Cc2ccc(N3CCOCC3)cc2Cl)CCN1C(=O)OC(C(F)(F)F)C(F)(F)F]

The title compound was synthesized directly from commercially available 2-chloro-4-(morpholin-4-yl)benzaldehyde and tert-butyl (2R)-2-methylpiperazine-1-carboxylate according to the representative procedure of Example 50: 1H NMR 400 MHz (CDCl3) δ 7.28 (t, J=7.6 Hz, 1H), 6.88 (d, J=1.2 Hz, 1H), 6.77-6.80 (m, 1H), 5.74-5.80 (m, 1H), 4.26 (br, 1H), 3.85 (t, J=4.8 Hz, 5H), 3.48-3.55 (m, 2H), 3.25 (br, 1H), 3.15 (t, J=4.8 Hz, 4H), 2.80-2.82 (m, 1H), 2.66 (d, J=7.8 Hz, 1H), 2.28-2.31 (m, 1H), 2.10-2.16 (m, 1H), 1.30 (d, J=6.8 Hz, 3H). LCMS (ESI, m/z): 504 [M+H]+.

Example 79

(S)-1,1,1,3,3,3-hexafluoropropan-2-yl 2-methyl-4-(4-morpholino-2-(trifluoromethoxy)benzyl)piperazine-1-carboxylate (9an)

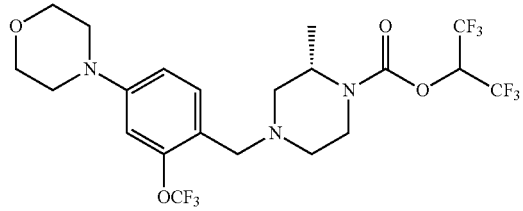

Step 1: Preparation of (S)-tert-butyl 2-methyl-4-(4-morpholino-2-(trifluoromethoxy)benzyl)piperazine-1-carboxylate

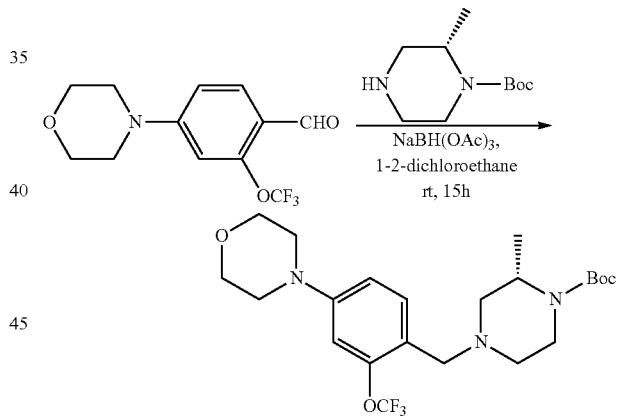

The title compound was synthesized according to the representative procedure of Example 48, Step 1 using 4-morpholino-2-(trifluoromethoxy)benzaldehyde: LCMS (ESI, m/z): 459 [M+H]+.

Step 2: Preparation of (S)-4-(4-((3-methylpiperazin-1-yl)methyl)-3-(trifluoromethoxy)phenyl)morpholine

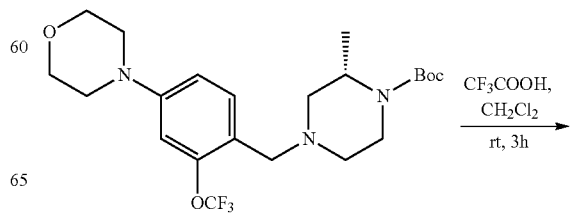

-continued

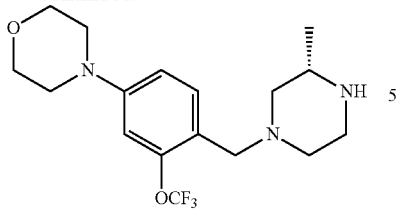

The title compound was synthesized according to the representative procedure of Example 48, Step 2 using 4-morpholino-2-(trifluoromethoxy)benzaldehyde: LCMS (ESI, m/z): 359 [M+H]+.

Step 3: Preparation of (S)-1,1,1,3,3,3-hexafluoropropan-2-yl 2-methyl-4-(4-morpholino-2-(trifluoromethoxy)benzyl)piperazine-1-carboxylate (9an)

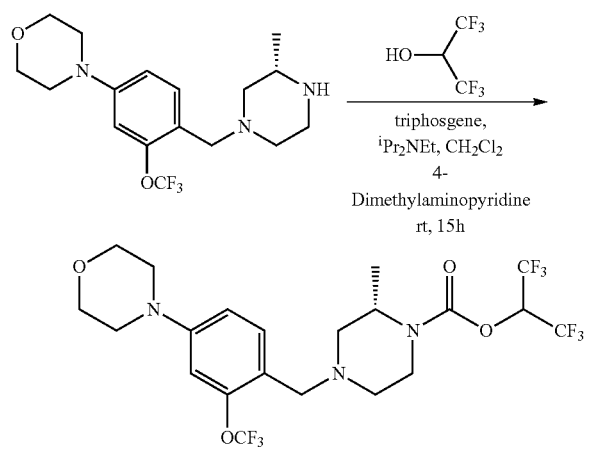

The title compound was synthesized according to the representative procedure of Example 48, Step 3 using 4-morpholino-2-(trifluoromethoxy)benzaldehyde: $^1$H NMR 300 MHz (CDCl$_3$) δ 7.36 (d, J=8.4 Hz, 1H), 6.73-6.83 (m, 2H), 5.70-5.82 (m, 1H), 4.26 (s, 1H), 3.86 (t, J=4.8 Hz, 5H), 3.37-3.60 (m, 2H), 3.15-3.28 (m, 5H), 2.78 (d, J=9.9 Hz, 1H), 2.64 (d, J=11.1 Hz, 1H), 2.22-2.28 (m, 1H), 2.05-2.13 (m, 1H), 1.51 (d, J=6.9 Hz, 3H). LCMS (ESI, m/z): 260 [M−C$_9$H$_{11}$F$_6$N$_2$O$_2$]+.

Example 80

(R)-1,1,1,3,3,3-hexafluoropropan-2-yl 2-methyl-4-(4-morpholino-2-(trifluoromethoxy)benzyl)piperazine-1-carboxylate (9ao)

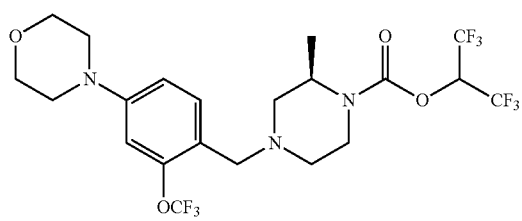 [SMILES: C[C@@H]1CN(Cc2ccc(N3CCOCC3)cc2OC(F)(F)F)CCN1C(=O)OC(C(F)(F)F)C(F)(F)F]

Step 1: Preparation of (R)-tert-butyl 2-methyl-4-(4-morpholino-2-(trifluoromethoxy)benzyl)piperazine-1-carboxylate

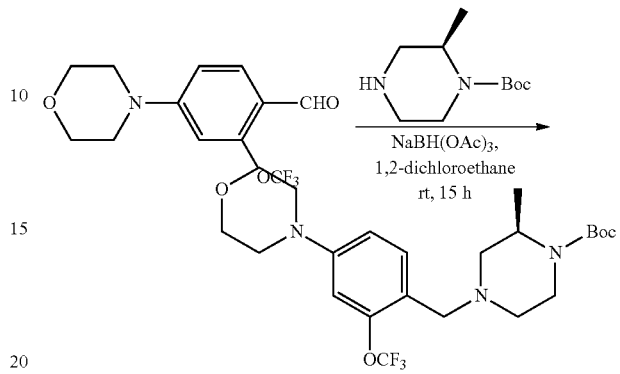

The title compound was synthesized from 4-morpholino-2-(trifluoromethoxy)benzaldehyde according to the representative procedure of Example 50, Step 1 (301 mg, 90%): LCMS (ESI, m/z): 459 [M+H]+.

Step 2: Preparation of (R)-4-(4-((3-methylpiperazin-1-yl)methyl)-3-(trifluoromethoxy)phenyl)morpholine

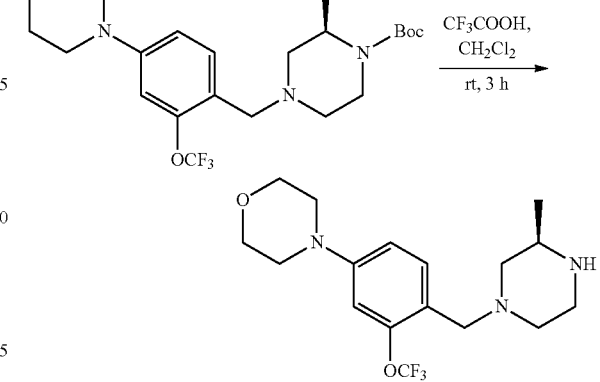

The title compound was synthesized from (R)-tert-butyl 2-methyl-4-(4-morpholino-2-(trifluoromethoxy)benzyl)piperazine-1-carboxylate according to the representative procedure of Example 50, Step 2: LCMS (ESI, m/z): 359 [M+H]+.

Step 3: Preparation of (R)-1,1,1,3,3,3-hexafluoropropan-2-yl 2-methyl-4-(4-morpholino-2-(trifluoromethoxy)benzyl)piperazine-1-carboxylate (9ao)

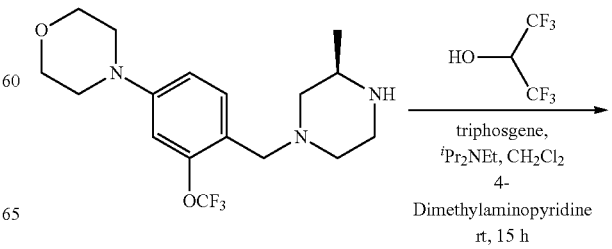

189

-continued

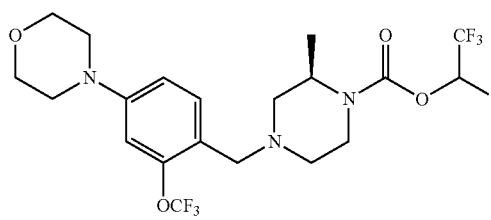

The title compound was synthesized from (R)-4-(4-((3-methylpiperazin-1-yl)methyl)-3-(trifluoromethoxy)phenyl)morpholine according to the representative procedure of Example 50, Step 3 (120 mg, 58%): $^1$H NMR 300 MHz (CDCl$_3$) δ 7.36 (d, J=8.4 Hz, 1H), 6.73-6.83 (m, 2H), 5.70-5.83 (m, 1H), 4.26 (s, 1H), 3.86 (t, J=4.8 Hz, 5H), 3.42-3.52 (m, 2H), 3.15-3.29 (m, 5H), 2.79 (d, J=10.2 Hz, 1H), 2.64 (d, J=11.1 Hz, 1H), 2.23-2.28 (m, 1H), 2.09 (t, J=10.2 Hz, 1H), 1.30 (d, J=6.6 Hz, 3H). LCMS (ESI, m/z): 260 [M–C$_9$H$_{11}$F$_6$N$_2$O$_2$]$^+$.

Example 81

1,1,1,3,3,3-hexafluoropropan-2-yl 4-(4-(pyrrolidin-1-yl)-2-(trifluoromethoxy)benzyl)piperazine-1-carboxylate (9ap)

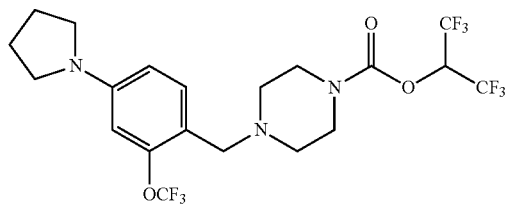 [SMILES: O=C(OC(C(F)(F)F)C(F)(F)F)N1CCN(Cc2ccc(N3CCCC3)cc2OC(F)(F)F)CC1]

Step 1: Preparation of tert-butyl 4-(4-bromo-2-(trifluoromethoxy)benzyl)piperazine-1-carboxylate

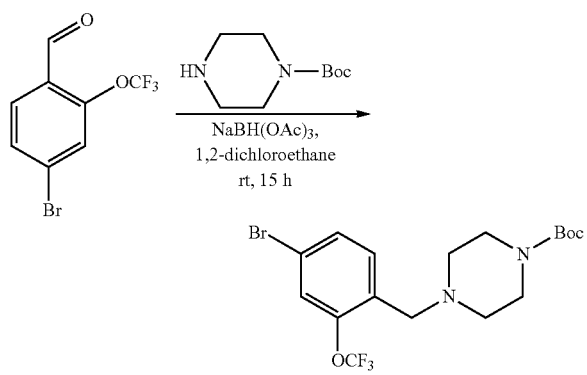

The title compound was synthesized from 4-bromo-2-(trifluoromethoxy)benzaldehyde according to the representative procedure of Example 67, Step 2 (2.3 g, 97%): LCMS (ESI, m/z): 438 [M+H]$^+$.

190

Step 2: Preparation of tert-butyl 4-(4-(pyrrolidin-1-yl)-2-(trifluoromethoxy)benzyl)piperazine-1-carboxylate

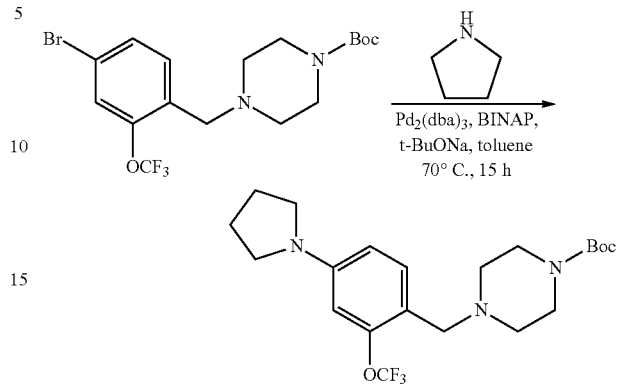

A 100 mL round-bottom flask purged and maintained with an inert atmosphere of nitrogen was charged with tert-butyl 4-[[4-bromo-2-(trifluoromethoxy)phenyl]methyl]piperazine-1-carboxylate (1.00 g, 2.28 mmol, 1.00 equiv), pyrrolidine (194 mg, 2.73 mmol, 1.20 equiv), t-BuONa (307 mg, 3.19 mmol, 1.40 equiv), Pd$_2$(dba)$_3$ (104 mg, 0.110 mmol, 0.05 equiv), BINAP (213 mg, 0.340 mmol, 0.150 equiv), toluene (20 mL). The resulting solution was stirred for 15 h at 70° C. in an oil bath. The reaction progress was monitored by LCMS. The resulting solution was diluted with water (15 mL). The resulting solution was extracted with dichloromethane (3×15 mL) and the organic layers were combined, dried over anhydrous sodium sulfate, filtered and concentrated under reduced pressure. The residue was chromatographed on a silica gel column with ethyl acetate/petroleum ether (1/4) to provide 940 mg (96% yield) of tert-butyl 4-[[4-(pyrrolidin-1-yl)-2-(trifluoromethoxy)phenyl]methyl]piperazine-1-carboxylate as light yellow oil.

Step 3: Preparation of 1-(4-(pyrrolidin-1-yl)-2-(trifluoromethoxy)benzyl)piperazine

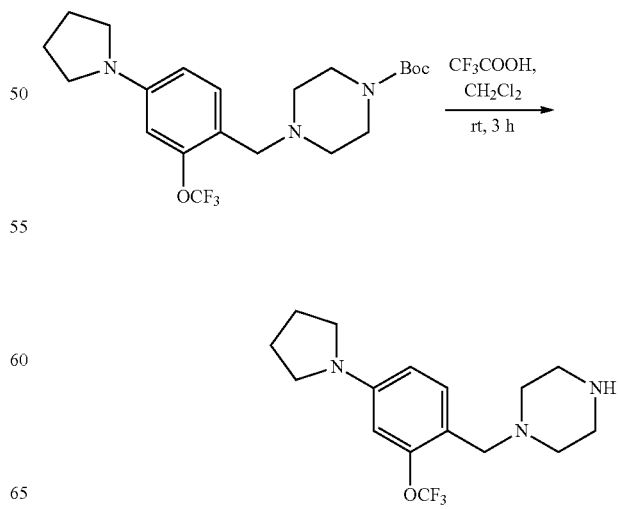

The title compound was synthesized from tert-butyl 4-(4-(pyrrolidin-1-yl)-2-(trifluoromethoxy)benzyl)piperazine-1-carboxylate according to the representative procedure of Example 42, step 3.

Step 4: Preparation of 1,1,1,3,3,3-hexafluoropropan-2-yl 4-(4-(pyrrolidin-1-yl)-2-(trifluoromethoxy)benzyl)piperazine-1-carboxylate (9ap)

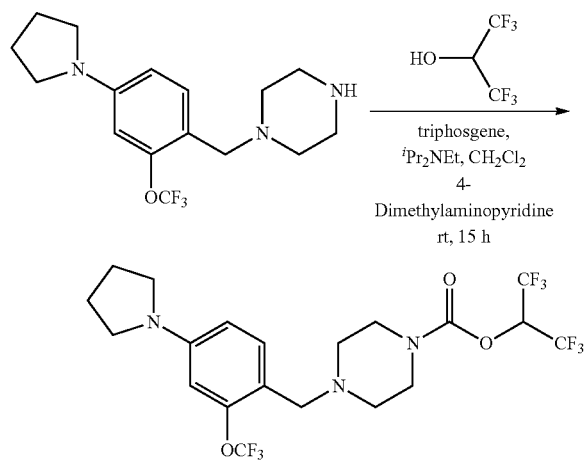

The title compound was synthesized from 1-(4-(pyrrolidin-1-yl)-2-(trifluoromethoxy)benzyl)piperazine as described in Example 42, step 4 (87 mg, 36%). $^1$H NMR 300 MHz (CDCl$_3$) δ 7.23 (d, J=8.4 Hz, 1H), 6.43-6.47 (m, 1H), 6.38 (s, 1H), 5.68-5.80 (m, 1H), 3.52 (d, J=9.0 Hz, 6H), 3.27 (t, J=6.6 Hz, 4H), 2.46 (s, 4H), 1.98-2.06 (m, 4H). LCMS (ESI, m/z): 244 [M−C$_8$H$_9$F$_6$N$_2$O$_2$]$^+$.

Example 82

1,1,1,3,3,3-hexafluoropropan-2-yl 4-(2-(pyrrolidin-1-yl)-4-(trifluoromethyl)benzyl)piperazine-1-carboxylate (9aq)

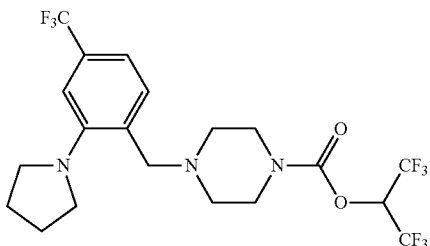

Step 1: Preparation of 2-(pyrrolidin-1-yl)-4-(trifluoromethyl)benzaldehyde

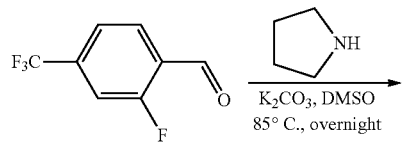

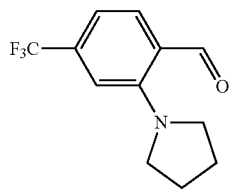

The title compound was synthesized from 2-fluoro-4-(trifluoromethyl)benzaldehyde and pyrrolidine as described in Example 67, Step 1 (1.6 g, 63%): LCMS (ESI, m/z): 244 [M+H]$^+$.

Step 2: Preparation of tert-butyl 4-(2-(pyrrolidin-1-yl)-4-(trifluoromethyl)benzyl)piperazine-1-carboxylate

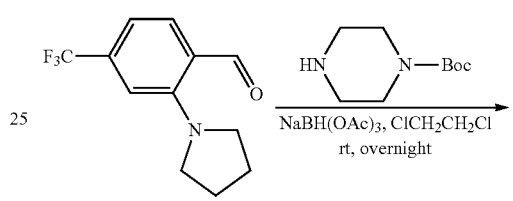

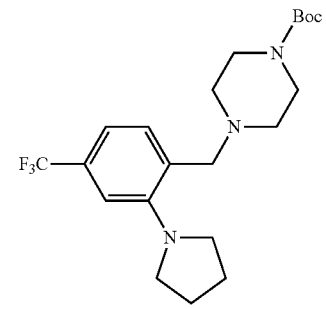

The title compound was synthesized from 2-(pyrrolidin-1-yl)-4-(trifluoromethyl)benzaldehyde as described in Example 67, Step 2 (2.10 g, 77%): LCMS (ESI, m/z): 414 [M+H]$^+$.

Step 3: Preparation of 1-(2-(pyrrolidin-1-yl)-4-(trifluoromethyl)benzyl)piperazine -continued

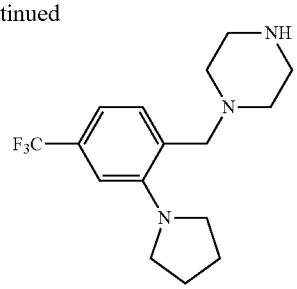

The title compound was synthesized from tert-butyl 4-(2-(pyrrolidin-1-yl)-4-(trifluoromethyl)benzyl)piperazine-1-carboxylate as described in Example 42, Step 3: LCMS (ESI, m/z): 314 [M+H]+.

Step 4: Preparation of 1,1,1,3,3,3-hexafluoropropan-2-yl 4-(2-(pyrrolidin-1-yl)-4-(trifluoromethyl)benzyl)piperazine-1-carboxylate (9aq)

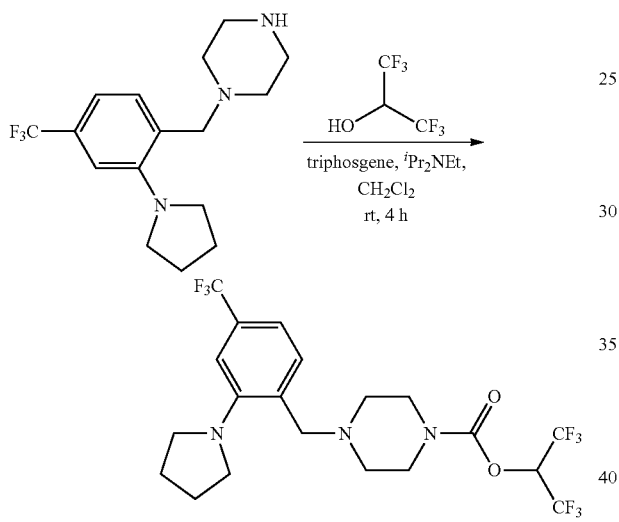

The title compound was synthesized from 1-(2-(pyrrolidin-1-yl)-4-(trifluoromethyl)benzyl)piperazine as described in Example 42, Step 4 (205 mg, 79%): ¹H NMR 300 MHz (CDCl₃) δ 7.52 (d, J=8.1 Hz, 1H), 7.08-7.11 (m, 2H), 5.74-5.84 (m, 1H), 3.58 (br, 6H), 3.22-3.26 (m, 4H), 2.46-2.49 (m, 4H), 1.90-1.98 (m, 4H). LCMS (ESI, m/z): 508 [M+H]+.

Example 83

1,1,1,3,3,3-hexafluoropropan-2-yl 4-(3-chloro-2-(pyrrolidin-1-yl)benzyl)piperazine-1-carboxylate (9ar)

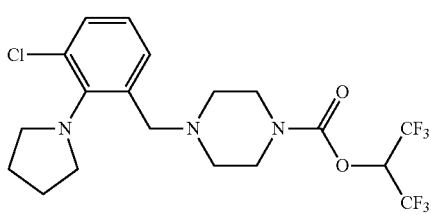

Step 1: Preparation of 3-chloro-2-(pyrrolidin-1-yl)benzaldehyde

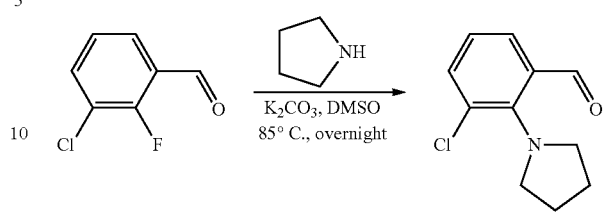

The title compound was synthesized from 3-chloro-2-fluorobenzaldehyde and pyrrolidine as described in Example 67, Step 1 (800 mg, 30%). ¹H NMR 300 MHz (CDCl₃) δ 10.36 (s, 1H), 7.71-7.73 (m, 1H), 7.59-7.61 (m, 1H), 7.18-7.26 (m, 1H), 3.33-3.42 (m, 4H), 2.01-2.10 (m, 4H). LCMS (ESI, m/z): 210 [M+H]+.

Step 2: Preparation of tert-butyl 4-(3-chloro-2-(pyrrolidin-1-yl)benzyl)piperazine-1-carboxylate

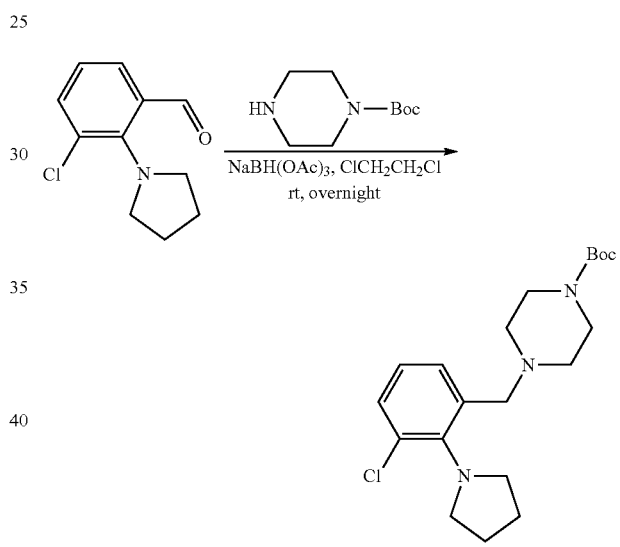

The title compound was synthesized from 3-chloro-2-(pyrrolidin-1-yl)benzaldehyde as described in Example 67, Step 2 (1.14 g, 79%). LCMS (ESI, m/z): 380 [M+H]+.

Step 3: Preparation of 1-(3-chloro-2-(pyrrolidin-1-yl)benzyl)piperazine

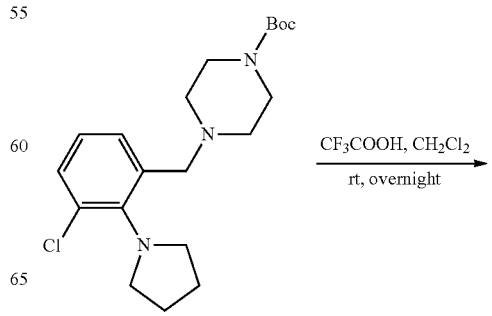

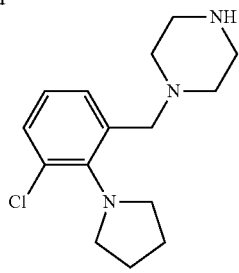

The title compound was synthesized from tert-butyl 4-(3-chloro-2-(pyrrolidin-1-yl)benzyl)piperazine-1-carboxylate as described in Example 42, Step 3: LCMS (ESI, m/z): 280 [M+H]⁺.

Step 4: Preparation of 1,1,1,3,3,3-hexafluoropropan-2-yl 4-(3-chloro-2-(pyrrolidin-1-yl)benzyl)piperazine-1-carboxylate (9ar)

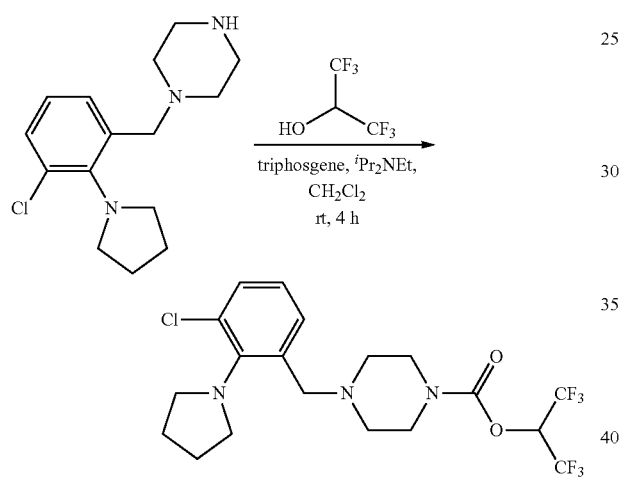

The title compound was synthesized from 1-(3-chloro-2-(pyrrolidin-1-yl)benzyl)piperazine as described in Example 42, Step 4: $^1$H NMR 300 MHz (CDCl$_3$) δ 7.25-7.36 (m, 2H), 7.05-7.10 (m, 1H), 5.71-5.84 (m, 1H), 3.54-3.60 (m, 6H), 3.19-3.24 (m, 4H), 2.46-2.47 (m, 4H), 1.93-2.03 (m, 4H). LCMS (ESI, m/z): 474 [M+H]⁺.

Example 84

1,1,1,3,3,3-hexafluoropropan-2-yl 4-(3-fluoro-2-(pyrrolidin-1-yl)benzyl)piperazine-1-carboxylate (9as)

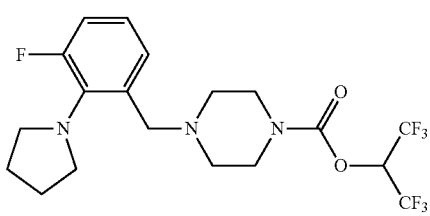

The title compound was prepared from 2,3-difluorobenzaldehyde and pyrrolidine as described in Example 75, Steps 1-4: $^1$H NMR 300 MHz (CDCl$_3$) δ 7.18-7.20 (m, 1H), 7.02-7.09 (m, 1H), 6.90-6.97 (m, 1H), 5.72-5.84 (m, 1H), 3.63 (br, 2H), 3.54-3.55 (m, 4H), 3.12-3.63 (m, 4H), 2.45-2.50 (m, 4H), 1.88-1.97 (m, 4H). LCMS (ESI, m/z): 458 [M+H]⁺.

Example 85

1,1,1,3,3,3-hexafluoropropan-2-yl 4-((3-isopropyl-[1,1'-biphenyl]-4-yl)methyl)piperazine-1-carboxylate (9at)

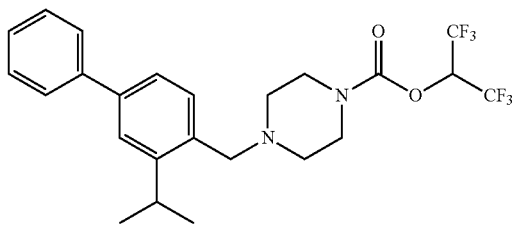 [SMILES: CC(C)c1cc(-c2ccccc2)ccc1CN1CCN(C(=O)OC(C(F)(F)F)C(F)(F)F)CC1]

The title compound was prepared from 2,3-difluorobenzaldehyde and pyrrolidine as described in Example 118: $^1$H NMR 300 MHz (CDCl$_3$) δ 7.64 (m, 2H), 7.60-7.63 (m, 1H), 7.49-7.50 (m, 2H), 7.47-7.48 (m, 2H), 7.32-7.35 (m, 1H), 5.75-5.83 (m, 1H), 3.58-3.61 (m, 6H), 3.38-3.47 (m, 1H), 2.52-2.53 (m, 4H), 1.32 (d, J=6.9 Hz, 6H). LCMS (ESI, m/z): 489 [M+H]⁺.

Example 86

1,1,1,3,3,3-hexafluoropropan-2-yl 4-(2-isopropyl-4-(pyrrolidin-1-yl)benzyl)piperazine-1-carboxylate (9au)

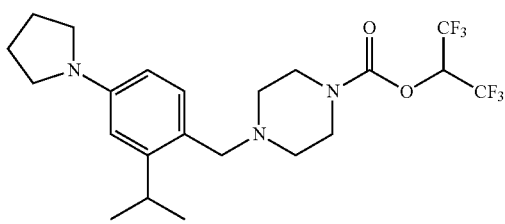 [SMILES: CC(C)c1cc(N2CCCC2)ccc1CN1CCN(C(=O)OC(C(F)(F)F)C(F)(F)F)CC1]

Step 1: Preparation of tert-butyl 4-(2-isopropyl-4-(pyrrolidin-1-yl)benzyl)piperazine-1-carboxylate

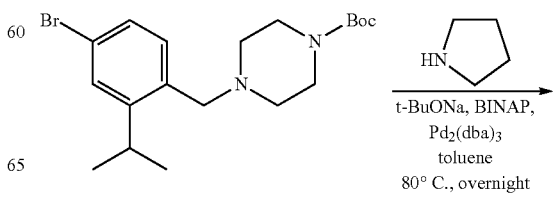

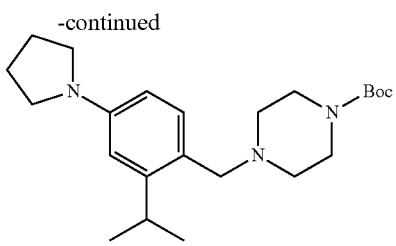

A 50 mL round-bottom flask was charged with tert-butyl 4-[[4-bromo-2-(propan-2-yl)phenyl]methyl]piperazine-1-carboxylate (50.0 mg, 0.130 mmol, 1.00 equiv), pyrrolidine (11.0 mg, 0.150 mmol, 1.20 equiv), t-BuONa (17.5 mg, 0.180 mmol, 1.45 equiv), $Pd_2(dba)_3$ (6.00 mg, 0.010 mmol, 0.050 equiv), BINAP (12.0 mg, 0.020 mmol, 0.15 equiv), toluene (2 mL). The resulting solution was stirred overnight at 80° C. with an inert atmosphere of nitrogen and then diluted with water (5 mL). The resulting solution was extracted with dichloromethane (3×5 mL) and the organic layers were combined, dried over anhydrous sodium sulfate, filtered and concentrated under reduced pressure. The residue was chromatographed on a silica gel column with ethyl acetate/petroleum ether (20/80) to provide 31.0 mg (61% yield) of tert-butyl 4-[[2-(propan-2-yl)-4-(pyrrolidin-1-yl)phenyl]methyl]piperazine-1-carboxylate as light yellow oil. LCMS (ESI, m/z): 338 [M+H]$^+$.

Step 2: Preparation of 1-(2-isopropyl-4-(pyrrolidin-1-yl)benzyl)piperazine

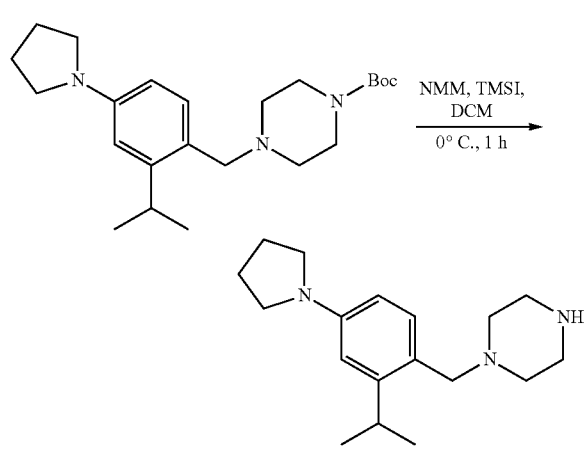

A 100 mL round-bottom flask was charged with tert-butyl 4-[[2-(propan-2-yl)-4-(pyrrolidin-1-yl)phenyl]methyl]piperazine-1-carboxylate (200 mg, 0.52 mmol, 1.00 equiv), dichloromethane (10 mL) with an inert atmosphere of nitrogen. 4-Methylmorpholine (265 mg, 2.62 mmol, 5.00 equiv) and iodotrimethylsilane (412 mg, 2.08 mmol, 4.00 equiv) were added at 0° C. The resulting solution was stirred for 1 h at 0° C. The resulting mixture was concentrated under reduced pressure to provide 150 mg (crude) of 1-[[2-(propan-2-yl)-4-(pyrrolidin-1-yl)phenyl]methyl]piperazine as light yellow oil. LCMS (ESI, m/z): 238 [M+H]$^+$.

Step 3: Preparation of 1,1,1,3,3,3-hexafluoropropan-2-yl 4-(2-isopropyl-4-(pyrrolidin-1-yl)benzyl)piperazine-1-carboxylate (9au)

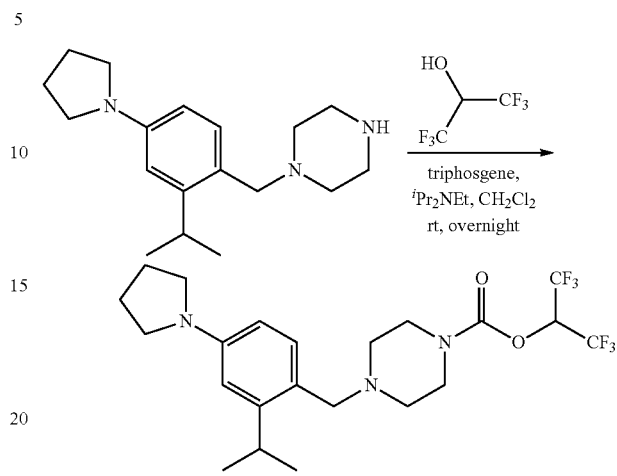

The title compound was synthesized from 1-(3-chloro-2-(pyrrolidin-1-yl)benzyl)piperazine as described in Example 42, Step 4: $^1$H NMR 300 MHz (CDCl$_3$) δ 7.00-7.02 (m, 1H), 6.50 (s, 1H), 6.33-6.36 (m, 1H), 5.70-5.79 (m, 1H), 3.44-3.49 (m, 6H), 3.29 (t, J=6.3 Hz, 5H), 2.42 (br, 4H), 1.97-2.01 (m, 4H), 1.23 (d, J=6.9 Hz, 6H). LCMS (ESI, m/z): 482 [M+H]$^+$.

Example 87

1,1,1,3,3,3-hexafluoropropan-2-yl 4-(4-chloro-2-(8-oxa-2-azaspiro[4.5]decan-2-yl)benzyl)piperazine-1-carboxylate (9av)

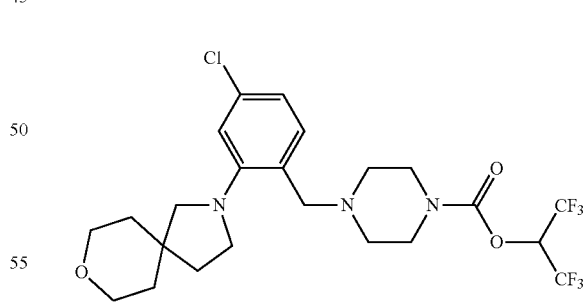

The title compound was prepared from 4-chloro-2-fluorobenzaldehyde and 8-oxa-2-azaspiro[4.5]decane as described in Example 75, Steps 1-4: $^1$H NMR 300 MHz (CDCl$_3$) δ 7.24 (t, J=7.05 Hz, 1H), 6.80-6.83 (m, 2H), 5.69-5.82 (m, 1H), 3.62-3.77 (m, 4H), 3.49-3.53 (m, 6H), 3.30 (t, J=7.05 Hz, 2H), 3.17 (s, 2H), 2.44 (br, 4H), 1.83 (t, J=7.05 Hz, 2H), 1.59-1.70 (m, 4H). LCMS (ESI, m/z): 544 [M+H]$^+$.

Example 88

1,1,1,3,3,3-hexafluoropropan-2-yl 4-(2-(4-acetylpiperazin-1-yl)-4-chlorobenzyl)piperazine-1-carboxylate (9aw)

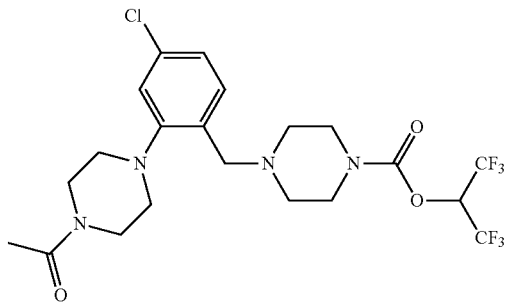 [SMILES: CC(=O)N1CCN(c2cc(Cl)ccc2CN2CCN(C(=O)OC(C(F)(F)F)C(F)(F)F)CC2)CC1]

The title compound was prepared from 4-chloro-2-fluorobenzaldehyde and 1-(piperazin-1-yl)ethanone as described in Example 75, Steps 1-4: $^1$H NMR 300 MHz (CDCl$_3$) δ 7.36 (d, J=8.4 Hz, 1H), 7.03-7.10 (m, 2H), 5.71-5.79 (m, 1H), 3.74 (br, 2H), 3.55-3.61 (m, 8H), 2.90-2.98 (m, 4H), 2.49 (br, 4H), 2.14 (s, 3H). LCMS (ESI, m/z): 531 [M+H]$^+$.

Example 89

1,1,1,3,3,3-hexafluoropropan-2-yl 4-(4-chloro-2-(1-oxo-2,8-diazaspiro[4.5]decan-8-yl)benzyl)piperazine-1-carboxylate (9ax)

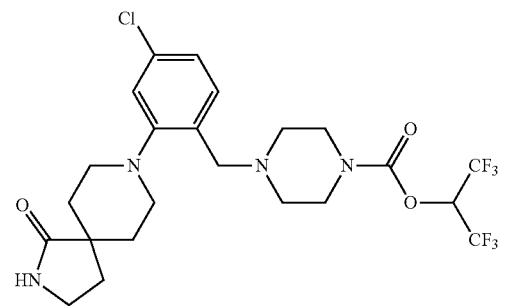 [SMILES: O=C(OC(C(F)(F)F)C(F)(F)F)N1CCN(Cc2ccc(Cl)cc2N2CCC3(CCNC3=O)CC2)CC1]

The title compound was prepared from 4-chloro-2-fluorobenzaldehyde and 1-(piperazin-1-yl)ethanone as described in Example 75, Steps 1-4: $^1$H NMR 300 MHz (CDCl$_3$) δ 7.35-7.37 (m, 1H), 7.03-7.07 (m, 2H), 6.29 (s, 1H), 5.69-5.82 (m, 1H), 3.55 (br, 6H), 3.36-3.41 (m, 2H), 3.17-3.21 (m, 2H), 2.68-2.76 (m, 2H), 2.49 (br, 4H), 2.01-2.16 (m, 4H), 1.53-1.57 (m, 2H). LCMS (ESI, m/z): 557 [M+H]$^+$.

Example 90

1,1,1,3,3,3-hexafluoropropan-2-yl 4-(2-(azetidin-1-yl)-4-chlorobenzyl)piperazine-1-carboxylate (9ay)

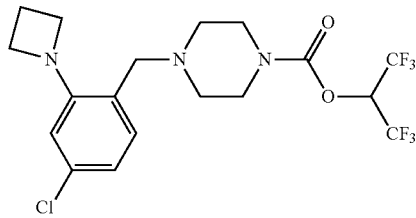 [SMILES: O=C(OC(C(F)(F)F)C(F)(F)F)N1CCN(Cc2ccc(Cl)cc2N2CCC2)CC1]

Step 1: Preparation of tert-butyl 4-(2-bromo-4-chlorobenzyl)piperazine-1-carboxylate

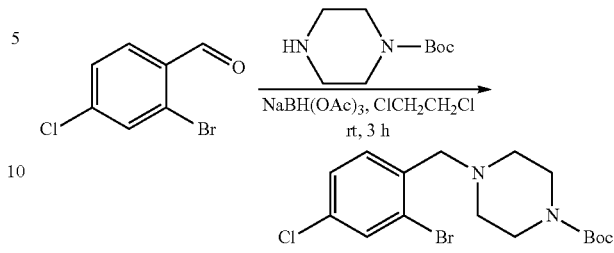

The title compound was synthesized from 2-bromo-4-chlorobenzaldehyde according to the representative procedure of Example 67, Step 2 (40.0 g, 75%). $^1$H NMR 300 MHz (CDCl$_3$) δ 7.56-7.57 (m, 1H), 7.43-7.46 (m, 1H), 7.29-7.30 (m, 1H), 3.61 (br, 2H), 3.46 (br, 4H), 2.49 (br, 4H), 1.46 (s, 9H). LCMS (ESI, m/z): 390 [M+H]$^+$.

Step 2: Preparation of tert-butyl 4-(2-(azetidin-1-yl)-4-chlorobenzyl)piperazine-1-carboxylate

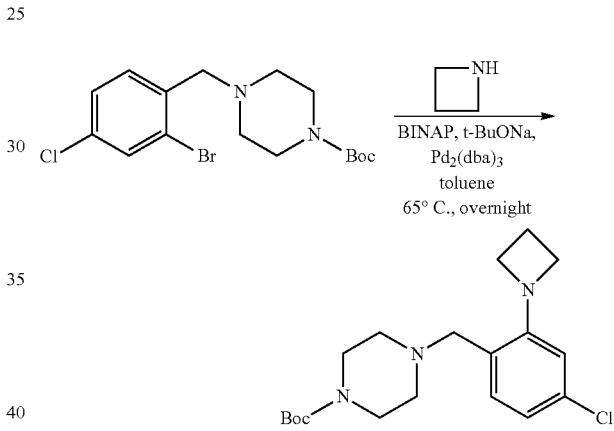

The title compound was prepared from tert-butyl 4-(2-bromo-4-chlorobenzyl)piperazine-1-carboxylate as described in Example 81, Step 2 (670 mg, 89%): LCMS (ESI, m/z): 366 [M+H]$^+$.

Step 3: Preparation of 1-(2-(azetidin-1-yl)-4-chlorobenzyl)piperazine

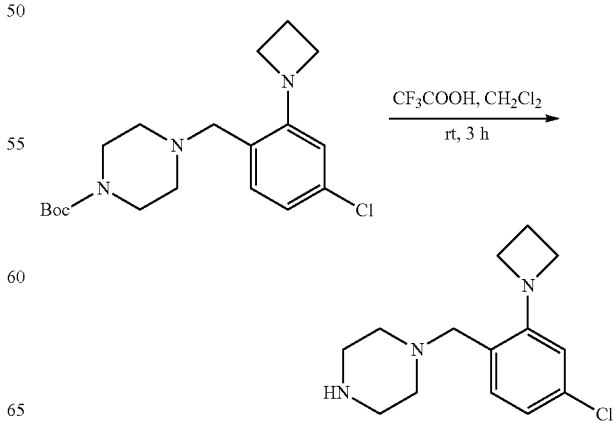

The title compound was prepared from tert-butyl 4-(2-(azetidin-1-yl)-4-chlorobenzyl)piperazine-1-carboxylate as described in Example 81, Step 2: LCMS (ESI, m/z): 266 [M+H]+.

Step 4: Preparation of 1,1,1,3,3,3-hexafluoropropan-2-yl 4-(2-(azetidin-1-yl)-4-chlorobenzyl)piperazine-1-carboxylate (9ay)

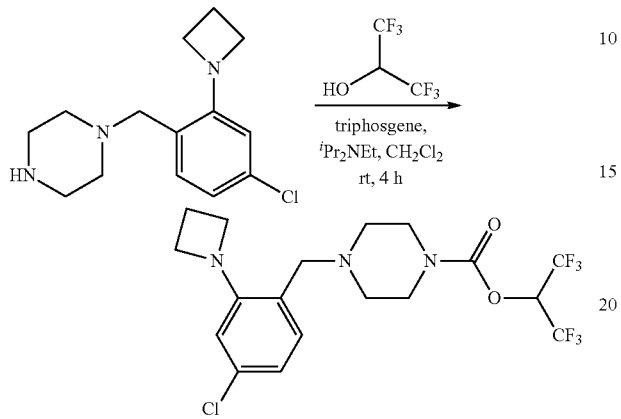

The title compound was prepared from 1-(2-(azetidin-1-yl)-4-chlorobenzyl)piperazine as described in Example 81, Step 2 (54 mg, 12%): $^1$H NMR 300 MHz (CDCl$_3$) δ 7.08 (d, J=8.1 Hz, 1H), 6.68-6.72 (m, 1H), 6.41 (s, 1H), 5.71-5.81 (m, 1H), 3.95-4.00 (m, 4H), 3.55 (br, 4H), 3.38 (br, 2H), 2.42-2.45 (m, 4H), 2.24-2.33 (m, 2H). LCMS (ESI, m/z): 460 [M+H]+.

Example 91

1,1,1,3,3,3-hexafluoropropan-2-yl 4-(3-fluoro-4-(1H-pyrazol-1-yl)benzyl)piperazine-1-carboxylate (9az)

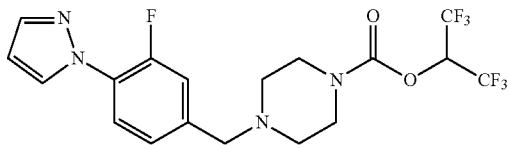 [SMILES: O=C(OC(C(F)(F)F)C(F)(F)F)N1CCN(Cc2ccc(-n3cccn3)c(F)c2)CC1]

The title compound was synthesized directly from commercially available 3-fluoro-4-(1H-pyrazol-1-yl)benzaldehyde and tert-butyl piperazine-1-carboxylate according to the representative procedure of Example 40: $^1$H NMR 400 MHz (CDCl$_3$) δ 7.93 (s, 1H), 7.83-7.74 (m, 1H), 7.67 (s, 1H), 7.18-7.09 (m, 2H), 6.45-6.37 (m, 1H), 5.75-5.60 (m, 1H), 3.58-3.34 (m, 6H), 2.53-2.17 (m, 4H). LCMS (ESI, m/z): 455.1 [M+H]+.

Example 92

(R)-1,1,1,3,3,3-hexafluoropropan-2-yl 4-(2-(3-acetamidopyrrolidin-1-yl)-4-chlorobenzyl)piperazine-1-carboxylate (9ba)

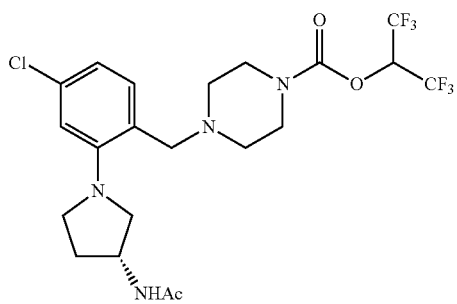

Step 1: Preparation of (R)-tert-butyl (1-(5-chloro-2-formylphenyl)pyrrolidin-3-yl)carbamate

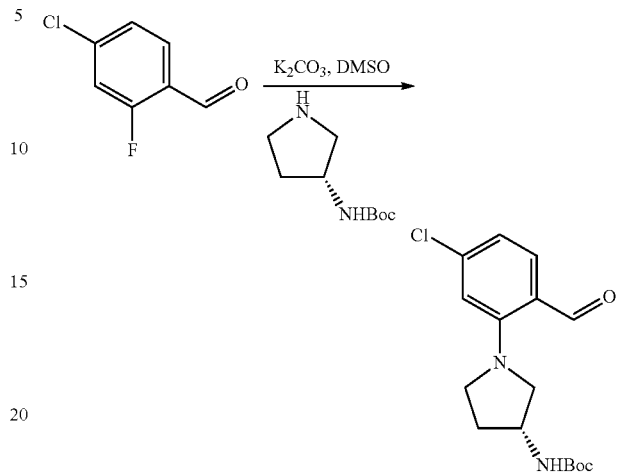

The title compound was prepared from 4-chloro-2-fluorobenzaldehyde and (R)-tert-butyl pyrrolidin-3-ylcarbamate as described in Example 70, Step 1 (30.0 mg, 81%). $^1$H NMR 400 MHz (CDCl$_3$) δ 9.98 (s, 1H), 7.63 (d, J=8.3 Hz, 1H), 6.89-6.79 (m, 2H), 4.77 (s, 1H), 3.57 (dd, J=10.7, 6.0 Hz, 2H), 3.34 (s, 1H), 3.25-3.18 (m, 1H), 2.28 (td, J=12.9, 7.0 Hz, 1H), 2.00 (td, J=12.5, 6.4 Hz, 2H), 1.46 (s, 9H). LCMS (ESI, an/z): 325 [M+H]+.

Step 2: Preparation of (R)-tert-butyl 4-(2-(3-((tert-butoxycarbonyl)amino)pyrrolidin-1-yl)-4-chlorobenzyl)piperazine-1-carboxylate

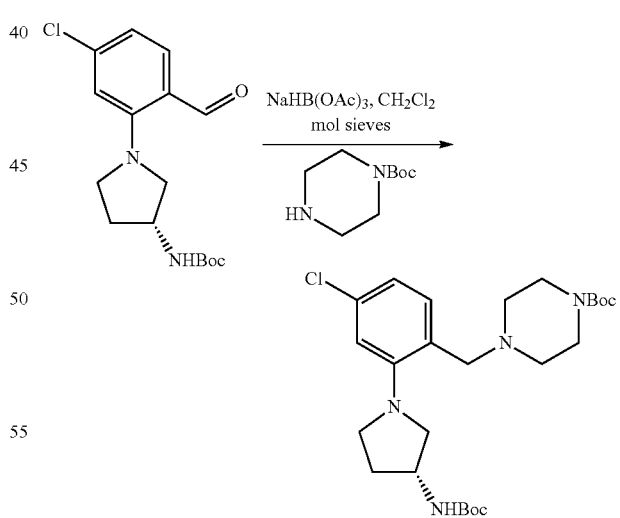

The title compound was prepared from 4-chlorobenzaldehyde as described in Example 40, Step 1 (2.1 g, 38%): $^1$H NMR 400 MHz (CDCl$_3$) δ 7.22 (d, J=8.1 Hz, 1H), 6.90-6.79 (m, 2H), 5.05 (d, J=7.9 Hz, 1H), 4.30 (s, 1H), 3.55-3.33 (m, 8H), 3.29-3.21 (m, 1H), 3.13 (td, J=8.8, 5.3 Hz, 1H), 2.36 (s, 4H), 2.32-2.17 (m, 1H), 1.94-1.82 (m, 1H), 1.46 (d, J=2.6 Hz, 9H). LCMS (ESI, m/z): 495 [M+H]⁺.

Step 3: Preparation of (R)-1,1,1,3,3,3-hexafluoropropan-2-yl 4-(2-(3-aminopyrrolidin-1-yl)-4-chlorobenzyl)piperazine-1-carboxylate

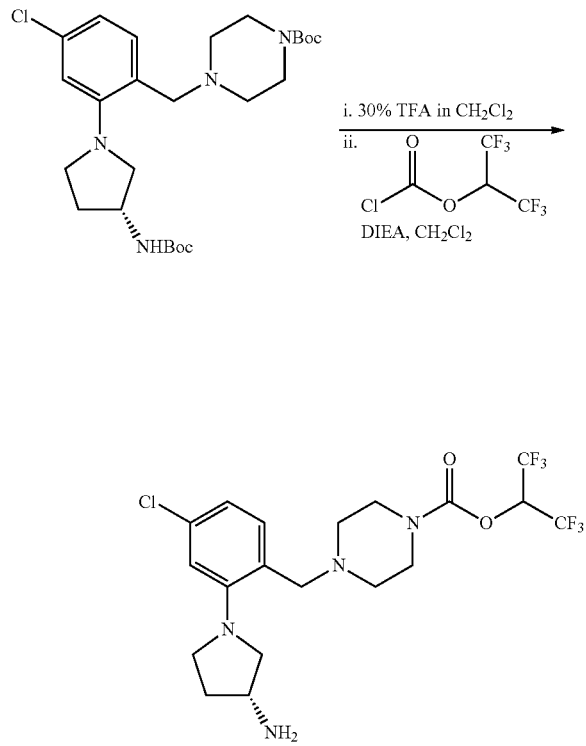

A round bottom flask was charged with triphosgene (18 mg, 0.061 mmol), CH$_2$Cl$_2$ (1 mL), and 1,1,1,3,3,3-hexafluoropropan-2-ol (30 mg, 0.202 mmol). DIPEA (104 µL, 0.606 mmol) was added to this solution dropwise and the chloroformate was allowed to form at room temperature for 2 h. A separate flask was charged with (R)-tert-butyl 4-(2-(3-((tert-butoxycarbonyl)amino)pyrrolidin-1-yl)-4-chlorobenzyl)piperazine-1-carboxylate (100 mg, 0.202 mmol) and CH$_2$Cl$_2$ (3 mL) and cooled to 0° C. Trifluoroacetic acid (1 mL) was added dropwise over 1 minute. The reaction was stirred at 0° C. for 15 min. The reaction was allowed to warm to room temperature. After 60 min, the reaction was concentrated under reduced pressure. Methanol was added and the solution was concentrated yielding crude diamine. The crude diamine was dissolved in CH$_2$Cl$_2$ (3 mL) and cooled to 4° C. DIPEA (150 µL, 0.876 mmol) was added followed by the chloroformate solution over 5 minutes. After stirring for 2 h at 0° C. the reaction was quenched by addition of sat Na$_2$CO$_3$ and extracted with CH$_2$Cl$_2$ (3×). The organics were dried (Na$_2$SO$_4$), filtered, and concentrated. The residue was chromatographed on a silica gel column (100% CH$_2$Cl$_2$ to 10% 2M NH$_3$ in MeOH) and yielded (R)-1,1,1,3,3,3-hexafluoropropan-2-yl 4-(2-(3-aminopyrrolidin-1-yl)-4-chlorobenzyl)piperazine-1-carboxylate (28 mg, 28%): ¹H NMR 400 MHz (CDCl$_3$) δ 7.29-7.22 (m, 1H), 6.92-6.76 (m, 2H), 5.82-5.66 (m, J=6.4 Hz, 1H), 3.54 (tddd, J=37.8, 22.2, 11.8, 6.2 Hz, 9H), 3.21 (ddd, J=15.3, 10.0, 5.8 Hz, 1H), 3.11-3.04 (m, 1H), 2.49-2.34 (m, 4H), 2.22 (ddd, J=19.5, 13.0, 6.6 Hz, 1H), 1.80 (dt, J=12.7, 6.4 Hz, 1H). LCMS (ESI, m/z): 489 [M+H]⁺.

Step 4: Preparation of (R)-1,1,1,3,3,3-hexafluoropropan-2-yl 4-(2-(3-acetamidopyrrolidin-1-yl)-4-chlorobenzyl)piperazine-1-carboxylate (9ba)

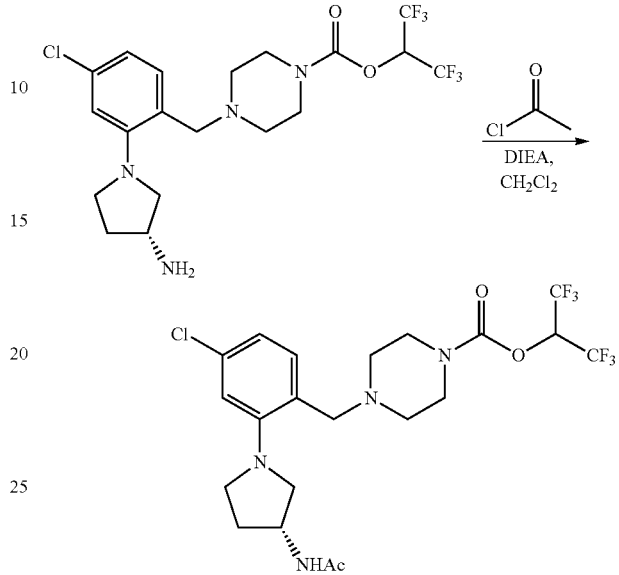

A 4 mL vial was charged with (R)-1,1,1,3,3,3-hexafluoropropan-2-yl 4-(2-(3-aminopyrrolidin-1-yl)-4-chlorobenzyl)piperazine-1-carboxylate (28 mg, 0.057 mmol), a magnetic stirbar, CH$_2$Cl$_2$ (2 mL), and DIPEA (30 µL, 0.172 mmol). The reaction was cooled to 0° C. and an acetyl chloride solution (7 mg, 0.086 mmol, in 1 mL CH$_2$Cl$_2$) was added dropwise. After stirring for 30 min at 0° C., the reaction was quenched with sat Na$_2$CO$_3$ and extracted with CH$_2$Cl$_2$ (3×). The organics were dried (Na$_2$SO$_4$), filtered, and concentrated. The residue was chromatographed on a silica gel column (100% to 10% MeOH in CH$_2$Cl$_2$) and yielded (R)-1,1,1,3,3,3-hexafluoropropan-2-yl 4-(2-(3-acetamidopyrrolidin-1-yl)-4-chlorobenzyl)piperazine-1-carboxylate (30 mg, 35%). ¹H NMR 400 MHz (CDCl$_3$) δ 7.31 (d, J=8.2 Hz, 1H), 6.91 (dd, J=8.1, 1.8 Hz, 1H), 6.86 (d, J=1.9 Hz, 1H), 5.84-5.70 (m, 2H), 4.62-4.50 (m, 1H), 3.59-3.53 (m, 4H), 3.50 (s, 2H), 3.48-3.44 (m, 1H), 3.43-3.33 (m, 1H), 3.20-3.10 (m, 2H), 2.50-2.42 (m, 4H), 2.34 (td, J=13.4, 7.6 Hz, 1H), 2.01 (s, 3H), 1.91-1.79 (m, 1H). LCMS (ESI, m/z): 531 [M+H]⁺.

Example 93

(S)-1,1,1,3,3,3-hexafluoropropan-2-yl 4-(2-(3-acetamidopyrrolidin-1-yl)-4-chlorobenzyl)piperazine-1-carboxylate (9bb)

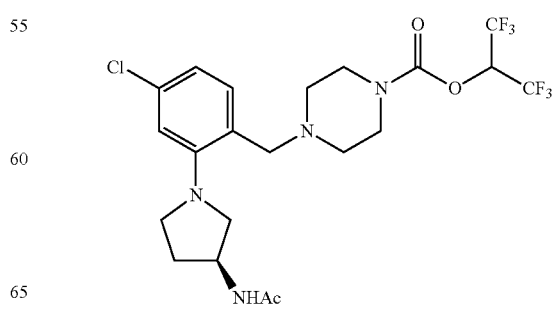

The title compound was prepared from 4-chloro-2-fluorobenzaldehyde and (S)-tert-butyl pyrrolidin-3-ylcarbamate as described in Example 92. $^1$H NMR 400 MHz (CDCl$_3$) δ 7.22 (d, J=8.2 Hz, 1H), 6.82 (dd, J=8.1, 1.8 Hz, 1H), 6.78 (d, J=1.9 Hz, 1H), 5.75-5.61 (m, 2H), 4.54-4.42 (m, 1H), 3.51-3.45 (m, 4H), 3.41 (s, 2H), 3.40-3.36 (m, 1H), 3.34-3.25 (m, 1H), 3.12-3.02 (m, 2H), 2.41-2.34 (m, 4H), 2.25 (td, J=13.4, 7.6 Hz, 1H), 1.93 (s, 3H), 1.83-1.70 (m, 1H). LCMS (ESI, m/z): 531 [M+H]$^+$.

Example 94

1,1,1,3,3,3-hexafluoropropan-2-yl 4-[[4-(morpholin-4-yl)-2-(propan-2-yl)phenyl]methyl]piperazine-1-carboxylate (9bc)

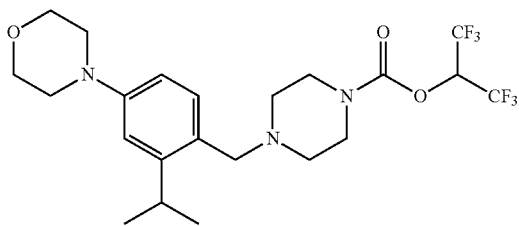 [SMILES: CC(C)c1cc(N2CCOCC2)ccc1CN1CCN(C(=O)OC(C(F)(F)F)C(F)(F)F)CC1]

The title compound was synthesized directly from tert-butyl 4-[[4-bromo-2-(propan-2-yl)phenyl]methyl]piperazine-1-carboxylate and morpholine according to the representative procedure of Example 76: $^1$H NMR 300 MHz (CDCl$_3$) δ 7.80 (d, J=8.4 Hz, 1H), 6.86 (d, J=2.4 Hz, 1H), 6.66-6.68 (m, 1H), 5.70-5.79 (m, 1H), 3.87 (t, J=4.8 Hz, 4H), 3.61-3.64 (m, 6H), 3.36-3.39 (m, 1H), 3.16 (t, J=4.8 Hz, 4H), 2.42 (br, 4H), 1.22 (d, J=6.9 Hz, 6H). LCMS: (ESI, m/z): 498 [M+H]$^+$.

Example 95

1,1,1,3,3,3-hexafluoropropan-2-yl 4-(2-chloro-4-(pyrrolidine-1-carbonyl)benzyl)piperazine-1-carboxylate (9bd)

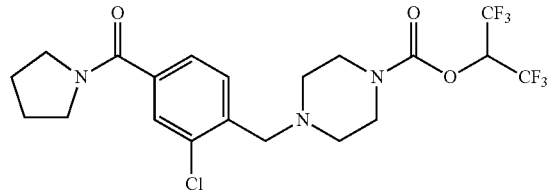 [SMILES: O=C(OC(C(F)(F)F)C(F)(F)F)N1CCN(Cc2ccc(C(=O)N3CCCC3)cc2Cl)CC1]

Step 1: Preparation of tert-butyl 4-(2-chloro-4-(methoxycarbonyl)benzyl)piperazine-1-carboxylate

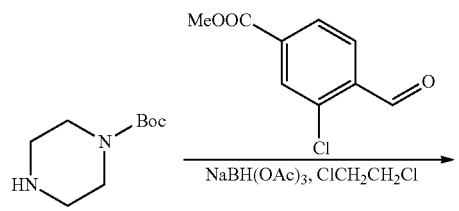

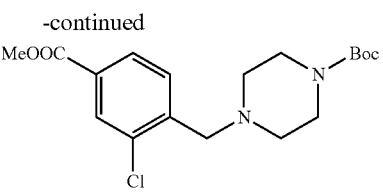

The title compound was prepared from methyl 3-chloro-4-formylbenzoate as described in Example 67, Step 2 (3.5 g, 95%): $^1$H NMR 300 MHz (CDCl$_3$) δ 8.03 (s, 1H), 7.90-7.92 (m, 1H), 7.58-7.61 (m, 1H), 3.92 (s, 3H), 3.66 (br, 2H), 3.46 (br, 4H), 2.47 (br, 4H), 1.46 (s, 9H). LCMS (ESI, m/z): 369 [M+H]$^+$.

Step 2: Preparation of 4-((4-(tert-butoxycarbonyl)piperazin-1-yl)methyl)-3-chlorobenzoic acid

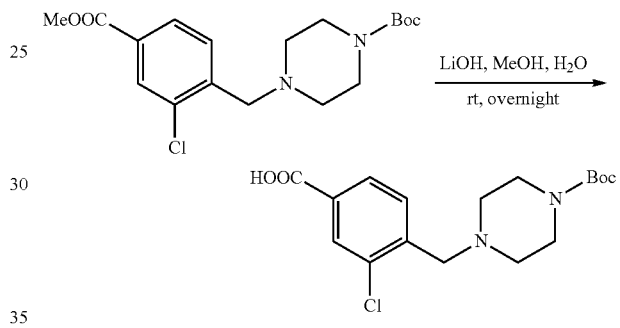

A 100 mL round-bottom flask was charged with tert-butyl 4-[[2-chloro-4-(methoxycarbonyl)phenyl]methyl]piperazine-1-carboxylate (3.54 g, 9.60 mmol, 1.00 equiv), methanol (20 mL), H$_2$O (10 mL), lithium hydroxide (0.690 g, 28.8 mmol, 3.00 equiv). The resulting solution was stirred overnight at room temperature. The pH value of the solution was adjusted to 6 with hydrogen chloride (1 mol/L). The resulting solution was extracted with dichloromethane (3×20 mL) and the organic layers were combined, washed with brine (1×20 mL), dried over anhydrous sodium sulfate, filtered and concentrated under reduced pressure to provide 2.90 g (crude) of 4-([4-[(tert-butoxy)carbonyl]piperazin-1-yl]methyl)-3-chlorobenzoic acid as a white solid. $^1$H NMR 300 MHz (CDCl$_3$) δ 7.89-8.06 (m, 3H), 3.88 (s, 2H), 3.56 (br, 4H), 2.68 (br, 4H), 1.46 (s, 9H). LCMS (ESI, m/z): 355 [M+H]$^+$.

Step 3: Preparation of tert-butyl 4-(2-chloro-4-(pyrrolidine-1-carbonyl)benzyl)piperazine-1-carboxylate

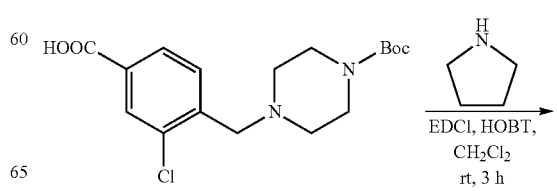

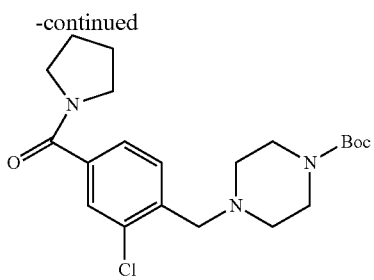

A 100 mL round-bottom flask was charged with 4-([4-[(tert-butoxy)carbonyl]piperazin-1-yl]methyl)-3-chlorobenzoic acid (600 mg, 1.69 mmol, 1.00 equiv), N-(3-dimethylaminopropyl)-N'-ethylcarbodiimide hydrochloride (487 mg, 2.54 mmol, 1.50 equiv), 1-Hydroxybenzotrizole (342 mg, 2.53 mmol, 1.50 equiv), dichloromethane (15 mL). The resulting solution was stirred for 30 min at room temperature and pyrrolidine (240 mg, 3.37 mmol, 2.00 equiv) was added. The resulting solution was stirred for 3 h at room temperature and diluted with H$_2$O (10 mL). The resulting solution was extracted with dichloromethane (3×15 mL) and the organic layers were combined, washed with brine (1×15 mL), dried over anhydrous sodium sulfate, filtered and concentrated under reduced pressure. The residue was chromatographed on a silica gel column with ethyl acetate/petroleum ether (80/20) to provide 430 mg (62% yield) of tert-butyl 4-([2-chloro-4-[(pyrrolidin-1-yl)carbonyl]phenyl]methyl)piperazine-1-carboxylate as a white solid. LCMS (ESI, m/z): 408 [M+H]$^+$.

Step 4: Preparation of (3-chloro-4-(piperazin-1-ylmethyl)phenyl)(pyrrolidin-1-yl)methanone

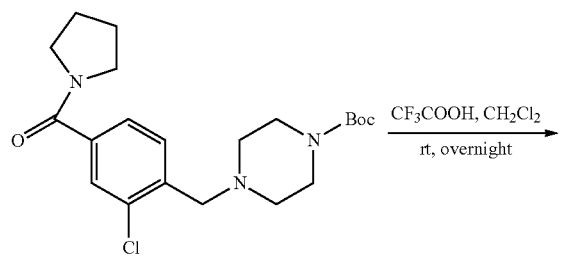

The title compound was prepared from tert-butyl 4-(2-chloro-4-(pyrrolidine-1-carbonyl)benzyl)piperazine-1-carboxylate as described in Example 42, Step 3. LCMS (ESI, m/z): 308 [M+H]$^+$.

Step 5: Preparation of 1,1,1,3,3,3-hexafluoropropan-2-yl 4-(2-chloro-4-(pyrrolidine-1-carbonyl)benzyl)piperazine-1-carboxylate (9bd)

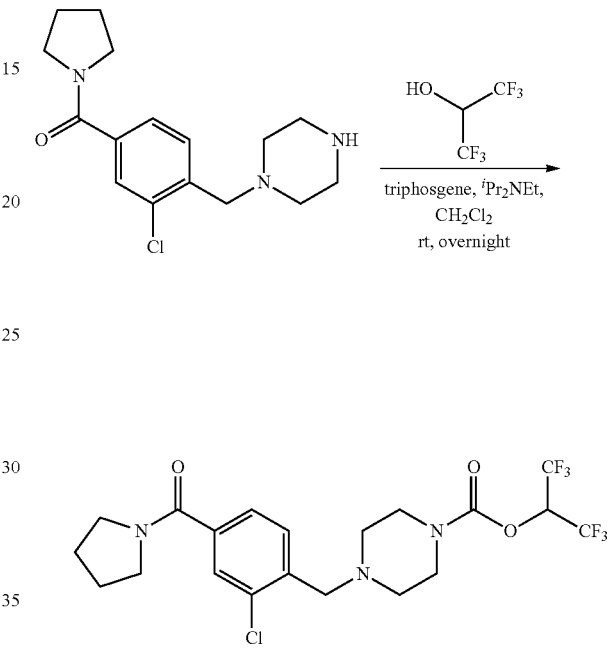

The title compound was prepared from tert-butyl 4-(2-chloro-4-(pyrrolidine-1-carbonyl)benzyl)piperazine-1-carboxylate as described in Example 42, Step 4. $^1$H NMR 300 MHz (CDCl$_3$) δ 7.39-7.61 (m, 3H), 5.69-5.81 (m, 1H), 3.57-3.66 (m, 8H), 3.42-3.46 (t, J=6.4 Hz, 2H), 2.53 (br, 4H), 1.85-2.02 (m, 4H). LCMS (ESI, m/z): 502 [M+H]$^+$.

Example 96

1,1,1,3,3,3-hexafluoropropan-2-yl 4-(4-(azetidine-1-carbonyl)-2-chlorobenzyl)piperazine-1-carboxylate (9be)

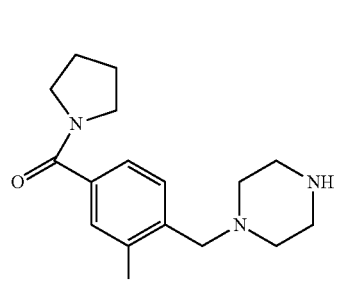

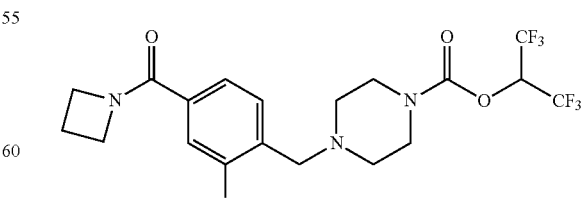

The title compound was prepared from methyl 3-chloro-4-formylbenzoate and azetidine as described in Example 95. $^1$H NMR 300 MHz (CDCl$_3$) δ 7.64 (s, 1H), 7.51 (s, 2H), 5.71-

5.81 (m, 1H), 4.21-4.35 (m, 4H), 3.66 (s, 2H), 3.56-3.58 (m, 4H), 2.50-2.56 (m, 4H), 2.31-2.42 (m, 2H). LCMS (ESI, m/z): 488 [M+H]$^+$.

Example 97

1,1,1,3,3,3-hexafluoropropan-2-yl 4-(3-chloro-2-(morpholine-4-carbonyl)benzyl)piperazine-1-carboxylate (9bf)

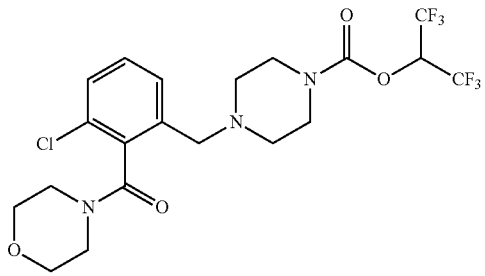 [SMILES: O=C(OC(C(F)(F)F)C(F)(F)F)N1CCN(Cc2cccc(Cl)c2C(=O)N2CCOCC2)CC1]

The title compound was prepared from methyl 2-chloro-6-formylbenzoate and morpholine as described in Example 95. $^1$H NMR 300 MHz (CDCl$_3$) δ 7.27-7.34 (m, 3H), 5.70-5.81 (m, 1H), 4.05-4.12 (m, 1H), 3.63-3.86 (m, 5H), 3.50-3.58 (m, 5H), 3.30-3.34 (m, 1H), 3.12-3.27 (m, 2H), 2.46-2.48 (m, 4H). LCMS (ESI, m/z): 518 [M+H]$^+$.

Example 98

1 1,1,1,3,3,3-hexafluoropropan-2-yl 4-(3-chloro-2-(pyrrolidine-1-carbonyl)benzyl)piperazine-1-carboxylate (9bg)

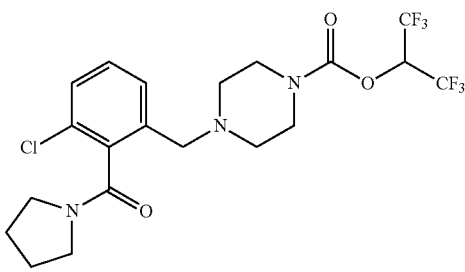 [SMILES: O=C(OC(C(F)(F)F)C(F)(F)F)N1CCN(Cc2cccc(Cl)c2C(=O)N2CCCC2)CC1]

The title compound was prepared from methyl 2-chloro-6-formylbenzoate and pyrrolidine as described in Example 95. $^1$H NMR 300 MHz (CDCl$_3$) δ 7.23-7.33 (m, 3H), 5.68-5.80 (m, 1H), 3.70-3.77 (m, 2H), 3.47-3.67 (m, 5H), 3.24-3.33 (m, 2H), 3.03-3.10 (m, 1H), 2.46-2.48 (m, 4H), 1.85-2.06 (m, 4H). LCMS (ESI, m/z): 502 [M+H]$^+$.

Example 99

1,1,1,3,3,3-hexafluoropropan-2-yl 4-(4-chloro-2-(5H-pyrrolo[3,4-b]pyridin-6(7H)-yl)benzyl)piperazine-1-carboxylate (9bh)

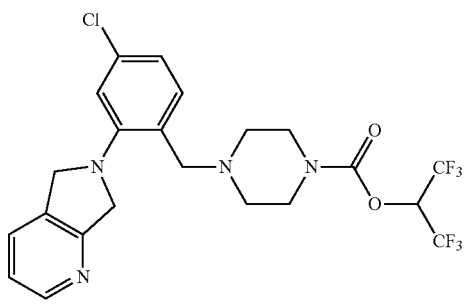 [SMILES: O=C(OC(C(F)(F)F)C(F)(F)F)N1CCN(Cc2ccc(Cl)cc2N2Cc3cccnc3C2)CC1]

The title compound was prepared from 4-chloro-2-fluorobenzaldehyde and 6,7-dihydro-5H-pyrrolo[3,4-b]pyridine as described in Example 75, Steps 1-4: $^1$H NMR 300 MHz (CDCl$_3$) δ 8.49 (s, 1H), 7.61 (d, J=7.5 Hz, 1H), 7.12-7.44 (m, 2H), 7.00 (s, 1H), 6.88-6.90 (m, 1H), 5.67-5.79 (m, 1H), 4.78-4.69 (m, 4H), 3.53-3.76 (m, 6H), 2.69 (br, 4H). LCMS (ESI, m/z): 523 [M+H]$^+$.

Example 100

(R)-1,1,1,3,3,3-hexafluoropropan-2-yl 4-(4-chloro-2-(hexahydropyrrolo[1,2-a]pyrazin-2(1H)-yl)benzyl)piperazine-1-carboxylate (9bi)

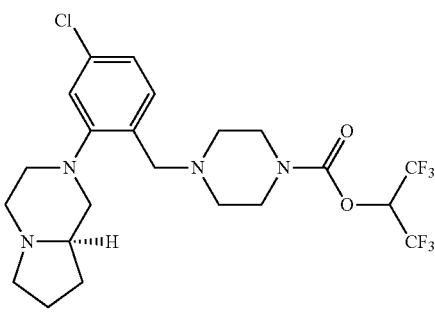 [SMILES: O=C(OC(C(F)(F)F)C(F)(F)F)N1CCN(Cc2ccc(Cl)cc2N2CCN3CCC[C@@H]3C2)CC1]

The title compound was prepared from methyl 2-chloro-6-formylbenzoate and pyrrolidine as described in Example 95. $^1$H NMR 300 MHz (CDCl$_3$) δ 7.32-7.35 (m, 1H), 7.02-7.08 (m, 2H), 5.71-5.80 (m, 1H), 3.52 (br, 6H), 3.27 (d, J=10.8 Hz, 1H), 3.08-3.17 (m, 3H), 2.90-2.95 (m, 1H), 2.38-2.62 (m, 6H), 2.23-2.26 (m, 2H), 1.76-1.93 (m, 3H), 1.45-1.52 (m, 1H). LCMS (ESI, m/z): 529 [M+H]$^+$.

Example 101

1,1,1,3,3,3-hexafluoropropan-2-yl 4-(4-chloro-2-(4-(methylsulfonyl)piperazin-1-yl)benzyl)piperazine-1-carboxylate (9bj)

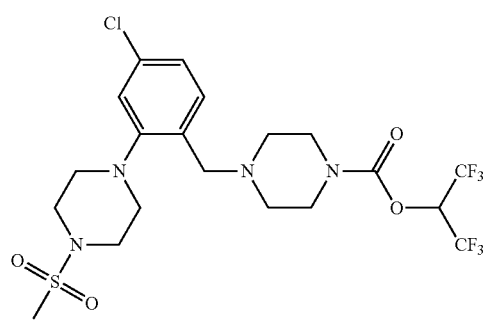 [SMILES: CS(=O)(=O)N1CCN(c2cc(Cl)ccc2CN2CCN(C(=O)OC(C(F)(F)F)C(F)(F)F)CC2)CC1]

The title compound was prepared from methyl 2-chloro-6-formylbenzoate and pyrrolidine as described in Example 95. $^1$H NMR 300 MHz (CDCl$_3$) δ 7.38-7.40 (m, 1H), 7.07-7.12

(m, 2H), 5.70-5.79 (m, 1H), 3.56 (br, 6H), 3.36-3.39 (m, 4H), 3.05-3.08 (m, 4H), 2.86 (s, 3H), 2.50 (br, 4H). LCMS (ESI, m/z): 567 [M+H]⁺.

Example 102

1,1,1,3,3,3-hexafluoropropan-2-yl 4-((5-(4-methoxyphenyl)isoxazol-3-yl)methyl)piperazine-1-carboxylate (10a)

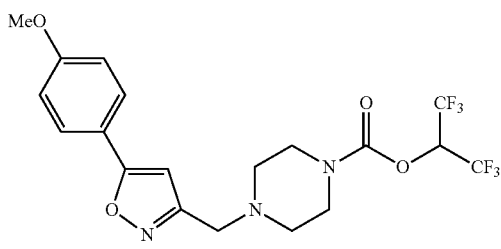 [SMILES: COc1ccc(-c2cc(CN3CCN(C(=O)OC(C(F)(F)F)C(F)(F)F)CC3)no2)cc1]

Step 1: Preparation of tert-butyl 4-((5-(4-methoxyphenyl)isoxazol-3-yl)methyl)piperazine-1-carboxylate

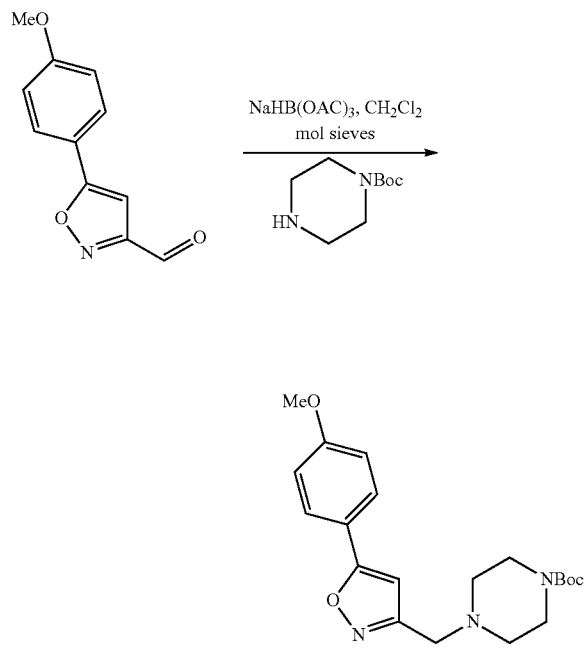

The title compound was prepared from 5-(4-methoxyphenyl)isoxazole-3-carbaldehyde as described in Example 40, Step 1 (300 mg, 80%). ¹H NMR 400 MHz (CDCl₃) δ 7.66 (d, J=8.1 Hz, 2H), 6.92 (d, J=8.8 Hz, 2H), 6.39 (s, 1H), 3.80 (s, 3H), 3.59 (s, 2H), 3.41 (s, 4H), 2.44 (s, 4H), 1.41 (s, 9H). LCMS (ESI, m/z): 374 [M+H]⁺.

Step 2: Preparation of 1,1,1,3,3,3-hexafluoropropan-2-yl 4-((5-(4-methoxyphenyl)isoxazol-3-yl)methyl)piperazine-1-carboxylate (10a)

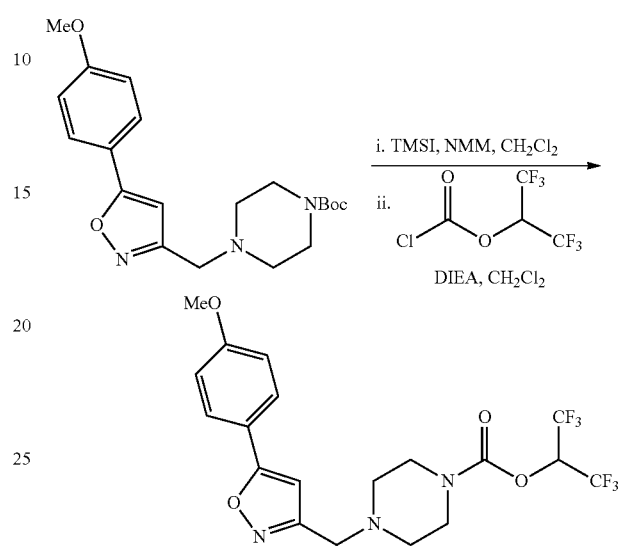

The title compound was prepared from tert-butyl 4-((5-(4-methoxyphenyl)isoxazol-3-yl)methyl)piperazine-1-carboxylate as described in Example 1, Step 2 (70 mg, 82%). ¹H NMR 400 MHz (CDCl₃) δ 7.73 (d, J=8.5 Hz, 2H), 6.99 (d, J=8.6 Hz, 2H), 6.44 (s, 1H), 5.77 (hept, J=6.3 Hz, 1H), 3.88 (s, 3H), 3.68 (s, 2H), 3.65-3.55 (m, 4H), 2.74-2.41 (m, 4H). LCMS (ESI, an/z): 468 [M+H]⁺.

Example 103

1,1,1,3,3,3-hexafluoropropan-2-yl 4-((5-phenylisoxazol-3-yl)methyl)piperazine-1-carboxylate (10b)

Step 1: Preparation of tert-butyl 4-((5-phenylisoxazol-3-yl)methyl)piperazine-1-carboxylate

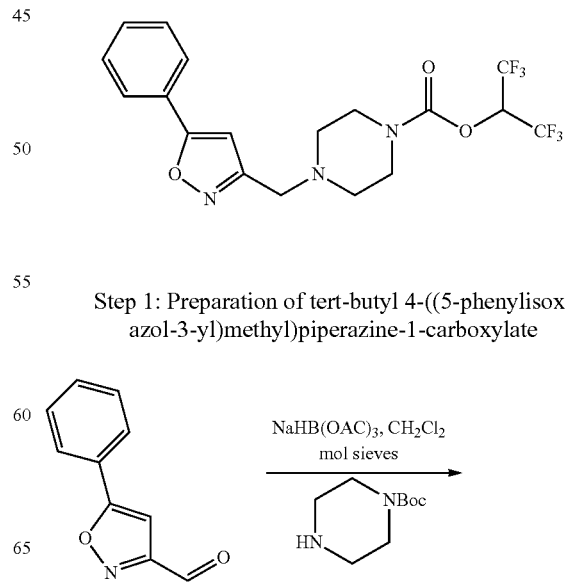

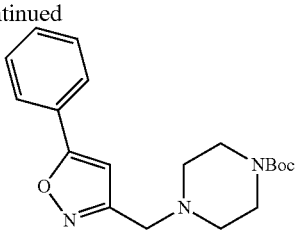

The title compound was prepared from 5-phenylisoxazole-3-carbaldehyde as described in Example 40, Step 1 (300 mg, 82%): $^1$H NMR 400 MHz (CDCl$_3$) δ 7.74-7.66 (m, 2H), 7.44-7.31 (m, 3H), 6.49 (s, 1H), 3.58 (s, 2H), 3.42-3.35 (m, 4H), 2.41 (s, 4H), 1.38 (s, 9H). LCMS (ESI, m/z): 344 [M+H]$^+$.

Step 2: Preparation of 1,1,1,3,3,3-hexafluoropropan-2-yl 4-((5-phenylisoxazol-3-yl)methyl)piperazine-1-carboxylate (10b)

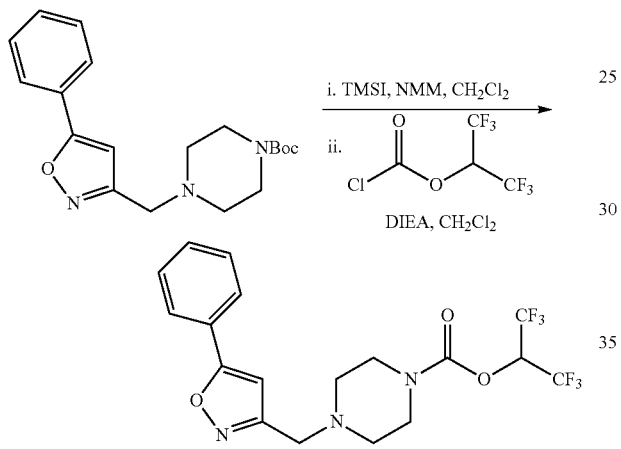

The title compound was prepared from tert-butyl 4-((5-phenylisoxazol-3-yl)methyl)piperazine-1-carboxylate as described in Example 1, step 2 (60 mg, 64%). $^1$H NMR 400 MHz (CDCl$_3$) δ 7.84-7.76 (m, 2H), 7.55-7.40 (m, 3H), 6.57 (s, 1H), 5.78 (hept, J=6.2 Hz, 1H), 3.70 (s, 2H), 3.68-3.57 (m, 4H), 2.64-2.53 (m, 4H). LCMS (ESI, m/z): 438 [M+H]$^+$.

Example 104

1,1,1,3,3,3-hexafluoropropan-2-yl 4-((3-methyl-1-phenyl-1H-pyrazol-4-yl)methyl)piperazine-1-carboxylate (10c)

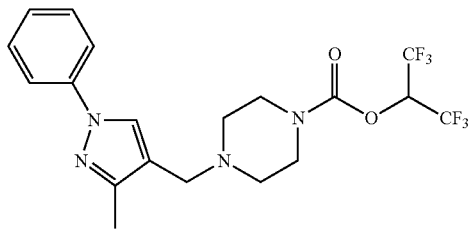 [SMILES: Cc1nn(-c2ccccc2)cc1CN1CCN(C(=O)OC(C(F)(F)F)C(F)(F)F)CC1]

The title compound was synthesized directly from commercially available 3-methyl-1-phenyl-1H-pyrazole-4-carboxaldehyde and tert-butyl piperazine-1-carboxylate according to the representative procedure of Example 40: $^1$H NMR 400 MHz (CDCl$_3$) δ 7.71 (s, 1H), 7.56 (d, J=7.5, 2H), 7.35 (t, J=7.4, 2H), 7.19 (t, J=7.4, 1H), 5.68 (hep, J=6.2, 1H), 3.53- 3.48 (m, 4H), 3.37 (s, 2H), 2.45-2.35 (m, 4H), 2.26 (s, 3H). LCMS (ESI, m/z): 451.1 [M+H]$^+$.

Example 105

1,1,1,3,3,3-hexafluoropropan-2-yl 4-((1-methyl-3-phenyl-1H-pyrazol-5-yl)methyl)piperazine-1-carboxylate (10d)

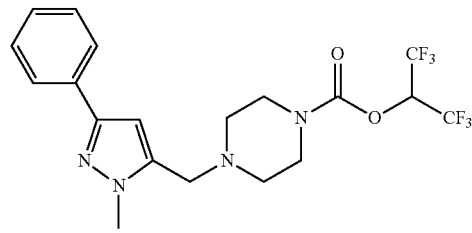 [SMILES: Cn1nc(-c2ccccc2)cc1CN1CCN(C(=O)OC(C(F)(F)F)C(F)(F)F)CC1]

The title compound was synthesized directly from commercially available 1-methyl-3-phenyl-1H-pyrazole-5-carboxaldehyde and tert-butyl piperazine-1-carboxylate according to the representative procedure of Example 40: $^1$H NMR 400 MHz (CDCl$_3$) δ 7.69 (d, J=7.4, 2H), 7.31 (d, J=7.4, 2H), 7.21 (t, J=7.4, 1H), 6.33 (s, 1H), 5.68 (hep, J=6.2, 1H), 3.86 (s, 3H), 3.55-3.45 (bs, 6H), 2.45-2.35 (m, 4H). LCMS (ESI, m/z): 451.1 [M+H]$^+$.

Example 106

1,1,1,3,3,3-hexafluoropropan-2-yl 4-((1-methyl-3-phenyl-1H-pyrazol-4-yl)methyl)piperazine-1-carboxylate (10e)

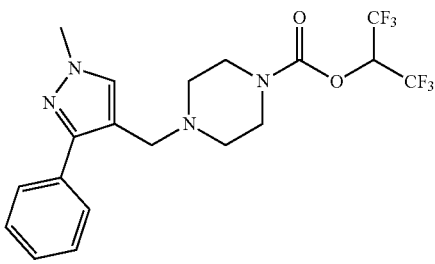 [SMILES: Cn1cc(CN2CCN(C(=O)OC(C(F)(F)F)C(F)(F)F)CC2)c(-c2ccccc2)n1]

The title compound was synthesized directly from commercially available 1-methyl-3-phenyl-1H-pyrazole-4-carbaldehyde and tert-butyl piperazine-1-carboxylate according to the representative procedure of Example 40: $^1$H NMR 400 MHz (CDCl$_3$) δ 7.79 (d, J=7.6 Hz, 2H), 7.40 (t, J=7.6 Hz, 2H), 7.37-7.28 (m, 2H), 5.75 (hep, J=6.2 Hz), 3.93 (s, 3H), 3.58-3.53 (m, 4H), 3.47 (s, 2H), 2.53-2.42 (m, 4H). LCMS (ESI, an/z): 451.1 [M+H]$^+$.

Example 107

1,1,1,3,3,3-hexafluoropropan-2-yl 4-((4-bromo-1-methyl-1H-pyrazol-5-yl)methyl)piperazine-1-carboxylate (10f)

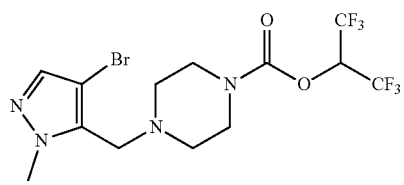 [SMILES: Cn1ncc(Br)c1CN1CCN(C(=O)OC(C(F)(F)F)C(F)(F)F)CC1]

215

Step 1: Preparation of tert-butyl 4-((4-bromo-1-methyl-1H-pyrazol-5-yl)methyl)piperazine-1-carboxylate

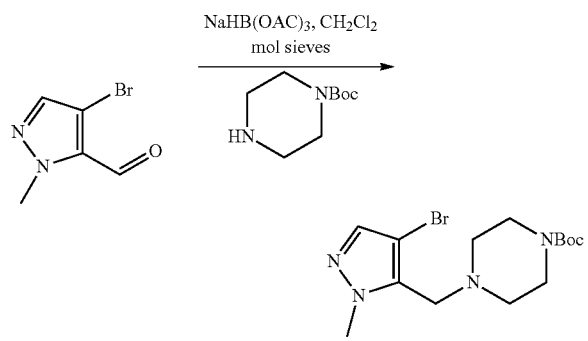

The title compound was prepared from 4-bromo-1-methyl-1H-pyrazole-5-carbaldehyde (200 mg, 1.06 mmol) as described in Example 40, Step 1 (310 mg, 81%). $^1$H NMR 400 MHz (CDCl$_3$) δ 7.37 (d, J=3.8 Hz, 1H), 3.98-3.86 (m, 3H), 3.50 (s, 2H), 3.38 (s, 4H), 2.38 (s, 4H), 1.44 (s, 9H). LCMS (ESI, m/z): 359 [M+H]$^+$.

Step 2: Preparation of 1,1,1,3,3,3-hexafluoropropan-2-yl 4-((4-bromo-1-methyl-1H-pyrazol-5-yl)methyl)piperazine-1-carboxylate (10f)

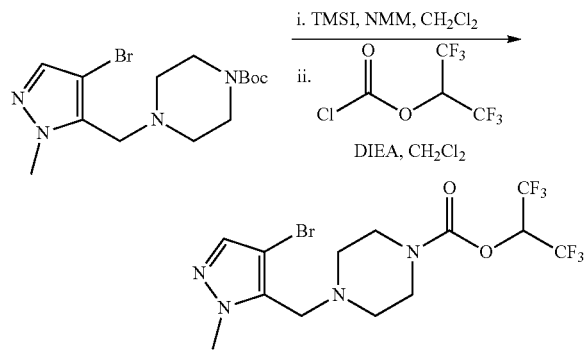

The title compound was prepared from tert-butyl 4-((4-bromo-1-methyl-1H-pyrazol-5-yl)methyl)piperazine-1-carboxylate as described in Example 1, step 2 (129 mg, 66%). $^1$H NMR 400 MHz (CDCl$_3$) δ 7.42 (s, 1H), 5.77 (hept, J=6.1 Hz, 1H), 3.93 (s, 3H), 3.55 (m, 4H), 2.49 (m, 4H). LCMS (ESI, m/z): 453 [M+H]$^+$.

Example 108

1,1,1,3,3,3-hexafluoropropan-2-yl 4-[[3-(2-chlorophenyl)-1-methyl-1H-pyrazol-4-yl]methyl]piperazine-1-carboxylate (10g)

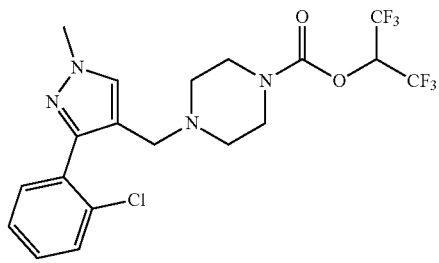 [SMILES: Cn1cc(CN2CCN(C(=O)OC(C(F)(F)F)C(F)(F)F)CC2)c(-c2ccccc2Cl)n1]

216

Step 1: (Z)-1-[1-(2-chlorophenyl)ethylidene]-2-methylhydrazine

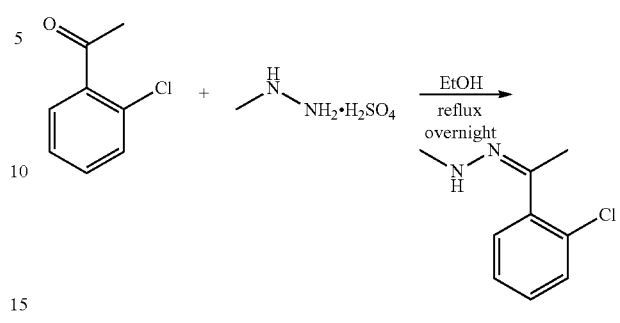

A 100 mL round-bottom flask purged and maintained with an inert atmosphere of nitrogen and charged with 1-(2-chlorophenyl)ethan-1-one (3.80 g, 24.6 mmol, 1.20 equiv), methylhydrazine sulfate (3.00 g, 20.8 mmol, 1.00 equiv) and ethanol (30 mL). The resulting solution was heated to reflux overnight. The reaction progress was monitored by LCMS. The resulting mixture was concentrated under reduced pressure to provide 7.0 g (crude) of (Z)-1-[1-(2-chlorophenyl)ethylidene]-2-methylhydrazine as yellow oil. LCMS (ESI, m/z): 183 [M+H]$^+$.

Step 2: 3-(2-chlorophenyl)-1-methyl-1H-pyrazole-4-carbaldehyde

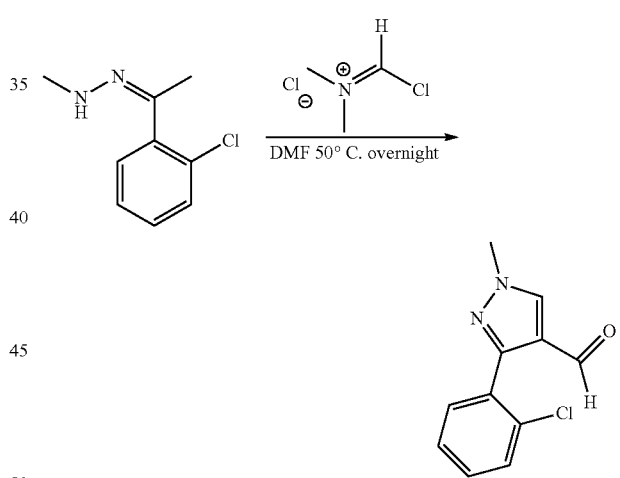

A 100 mL round-bottom flask was purged and maintained with an inert atmosphere of nitrogen and charged with (Z)-1-[1-(2-chlorophenyl)ethylidene]-2-methylhydrazine (2.00 g, 10.9 mmol, 1.00 equiv), (chloromethylidene)dimethylazanium chloride (12.7 g, 99.2 mmol, 9.06 equiv) and N,N-dimethylformamide (40 mL). The resulting solution was stirred overnight at 50° C. The reaction progress was monitored by LCMS. The reaction was then quenched by the addition of saturated sodium carbonate solution (100 mL). The resulting solution was extracted with ethyl acetate (3×100 mL) and the organic layers were combined, washed with brine (2×100 mL), dried over sodium sulfate and concentrated under reduced pressure. The residue was chromatographed on a silica gel column with ethyl acetate/petroleum ether (1/1) to yield 1.00 g (41% yield) of 3-(2-chlorophenyl)-

1-methyl-1H-pyrazole-4-carbaldehyde as a yellow solid. LCMS (ESI, m/z): 221 [M+H]+.

Step 3-5: Preparation of 1,1,1,3,3,3-hexafluoropropan-2-yl 4-[[3-(2-chlorophenyl)-1-methyl-1H-pyrazol-4-yl]methyl]piperazine-1-carboxylate (10g)

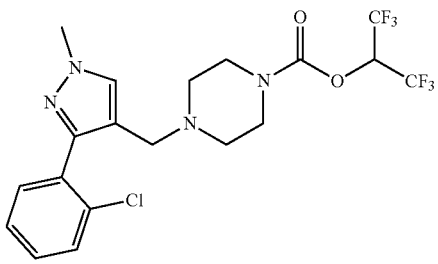 [SMILES: Cn1cc(CN2CCN(C(=O)OC(C(F)(F)F)C(F)(F)F)CC2)c(-c2ccccc2Cl)n1]

The title compound was synthesized according to the representative procedure of Example 40 using 3-(2-chlorophenyl)-1-methyl-1H-pyrazole-4-carbaldehyde from Step 2 of this example. ¹H NMR 300 MHz (CDCl₃) δ 7.26-7.46 (m, 5H), 5.67-5.75 (m, 1H), 3.94 (s, 3H), 3.40 (br, 6H), 2.31 (br, 4H). LCMS (ESI, m/z): 485 [M+H]+

Example 109

1,1,1,3,3,3-hexafluoropropan-2-yl 4-[[3-phenyl-1-(propan-2-yl)-1H-pyrazol-4-yl]methyl]piperazine-1-carboxylate (10h)

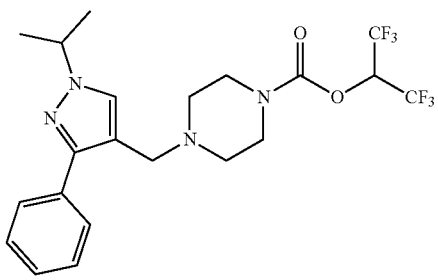 [SMILES: CC(C)n1cc(CN2CCN(C(=O)OC(C(F)(F)F)C(F)(F)F)CC2)c(-c2ccccc2)n1]

The title compound was synthesized according to the representative procedure of Example 131 Steps 1-5 using commercially available propan-2-ylhydrazine hydrochloride and 1-phenylethan-1-one. ¹H NMR 300 MHz (CDCl₃) δ 7.81 (d, J=7.2 Hz, 2H), 7.29-7.42 (m, 4H), 5.70-5.79 (m, 1H), 4.48-4.57 (m, 1H), 3.56 (br, 4H), 3.47 (s, 2H), 2.48-2.51 (m, 4H), 1.55 (d, J=6.6 Hz, 6H). LCMS (ESI, m/z): 479 [M+H]+.

Example 110

1,1,1,3,3,3-hexafluoropropan-2-yl 4-[[3-(2-chlorophenyl)-1-(propan-2-yl)-1H-pyrazol-4-yl]methyl]piperazine-1-carboxylate (10i)

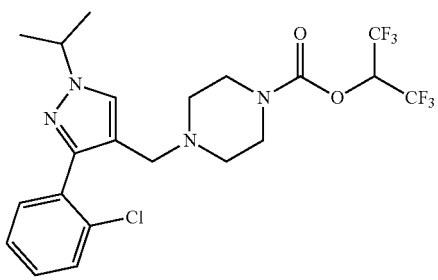 [SMILES: CC(C)n1cc(CN2CCN(C(=O)OC(C(F)(F)F)C(F)(F)F)CC2)c(-c2ccccc2Cl)n1]

The title compound was synthesized according to the representative procedure of Example 131 Steps 1-5 using commercially available isopropylhydrazine hydrochloride and 1-(2-chlorophenyl)ethan-1-one. ¹H NMR 300 MHz (CDCl₃) δ 7.36-7.46 (m, 3H), 7.25-7.33 (m, 2H), 5.67-5.75 (m, 1H), 4.48-4.57 (m, 1H), 3.40 (s, 6H), 2.31 (br, 4H), 1.56 (s, 3H), 1.54 (s, 3H). LCMS (ESI, m/z): 513 [M+H]+.

Example 111

1,1,1,3,3,3-hexafluoropropan-2-yl 3-methyl-4-[(4-phenylphenyl)methyl]piperazine-1-carboxylate (11a)

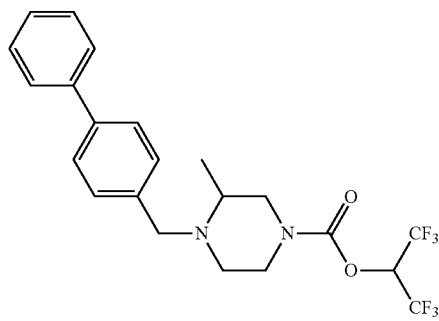 [SMILES: CC1CN(C(=O)OC(C(F)(F)F)C(F)(F)F)CCN1Cc1ccc(-c2ccccc2)cc1]

Step 1: Preparation of tert-butyl 3-methyl-4-[(4-phenylphenyl)methyl]piperazine-1-carboxylate

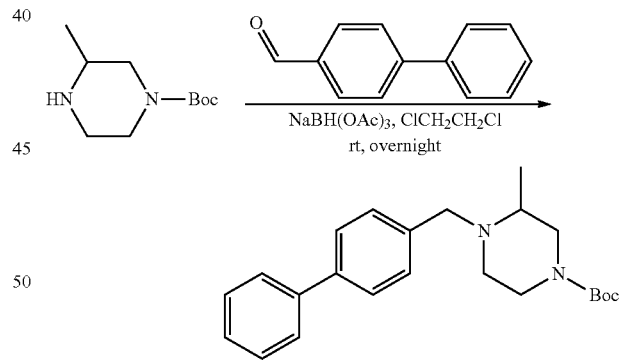

A 100 mL round-bottom flask was charged with tert-butyl 3-methylpiperazine-1-carboxylate (1.00 g, 4.99 mmol, 1.00 equiv), 4-phenylbenzaldehyde (1.00 g, 5.49 mmol, 1.10 equiv), sodium triacetoxyborohydride (3.18 g, 15.0 mmol, 3.01 equiv), 1,2-dichloroethane (30 mL). The resulting solution was stirred overnight at room temperature. The resulting solution was washed with water (1×120 mL) and extracted with dichloromethane (3×20 mL) and the organic layers were combined, dried over anhydrous sodium sulfate, filtered and concentrated under reduced pressure. The residue was chromatographed on a silica gel column with ethyl acetate/petroleum ether (1/5) to yield 1.71 g (93% yield) of tert-butyl 3-methyl-4-[(4-phenylphenyl)methyl]piperazine-1-carboxylate as a light yellow solid. LCMS (ESI, m/z): 367 [M+H]⁺.

Step 2: Preparation of
2-methyl-1-[(4-phenylphenyl)methyl]piperazine

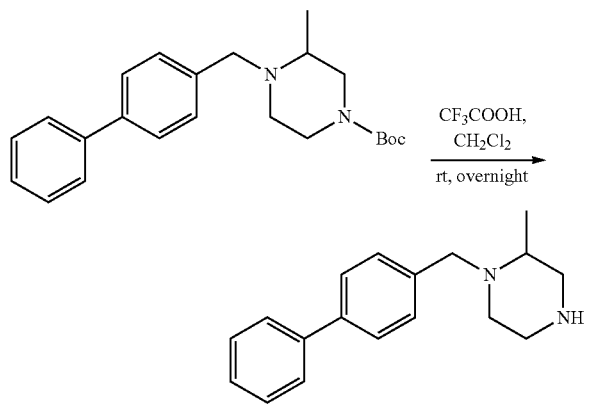

A 100 mL round-bottom flask was charged with tert-butyl 3-methyl-4-[(4-phenylphenyl)methyl]piperazine-1-carboxylate (600 mg, 1.64 mmol, 1.00 equiv), dichloromethane (25 mL). Trifluoroacetic acid (1 mL) was added dropwise. The resulting solution was stirred overnight at room temperature. The resulting solution was concentrated under reduced pressure to yield 532 mg (crude) of 2-methyl-1-[(4-phenylphenyl)methyl]piperazine as brown oil. LCMS (ESI, m/z): 267 [M+H]⁺.

Step 3: Preparation of 1,1,1,3,3,3-hexafluoropropan-2-yl 3-methyl-4-[(4-phenylphenyl)methyl]piperazine-1-carboxylate (11a)

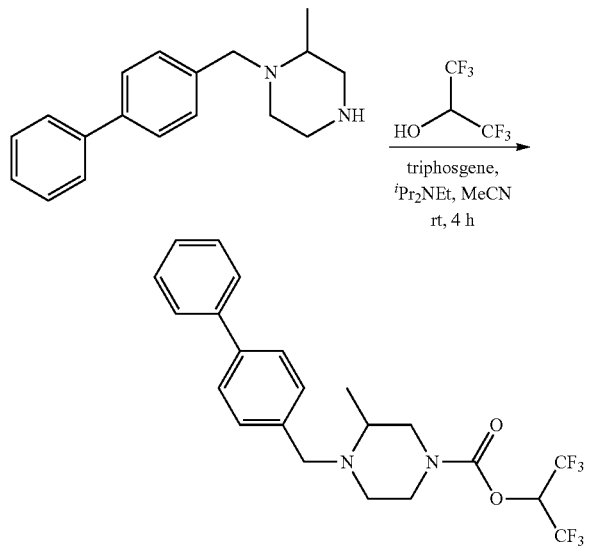

A 50 mL round-bottom flask was charged with 1,1,1,3,3,3-hexafluoropropan-2-ol (168 mg, 1.00 mmol, 1.00 equiv), triphosgene (99.0 mg, 0.330 mmol, 0.33 equiv), and acetonitrile (10 mL). N,N-diisopropylethylamine (471 mg, 3.64 mmol, 3.65 equiv) was added dropwise. The mixture was stirred at room temperature for 2 hours. 2-Methyl-1-[(4-phenylphenyl)methyl]piperazine (266 mg, 1.00 mmol, 1.00 equiv) was added. The resulting solution was stirred for 2 hours at room temperature and diluted with water (20 mL). The resulting solution was extracted with dichloromethane (3×20 mL) and the organic layers were dried over anhydrous sodium sulfate, filtered and concentrated under reduced pressure. The residue was chromatographed on a silica gel column with ethyl acetate/petroleum ether (1/3). The product (208 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep $C_{18}$, 19*150 mm 5 um; Mobile phase: Phase A: aqueous NH₄HCO₃ (0.05%); Phase B: CH₃CN; Detector, UV220 & 254 nm. Purification resulted in 91.3 mg (20% yield) of 1,1,1,3,3,3-hexafluoropropan-2-yl 3-methyl-4-[(4-phenylphenyl)methyl]piperazine-1-carboxylate as colorless oil. ¹H NMR 400 MHz (CDCl₃) δ 7.54-7.62 (m, 4H), 7.33-7.49 (m, 5H), 5.75-5.80 (m, 1H), 3.98-4.23 (m, 1H), 3.75-3.86 (m, 2H), 3.01-3.48 (m, 3H), 2.62-2.77 (m, 2H), 2.20-2.27 (m, 1H), 1.19 (br, 3H). LCMS (ESI, m/z): 461 [M+H]⁺.

Example 112

1,1,1,3,3,3-hexafluoropropan-2-yl 4-[[2-methyl-6-(2-methylphenyl)pyridin-3-yl]methyl]piperazine-1-carboxylate (11b)

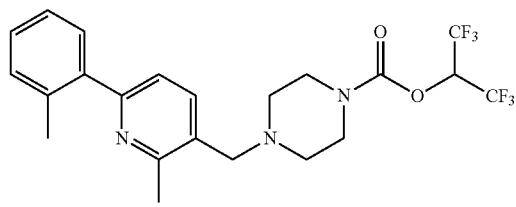 [SMILES: Cc1ccccc1-c1ccc(CN2CCN(C(=O)OC(C(F)(F)F)C(F)(F)F)CC2)c(C)n1]

Step 1: Preparation of tert-butyl 4-[(6-bromo-2-methylpyridin-3-yl)methyl]piperazine-1-carboxylate

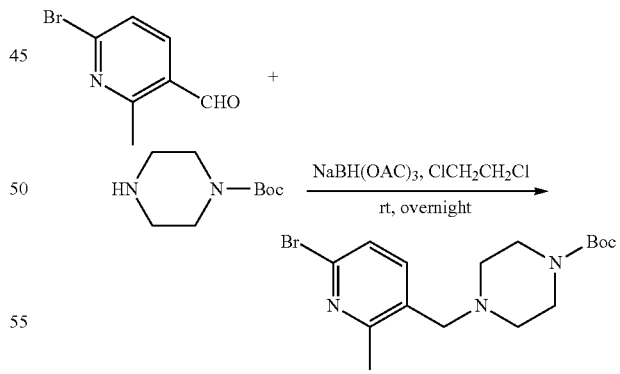

A 100 mL round-bottom flask was charged with 6-bromo-2-methylpyridine-3-carbaldehyde (2.50 g, 12.6 mmol, 1.00 equiv), tert-butyl piperazine-1-carboxylate (2.34 g, 12.6 mmol, 1.00 equiv), and dichloromethane (50 mL). The resulting solution was stirred for 30 min at room temperature. Sodium triacetoxyborohydride (8.00 g, 37.8 mmol, 3.00 equiv) was added. The resulting solution was stirred overnight at room temperature and then diluted with water (30 mL). The resulting mixture was extracted with dichloromethane (3×20 mL) and the organic layers were combined, dried over anhydrous sodium sulfate, filtered and concentrated under reduced pressure. The residue was chromatographed on a silica gel column with ethyl acetate/petroleum ether (22/78) to provide 3.80 g (82% yield) of tert-butyl 4-[(6-bromo-2-methylpyridin-3-yl)methyl]piperazine-1-carboxylate as a white solid. LCMS (ESI, m/z): 370 [M+H]+.

Step 2: Preparation of tert-butyl 4-[[2-methyl-6-(2-methylphenyl)pyridin-3-yl]methyl]piperazine-1-carboxylate

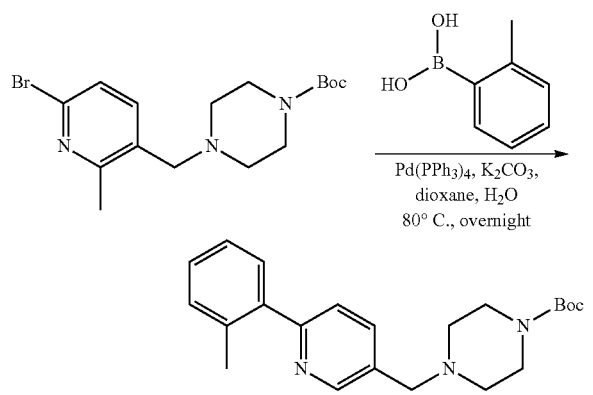

A 50 mL round-bottom flask was purged with and maintained under an inert atmosphere of nitrogen then charged with tert-butyl 4-[(6-bromo-2-methylpyridin-3-yl)methyl]piperazine-1-carboxylate (800 mg, 2.16 mmol, 1.00 equiv), (2-methylphenyl)boronic acid (590 mg, 4.34 mmol, 2.00 equiv), tetrakis(triphenylphosphine)palladium (250 mg, 0.220 mmol, 0.10 equiv), potassium carbonate (898 mg, 6.50 mmol, 3.00 equiv), dioxane (12 mL), and water (2 mL). The resulting solution was stirred overnight at 80° C. and then diluted with water (10 mL) and extracted with dichloromethane (3×10 mL). The organic layers were combined, dried over anhydrous sodium sulfate, filtered and concentrated under reduced pressure. The residue was chromatographed on a silica gel column with ethyl acetate/petroleum ether (22/78) to provide 800 mg (97% yield) of tert-butyl 4-[[2-methyl-6-(2-methylphenyl)pyridin-3-yl]methyl]piperazine-1-carboxylate as a yellow oil. LCMS (ESI, m/z): 382 [M+H]+.

Step 3: Preparation of 1-[[2-methyl-6-(2-methylphenyl)pyridin-3-yl]methyl]piperazine

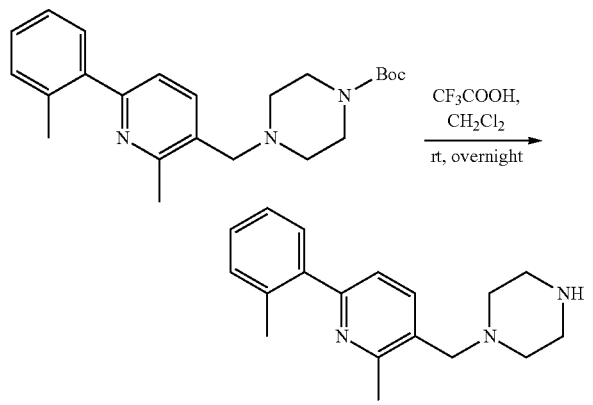

A 100 mL round-bottom flask was charged with tert-butyl 4-[[2-methyl-6-(2-methylphenyl)pyridin-3-yl]methyl]piperazine-1-carboxylate (800 mg, 2.40 mmol, 1.00 equiv), dichloromethane (20 mL), trifluoroacetic acid (4 mL) was added dropwise. The resulting solution was stirred overnight at room temperature. The resulting mixture was concentrated under reduced pressure to provide 590 mg (crude) of 1-[[2-methyl-6-(2-methylphenyl)pyridin-3-yl]methyl]piperazine as yellow oil. LCMS (ESI, m/z): 282 [M+H]+.

Step 4: Preparation of 1,1,1,3,3,3-hexafluoropropan-2-yl 4-[[2-methyl-6-(2-methylphenyl)pyridin-3-yl]methyl]piperazine-1-carboxylate (11b)

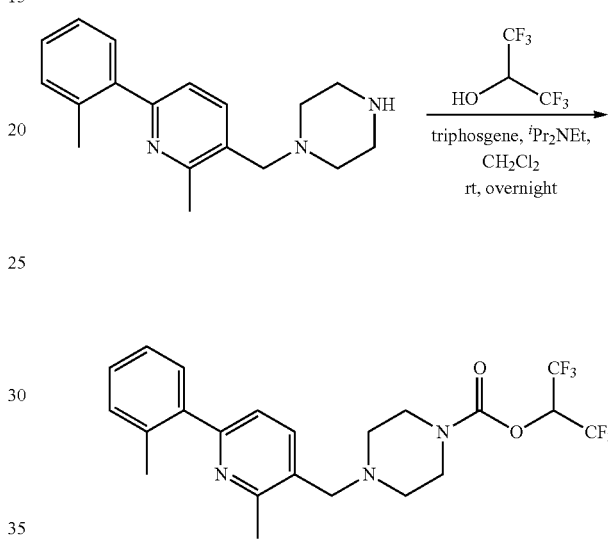

A 100 mL round-bottom flask, was charged with triphosgene (63.0 mg, 0.200 mmol, 0.30 equiv), dichloromethane (10 mL), 1,1,1,3,3,3-hexafluoropropan-2-ol (119 mg, 0.710 mmol, 1.00 equiv). N,N-Di-isopropylethylamine (174 mg, 1.35 mmol, 2.00 equiv) was added drop-wise. The resulting solution was stirred for 2 h at room temperature. 1-[[2-Methyl-6-(2-methylphenyl)pyridin-3-yl]methyl]piperazine (200 mg, 0.710 mmol, 1.00 equiv) was added. The resulting solution was stirred overnight at room temperature and then diluted with water (10 mL). The resulting mixture was extracted with dichloromethane (3×10 mL) and the organic layers were combined, dried over anhydrous sodium sulfate, filtered and concentrated under reduced pressure. The crude product (230 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 146.2 mg (43% yield) of 1,1,1,3,3,3-hexafluoropropan-2-yl 4-[[2-methyl-6-(2-methylphenyl)pyridin-3-yl]methyl]piperazine-1-carboxylate as a off-white solid. $^1$H NMR 300 MHz (CDCl$_3$) δ 7.62 (d, J=7.8 Hz, 1H), 7.37-7.40 (m, 1H), 7.31-7.35 (m, 3H), 7.19-7.28 (m, 1H), 5.72-5.80 (m, 1H), 3.56-3.59 (m, 6H), 2.64 (s, 3H), 2.51-2.56 (m, 4H), 2.36 (s, 3H). LCMS (ESI, m/z): 476 [M+H]⁺.

Example 113

1,1,1,3,3,3-hexafluoropropan-2-yl 4-[[6-(2-fluorophenyl)-2-methylpyridin-3-yl]methyl]piperazine-1-carboxylate (11c)

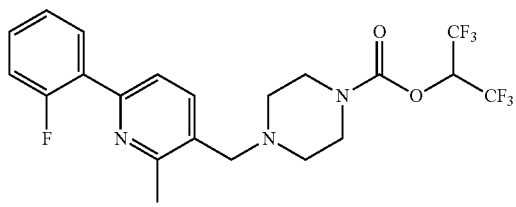 [SMILES: Cc1nc(-c2ccccc2F)ccc1CN1CCN(C(=O)OC(C(F)(F)F)C(F)(F)F)CC1]

The title compound was synthesized according to the representative procedure of Example 112 Steps 1-4 using (2-fluorophenyl)boronic acid: ¹H NMR 300 MHz (CDCl₃) δ 7.97-8.02 (m, 1H), 7.61 (m, 2H), 7.32-7.40 (m, 1H), 7.23-7.28 (m, 1H), 7.11-7.18 (m, 1H), 5.72-5.80 (m, 1H), 3.56 (br, 6H), 2.66 (s, 3H), 2.52 (br, 4H). LCMS (ESI, m/z): 480 [M+H]⁺.

Example 114

1,1,1,3,3,3-hexafluoropropan-2-yl 4-[[2-methyl-6-(3-methylphenyl)pyridin-3-yl]methyl]piperazine-1-carboxylate (11d)

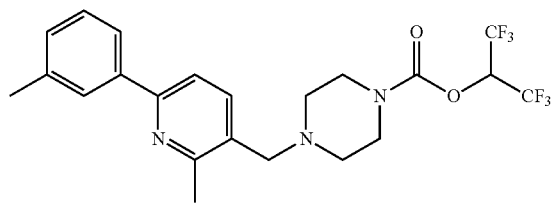 [SMILES: Cc1cccc(-c2ccc(CN3CCN(C(=O)OC(C(F)(F)F)C(F)(F)F)CC3)c(C)n2)c1]

The title compound was synthesized according to the representative procedure of Example 112 Steps 1-4 using (3-methylphenyl)boronic acid: ¹H NMR 300 MHz (CDCl₃) δ 7.83 (s, 1H), 7.75 (d, J=7.8 Hz, 1H), 7.60-7.63 (m, 1H), 7.52 (d, J=7.8 Hz, 1H), 7.35 (t, J=7.6 Hz, 1H), 7.23 (d, J=8.7 Hz, 1H), 5.71-5.80 (m, 1H), 3.56-3.58 (m, 6H), 2.67 (s, 3H), 2.51 (br, 4H), 2.44 (s, 3H). LCMS (ESI, m/z): 476 [M+H]⁺.

Example 115

1,1,1,3,3,3-hexafluoropropan-2-yl 4-[[6-(3-fluorophenyl)-2-methylpyridin-3-yl]methyl]piperazine-1-carboxylate (11e)

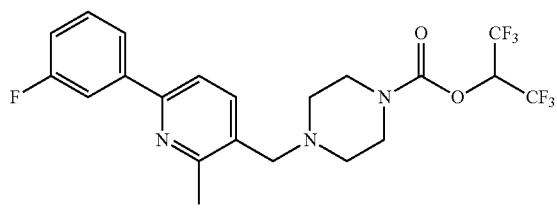 [SMILES: Cc1nc(-c2cccc(F)c2)ccc1CN1CCN(C(=O)OC(C(F)(F)F)C(F)(F)F)CC1]

The title compound was synthesized according to the representative procedure of Example 112 Steps 1-4 using (3-fluorophenyl)boronic acid: ¹H NMR 300 MHz (CDCl₃) δ 7.76-7.81 (m, 2H), 7.64 (d, J=8.1 Hz, 1H), 7.54 (d, J=7.8 Hz, 1H), 7.40-7.48 (m, 1H), 7.08-7.14 (m, 1H), 5.57-5.84 (m, 1H), 3.56-3.60 (m, 6H), 2.68 (s, 3H), 2.49-2.55 (m, 4H). LCMS (ESI, m/z): 480 [M+H]⁺.

Example 116

1,1,1,3,3,3-hexafluoropropan-2-yl 4-((3-morpholino-[1,1'-biphenyl]-4-yl)methyl)piperazine-1-carboxylate (11f)

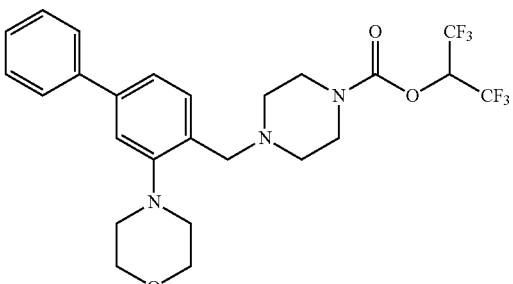

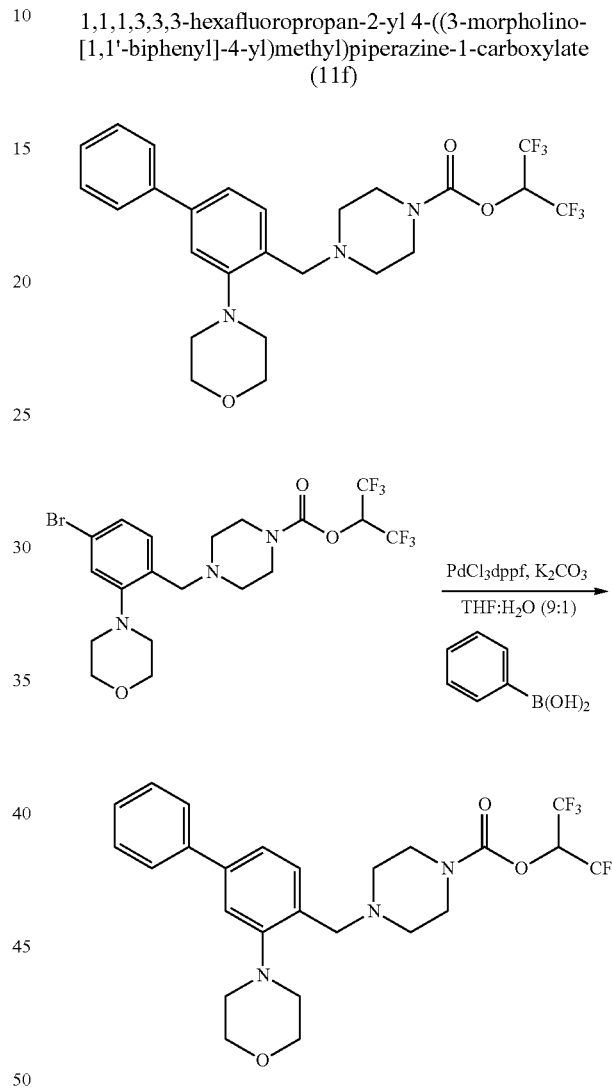

A round bottom flask was charged with 1,1,1,3,3,3-hexafluoropropan-2-yl 4-(4-bromo-2-morpholinobenzyl)piperazine-1-carboxylate (Example 57, 30 mg, 0.0562 mmol), Bis(diphenylphosphino)ferrocene-palladium(II) dichloride (5 mg, 6.13 µmol), phenylboronic acid (10 mg, 82.0 µmol), and K₂CO₃ (21 mg, 152 µmol). THF (4 mL) and H₂O (0.4 mL) were added and the reaction was heated to 70° C. for 2 h. The reaction was diluted in CH₂Cl₂ and washed with sat Na₂CO₃ (2×) and brine (1×). The organics were dried (Na₂SO₄), filtered, and concentrated under reduced pressure. The residue was chromatographed on a silica gel column (100% to 80% hexanes in EtOAc) and yielded 1,1,1,3,3,3-hexafluoropropan-2-yl 4-((3-morpholino-[1,1'-biphenyl]-4-yl)methyl)piperazine-1-carboxylate (18 mg, 60%). ¹H NMR 400 MHz (CDCl₃) δ 7.54-7.48 (m, 2H), 7.45-7.34 (m, 3H), 7.31-7.20 (m, 3H), 5.68 (h, J=6.3 Hz, 1H), 3.84-3.71 (m, 4H), 3.57 (s, 2H), 3.53-3.39 (m, 4H), 3.00-2.93 (m, 4H), 2.47 (dt, J=9.9, 5.0 Hz, 4H). LCMS (ESI, m/z): 532 [M+H]+.

Example 117

1,1,1,3,3,3-hexafluoropropan-2-yl 4-[[2-fluoro-4-(2-methylpyridin-4-yl)phenyl]methyl]piperazine-1-carboxylate (11g)

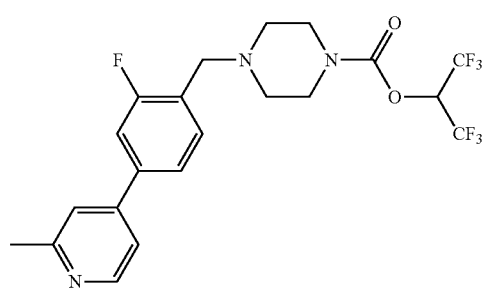 [SMILES: Cc1cc(-c2ccc(CN3CCN(C(=O)OC(C(F)(F)F)C(F)(F)F)CC3)c(F)c2)ccn1]

Step 1: tert-butyl 4-[(4-bromo-2-fluorophenyl)methyl]piperazine-1-carboxylate

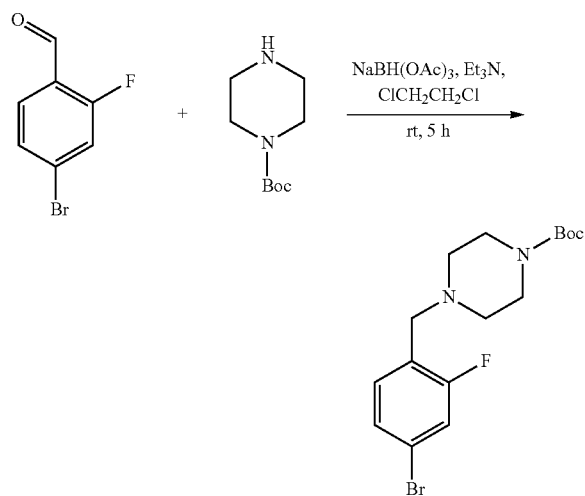

A 500 mL round-bottom flask was charged with 4-bromo-2-fluorobenzaldehyde (12.0 g, 59.1 mmol, 1.10 equiv), tert-butyl piperazine-1-carboxylate (10.0 g, 53.7 mmol, 1.00 equiv), triethylamine (8.10 g, 80.0 mmol, 1.49 equiv) and dichloroethane (100 mL). The resulting solution was stirred for 30 min at room temperature. Solid sodium triacetoxyborohydride (34.2 g, 161 mmol, 3.01 equiv) was added. The resulting solution was stirred 5 h at room temperature. The reaction progress was monitored by LCMS. The reaction was then quenched by the addition of water (200 mL). The resulting solution was extracted with dichloromethane (3×200 mL) and the organic layers were combined, washed with brine (2×200 mL), dried over anhydrous sodium sulfate and concentrated under reduced pressure. The residue was chromatographed on a silica gel column with ethyl acetate/petroleum ether (2/3) to yield 16.0 g (80% yield) of tert-butyl 4-[(4-bromo-2-fluorophenyl)methyl]piperazine-1-carboxylate as yellow oil. LCMS (ESI, m/z): 373 [M+H]+.

Step 2: tert-butyl 4-[[2-fluoro-4-(2-methylpyridin-4-yl)phenyl]methyl]piperazine-1-carboxylate

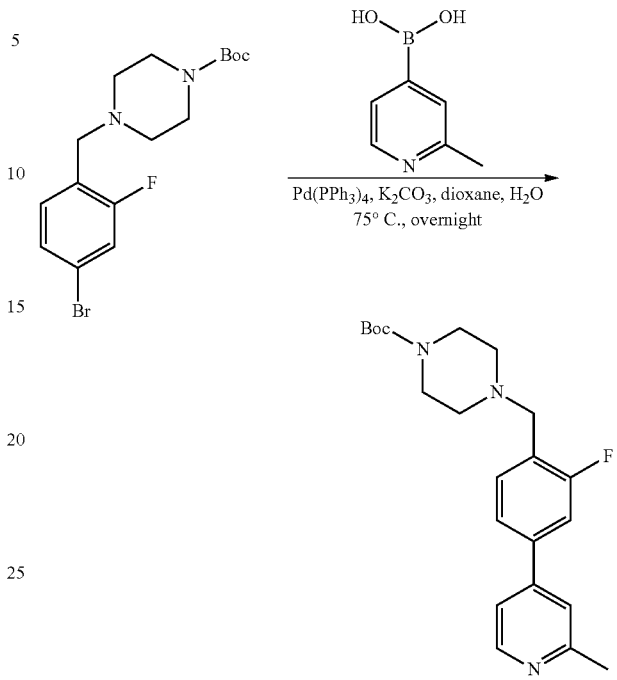

A 25 mL round-bottom flask was purged with and maintained under an inert atmosphere of nitrogen then charged with tert-butyl 4-[(4-bromo-2-fluorophenyl)methyl]piperazine-1-carboxylate (1.00 g, 2.68 mmol, 1.00 equiv), (2-methylpyridin-4-yl)boronic acid (0.737 g, 5.38 mmol, 2.01 equiv), Tetrakis(triphenylphosphine)palladium (0.311 g, 0.270 mmol, 0.10 equiv), potassium carbonate (1.10 g, 7.96 mmol, 2.97 equiv), dioxane (10 mL) and water (2 mL). The resulting solution was stirred overnight at 75° C. The reaction progress was monitored by LCMS. The reaction was then quenched by the addition of water (10 mL). The resulting solution was extracted with ethyl acetate (3×10 mL) and the organic layers were combined, washed with brine (2×10 mL), dried over anhydrous sodium sulfate and concentrated under reduced pressure. The residue was chromatographed on a silica gel column with ethyl acetate/petroleum ether (1/2) to yield 0.600 g (58% yield) of tert-butyl 4-[[2-fluoro-4-(2-methylpyridin-4-yl)phenyl]methyl]piperazine-1-carboxylate as yellow oil. LCMS (ESI, m/z): 386 [M+H]+.

Step 3: 1-[[2-fluoro-4-(2-methylpyridin-4-yl)phenyl]methyl]piperazine

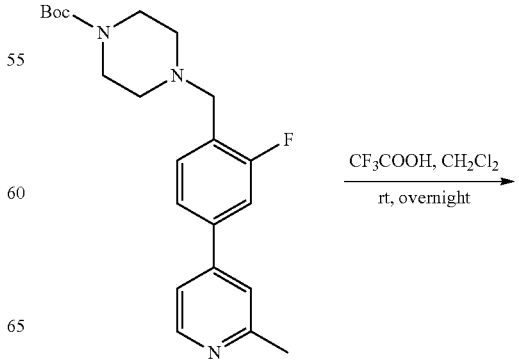

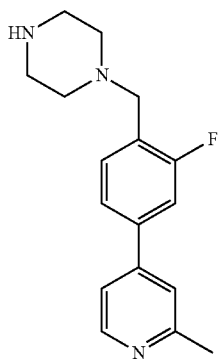

A 100 mL round-bottom flask was purged with and maintained under an inert atmosphere of nitrogen then charged with tert-butyl 4-[[2-fluoro-4-(2-methylpyridin-4-yl)phenyl]methyl]piperazine-1-carboxylate (1.00 g, 2.59 mmol, 1.00 equiv) and dichloromethane (20 mL). Trifluoroacetic acid (2.5 mL) was added dropwise at 0° C. The resulting solution was stirred overnight at room temperature. The reaction progress was monitored by LCMS. The reaction was then quenched by the addition of water (20 mL). The resulting solution was extracted with dichloromethane (3×20 mL) and the organic layers were combined, washed with brine (2×20 mL), dried over anhydrous sodium sulfate and concentrated under reduced pressure to provide 0.300 g (41% yield) of 1-[[2-fluoro-4-(2-methylpyridin-4-yl)phenyl]methyl]piperazine as yellow oil. LCMS (ESI, m/z): 286 [M+H]+.

Step 4: 1,1,1,3,3,3-hexafluoropropan-2-yl 4-[[2-fluoro-4-(2-methylpyridin-4-yl)phenyl]methyl]piperazine-1-carboxylate (11g)

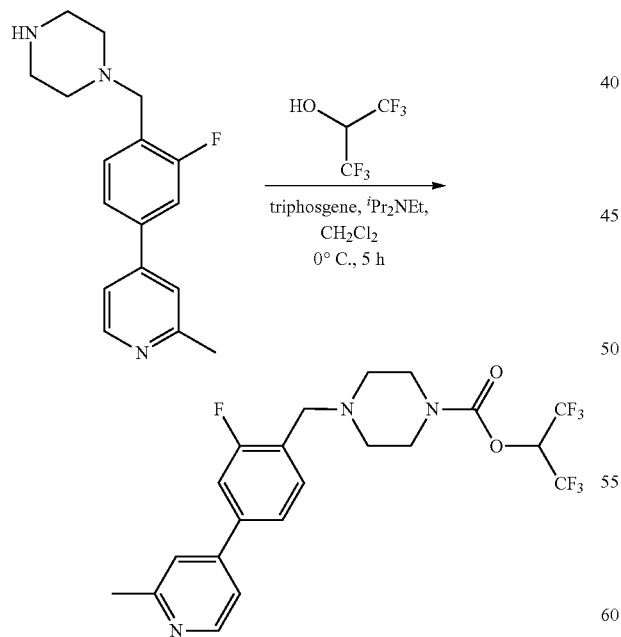

A 25 mL round-bottom flask was purged with and maintained under an inert atmosphere of nitrogen then charged with triphosgene (55.0 mg, 0.190 mmol, 0.35 equiv), 1,1,1,3,3,3-hexafluoropropan-2-ol (143 mg, 0.530 mmol, 1.00 equiv) and dichloromethane (3 mL). N,N-Di-isopropylethylamine (205 mg, 1.59 mmol, 3.02 equiv) was added dropwise at 0° C. The resulting solution was stirred for 2 h at 0° C. 1-[[2-Fluoro-4-(2-methylpyridin-4-yl)phenyl]methyl]piperazine (150 mg, 0.530 mmol, 1.00 equiv) in dichloromethane (2 mL) was added dropwise at 0° C. The resulting solution was stirred for 5 h at 0° C. The reaction progress was monitored by LCMS. The reaction was then quenched by the addition of water (10 mL). The resulting solution was extracted with dichloromethane (3×10 mL) and the organic layers were combined, washed with (2×10 mL) of brine, dried over anhydrous sodium sulfate and concentrated under reduced pressure. The crude product (300 mg) was purified by preparative HPLC using the following gradient conditions: 30% CH₃CN/70% Phase A increasing to 70% CH₃CN over 10 min, then to 100% CH₃CN over 0.1 min, holding at 100% CH₃CN for 1.9 min, then reducing to 30% CH₃CN over 0.1 min, and holding at 30% for 1.9 min, on a Waters 2767-5 Chromatograph. Column: Xbridge Prep $C_{18}$, 19*150 mm 5 um; Mobile phase: Phase A: aqueous $NH_4HCO_3$ (0.05%); Phase B: $CH_3CN$; Detector, UV220 & 254 nm. Purification resulted in 120 mg (48% yield) of 1,1,1,3,3,3-hexafluoropropan-2-yl 4-[[2-fluoro-4-(2-methylpyridin-4-yl)phenyl]methyl]piperazine-1-carboxylate as yellow oil. 1H NMR 400 MHz (CDCl₃) δ 8.59 (d, J=5.2 Hz, 1H), 7.44-7.54 (m, 1H), 7.38-7.44 (m, 1H), 7.32-7.37 (m, 3H), 5.74-5.80 (m, 1H), 3.61-3.70 (m, 6H), 2.67 (s, 3H), 2.51-2.58 (m, 4H). LCMS (ESI, m/z): 480 [M+H]+.

Example 118

1,1,1,3,3,3-hexafluoropropan-2-yl 4-[[2-methyl-4-(3-methylphenyl)phenyl]methyl]piperazine-1-carboxylate (11h)

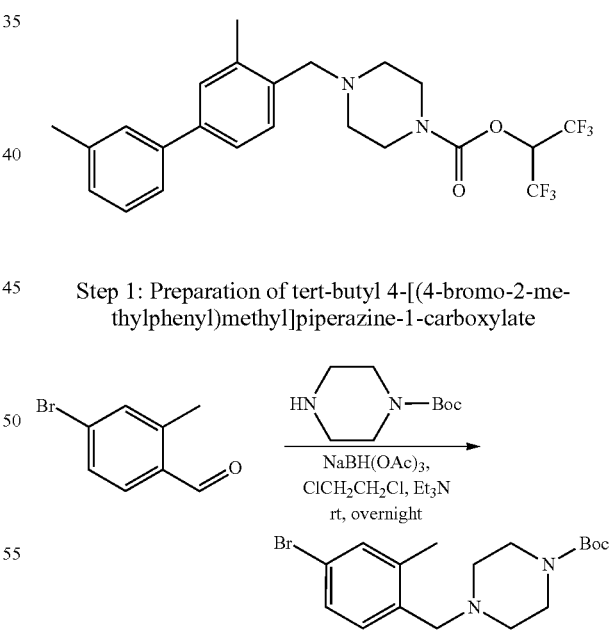

Step 1: Preparation of tert-butyl 4-[(4-bromo-2-methylphenyl)methyl]piperazine-1-carboxylate A 250 mL round-bottom flask was charged with tert-butyl piperazine-1-carboxylate (2.80 g, 15.0 mmol, 1.00 equiv), 4-bromo-2-methylbenzaldehyde (3.28 g, 16.5 mmol, 1.10 equiv), dichloromethane (80 mL). Triethylamine (4.56 g, 45.1 mmol, 3.00 equiv) was added. The resulting solution was stirred for 30 mins at room temperature. Sodium triacetoxyborohydride (9.60 g, 45.3 mmol, 3.00 equiv) was added. The resulting solution was stirred overnight at room temperature and then diluted with water (100 mL). The resulting solution was extracted with dichloromethane (3×60 mL) and the organic layers were combined, dried over Na$_2$SO$_4$, filtered and concentrated under reduced pressure. The residue was chromatographed on a silica gel column with ethyl acetate/petroleum ether (20/80) to provide 5.70 g (98% yield) of tert-butyl 4-[(4-bromo-2-methylphenyl)methyl]piperazine-1-carboxylate as light yellow oil. LCMS (ESI, m/z): 369 [M+H]$^+$.

Step 2: Preparation of tert-butyl 4-[[2-methyl-4-(3-methylphenyl)phenyl]methyl]piperazine-1-carboxylate

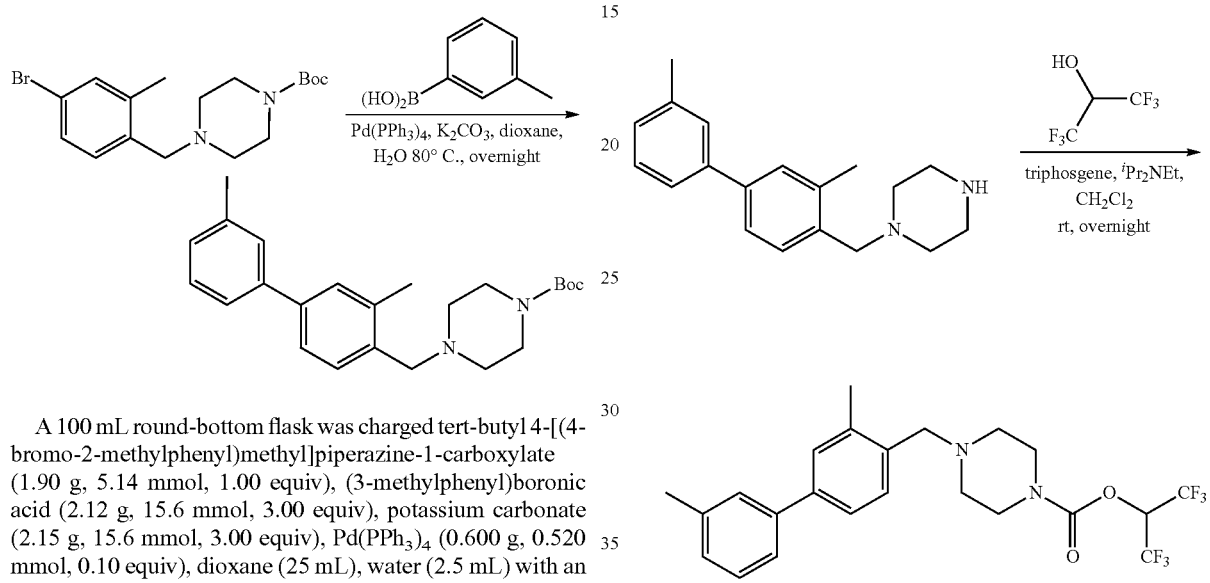

A 100 mL round-bottom flask was charged tert-butyl 4-[(4-bromo-2-methylphenyl)methyl]piperazine-1-carboxylate (1.90 g, 5.14 mmol, 1.00 equiv), (3-methylphenyl)boronic acid (2.12 g, 15.6 mmol, 3.00 equiv), potassium carbonate (2.15 g, 15.6 mmol, 3.00 equiv), Pd(PPh$_3$)$_4$ (0.600 g, 0.520 mmol, 0.10 equiv), dioxane (25 mL), water (2.5 mL) with an inert atmosphere of nitrogen. The resulting solution was stirred overnight at 80° C., diluted with water (50 mL), extracted with dichloromethane (3×40 mL) and the organic layers were combined, dried over Na$_2$SO$_4$, filtered and concentrated under reduced pressure. The residue was chromatographed on a silica gel column with ethyl acetate/petroleum ether (20/80) to provide in 2.00 g (95% yield) of tert-butyl 4-[[2-methyl-4-(3-methylphenyl)phenyl]methyl]piperazine-1-carboxylate as light yellow oil. LCMS (ESI, m/z): 381 [M+H]$^+$.

Step 3: Preparation of 1-[[2-methyl-4-(3-methylphenyl)phenyl]methyl]piperazine

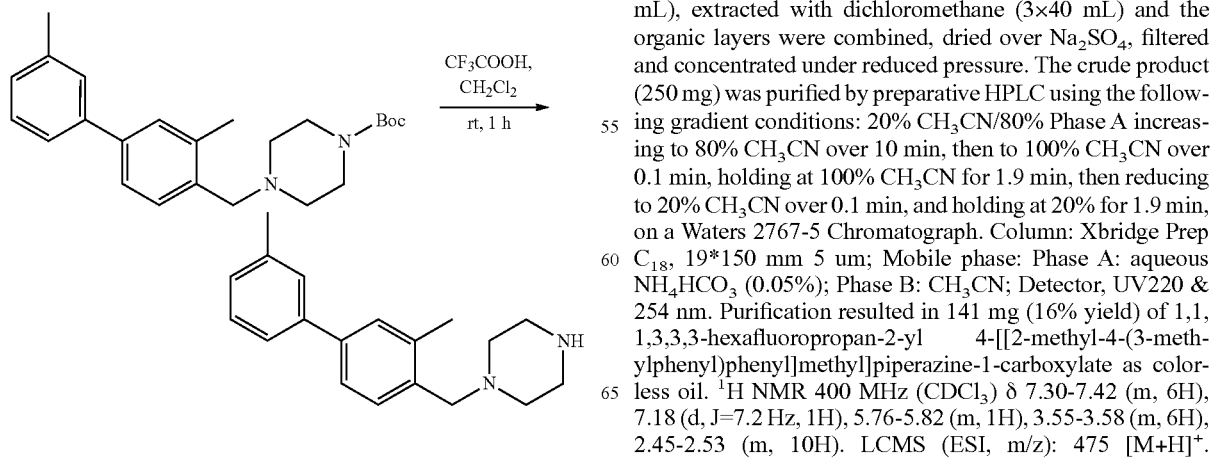

A 100 mL round-bottom flask was charged with tert-butyl 4-[[2-methyl-4-(3-methylphenyl)phenyl]methyl]piperazine-1-carboxylate (2.00 g, 5.26 mmol, 1.00 equiv), trifluoroacetic acid (8 mL), dichloromethane (40 mL). The resulting solution was stirred for 1 h at room temperature and concentrated under reduced pressure to yield 1.50 g (crude) of 1-[[2-methyl-4-(3-methylphenyl)phenyl]methyl]piperazine as light yellow oil. LCMS (ESI, m/z): 281 [M+H]$^+$.

Step 4: Preparation of 1,1,1,3,3,3-hexafluoropropan-2-yl 4-[[2-methyl-4-(3-methylphenyl)phenyl]methyl]piperazine-1-carboxylate (11h)

A 100 mL round-bottom flask was charged with triphosgene (160 mg, 0.540 mmol, 0.30 equiv), dichloromethane (20 mL). 1,1,1,3,3,3-Hexafluoropropan-2-ol (302 mg, 1.80 mmol, 1.00 equiv) and N,N-diisopropylethylamine (441 mg, 3.41 mmol, 1.90 equiv) were added. The resulting solution was stirred for 2 h at room temperature. 1-[[2-methyl-4-(3-methylphenyl)phenyl]methyl]piperazine (500 mg, 1.78 mmol, 1.00 equiv) was added. The resulting solution was stirred overnight at room temperature, diluted with water (50 mL), extracted with dichloromethane (3×40 mL) and the organic layers were combined, dried over Na$_2$SO$_4$, filtered and concentrated under reduced pressure. The crude product (250 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 141 mg (16% yield) of 1,1,1,3,3,3-hexafluoropropan-2-yl 4-[[2-methyl-4-(3-methylphenyl)phenyl]methyl]piperazine-1-carboxylate as colorless oil. $^1$H NMR 400 MHz (CDCl$_3$) δ 7.30-7.42 (m, 6H), 7.18 (d, J=7.2 Hz, 1H), 5.76-5.82 (m, 1H), 3.55-3.58 (m, 6H), 2.45-2.53 (m, 10H). LCMS (ESI, m/z): 475 [M+H]$^+$.

Example 119

1,1,1,3,3,3-hexafluoropropan-2-yl 4-[[2-methyl-4-(2-methylpyridin-4-yl)phenyl]methyl]piperazine-1-carboxylate (11i)

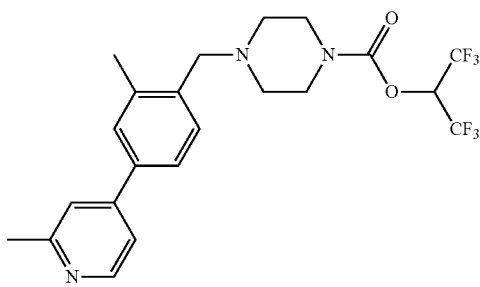 [SMILES: Cc1cc(-c2ccc(CN3CCN(C(=O)OC(C(F)(F)F)C(F)(F)F)CC3)c(C)c2)ccn1]

The title compound was synthesized according to the representative procedure of Example 118 Steps 1-4 using (2-methylpyridin-4-yl)boronic acid: $^1$H NMR 400 MHz (CDCl$_3$) δ 8.55 (d, J=5.2 Hz, 1H), 7.34-7.46 (m, 5H), 5.75-5.81 (m, 1H), 3.56-3.58 (m, 6H), 3.66 (s, 3H), 2.49-2.54 (m, 4H), 2.47 (s, 3H). LCMS (ESI, m/z): 476 [M+H]$^+$.

Example 120

1,1,1,3,3,3-hexafluoropropan-2-yl 4-[(2-methoxy-4-phenylphenyl)methyl]piperazine-1-carboxylate (11j)

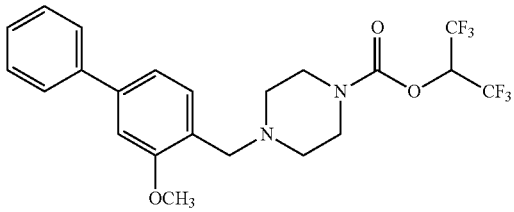 [SMILES: COc1cc(-c2ccccc2)ccc1CN1CCN(C(=O)OC(C(F)(F)F)C(F)(F)F)CC1]

Step 1: Preparation of tert-butyl 4-[(4-bromo-2-methoxyphenyl)methyl]piperazine-1-carboxylate

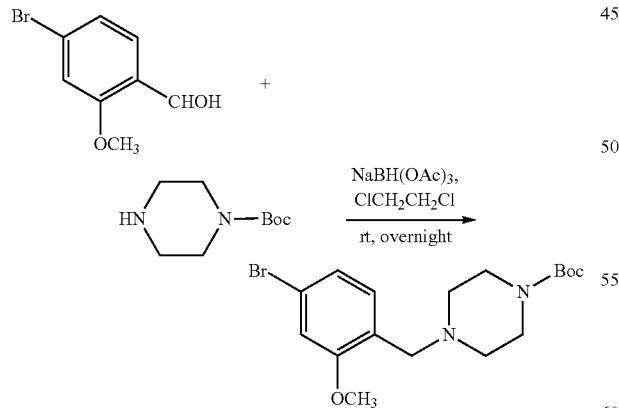

A 100 mL round-bottom flask was charged with 4-bromo-2-methoxybenzaldehyde (1.90 g, 8.84 mmol, 1.10 equiv), tert-butyl piperazine-1-carboxylate (1.50 g, 8.05 mmol, 1.00 equiv), and dichloromethane (30 mL). The resulting solution was stirred for 30 min at room temperature. Sodium triacetoxyborohydride (5.10 g, 24.0 mmol, 3.00 equiv) was added. The resulting solution was stirred for overnight at room temperature and then diluted with water (30 mL). The resulting mixture was extracted with dichloromethane (2×20 mL) and the organic layers were combined, dried over anhydrous sodium sulfate, filtered and concentrated under reduced pressure. The residue was chromatographed on a silica gel column with ethyl acetate/petroleum ether (20/80) to provide 2.66 g (86% yield) of tert-butyl 4-[(4-bromo-2-methoxyphenyl)methyl]piperazine-1-carboxylate as a white solid. LCMS (ESI, m/z): 385 [M+H]$^+$.

Step 2: Preparation of tert-butyl 4-[(2-methoxy-4-phenylphenyl)methyl]piperazine-1-carboxylate

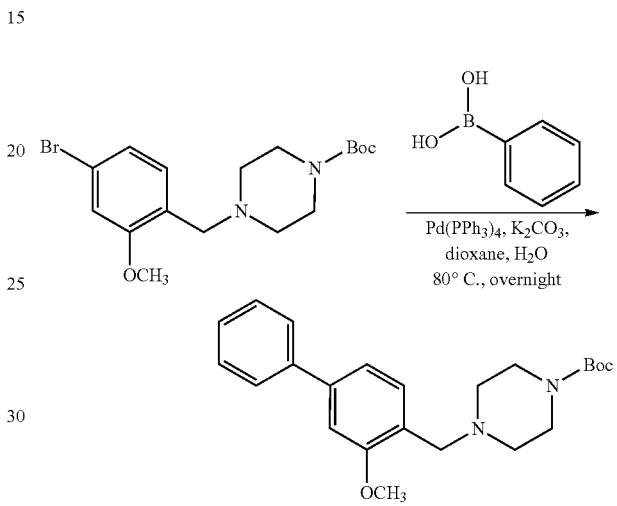

A 100 mL round-bottom flask was purged with and maintained under an inert atmosphere of nitrogen then charged with tert-butyl 4[(4-bromo-2-methoxyphenyl)methyl]piperazine-1-carboxylate (1.00 g, 2.60 mmol, 1.00 equiv), phenylboronic acid (0.640 g, 5.25 mmol, 2.02 equiv), Tetrakis(triphenylphosphine)palladium (0.300 g, 0.260 mmol, 0.10 equiv), potassium carbonate (1.08 g, 7.81 mmol, 3.01 equiv), dioxane (24 mL), and water (4 mL). The resulting solution was stirred overnight at 80° C. and then diluted with water (10 mL) and extracted with ethyl acetate (3×5 mL). The organic layers were combined, dried over anhydrous sodium sulfate, filtered and concentrated under reduced pressure. The residue was chromatographed on a silica gel column with ethyl acetate/petroleum ether (3/7) to provide 0.850 g (86% yield) of tert-butyl 4-[(2-methoxy-4-phenylphenyl)methyl]piperazine-1-carboxylate as yellow oil. LCMS (ESI, m/z): 383 [M+H]$^+$.

Step 3: Preparation of 1-[(2-methoxy-4-phenylphenyl)methyl]piperazine

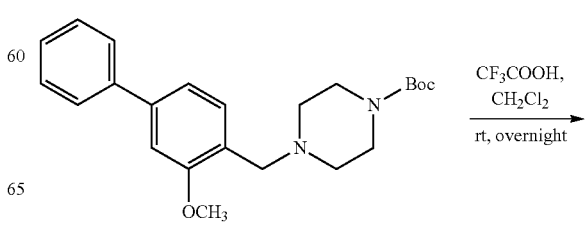

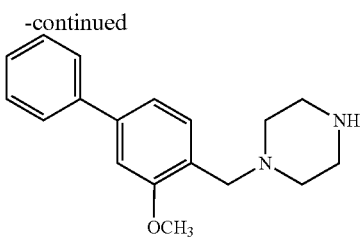

A 100 mL round-bottom flask was charged with tert-butyl 4-[(2-methoxy-4-phenylphenyl)methyl]piperazine-1-carboxylate (850 mg, 2.22 mmol, 1.00 equiv), dichloromethane (15 mL), trifluoroacetic acid (1.50 mL). The resulting solution was stirred overnight at room temperature. The resulting mixture was concentrated under reduced pressure to provide 600 mg (crude) of 1-[(2-methoxy-4-phenylphenyl)methyl]piperazine as yellow oil. LCMS (ESI, m/z): 283 [M+H]⁺.

Step 4: Preparation of 1,1,1,3,3,3-hexafluoropropan-2-yl 4-[(2-methoxy-4-phenylphenyl)methyl]piperazine-1-carboxylate (11j)

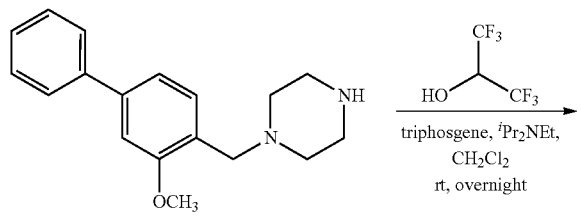

A 100 mL round-bottom flask was charged with triphosgene (63.0 mg, 0.210 mmol, 0.30 equiv), dichloromethane (20 mL), 1,1,1,3,3,3-hexafluoropropan-2-ol (119 mg, 0.710 mmol, 1.00 equiv). N,N-Diisopropylethylamine (174 mg, 1.35 mmol, 1.90 equiv) was added dropwise. The resulting solution was stirred for 2 h at room temperature. 1-[(2-Methoxy-4-phenylphenyl)methyl]piperazine (200 mg, 0.710 mmol, 1.00 equiv) was added. The resulting solution was stirred overnight at room temperature and then diluted with water (5 mL). The resulting mixture was extracted with dichloromethane (3×5 mL) and the organic layers were combined, dried over anhydrous sodium sulfate, filtered and concentrated under reduced pressure. The crude product (260 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm 5 um; Mobile phase: Phase A: aqueous NH₄HCO₃ (0.05%); Phase B: CH₃CN; Detector, UV220 & 254 nm. Purification resulted in 120 mg (36% yield) of 1,1,1,3,3,3-hexafluoropropan-2-yl 4-[(2-methoxy-4-phenylphenyl)methyl]piperazine-1-carboxylate as yellow oil. $^1$H NMR 300 MHz (CDCl₃) δ 7.60 (t, J=4.2 Hz, 2H), 7.32-7.46 (m, 4H), 7.15-7.18 (m, 1H), 7.60 (d, J=1.2 Hz, 1H), 5.72-5.80 (m, 1H), 3.88 (s, 3H), 3.58-3.63 (m, 6H), 2.51-2.57 (m, 4H). LCMS: (ESI, m/z): 477 [M+H]⁺.

Example 121

1,1,1,3,3,3-hexafluoropropan-2-yl 4-[[5-(3-fluorophenyl)pyridin-2-yl]methyl]piperazine-1-carboxylate (11k)

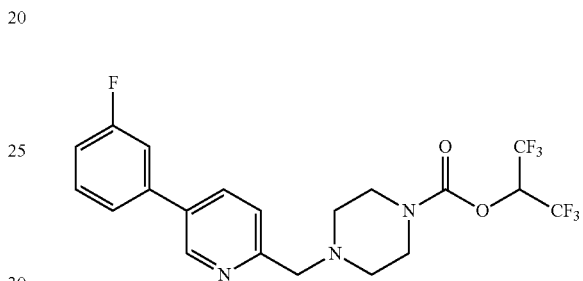

Step 1: Preparation of tert-butyl 4-[(4-bromopyridin-2-yl)methyl]piperazine-1-carboxylate

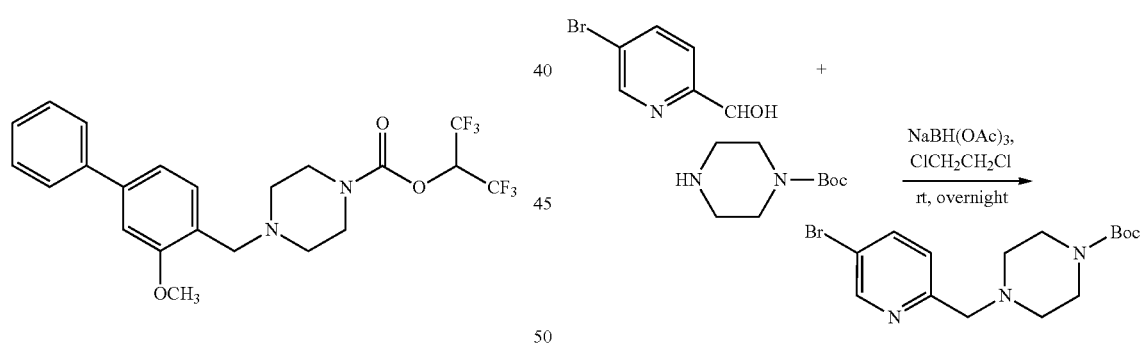

A 100 mL round-bottom flask was charged with 4-bromopyridine-2-carbaldehyde (1.60 g, 8.60 mmol, 1.07 equiv), tert-butyl piperazine-1-carboxylate (1.50 g, 8.05 mmol, 1.00 equiv), and dichloromethane (30 mL). The mixture was stirred for 30 min at room temperature. Sodium triacetoxyborohydride (5.10 g, 24.1 mmol, 3.00 equiv) was added. The resulting solution was stirred for overnight at room temperature and then diluted with water (30 mL). The resulting mixture was extracted with dichloromethane (2×20 mL) and the organic layers were combined, dried over anhydrous sodium sulfate, filtered and concentrated under reduced pressure. The residue was chromatographed on a silica gel column with ethyl acetate/petroleum ether (45/55) to provide 2.70 g (94% yield) of tert-butyl 4-[(4-bromopyridin-2-yl)methyl]piperazine-1-carboxylate as a yellow solid. LCMS (ESI, m/z): 356 [M+H]⁺.

Step 2: Preparation of tert-butyl 4-[[5-(3-fluorophenyl)pyridin-2-yl]methyl]piperazine-1-carboxylate

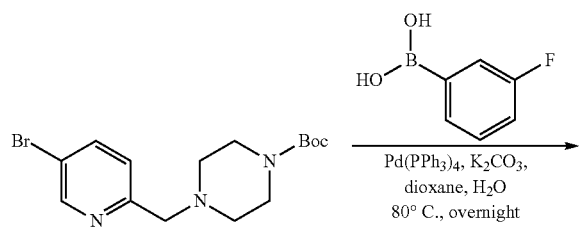

A 100 mL round-bottom flask was purged with and maintained an inert atmosphere of nitrogen then charged with tert-butyl 4-[(5-bromopyridin-2-yl)methyl]piperazine-1-carboxylate (1.00 g, 2.81 mmol, 1.00 equiv), (3-fluorophenyl) boronic acid (0.790 g, 5.65 mmol, 2.00 equiv), Tetrakis(triphenylphosphine)palladium (0.325 g, 0.280 mmol, 0.10 equiv), potassium carbonate (1.17 g, 8.47 mmol, 3.00 equiv), dioxane (24 mL), and water (4 mL). The resulting solution was stirred overnight at 80° C. and then diluted with water (10 mL) and extracted with ethyl acetate (3×5 mL). The organic layers were combined, dried over anhydrous sodium sulfate, filtered and concentrated under reduced pressure. The residue was chromatographed on a silica gel column with ethyl acetate/petroleum ether (1/1) to provide 0.955 g (92% yield) of tert-butyl 4-[[5-(3-fluorophenyl)pyridin-2-yl]methyl]piperazine-1-carboxylate as yellow oil. LCMS (ESI, m/z): 372 [M+H]$^+$.

Step 3: Preparation of 1-[[5-(3-fluorophenyl)pyridin-2-yl]methyl]piperazine

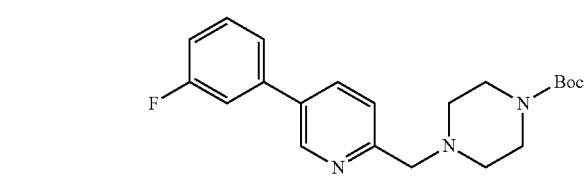

A 100 mL round-bottom flask, was charged with tert-butyl 4-[[5-(3-fluorophenyl)pyridin-2-yl]methyl]piperazine-1-carboxylate (950 mg, 2.56 mmol, 1.00 equiv), dichloromethane (15 mL), trifluoroacetic acid (2 mL). The resulting solution was stirred for overnight at room temperature. The resulting mixture was concentrated under reduced pressure to provide 500 mg (crude) of 1-[[5-(3-fluorophenyl)pyridin-2-yl]methyl]piperazine as yellow oil. LCMS (ESI, m/z): 272 [M+H]$^+$.

Step 4: Preparation of 1,1,1,3,3,3-hexafluoropropan-2-yl 4-[[5-(3-fluorophenyl)pyridin-2-yl]methyl]piperazine-1-carboxylate (11k)

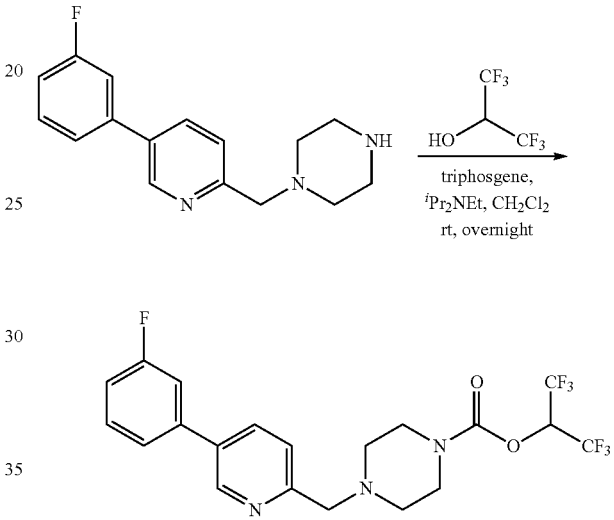

A 100 mL round-bottom flask was charged with triphosgene (66.0 mg, 0.220 mmol, 0.30 equiv), dichloromethane (20 mL), 1,1,1,3,3,3-hexafluoropropan-2-ol (124 mg, 0.740 mmol, 1.00 equiv). N,N-Diisopropylethylamine (181 mg, 1.40 mmol, 1.90 equiv) was added dropwise. The resulting solution was stirred for 2 h at room temperature. 1-[[5-(3-Fluorophenyl)pyridin-2-yl]methyl]piperazine (200 mg, 0.740 mmol, 1.00 equiv) was added. The resulting solution was stirred overnight at room temperature and then diluted with water (5 mL). The resulting mixture was extracted with dichloromethane (3×5 mL) and the organic layers were combined, dried over anhydrous sodium sulfate, filtered and concentrated under reduced pressure. The crude product (352 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 164 mg (48% yield) of 1,1,1,3,3,3-hexafluoropropan-2-yl 4-[[5-(3-fluorophenyl)pyridin-2-yl]methyl]piperazine-1-carboxylate as a white solid. $^1$H NMR 300 MHz (CDCl$_3$) δ 8.79 (s, 1H), 7.84-7.87 (m, 1H), 7.42-7.49 (m, 2H), 7.36 (d, J=7.8 Hz, 1H), 7.29-7.30 (m, 1H), 7.08-7.14 (m, 1H), 5.69-5.82 (m, 1H), 3.84 (s, 2H), 3.62 (br, 4H), 2.58 (br, 4H). LCMS (ESI, m/z): 466 [M+H]$^+$.

Example 122

1,1,1,3,3,3-hexafluoropropan-2-yl 4-[[2-methyl-4-(pyridin-3-yl)phenyl]methyl]piperazine-1-carboxylate (11l)

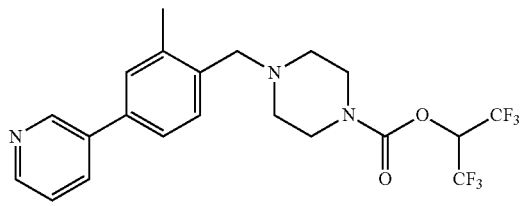 [SMILES: Cc1cc(-c2cccnc2)ccc1CN1CCN(C(=O)OC(C(F)(F)F)C(F)(F)F)CC1]

The title compound was synthesized according to the representative procedure of Example 118 Steps 1-4 using (pyridin-3-yl)boronic acid: $^1$H NMR 300 MHz (CDCl$_3$) d 8.85 (d, J=1.8 Hz, 1H), 8.58-8.60 (m, 1H), 7.85-7.89 (m, 1H), 7.34-7.40 (m, 4H), 5.72-5.80 (m, 1H)), 3.56 (s, 6H), 2.49-2.51 (m, 7H). LCMS (ESI, m/z): 462 [M+H]$^+$.

Example 123

1,1,1,3,3,3-hexafluoropropan-2-yl 4-[[4-(2,6-dimethylpyridin-4-yl)-2-methylphenyl]methyl]piperazine-1-carboxylate (11m)

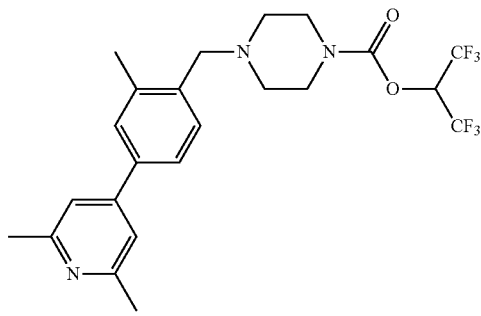 [SMILES: Cc1cc(-c2ccc(CN3CCN(C(=O)OC(C(F)(F)F)C(F)(F)F)CC3)c(C)c2)cc(C)n1]

Step 1: Preparation of tert-butyl 4-[(4-bromo-2-methylphenyl)methyl]piperazine-1-carboxylate

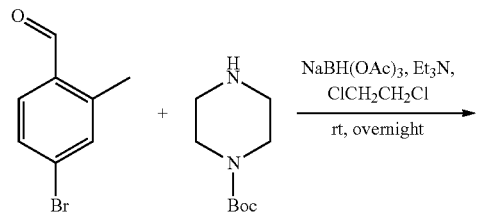

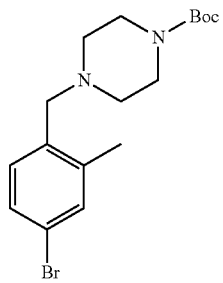

A 500 mL round-bottom flask was charged with 4-bromo-2-methylbenzaldehyde (8.00 g, 40.2 mmol, 1.00 equiv), tert-butyl piperazine-1-carboxylate (9.40 g, 50.5 mmol, 1.26 equiv), triethylamine (6.50 g, 64.2 mmol, 1.60 equiv) and dichloroethane (200 mL). The resulting solution was stirred for 30 min at room temperature. Solid sodium triacetoxyborohydride (27.0 g, 127 mmol, 3.17 equiv) was added. The resulting solution was stirred overnight at room temperature. The reaction progress was monitored by LCMS. The reaction was then quenched by the addition of water (100 mL). The resulting solution was extracted with dichloromethane (3×200 mL) and the organic layers were combined, washed with brine (2×200 mL), dried over anhydrous sodium sulfate and concentrated under reduced pressure. The residue was chromatographed on a silica gel column with ethyl acetate/petroleum ether (2/3) to yield 10.0 g (67% yield) of tert-butyl 4-[(4-bromo-2-methylphenyl)methyl]piperazine-1-carboxylate as a white solid. LCMS (ESI, m/z): 369 [M+H]$^+$.

Step 2: Preparation of tert-butyl 4-[[4-(2,6-dimethylpyridin-4-yl)-2-methylphenyl]methyl]piperazine-1-carboxylate

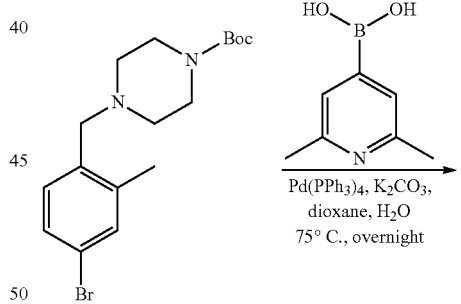

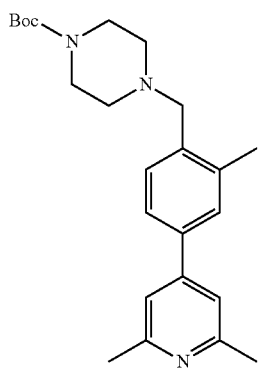

A 25 mL round-bottom flask maintained with an inert atmosphere of nitrogen was charged with tert-butyl 4[(4- bromo-2-methylphenyl)methyl]piperazine-1-carboxylate (368 mg, 1.00 mmol, 1.00 equiv), (2,6-dimethylpyridin-4-yl) boronic acid (300 mg, 1.99 mmol, 1.99 equiv), Pd(PPh$_3$)$_4$ (116 mg, 0.100 mmol, 0.10 equiv), potassium carbonate (414 mg, 3.00 mmol, 3.01 equiv), dioxane (6 mL) and water (1 mL). The resulting solution was stirred overnight at 75° C. The reaction progress was monitored by LCMS. The reaction was then quenched by the addition of water (10 mL). The resulting solution was extracted with ethyl acetate (3×10 mL) and the organic layers were combined, washed with brine (2×10 mL), dried over anhydrous sodium sulfate and concentrated under reduced pressure. The residue was chromatographed on a silica gel column with ethyl acetate/petroleum ether (1/1) to yield 350 mg (89% yield) of tert-butyl 4-[[4-(2,6-dimethylpyridin-4-yl)-2-methylphenyl]methyl]piperazine-1-carboxylate as yellow oil. LCMS (ESI, m/z): 396 [M+H]$^+$.

Step 3: Preparation of 1-[[4-(2,6-dimethylpyridin-4-yl)-2-methylphenyl]methyl]piperazine

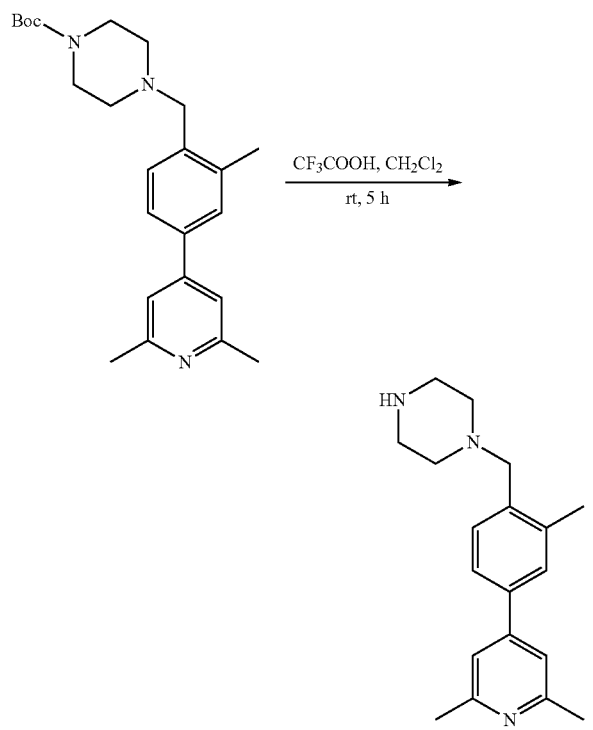

A 50 mL round-bottom flask maintained with an inert atmosphere of nitrogen was charged with tert-butyl 4-[[4-(2,6-dimethylpyridin-4-yl)-2-methylphenyl]methyl]piperazine-1-carboxylate (350 mg, 0.880 mmol, 1.00 equiv) and dichloromethane (5 mL). Trifluoroacetic acid (0.5 mL) was added dropwise at 0° C. The resulting solution was stirred for 5 h at room temperature. The reaction progress was monitored by LCMS. The reaction was then quenched by the addition of water (10 mL). The resulting solution was extracted with dichloromethane (3×10 mL) and the organic layers were combined, washed with brine (2×10 mL), dried over anhydrous sodium sulfate and concentrated under reduced pressure to yield 270 mg (crude) of 1-[[4-(2,6-dimethylpyridin-4-yl)-2-methylphenyl]methyl]piperazine as yellow oil. LCMS (ESI, m/z): 296 [M+H]$^+$.

Step 4: Preparation of 1,1,1,3,3,3-hexafluoropropan-2-yl 4-[[4-(2,6-dimethylpyridin-4-yl)-2-methylphenyl]methyl]piperazine-1-carboxylate (11m)

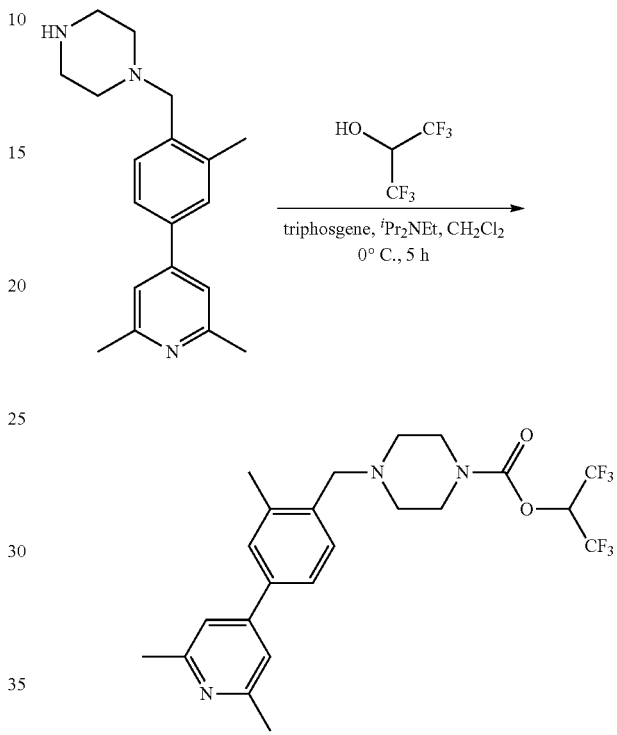

A 25 mL round-bottom flask maintained with an inert atmosphere of nitrogen was charged with triphosgene (46.0 mg, 0.150 mmol, 0.35 equiv), 1,1,1,3,3,3-hexafluoropropan-2-ol (111 mg, 0.660 mmol, 1.50 equiv) and dichloromethane (3 mL). N,N-diisopropylethylamine (170 mg, 1.32 mmol, 2.99 equiv) was added dropwise at 0° C. The resulting solution was stirred for 2 h at 0° C. 1-[[4-(2,6-Dimethylpyridin-4-yl)-2-methylphenyl]methyl]piperazine (130 mg, 0.440 mmol, 1.00 equiv) in dichloromethane (2 mL) was added dropwise at 0° C. The resulting solution was stirred for 3 h at 0° C. The reaction was then quenched by the addition of water (20 mL). The resulting solution was extracted with dichloromethane (3×20 mL) and the organic layers were combined, washed with brine (2×20 mL), dried over anhydrous sodium sulfate and concentrated under reduced pressure. The crude product (300 mg) was purified by preparative HPLC using the following gradient conditions: 30% CH$_3$CN/70% Phase A increasing to 70% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 101 mg (47% yield) of 1,1,1,3,3,3-hexafluoropropan-2-yl 4-[[4-(2,6-dimethylpyridin-4-yl)-2-methylphenyl]methyl]piperazine-1-carboxylate as yellow oil. $^1$H NMR 400 MHz (CDCl$_3$) δ 7.42-7.45 (m, 2H), 7.35-7.37 (m, 1H), 7.21 (s, 2H), 5.75-5.81

(m, 1H), 3.56-3.58 (m, 6H), 3.62 (s, 6H), 2.48-2.53 (m, 4H), 2.46 (s, 3H). LCMS (ESI, m/z): 490 [M+H]+.

Example 124

1,1,1,3,3,3-hexafluoropropan-2-yl 4-[[2-methyl-4-(3-methylpyridin-4-yl)phenyl]methyl]piperazine-1-carboxylate (11n)

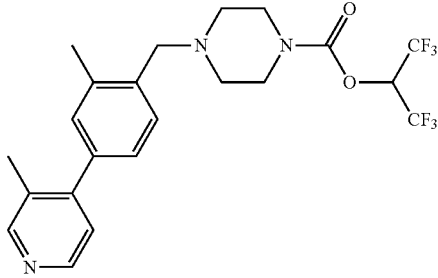 [SMILES: Cc1cc(-c2ccncc2C)ccc1CN1CCN(C(=O)OC(C(F)(F)F)C(F)(F)F)CC1]

The title compound was synthesized according to the representative procedure of Example 118 Steps 1-4 using (3-methylpyridin-4-yl)boronic acid: $^1$H NMR 300 MHz (CDCl$_3$) δ 8.51 (d, J=13.6 Hz, 2H), 7.35-7.37 (m, 1H), 7.14-7.19 (m, 3H), 5.75-5.81 (m, 1H), 3.58-3.60 (m, 6H), 2.51-2.60 (m, 4H), 2.44 (s, 3H), 2.32 (s, 3H). LCMS (ESI, m/z): 476 [M+H]+.

Example 125

1,1,1,3,3,3-hexafluoropropan-2-yl 4-[[2-fluoro-4-(3-fluorophenyl)phenyl]methyl]piperazine-1-carboxylate (11o)

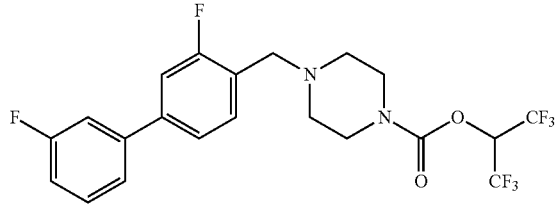 [SMILES: O=C(OC(C(F)(F)F)C(F)(F)F)N1CCN(Cc2ccc(-c3cccc(F)c3)cc2F)CC1]

The title compound was synthesized according to the representative procedure of Example 117 Steps 1-4 using (3-fluorophenyl)boronic acid: $^1$H NMR 300 MHz (CDCl$_3$) δ 7.33-7.51 (m, 4H), 7.28 (s, 1H), 7.25-7.27 (m, 1H), 7.03-7.10 (m, 1H), 5.69-5.81 (m, 1H), 3.59-3.81 (m, 6H), 2.54 (br, 4H). LCMS (ESI, m/z): 483 [M+H]+.

Example 126

1,1,1,3,3,3-hexafluoropropan-2-yl 4-[(2-fluoro-4-phenylphenyl)methyl]piperazine-1-carboxylate (11p)

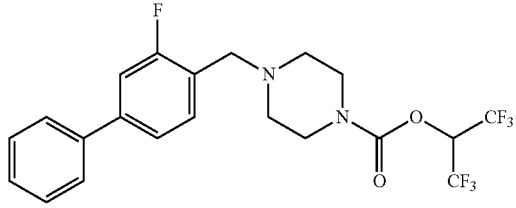 [SMILES: O=C(OC(C(F)(F)F)C(F)(F)F)N1CCN(Cc2ccc(-c3ccccc3)cc2F)CC1]

The title compound was synthesized according to the representative procedure of Example 117 Steps 1-4 using phenylboronic acid: $^1$H NMR 300 MHz (CDCl$_3$) δ 7.60 (d, J=8.0 Hz, 2H), 7.29-7.50 (m, 6H), 5.74-5.80 (m, 1H), 3.42-3.68 (m, 6H), 2.57-2.74 (m, 4H). LCMS (ESI, m/z): 465 [M+H]+.

Example 127

1,1,1,3,3,3-hexafluoropropan-2-yl 4-[(2-methyl-4-phenylphenyl)methyl]piperazine-1-carboxylate (11q)

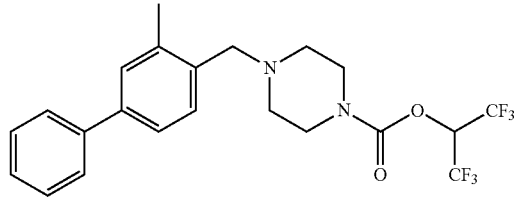 [SMILES: Cc1cc(-c2ccccc2)ccc1CN1CCN(C(=O)OC(C(F)(F)F)C(F)(F)F)CC1]

The title compound was synthesized according to the representative procedure of Example 118 Steps 1-4 using phenylboronic acid: $^1$H NMR 400 MHz (CDCl$_3$) d 7.57-7.60 (m, 2H), 7.31-7.60 (m, 6H), 5.72-5.80 (m, 1H), 3.53-3.55 (m, 6H), 2.43-2.49 (m, 7H). LCMS (ESI, m/z): 461 [M+H]+.

Example 128

1,1,1,3,3,3-hexafluoropropan-2-yl 4-[[4-(3-methylphenyl)-2-phenoxyphenyl]methyl]piperazine-1-carboxylate (11r)

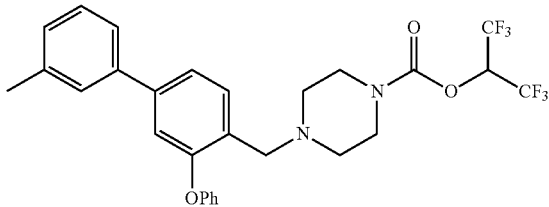 [SMILES: Cc1cccc(-c2ccc(CN3CCN(C(=O)OC(C(F)(F)F)C(F)(F)F)CC3)c(Oc3ccccc3)c2)c1]

Step 1: Preparation of 4-bromo-2-phenoxybenzaldehyde

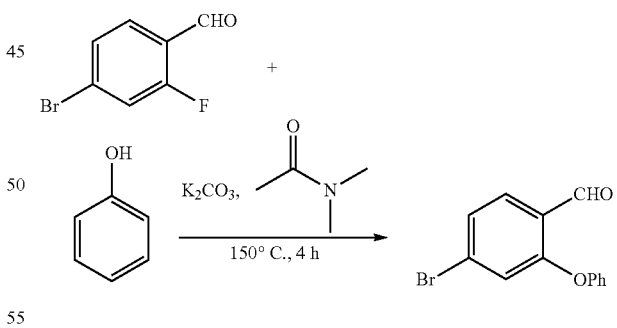

A 250 mL round-bottom flask was purged with and maintained under an inert atmosphere of nitrogen then charged with 4-bromo-2-fluorobenzaldehyde (2.00 g, 9.85 mmol, 1.00 equiv), phenol (0.926 g, 9.84 mmol, 1.00 equiv), potassium carbonate (1.35 g, 9.77 mmol, 0.99 equiv), and N,N-dimethylacetamide (30 mL). The resulting solution stirred for 4 h at 150° C. and then diluted with water (30 mL) and extracted with ethyl acetate (3×20 mL). The organic layers were combined, dried over anhydrous sodium sulfate, filtered and concentrated under reduced pressure. The residue was chromatographed on a silica gel column with ethyl acetate/petroleum ether (1/99) to provide 2.40 g (88% yield) of 4-bromo-2-phenoxybenzaldehyde as a light yellow solid. $^1$H NMR 400 MHz (CDCl$_3$) δ 10.51 (s, 1H), 7.82 (d, J=8.4 Hz, 1H), 7.41-7.48 (m, 1H), 7.33 (d, J=8.4 Hz, 1H), 7.25-7.29 (m, 1H), 7.12 (d, J=7.6 Hz, 2H), 7.04 (s, 1H). LCMS (ESI, m/z): 277 [M+H]$^+$.

Step 2: Preparation of 4-[(4-bromo-2-phenoxyphenyl)methyl]piperazine-1-carboxylate

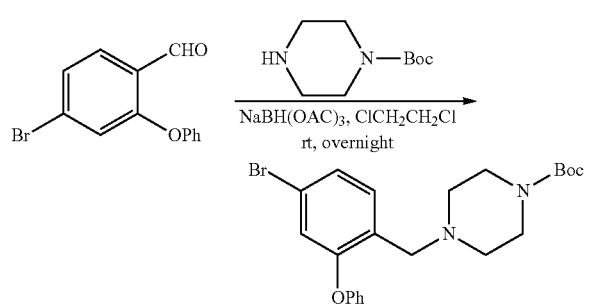

A 100 mL round-bottom flask, was charged with 4-bromo-2-phenoxybenzaldehyde (1.00 g, 3.61 mmol, 1.00 equiv), tert-butyl piperazine-1-carboxylate (0.674 g, 3.62 mmol, 1.00 equiv), and dichloromethane (30 mL). The resulting solution was stirred for 30 min at room temperature. Sodium triacetoxyborohydride (2.30 g, 10.8 mmol, 3.01 equiv) was added. The resulting solution was stirred for overnight at room temperature and then diluted with H$_2$O (10 mL). The resulting mixture was extracted with dichloromethane (2×10 mL) and the organic layers were combined, dried over anhydrous sodium sulfate, filtered and concentrated under reduced pressure. The residue was chromatographed on a silica gel column with ethyl acetate/petroleum ether (8/92) to provide 1.20 g (74% yield) of tert-butyl 4-[(4-bromo-2-phenoxyphenyl)methyl]piperazine-1-carboxylate as yellow oil. LCMS (ESI, m/z): 447 [M+H]$^+$.

Step 3: Preparation of tert-butyl 4-[[4-(3-methylphenyl)-2-phenoxyphenyl]methyl]piperazine-1-carboxylate

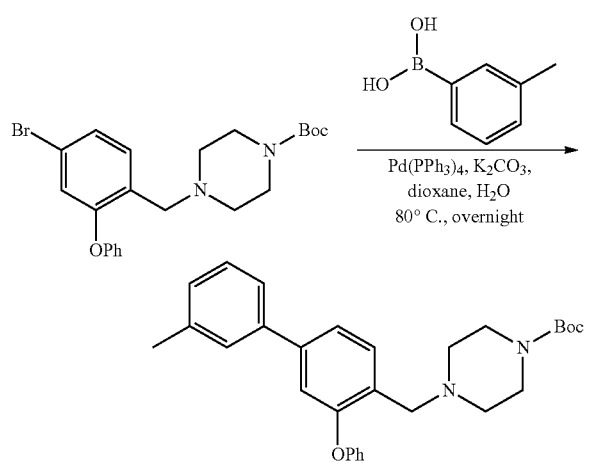

A 100 mL round-bottom flask was purged with and maintained an inert atmosphere of nitrogen then charged with tert-butyl 4-[(4-bromo-2-phenoxyphenyl)methyl]piperazine-1-carboxylate (1.20 g, 2.68 mmol, 1.00 equiv), (3-methylphenyl)boronic acid (0.730 g, 5.37 mmol, 2.00 equiv), Pd(PPh$_3$)$_4$ (0.310 g, 0.270 mmol, 0.10 equiv), potassium carbonate (1.10 g, 7.96 mmol, 2.97 equiv), dioxane (12 mL), and water (2 mL). The resulting solution was stirred overnight at 80° C. and then diluted with water (10 mL) and extracted with ethyl acetate (3×10 mL). The organic layers were combined, dried over anhydrous sodium sulfate, filtered and concentrated under reduced pressure. The residue was chromatographed on a silica gel column with ethyl acetate/petroleum ether (1/9) to provide 1.00 g (81% yield) of tert-butyl 4-[[4-(3-methylphenyl)-2-phenoxyphenyl]methyl]piperazine-1-carboxylate as yellow oil. LCMS (ESI, m/z): 459 [M+H]$^+$.

Step 4: Preparation of 1-[[4-(3-methylphenyl)-2-phenoxyphenyl]methyl]piperazine

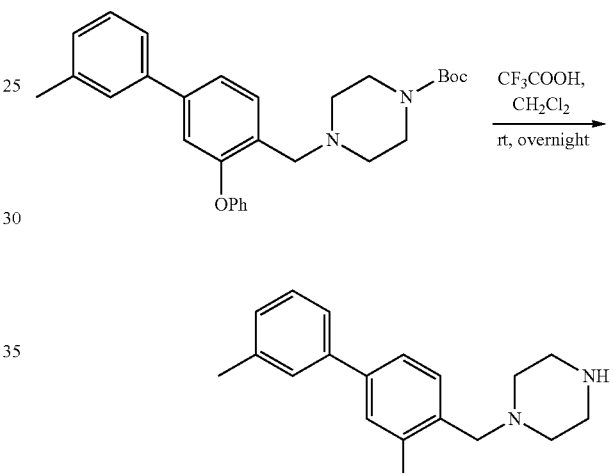

A 100 mL round-bottom flask, was charged with tert-butyl 4-[[4-(3-methylphenyl)-2-phenoxyphenyl]methyl]piperazine-1-carboxylate (1.00 g, 2.18 mmol, 1.00 equiv), trifluoroacetic acid (1 mL), dichloromethane (10 mL). The resulting solution was stirred overnight at room temperature and concentrated under reduced pressure to provide 0.800 g (crude) of 1-[[4-(3-methylphenyl)-2-phenoxyphenyl]methyl]piperazine as yellow oil LCMS (ESI, m/z): 359 [M+H]$^+$.

Step 5: Preparation of 1,1,1,3,3,3-hexafluoropropan-2-yl 4-[[4-(3-methylphenyl)-2-phenoxyphenyl]methyl]piperazine-1-carboxylate (11r)

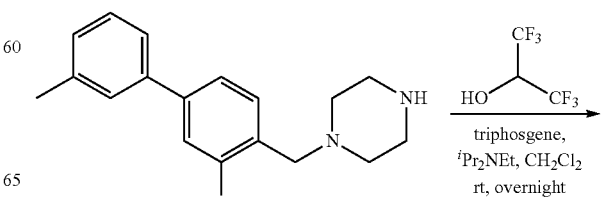

-continued

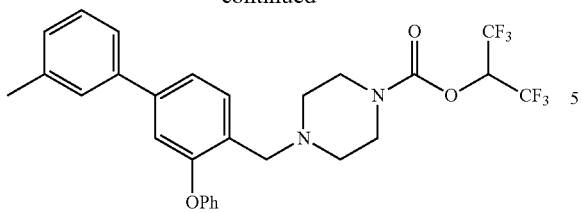

A 100 mL round-bottom flask, was charged with triphosgene (50.0 mg, 0.170 mmol, 0.30 equiv), dichloromethane (10 mL), 1,1,1,3,3,3-hexafluoropropan-2-ol (94.0 mg, 0.560 mmol, 1.00 equiv). N,N-Diisopropylethylamine (144 mg, 1.00 mmol, 2.00 equiv) was added dropwise. The resulting solution was stirred for 2 h at room temperature. 1-[[4-(3-Methylphenyl)-2-phenoxyphenyl]methyl]piperazine (200 mg, 0.560 mmol, 1.00 equiv) was added. The resulting solution was stirred overnight at room temperature and then diluted with water (5 mL). The resulting mixture was extracted with dichloromethane (2×10 mL) and the organic layers were combined, dried over anhydrous sodium sulfate, filtered and concentrated under reduced pressure. The crude product (230 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 173 mg (56% yield) of 1,1,1,3,3,3-hexafluoropropan-2-yl 4-[[4-(3-methylphenyl)-2-phenoxyphenyl]methyl]piperazine-1-carboxylate as yellow oil. $^1$H NMR 300 MHz (CDCl$_3$) δ 7.51 (d, J=7.8 Hz, 1H), 7.27-7.39 (m, 5H), 7.21-7.248 (m, 1H), 7.18 (d, J=1.5 Hz, 1H), 7.12-7.14 (m, 1H), 7.02-7.07 (m, 1H), 6.92-6.96 (m, 2H), 5.71-5.79 (m, 1H), 3.62 (s, 2H), 3.50 (br, 4H), 2.50-2.51 (m, 4H), 2.37 (s, 3H). LCMS (ESI, m/z): 553 [M+H]$^+$.

Example 129

1,1,1,3,3,3-hexafluoropropan-2-yl 4-[[2-methyl-4-(2-methylpyridin-3-yl)phenyl]methyl]piperazine-1-carboxylate (11s)

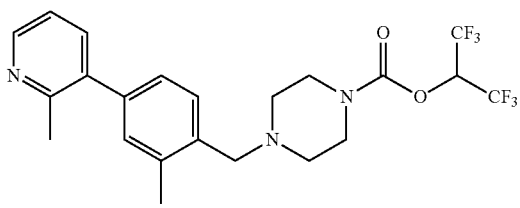 [SMILES: Cc1cc(-c2cccnc2C)ccc1CN1CCN(C(=O)OC(C(F)(F)F)C(F)(F)F)CC1]

The title compound was synthesized according to the representative procedure of Example 118 Steps 1-4 using (2-methylpyridin-3-yl)boronic acid: $^1$H NMR 400 MHz (CDCl$_3$) d 8.51 (d, J=4.8 Hz, 1H), 7.52 (d, J=7.6 Hz, 1H), 7.33 (d, J=7.6 Hz, 1H), 7.12-7.20 (m, 3H), 5.76-5.82 (m, 1H), 3.56-3.59 (m, 6H), 2.51-2.54 (m, 7H), 2.43 (s, 3H). LCMS (ESI, m/z): 476 [M+H]$^+$.

Example 130

1,1,1,3,3,3-hexafluoropropan-2-yl 4-[[2-fluoro-4-(2-methylpyridin-3-yl)phenyl]methyl]piperazine-1-carboxylate (11t)

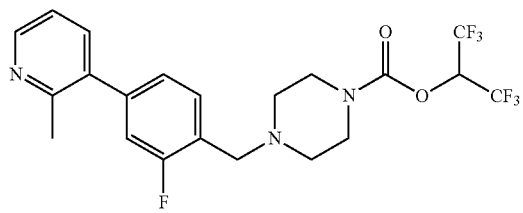 [SMILES: Cc1ncccc1-c1ccc(CN2CCN(C(=O)OC(C(F)(F)F)C(F)(F)F)CC2)c(F)c1]

The title compound was synthesized according to the representative procedure of Example 117 Steps 1-4 using (2-methylpyridin-3-yl)boronic acid: $^1$H NMR 300 MHz (CDCl$_3$) d 8.54 (d, J=4.8 Hz, 1H), 7.44-7.53 (m, 2H), 7.20-7.23 (m, 1H), 7.04-7.12 (m, 2H), 5.74-5.80 (m, 1H), 3.61-3.68 (m, 6H), 2.54-2.58 (m, 7H). LCMS (ESI, m/z): 480 [M+H]$^+$.

Example 131

1,1,1,3,3,3-hexafluoropropan-2-yl 4-[[6-methyl-5-(2-methylphenyl)pyridin-2-yl]methyl]piperazine-1-carboxylate (11u)

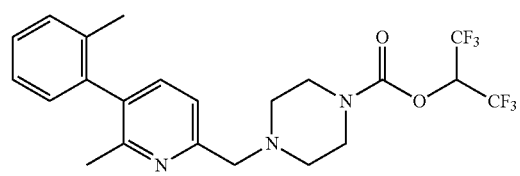 [SMILES: Cc1ccccc1-c1ccc(CN2CCN(C(=O)OC(C(F)(F)F)C(F)(F)F)CC2)nc1C]

Step 1: 5-bromo-6-methylpyridine-2-carbaldehyde

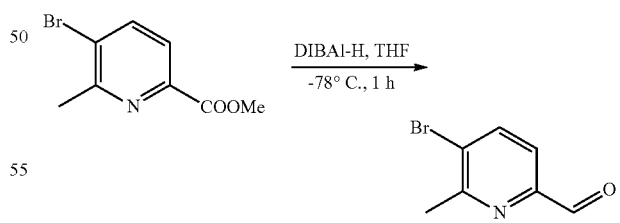

A 250 mL round-bottom flask was purged with and maintained under an inert atmosphere of nitrogen then charged with methyl 5-bromo-6-methylpyridine-2-carboxylate (7.00 g, 30.6 mmol, 1.00 equiv), tetrahydrofuran (150 mL). Diisobutylaluminium hydride (60 mL, 1 mol/L in hexane) was added dropwise at −78° C. The resulting solution was stirred for 60 min at −78° C., quenched by ammonium chloride (50 mL), extracted with ethyl acetate (2×100 mL). The organic layers were combined, dried over anhydrous sodium sulfate, filtered and concentrated under reduced pressure. The residue was chromatographed on a silica gel column with ethyl acetate/petroleum ether (10/90) to provide 4.90 g (76% yield) of 5-bromo-6-methylpyridine-2-carbaldehyde as a light yellow solid. ¹H NMR 300 MHz (CDCl₃) δ 10.04 (s, 1H), 8.02 (d, J=8.1 Hz, 1H), 7.67 (d, J=8.4 Hz, 1H), 2.78 (s, 3H). LCMS (ESI, m/z): 200 [M+H]⁺.

Step 2: Preparation tert-butyl 4-[(5-bromo-6-methylpyridin-2-yl)methyl]piperazine-1-carboxylate

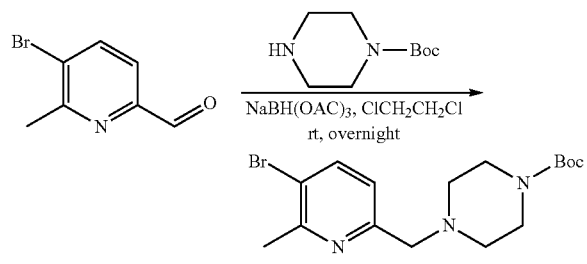

A 250 mL round-bottom flask was charged with 5-bromo-6-methylpyridine-2-carbaldehyde (4.90 g, 24.6 mmol, 1.00 equiv), tert-butyl piperazine-1-carboxylate (4.60 g, 24.7 mmol, 1.01 equiv), 1,2-dichloroethane (150 mL). The resulting solution was stirred for 30 min at room temperature. Sodium triacetoxyborohydride (15.6 g, 73.6 mmol, 3.00 equiv) was added. The resulting solution was stirred overnight at room temperature and diluted with water (50 mL), extracted with dichloromethane (2×100 mL). The organic layers were combined, dried over anhydrous sodium sulfate, filtered and concentrated under reduced pressure. The residue was chromatographed on a silica gel column with ethyl acetate/petroleum ether (30/70) to provide 7.80 g (82% yield) of tert-butyl 4[(5-bromo-6-methylpyridin-2-yl)methyl]piperazine-1-carboxylate as a light yellow solid. LCMS (ESI, m/z): 370 [M+H]⁺.

Step 3: Preparation of tert-butyl 4-[[6-methyl-5-(2-methylphenyl)pyridin-2-yl]methyl]piperazine-1-carboxylate

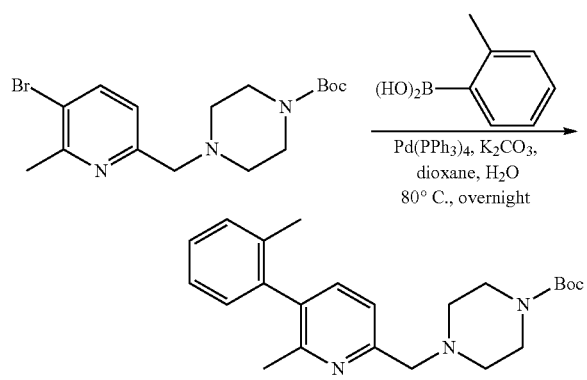

A 40 mL vial was purged with and maintained under an inert atmosphere of nitrogen then charged with tert-butyl 4[(5-bromo-6-methylpyridin-2-yl)methyl]piperazine-1-carboxylate (1.00 g, 2.70 mmol, 1.00 equiv), (2-methylphenyl)boronic acid (0.730 g, 5.40 mmol, 2.00 equiv), tetrakis(triphenylphosphine)palladium (0.310 g, 0.270 mmol, 0.10 equiv), potassium carbonate (1.15 g, 8.32 mmol, 3.08 equiv), dioxane (15 mL), water (3 mL). The resulting solution was stirred overnight at 80° C. and diluted with water (20 mL). The resulting solution was extracted with ethyl acetate (2×20 mL) and the organic layers were dried over anhydrous sodium sulfate, filtered and concentrated under reduced pressure. The residue was chromatographed on a silica gel column with ethyl acetate/petroleum ether (60/40) to provide 1.00 g (92% yield) of tert-butyl 4-[[6-methyl-5-(2-methylphenyl)pyridin-2-yl]methyl]piperazine-1-carboxylate as yellow oil. LCMS (ESI, m/z): 382 [M+H]⁺.

Step 4: Preparation of 1-[[6-methyl-5-(2-methylphenyl)pyridin-2-yl]methyl]piperazine

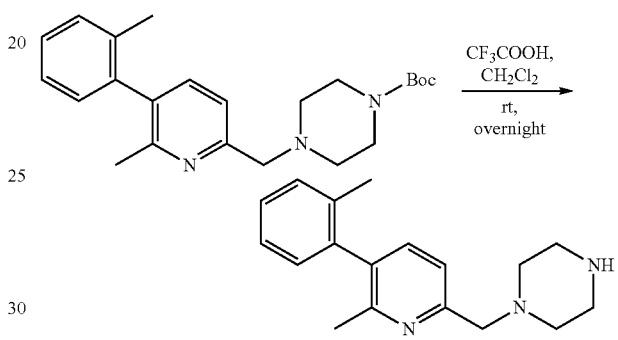

A 100 mL round-bottom flask was charged with tert-butyl 4-[[6-methyl-5-(2-methylphenyl)pyridin-2-yl]methyl]piperazine-1-carboxylate (1.00 g, 2.62 mmol, 1.00 equiv), dichloromethane (20 mL). Trifluoroacetic acid (2.5 mL) was added dropwise at 0° C. The resulting solution was stirred overnight at room temperature and concentrated under reduced pressure to yield 0.800 g (crude) of 1-[[6-methyl-5-(2-methylphenyl)pyridin-2-yl]methyl]piperazine as a yellow solid. LCMS (ESI, m/z): 282 [M+H]⁺.

Step 5: Preparation of 1,1,1,3,3,3-hexafluoropropan-2-yl 4-[[6-methyl-5-(2-methylphenyl)pyridin-2-yl]methyl]piperazine-1-carboxylate (11u)

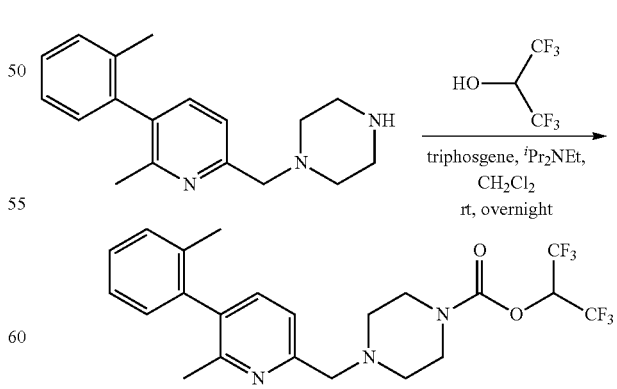

A 40 mL vial was charged with a solution of triphosgene (83.0 mg, 0.280 mmol, 0.39 equiv) in dichloromethane (20 mL), 1,1,1,3,3,3-hexafluoropropan-2-ol (141 mg, 0.840 mmol, 1.18 equiv). N,N-Diisopropylethylamine (542 mg, 4.19 mmol, 5.90 equiv) was added dropwise at 0° C. The mixture was stirred for 2 hours at room temperature. 1-[[6-Methyl-5-(2-methylphenyl)pyridin-2-yl]methyl]piperazine (200 mg, 0.710 mmol, 1.00 equiv) was added. The resulting solution was stirred overnight at room temperature and concentrated under reduced pressure. The residue was chromatographed on a $C_{18}$ column with acetonitrile/water (40/60) to provide 219 mg (65% yield) of 1,1,1,3,3,3-hexafluoropropan-2-yl 4-[[6-methyl-5-(2-methylphenyl)pyridin-2-yl]methyl]piperazine-1-carboxylate as yellow oil. $^1$H NMR 300 MHz (CDCl$_3$) δ 7.43 (d, J=7.5 Hz, 1H), 7.28-7.34 (m, 4H), 7.09 (d, J=6.9 Hz, 1H), 5.72-5.80 (m, 1H), 3.77 (s, 2H), 3.65 (br, 4H), 2.63 (br, 4H), 2.31 (s, 3H), 2.07 (s, 3H). LCMS (ESI, m/z): 476 [M+H]$^+$.

Example 132

1,1,1,3,3,3-hexafluoropropan-2-yl 4-[[5-(2-fluorophenyl)-6-methyl-pyridin-2-yl]methyl]piperazine-1-carboxylate (11v)

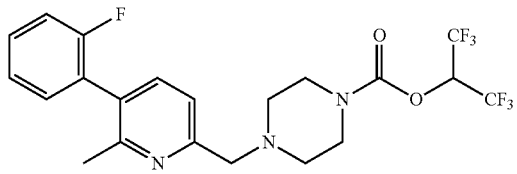 [SMILES: Cc1nc(CN2CCN(C(=O)OC(C(F)(F)F)C(F)(F)F)CC2)ccc1-c1ccccc1F]

The title compound was synthesized according to the representative procedure of Example 131 Steps 3-5 using (2-fluorophenyl)boronic acid. $^1$H NMR 300 MHz (CDCl$_3$) δ 7.52 (d, J=7.8 Hz, 1H), 7.32-7.43 (m, 2H), 7.14-7.26 (m, 3H), 5.72-5.82 (m, 1H), 3.74 (s, 2H), 3.63 (br, 4H), 2.60 (br, 4H), 2.44 (s, 3H). LCMS (ESI, m/z): 480 [M+H]$^+$.

Example 133

1,1,1,3,3,3-hexafluoropropan-2-yl 4-[[5-(3-fluorophenyl)-6-methylpyridin-2-yl]methyl]piperazine-1-carboxylate (11w)

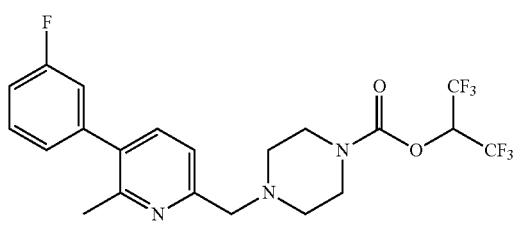 [SMILES: Cc1nc(CN2CCN(C(=O)OC(C(F)(F)F)C(F)(F)F)CC2)ccc1-c1cccc(F)c1]

The title compound was synthesized according to the representative procedure of Example 131 Steps 3-5 using (3-fluorophenyl)boronic acid. $^1$H NMR 300 MHz (CDCl$_3$) δ 7.50 (d, J=7.8 Hz, 1H), 7.26-7.45 (m, 2H), 7.01-7.11 (m, 3H), 5.72-5.80 (m, 1H), 3.73 (s, 2H), 3.62 (br, 4H), 2.59 (br, 4H), 2.50 (s, 3H). LCMS (ESI, m/z): 480 [M+H]$^+$.

Example 134

1,1,1,3,3,3-hexafluoropropan-2-yl 4-[[2-(dimethylcarbamoyl)-4-phenylphenyl]methyl]piperazine-1-carboxylate (11x)

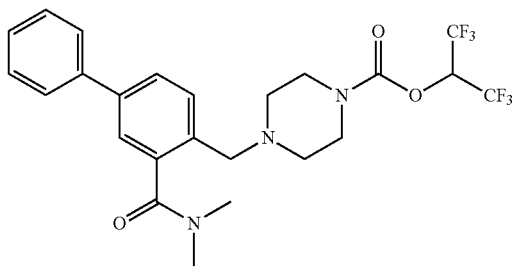 [SMILES: CN(C)C(=O)c1cc(-c2ccccc2)ccc1CN1CCN(C(=O)OC(C(F)(F)F)C(F)(F)F)CC1]

Step 1: Preparation of 5-bromo-2-formylbenzoic acid

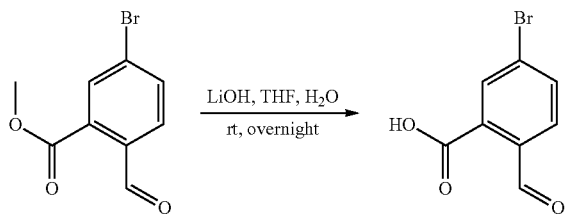

A 50 mL round-bottom flask was charged with methyl 5-bromo-2-formylbenzoate (1.00 g, 4.11 mmol, 1.00 equiv), lithium hydroxide (2.00 g, 83.5 mmol, 20.0 equiv), tetrahydrofuran (10 mL), and H$_2$O (10 mL). The resulting solution was stirred for 3 h at room temperature. The pH value of the solution was adjusted to 6 with hydrogen chloride solution (2 mol/L). The solid were collected by filtration to yield 0.700 g (crude) of 5-bromo-2-formylbenzoic acid as a light yellow solid. LCMS (ESI, m/z): 227 [M−H]$^-$.

Step 2: Preparation of 5-bromo-2-formyl-N,N-dimethylbenzamide

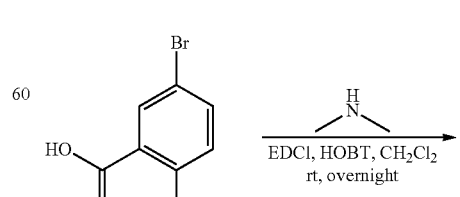

-continued

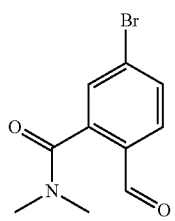

A 100 mL round-bottom flask was charged with 5-bromo-2-formylbenzoic acid (350 mg, 1.53 mmol, 1.00 equiv), N-(3-dimethylaminopropyl)-N'-ethylcarbodiimide hydrochloride (355 mg, 1.85 mmol, 1.20 equiv), 1-hydroxybenzotrizole (315 mg, 2.33 mmol, 1.50 equiv), dichloromethane (10 mL). The resulting solution was stirred for 15 min at room temperature. Dimethylamine (208 mg, 4.61 mmol, 3.00 equiv) was added. The resulting solution was stirred overnight at room temperature, diluted with water (20 mL), extracted with dichloromethane (3×20 mL) and the organic layers were combined, dried over $Na_2SO_4$, filtered and concentrated under reduced pressure. The residue was chromatographed on a silica gel column with ethyl acetate/petroleum ether (50/50) to provide 86.0 mg (22% yield) of 5-bromo-2-formyl-N,N-dimethylbenzamide as light yellow oil. LCMS (ESI, m/z): 256 $[M+H]^+$.

Step 3: Preparation of tert-butyl 4-[[4-bromo-2-(dimethylcarbamoyl)phenyl]methyl]piperazine-1-carboxylate

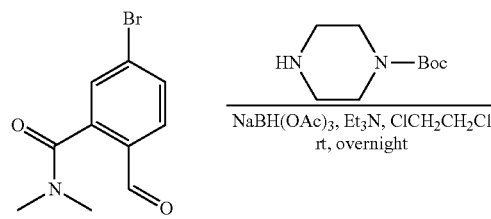

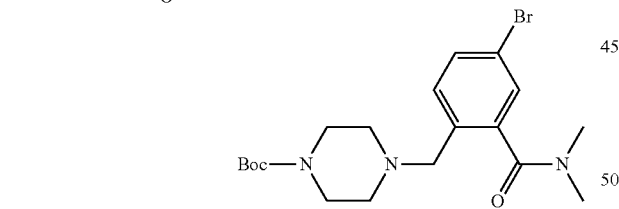

A 100 mL round-bottom flask was charged with tert-butyl piperazine-1-carboxylate (86.0 mg, 0.460 mmol, 1.00 equiv), 5-bromo-2-formyl-N,N-dimethylbenzamide (130 mg, 0.510 mmol, 1.10 equiv), dichloromethane (10 mL). Triethylamine (139 mg, 1.37 mmol, 3.00 equiv) was added. The mixture was stirred for 30 min at room temperature. Sodium triacetoxyborohydride (293 mg, 1.38 mmol, 3.00 equiv) was added. The resulting solution was stirred overnight at room temperature, diluted with water (15 mL), extracted with dichloromethane (3×15 mL) and the organic layers were combined, dried over $Na_2SO_4$, filtered and concentrated under reduced pressure. The residue was chromatographed on a silica gel column with ethyl acetate/petroleum ether (50/50) to provide 170 mg (87% yield) of tert-butyl 4-[[4-bromo-2-(dimethylcarbamoyl)phenyl]methyl]piperazine-1-carboxylate as light yellow oil. LCMS (ESI, m/z): 426 $[M+H]^+$.

Step 4: Preparation of tert-butyl 4-[[2-(dimethylcarbamoyl)-4-phenylphenyl]methyl]piperazine-1-carboxylate

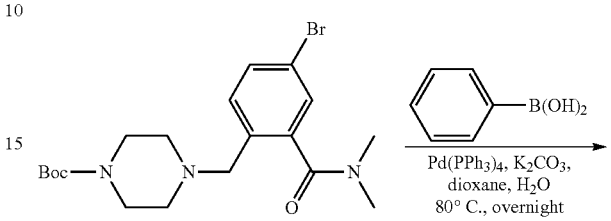

A 100 mL round-bottom flask purged and maintained with an inert atmosphere of nitrogen, was charged with tert-butyl 4-[[4-bromo-2-(dimethylcarbamoyl)phenyl]methyl]piperazine-1-carboxylate (130 mg, 0.300 mmol, 1.00 equiv), phenylboronic acid (113 mg, 0.930 mmol, 3.00 equiv), potassium carbonate (128 mg, 0.930 mmol, 3.00 equiv), tetrakis(triphenylphosphine)palladium (36.0 mg, 0.030 mmol, 0.10 equiv), dioxane (4 mL), $H_2O$ (0.4 mL). The resulting solution was stirred overnight at 80° C. and concentrated under reduced pressure. The residue was chromatographed on a silica gel column with ethyl acetate/petroleum ether (25/75) to provide 100 mg (79% yield) of tert-butyl 4-[[2-(dimethylcarbamoyl)-4-phenylphenyl]methyl]piperazine-1-carboxylate as light yellow oil. LCMS (ESI, m/z): 424 $[M+H]^+$.

Step 5: Preparation of N,N-dimethyl-5-phenyl-2-(piperazin-1-ylmethyl)benzamide

-continued

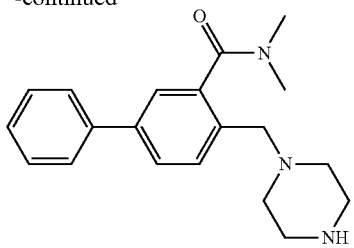

A 50 mL round-bottom flask was charged with tert-butyl 4-[[2-(dimethylcarbamoyl)-4-phenylphenyl]methyl]piperazine-1-carboxylate (300 mg, 0.710 mmol, 1.00 equiv), dichloromethane (5 mL), trifluoroacetic acid (1 mL). The resulting solution was stirred for 1 h at room temperature, concentrated under reduced pressure to yield 229 mg (crude) of N,N-dimethyl-5-phenyl-2-(piperazin-1-ylmethyl)benzamide as light yellow oil. LCMS (ESI, m/z): 324 [M+H]$^+$.

Step 6: Preparation of 1,1,1,3,3,3-hexafluoropropan-2-yl 4-[[2-(dimethylcarbamoyl)-4-phenylphenyl]methyl]piperazine-1-carboxylate (11x)

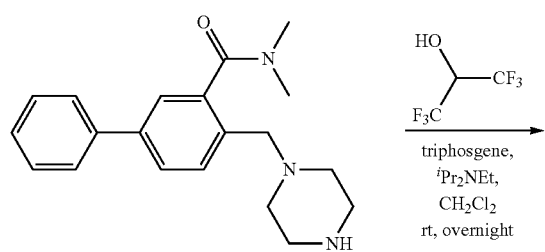

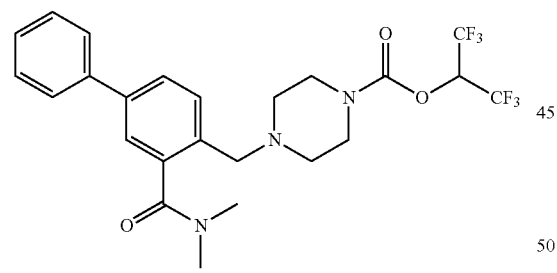

A 100 mL round-bottom flask was charged with triphosgene (55.0 mg, 0.190 mmol, 0.30 equiv) in dichloromethane (10 mL). 1,1,1,3,3,3-Hexafluoropropan-2-ol (104 mg, 0.620 mmol, 1.00 equiv) and N,N-diisopropylethylamine (152 mg, 1.18 mmol, 1.90 equiv) were added dropwise. The mixture was stirred for 30 min at room temperature. N,N-Dimethyl-5-phenyl-2-(piperazin-1-ylmethyl)benzamide (200 mg, 0.620 mmol, 1.00 equiv) was added. The resulting solution was stirred overnight at room temperature, diluted with water (20 mL), extracted with dichloromethane (3×20 mL) and the organic layers were combined, dried over Na$_2$SO$_4$, filtered and concentrated under reduced pressure. The crude product (240 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 93.2 mg (28% yield) of 1,1,1,3,3,3-hexafluoropropan-2-yl 4-[[2-(dimethylcarbamoyl)-4-phenylphenyl]methyl]piperazine-1-carboxylate as light yellow oil. $^1$H NMR 300 MHz (CDCl$_3$) δ 7.36-7.81 (m, 8H), 5.70-5.80 (m, 1H), 3.41-3.67 (m, 4H), 3.03-3.30 (m, 4H), 2.84-3.02 (m, 4H), 2.40-2.66 (m, 4H). LCMS (ESI, m/z): 518 [M+H]$^+$.

Example 135

1,1,1,3,3,3-hexafluoropropan-2-yl 4-([4-phenyl-2-[(pyrrolidin-1-yl)carbonyl]phenyl]methyl)piperazine-1-carboxylate (11y)

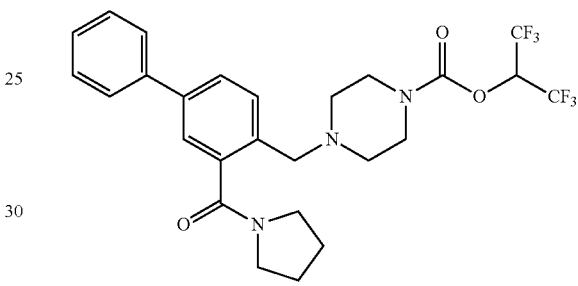

The title compound was synthesized according to the representative procedure of Example 131 Steps 3-5 using (3-fluorophenyl)boronic acid. $^1$H NMR 300 MHz (CDCl$_3$) δ 7.26-7.70 (m, 8H), 5.72-5.78 (m, 1H), 3.64-3.68 (m, 4H), 3.27-3.50 (m, 4H), 3.23-3.24 (m, 2H), 2.49-2.50 (m, 4H), 1.88-2.05 (m, 4H). LCMS (ESI, m/z): 544 [M+H]$^+$.

Example 136

1,1,1,3,3,3-hexafluoropropan-2-yl 4-[[2-methyl-4-(6-methylpyridin-2-yl)phenyl]methyl]piperazine-1-carboxylate (11z)

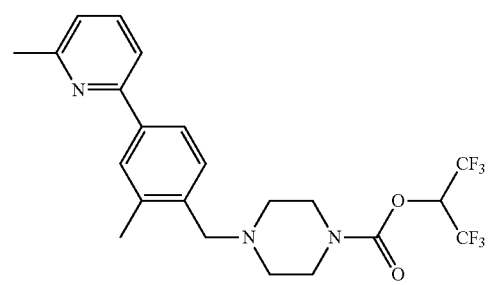

The title compound was synthesized according to the representative procedure of Example 139 Steps 1-4 using tert-butyl 4[(4-bromo-2-methylphenyl)methyl]piperazine-1-carboxylate: $^1$H NMR 400 MHz (CDCl$_3$) d 7.82 (s, 1H), 7.74 (d, J=7.6 Hz, 1H), 7.63-7.67 (m, 1H), 7.52 (d, J=8.0 Hz, 1H), 7.34-7.35 (m, 1H), 7.11 (d, J=7.6 Hz, 1H), 5.75-5.81 (m, 1H), 3.56 (br, 6H), 2.63 (s, 3H), 2.50 (br, 4H), 2.47 (s, 3H). LCMS (ESI, m/z): 476 [M+H]⁺.

Example 137

1,1,1,3,3,3-hexafluoropropan-2-yl 4-[[4-(2,6-dimethylpyridin-4-yl)-2-fluorophenyl]methyl]piperazine-1-carboxylate (11aa)

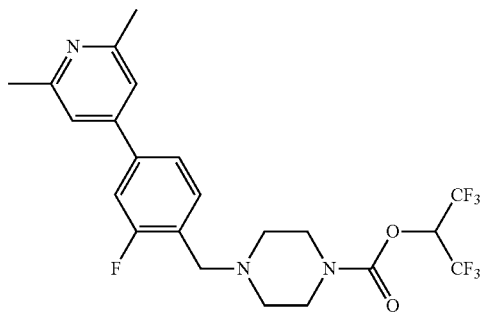 [SMILES: Cc1cc(-c2ccc(CN3CCN(C(=O)OC(C(F)(F)F)C(F)(F)F)CC3)c(F)c2)cc(C)n1]

The title compound was synthesized according to the representative procedure of Example 117 Steps 1-4 using (2,6-dimethylpyridin-4-yl)boronic acid: ¹H NMR 300 MHz (CDCl₃) d 7.46-7.50 (m, 1H), 7.40-7.42 (m, 1H), 7.32-7.35 (m, 1H), 7.18 (s, 2H), 5.74-5.80 (m, 1H), 3.68 (s, 2H), 3.60 (br, 4H), 2.62 (s, 6H), 2.52-2.58 (m, 4H). LCMS (ESI, m/z): 494 [M+H]⁺.

Example 138

1,1,1,3,3,3-hexafluoropropan-2-yl 4-[[2-fluoro-4-(3-methylpyridin-4-yl)phenyl]methyl]piperazine-1-carboxylate (11ab)

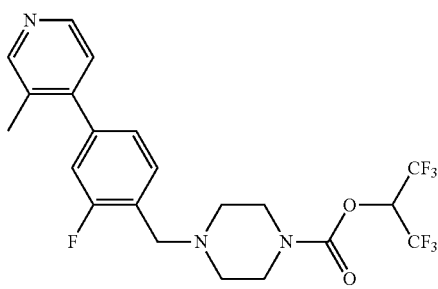 [SMILES: Cc1cnccc1-c1ccc(CN2CCN(C(=O)OC(C(F)(F)F)C(F)(F)F)CC2)c(F)c1]

The title compound was synthesized according to the representative procedure of Example 117 Steps 1-4 using (3-methylpyridin-4-yl)boronic acid: ¹H NMR 300 MHz (CDCl₃) d 8.51-8.55 (m, 2H), 7.54 (t, J=14.4 Hz, 1H), 7.13-7.18 (m, 2H), 7.06-7.09 (m, 1H), 5.75-5.80 (m, 1H), 3.66-3.74 (m, 6H), 2.63 (br, 4H), 2.32 (s, 3H). LCMS (ESI, m/z): 480 [M+H]⁺.

Example 139

1,1,1,3,3,3-hexafluoropropan-2-yl 4-[[2-fluoro-4-(6-methylpyridin-2-yl)phenyl]methyl]piperazine-1-carboxylate (11ac)

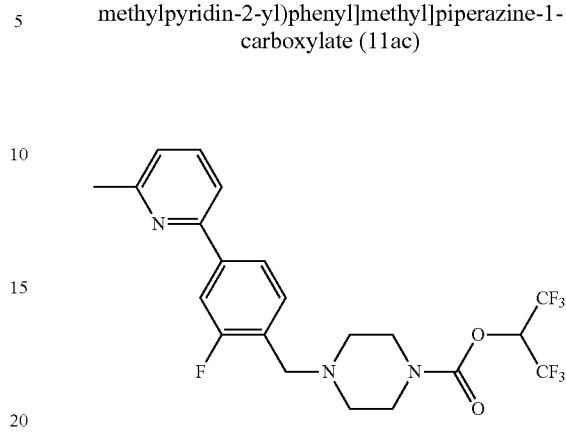

Step 1: Preparation of tert-butyl 4-[[2-fluoro-4-(tetramethyl-1,3,2-dioxaborolan-2-yl)phenyl]methyl]piperazine-1-carboxylate

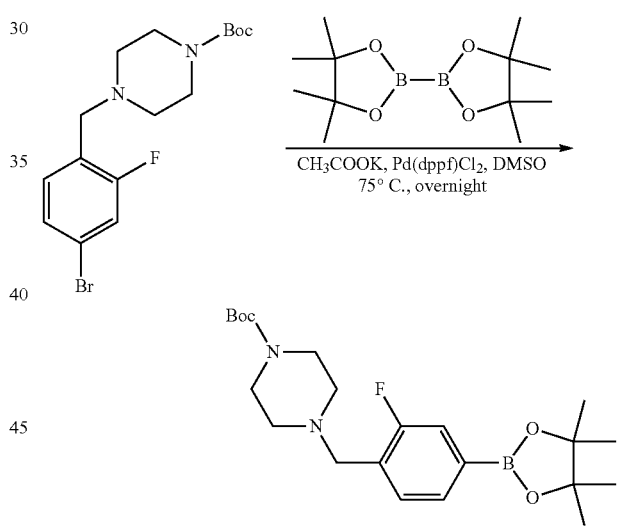

A 100 mL round-bottom flask was purged with and maintained under an inert atmosphere of nitrogen then charged with tert-butyl 4-[(4-bromo-2-fluorophenyl)methyl]piperazine-1-carboxylate (2.00 g, 5.36 mmol, 1.00 equiv, Example 117, Step 1), 4,4,5,5-tetramethyl-2-(tetramethyl-1,3,2-dioxaborolan-2-yl)-1,3,2-dioxaborolane (1.50 g, 5.91 mmol, 1.10 equiv), potassium acetate (1.05 g, 10.7 mmol, 2.00 equiv), [1,1'-Bis(diphenylphosphino)ferrocene]palladium(II) chloride (0.197 g, 0.270 mmol, 0.05 equiv) and dimethyl sulfoxide (20 mL). The resulting solution was stirred overnight at 75° C. The reaction progress was monitored by LCMS. The reaction was then quenched by the addition of water (30 mL). The resulting solution was extracted with ethyl acetate (3×30 mL) and the organic layers were combined, washed with brine (2×30 mL), dried over anhydrous sodium sulfate and concentrated under reduced pressure. The residue was chromatographed on a silica gel column with ethyl acetate/petroleum ether (1/2) to yield 1.50 g (67% yield) of tert-butyl 4-[[2-fluoro-4-(tetramethyl-1,3,2-dioxaborolan-2-yl)phenyl]methyl]piperazine-1-carboxylate as greenish oil. LCMS (ESI, m/z): 421 [M+H]+

Step 2: Preparation of tert-butyl 4-[[2-fluoro-4-(6-methylpyridin-2-yl)phenyl]methyl]piperazine-1-carboxylate

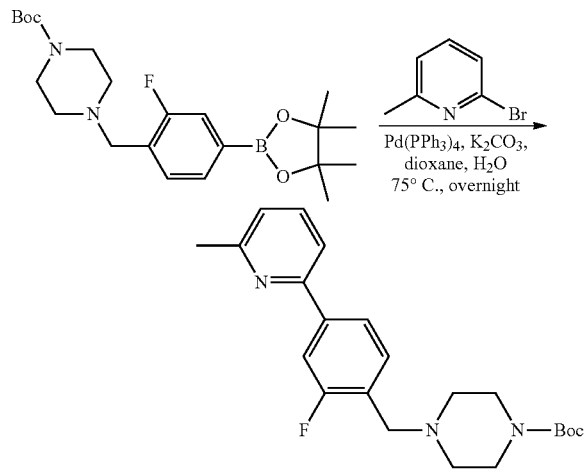

A 25 mL round-bottom flask purged and maintained with an inert atmosphere of nitrogen and charged with tert-butyl 4-[[2-fluoro-4-(tetramethyl-1,3,2-dioxaborolan-2-yl)phenyl]methyl]piperazine-1-carboxylate (1.50 g, 3.57 mmol, 1.00 equiv), 2-bromo-6-methylpyridine (0.916 g, 5.32 mmol, 1.49 equiv), Tetrakis(triphenylphosphine)palladium (0.413 g, 0.360 mmol, 0.10 equiv), potassium carbonate (1.50 g, 10.8 mmol, 3.04 equiv), dioxane (15 mL) and water (3 mL). The resulting solution was stirred overnight at 75° C. The reaction progress was monitored by LCMS. The reaction was then quenched by the addition of water (20 mL). The resulting solution was extracted with ethyl acetate (3×20 mL) and the organic layers were combined, washed with brine (2×20 mL), dried over anhydrous sodium sulfate and concentrated under reduced pressure. The residue was chromatographed on a silica gel column with ethyl acetate/petroleum ether (1/3) to yield 1.10 g (80% yield) of tert-butyl 4-[[2-fluoro-4-(6-methylpyridin-2-yl)phenyl]methyl]piperazine-1-carboxylate as yellow oil. LCMS (ESI, m/z): 386 [M+H]+.

Step 3: Preparation of 1-[[2-fluoro-4-(6-methylpyridin-2-yl)phenyl]methyl]piperazine

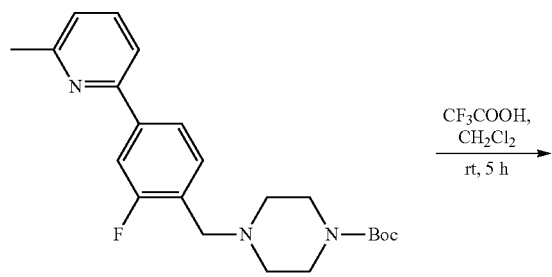

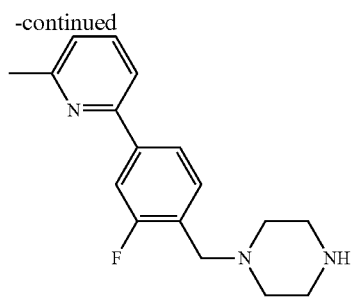

A 50 mL round-bottom flask was purged with and maintained under an inert atmosphere of nitrogen then charged with tert-butyl 4-[[2-fluoro-4-(6-methylpyridin-2-yl)phenyl]methyl]piperazine-1-carboxylate (1.10 g, 2.85 mmol, 1.00 equiv) and dichloromethane (12 mL). Trifluoroacetic acid (2 mL) was added dropwise at 0° C. The resulting solution was stirred for 5 h at room temperature. The reaction progress was monitored by LCMS. The reaction was then quenched by the addition of water (20 mL). The resulting solution was extracted with dichloromethane (3×20 mL) and the organic layers were combined, washed with brine (2×20 mL), dried over anhydrous sodium sulfate and concentrated under reduced pressure to provide 0.700 g (86% yield) of 1-[[2-fluoro-4-(6-methylpyridin-2-yl)phenyl]methyl]piperazine as yellow oil. LCMS (ESI, m/z): 286 [M+H]+.

Step 4: Preparation of 1,1,1,3,3,3-hexafluoropropan-2-yl 4-[[2-fluoro-4-(6-methylpyridin-2-yl)phenyl]methyl]piperazine-1-carboxylate (11ac)

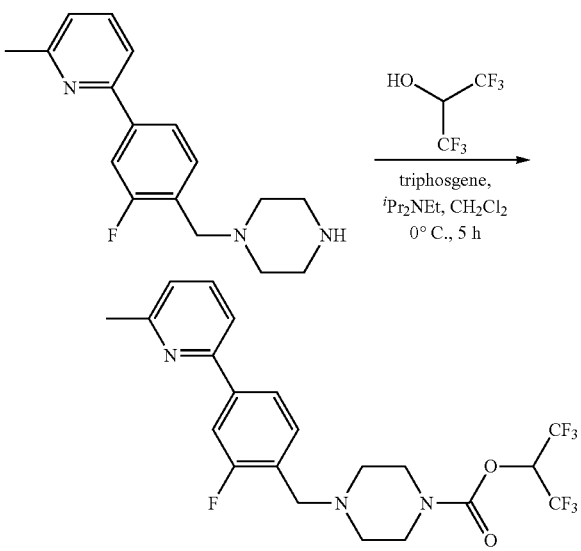

A 25 mL round-bottom flask was purged with and maintained under an inert atmosphere of nitrogen then charged with triphosgene (55.0 mg, 0.190 mmol, 0.35 equiv), 1,1,1,3,3,3-hexafluoropropan-2-ol (133 mg, 0.790 mmol, 1.51 equiv) and dichloromethane (3 mL). N,N-diisopropylethylamine (204 mg, 1.58 mmol, 3.00 equiv) was added dropwise at 0° C. The resulting solution was stirred for 2 h at 0° C. 1-[[2-Fluoro-4-(6-methylpyridin-2-yl)phenyl]methyl]piperazine (150 mg, 0.530 mmol, 1.00 equiv) in dichloromethane (2 mL) was added dropwise at 0° C. The resulting solution was stirred for 3 h at 0° C. The reaction progress was monitored by LCMS. The reaction was then quenched by the addition of water (10 mL). The resulting solution was extracted with dichloromethane (3×10 mL) and the organic layers were combined, washed with brine (2×10 mL), dried over anhydrous sodium sulfate and concentrated under reduced pressure. The crude product (320 mg) was purified by preparative HPLC using the following gradient conditions: 30% $CH_3CN$/70% Phase A increasing to 70% $CH_3CN$ over 10 min, then to 100% $CH_3CN$ over 0.1 min, holding at 100% $CH_3CN$ for 1.9 min, then reducing to 30% $CH_3CN$ over 0.1 min, and holding at 30% for 1.9 min, on a Waters 2767-5 Chromatograph. Column: Xbridge Prep $C_{18}$, 19*150 mm 5 um; Mobile phase: Phase A: aqueous $NH_4HCO_3$ (0.05%); Phase B: $CH_3CN$; Detector, UV220 & 254 nm. Purification resulted in 102 mg (40% yield) of 1,1,1,3,3,3-hexafluoropropan-2-yl 4-[[2-fluoro-4-(6-methylpyridin-2-yl)phenyl]methyl]piperazine-1-carboxylate as a white solid. $^1$H NMR 400 MHz ($CDCl_3$) δ 7.73-7.76 (m, 2H), 7.65-7.69 (m, 1H), 7.47-7.53 (m, 2H), 7.15 (d, J=7.6 Hz, 1H), 5.74-5.80 (m, 1H), 3.60-3.69 (m, 6H), 2.65 (s, 3H), 2.49 (br, 4H). LCMS (ESI, m/z): 480 $[M+H]^+$.

Example 140

1,1,1,3,3,3-hexafluoropropan-2-yl 4-[[6-methyl-5-(3-methylphenyl)pyridin-2-yl]methyl]piperazine-1-carboxylate (11ad)

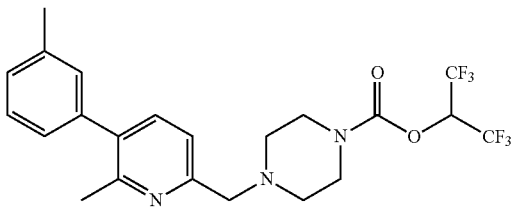 [SMILES: Cc1cccc(-c2ccc(CN3CCN(C(=O)OC(C(F)(F)F)C(F)(F)F)CC3)nc2C)c1]

The title compound was synthesized according to the representative procedure of Example 131 Steps 3-5 using (3-methylphenyl)boronic acid. $^1$H NMR 300 MHz ($CDCl_3$) δ 7.51 (d, J=7.8 Hz, 1H), 7.26-7.36 (m, 2H), 7.20 (d, J=7.8 Hz, 1H), 7.11-7.13 (m, 2H), 5.72-5.80 (m, 1H), 3.73 (s, 2H), 3.62 (br, 4H), 2.58-2.60 (m, 4H), 2.51 (s, 3H), 2.41 (s, 3H). LCMS: (ESI, m/z): 476 $[M+H]^+$.

Example 141

Compounds are tested to assess their MAGL and serine hydrolase activity using the following in vitro and in vivo assays.

In Vitro Competitive Activity-Based Protein Profiling.

Proteomes (mouse brain membrane fraction or cell lysates) (50 pt, 1.0 mg/mL total protein concentration) were preincubated with varying concentrations of inhibitors at 37° C. After 30 min, FP-Rh (1.0 μL, 50 μM in DMSO) was added and the mixture was incubated for another 30 min at 37° C. Reactions were quenched with SDS loading buffer (50 μL—4×) and run on SDS-PAGE. Following gel imaging, serine hydrolase activity was determined by measuring fluorescent intensity of gel bands corresponding to MAGL, ABHD6 and FAAH using ImageJ 1.43u software.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) *ACS Chem. Neurosci.* and Long, J. Z., et al. *Nat. Chem. Biol.* 5:37-44)

Recombinant Expression of Human MAGL in HEK293T Cells.

hMAGL was expressed in HEK293T cells according to previously reported methods (see Niphakis, Long, and Blankman, J. L., et al. (2007) *Chem. Biol.* 14:1347-1356). Cell lysates were diluted with mock proteomes for use in competitive ABPP experiments.

Compounds demonstrated activity in the assays of this Example as indicated in the following tables (Table 6, 7, and 8). Compound A is 4-nitrophenyl 4-(dibenzo[d][1,3]dioxol-5-yl(hydroxy)methyl)piperidine-1-carboxylate.

TABLE 6

| Compound | Mouse (IC50 value, nM) | | | Mouse brain MAGL (% inhibition at 20 mg/kg, p.o.) | Human MAGL (IC50 value, nM) |
|---|---|---|---|---|---|
| | MAGL | FAAH | ABHD6 | | |
| A | *** | 4700 | ** | >95 | *** |
| 1a | *** | >10,000 | * | >95 | *** |
| 1b | *** | >10,000 | ** | 13 | — |
| 1c | *** | >10,000 | * | >95 | *** |
| 1d | *** | >10,000 | ** | — | *** |
| 2a | *** | >10,000 | * | >95 | *** |
| 2b | *** | >10,000 | * | >95 | *** |
| 2c | ** | >10,000 | * | 94 | *** |
| 2d | *** | >10,000 | ** | >95 | *** |
| 2e | *** | >10,000 | ** | — | *** |
| 2f | *** | >10,000 | * | — | *** |
| 2g | * | >10,000 | * | — | — |
| 2i | * | >6,000 | ** | — | — |
| 2j | ** | >10,000 | * | — | — |
| 2l | *** | >10,000 | ** | — | — |
| 3a | *** | >10,000 | *** | >95 | *** |
| 3b | ** | >10,000 | * | — | *** |
| 3c | * | >10,000 | * | — | * |
| 3d | * | >10,000 | * | — | — |
| 3e | * | >10,000 | ** | — | ** |
| 3f | ** | >10,000 | ** | — | — |
| 3g | ** | >10,000 | *** | 93 | *** |
| 3h | * | >10,000 | * | — | *** |
| 3i | ** | >10,000 | * | — | ** |
| 3j | ** | >10,000 | ** | — | *** |
| 4a | ** | >10,000 | ** | — | ** |
| 4b | *** | >10,000 | ** | — | *** |
| 4c | *** | >10,000 | * | >95 | *** |
| 4d | ** | >10,000 | * | — | ** |
| 4e | * | >10,000 | * | — | * |
| 4f | * | >10,000 | * | — | * |
| 4g | ** | >10,000 | ** | — | ** |
| 4h | *** | >10,000 | * | — | * |
| 4i | ** | >10,000 | * | — | ** |
| 6h | ** | >10,000 | ** | — | — |
| 6i | * | >10,000 | * | — | — |
| 6j | ** | >10,000 | *** | >95 | — |
| 7k | * | >10,000 | * | — | — |
| 9b | *** | >10,000 | ** | >95 | — |

*** is less than 100 nM;
** is between 1000 and 100 nM;
* is greater than 1000 nM

TABLE 7

| Compound | Mouse (IC50 value, nM) | | | Mouse brain MAGL (% inhibition at 5 mg/kg, p.o.) | Mouse brain MAGL (ED50, mg/kg, p.o.) | Human MAGL (IC50 value, nM) |
|---|---|---|---|---|---|---|
| | MAGL | FAAH | ABHD6 | | | |
| 9a | ** | >10,000 | ** | — | — | — |
| 9c | *** | >10,000 | * | 100 | — | — |
| 9d | *** | >10,000 | * | — | ### | — |
| 9e | ** | >5,000 | ** | — | — | — |
| 9f | ** | >10,000 | ** | — | — | — |
| 9g | ** | >10,000 | * | — | — | — |
| 9h | ** | >10,000 | ** | — | — | — |
| 9n | *** | >10,000 | * | 75 | — | — |
| 9o | *** | — | — | — | — | — |
| 9p | *** | — | — | — | — | — |
| 9q | ** | — | — | — | — | — |
| 9r | *** | — | — | — | — | — |
| 9s | *** | >6,250 | ** | — | ### | *** |
| 9t | *** | >6,250 | * | — | # | — |
| 9u | ** | >6,250 | * | — | — | — |
| 9v | *** | >6,250 | ** | — | — | — |
| 9w | *** | >1,250 | * | — | — | — |
| 9x | *** | >250 | — | — | — | — |
| 9y | *** | >250 | — | — | — | — |
| 9z | *** | >10,000 | * | — | ### | *** |
| 9aa | ** | >10,000 | ** | — | — | — |
| 9ab | ** | >10,000 | * | — | — | — |
| 9ad | *** | >10,000 | * | — | ### | — |
| 9ae | ** | >10,000 | ** | — | — | — |
| 9af | ** | >10,000 | * | — | ### | — |
| 9ag | *** | >10,000 | * | — | ### | — |
| 9ah | *** | >10,000 | *** | — | — | — |
| 9ai | *** | >10,000 | ** | — | — | — |
| 9ap | ** | >10,000 | * | — | — | — |
| 9aq | *** | >10,000 | * | 100 | — | — |
| 9ar | *** | >10,000 | * | 75 | — | — |
| 9as | ** | >10,000 | * | — | — | — |
| 9au | * | >10,000 | * | — | — | — |
| 9av | *** | >10,000 | * | 75 | — | — |
| 9aw | ** | >10,000 | * | — | — | — |
| 9ax | *** | >10,000 | * | 75 | — | — |
| 9ay | *** | >10,000 | * | 50 | — | — |
| 9az | ** | >10,000 | ** | — | — | — |
| 9ba | *** | >10,000 | * | — | — | — |
| 9bb | *** | >10,000 | * | — | — | — |
| 9be | ** | >10,000 | ** | — | — | — |
| 9bg | ** | >10,000 | * | — | — | — |
| 9bh | *** | >10,000 | ** | 25 | — | — |
| 9bi | *** | >10,000 | * | 50 | — | — |
| 9bj | *** | >10,000 | ** | 75 | — | — |
| 10b | ** | — | — | — | — | — |
| 10c | *** | >6,250 | ** | — | — | — |
| 10d | ** | >10,000 | ** | — | — | — |
| 10e | *** | >10,000 | *** | — | — | — |
| 10f | ** | — | — | — | — | — |
| 10g | *** | >10,000 | ** | 75 | — | — |
| 10h | ** | >10,000 | ** | — | — | — |
| 10i | *** | >10,000 | ** | 75 | — | — |
| 11f | * | — | — | — | — | — |
| 11j | *** | >10,000 | * | — | — | — |
| 11p | *** | >10,000 | * | — | — | — |
| 11q | ** | >10,000 | * | — | — | — |
| 11x | ** | >10,000 | * | — | — | — |
| 11y | *** | >10,000 | * | 75 | — | — |

\*\*\*is less than 100 nM; \*\*is between 1000 and 100 nM; \*is greater than 1000 nM ### is less than 4 mg/kg; ## is between 4 and 8 mg/kg; # is greater than 8 mg/kg

TABLE 8

| | % Inhibition at 1 uM | | |
|---|---|---|---|
| Compound | MAGL | FAAH | ABHD6 |
| 2h | ** | * | ** |
| 2k | ** | * | ** |
| 9i | ** | * | ** |
| 9j | ** | * | ** |
| 9k | * | * | * |
| 9l | * | * | * |
| 9m | ** | * | ** |
| 9ac | * | * | ** |
| 9aj | ** | * | ** |
| 9ak | *** | * | ** |
| 9al | ** | * | ** |
| 9am | * | * | * |
| 9n | ** | * | ** |
| 9o | * | * | * |
| 9at | ** | * | * |
| 9bc | ** | * | * |
| 9bd | ** | * | ** |
| 9bf | ** | * | * |
| 10a | *** | * | ** |
| 11a | ** | * | ** |
| 11b | *** | * | ** |
| 11c | ** | * | ** |
| 11d | *** | * | ** |
| 11e | *** | * | ** |
| 11g | *** | * | *** |
| 11h | ** | * | * |
| 11i | ** | * | ** |
| 11k | *** | * | ** |
| 11l | *** | * | *** |
| 11m | ** | * | ** |
| 11n | *** | * | *** |
| 11o | *** | * | ** |
| 11r | ** | * | * |
| 11s | ** | * | ** |
| 11t | *** | * | ** |
| 11u | ** | * | ** |
| 11v | *** | * | *** |
| 11w | *** | * | ** |
| 11z | ** | * | ** |
| 11aa | *** | * | ** |
| 11ab | *** | * | ** |
| 11ac | *** | * | ** |
| 11ad | *** | * | ** |

\*\*\* is >75%;
\*\* is between 25 and 75%;
\* is <25%

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the disclosure have been discussed, the above specification is illustrative and not restrictive. Many variations will become apparent to those skilled in the art upon review of this specification. The full scope of the disclosure should be determined by reference to the claims, along with their full scope of equivalents, and the specification, along with such variations. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specifica-

What is claimed is:

1. A compound represented by:

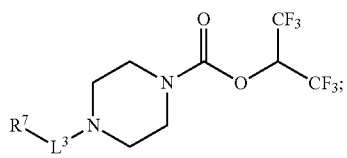

wherein
$L^3$ is a bond, —$CH_2$—, —$S(O)_2$—, or —$C(O)$—;
$R^7$ is phenyl; wherein $R^7$ is optionally substituted by one, two, or three moieties independently selected from $R^h$;
$R^a$ and $R^b$ are independently selected, for each occurrence, from the group consisting of hydrogen and $C_{1-3}$alkyl; wherein $C_{1-3}$alkyl is optionally substituted by one or more substituents selected from halogen, cyano, oxo, hydroxyl, heterocycle, and phenyl;
or $R^a$ and $R^b$, when they occur together with the nitrogen to which they are attached, form a 4-6 membered saturated heterocyclic ring, which may have an additional heteroatom selected from O, S, and N, or a spirocyclic ring selected from 8-oxa-2-azaspiro[4.5]decane and 2,8-diazaspiro[4.5]decane, wherein the 4-6 membered saturated heterocyclic ring or the spirocyclic ring are optionally substituted by one or more substituents selected from the group consisting of halogen, cyano, oxo, $C_{1-6}$alkyl, —$S(O)_w$—$C_{1-6}$alkyl (where w is 0, 1 or 2), hydroxyl, —$C(O)$—$C_{1-6}$alkyl, —$NH_2$, and —NH—$C(O)$—$C_{1-6}$alkyl;
$R^c$ is selected from the group consisting of halogen, hydroxyl, $C_{1-6}$alkyl (optionally substituted by one, two, or three halogens), and $C_{1-6}$alkoxy (optionally substituted by one, two, or three halogens); and
$R^h$ is selected from the group consisting of: halogen, phenyl (optionally substituted by one, two, or three moieties each independently selected from $R^c$), hydroxyl, cyano, $C_{1-6}$alkyl (optionally substituted by one, two or three halogens), $C_{1-6}$alkoxy (optionally substituted by one, two or three halogens), $R^aR^bN$—, $R^a$—$C(O)NR^a$—, $R^aR^bN$—$SO_2$—, $R^aR^bN$—$C(O)$—, $R^a$—$S(O)_w$— (wherein w is 0, 1 or 2), $R^a$—$SO_2$—$NR^b$—, and heteroaryl (optionally substituted by one, two or three moieties each independently selected from $R^c$);
or a stereoisomer or pharmaceutically acceptable salt thereof.

2. The compound of claim 1, or a stereoisomer or pharmaceutically acceptable salt thereof, wherein $L^3$ is a —$CH_2$—.

3. The compound of claim 1, or a stereoisomer or pharmaceutically acceptable salt thereof, wherein $L^3$ is a —$CH_2$—; and $R^h$ is selected from the group consisting of: halogen, phenyl (optionally substituted by one, two, or three moieties each independently selected from halogen, methyl, ethyl, propyl, t-butyl, and $CF_3$), $C_{1-6}$alkyl (optionally substituted by one, two or three halogens), $C_{1-6}$alkoxy (optionally substituted by one, two or three halogens), $R^aR^bN$—, $R^aR^bN$—$C(O)$—, and heteroaryl (optionally substituted by one, two or three moieties each independently selected from $C_{1-6}$alkyl or halogen).

4. The compound of claim 1, or a stereoisomer or pharmaceutically acceptable salt thereof, wherein $L^3$ is a —$CH_2$—; and $R^h$ is selected from the group consisting of: halogen, $C_{1-6}$alkyl (optionally substituted by one, two or three halogens), $C_{1-6}$alkoxy (optionally substituted by one, two or three halogens), and $R^aR^bN$—.

5. The compound of claim 4, or a stereoisomer or pharmaceutically acceptable salt thereof, wherein $R^7$ is substituted by two moieties independently selected from $R^h$.

6. The compound of claim 1, or a stereoisomer or pharmaceutically acceptable salt thereof, wherein $L^3$ is a —$CH_2$—; and $R^7$ is substituted by $R^aR^bN$— and a moiety selected from the group consisting of: halogen, $C_{1-6}$alkyl (optionally substituted by one, two or three halogens), and $C_{1-6}$alkoxy (optionally substituted by one, two or three halogens).

7. The compound of claim 6, or a stereoisomer or pharmaceutically acceptable salt thereof, wherein $R^a$ and $R^b$, together with the nitrogen to which they are attached, form a 4-6 membered saturated heterocyclic ring, which may have an additional heteroatom selected from O, S, and N, and the 4-6 membered saturated heterocyclic ring is optionally substituted by one or more substituents selected from the group consisting of halogen, cyano, oxo, $C_{1-6}$alkyl, —$S(O)_w$—$C_{1-6}$alkyl (where w is 0, 1 or 2), hydroxyl, —$C(O)$—$C_{1-6}$alkyl, —$NH_2$, and —NH—$C(O)$—$C_{1-6}$alkyl.

8. The compound of claim 7, or a stereoisomer or pharmaceutically acceptable salt thereof, wherein the 4-6 membered saturated heterocyclic ring is selected from azetidine, pyrrolidine, piperidine, piperazine, and morpholine, and the 4-6 membered saturated heterocyclic ring is optionally substituted by one or more substituents selected from the group consisting of halogen, cyano, oxo, $C_{1-6}$alkyl, —$S(O)_w$—$C_{1-6}$alkyl (where w is 0, 1 or 2), hydroxyl, —$C(O)$—$C_{1-6}$alkyl, —$NH_2$, and —NH—$C(O)$—$C_{1-6}$alkyl.

9. The compound of claim 7, or a stereoisomer or pharmaceutically acceptable salt thereof, wherein the 4-6 membered saturated heterocyclic ring is pyrrolidine.

10. The compound of claim 7, or a stereoisomer or pharmaceutically acceptable salt thereof, wherein the 4-6 membered saturated heterocyclic ring is morpholine.

11. The compound of claim 7, or a stereoisomer or pharmaceutically acceptable salt thereof, wherein the 4-6 membered saturated heterocyclic ring is piperidine.

12. The compound of claim 1, or a stereoisomer or pharmaceutically acceptable salt thereof, wherein $L^3$ is a —$CH_2$—; and $R^b$ is selected from the group consisting of: halogen, phenyl (optionally substituted by one, two, or three moieties each independently selected from halogen, methyl, ethyl, propyl, t-butyl, and $CF_3$), $C_{1-6}$alkyl (optionally substituted by one, two or three halogens), $C_{1-6}$alkoxy (optionally substituted by one, two or three halogens), and heteroaryl (optionally substituted by one, two or three moieties each independently selected from $C_{1-6}$alkyl or halogen).

13. The compound of claim 12, or a stereoisomer or pharmaceutically acceptable salt thereof, wherein $R^7$ is substituted by two moieties independently selected from $R^b$.

14. The compound of claim 1, or a stereoisomer or pharmaceutically acceptable salt thereof, wherein $L^3$ is a —$CH_2$—; and $R^h$ is selected from the group consisting of: halogen, $C_{1-6}$alkyl (optionally substituted by one, two or three halogens), $C_{1-6}$alkoxy (optionally substituted by one, two or three halogens), and $R^aR^bN$—$C(O)$—.

15. The compound of claim 14, or a stereoisomer or pharmaceutically acceptable salt thereof, wherein $R^7$ is substituted by two moieties independently selected from $R^h$.

16. The compound of claim 1, or a stereoisomer or pharmaceutically acceptable salt thereof, wherein $L^3$ is —$S(O)_2$—.

17. The compound of claim 1, or a stereoisomer or pharmaceutically acceptable salt thereof, wherein $L^3$ is —C(O)—.

18. The compound of claim 1, or a stereoisomer or pharmaceutically acceptable salt thereof, wherein $L^3$ is a bond.

19. The compound of claim 1, wherein the compound is 1,1,1,3,3,3-hexafluoropropan-2-yl 4-[[2-(morpholin-4-yl)-4-(trifluoromethyl)phenyl]methyl]piperazine-1-carboxylate, or a pharmaceutically acceptable salt thereof.

20. The compound of claim 1, wherein the compound is 1,1,1,3,3,3-hexafluoropropan-2-yl 4-[[3-fluoro-2-(morpholin-4-yl)phenyl]methyl]piperazine-1-carboxylate, or a pharmaceutically acceptable salt thereof.

21. The compound of claim 1, wherein the compound is 1,1,1,3,3,3-hexafluoropropan-2-yl 4-(4-chloro-2-(pyrrolidin-1-yl)benzyl)piperazine-1-carboxylate, or a pharmaceutically acceptable salt thereof.

22. The compound of claim 1, wherein the compound is 1,1,1,3,3,3-hexafluoropropan-2-yl 4-[[3-chloro-2-(morpholin-4-yl)phenyl]methyl]piperazine-1-carboxylate, or a pharmaceutically acceptable salt thereof.

23. The compound of claim 1, wherein the compound is 1,1,1,3,3,3-hexafluoropropan-2-yl 4-[[5-chloro-2-(morpholin-4-yl)phenyl]methyl]piperazine-1-carboxylate, or a pharmaceutically acceptable salt thereof.

24. The compound of claim 1, wherein the compound is 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt thereof.

25. The compound of claim 1, wherein the compound is 1,1,1,3,3,3-hexafluoropropan-2-yl 4-(2-(3-acetamidopyrrolidin-1-yl)-4-chlorobenzyl)piperazine-1-carboxylate, or a solvate, hydrate, stereoisomer, or pharmaceutically acceptable salt thereof.

26. The compound of claim 1, wherein the compound is 1,1,1,3,3,3-hexafluoropropan-2-yl 4-(4-chloro-2-(8-oxa-2-azaspiro[4.5]decan-2-yl)benzyl)piperazine-1-carboxylate, or a solvate, hydrate, or pharmaceutically acceptable salt thereof.

27. The compound of claim 1, wherein the compound is 1,1,1,3,3,3-hexafluoropropan-2-yl 4-(4-chloro-2-(4-(methylsulfonyl)piperazin-1-yl)benzyl)piperazine-1-carboxylate, or a solvate, hydrate, or pharmaceutically acceptable salt thereof.

28. A pharmaceutically acceptable composition comprising a compound of claim 1, and a pharmaceutically acceptable excipient.

29. A method of treating pain in a patient in need thereof, comprising administering to a patient in need thereof an effective amount of a compound of claim 1.

* * * * *

UNITED STATES PATENT AND TRADEMARK OFFICE
CERTIFICATE OF CORRECTION

| | | |
|---|---|---|
| PATENT NO. | : 9,133,148 B2 | Page 1 of 1 |
| APPLICATION NO. | : 14/599105 | |
| DATED | : September 15, 2015 | |
| INVENTOR(S) | : Justin S. Cisar et al. | |

It is certified that error appears in the above-identified patent and that said Letters Patent is hereby corrected as shown below:

In the Specification

In column 1, line 17, insert the following government grant information

--STATEMENT AS TO FEDERALLY SPONSORED RESEARCH

This invention was made with government support under Grant Number DA025285 awarded by the National Institutes of Health. The Government has certain rights in the invention.--

Signed and Sealed this
Twenty-eighth Day of June, 2016

Michelle K. Lee
*Director of the United States Patent and Trademark Office*